US012617776B2

(12) United States Patent
Inami et al.

(10) Patent No.: US 12,617,776 B2
(45) **Date of Patent: *May 5, 2026**

(54) STABLE SALT AND CRYSTAL FORMS OF 2-[3-({1-[2-(DIMETHYLAMINO)ETHYL]-2-(2,2-DIMETHYLPROPYL)-1H-1,3-BENZODIAZOL-5-YL}SULFONYL) AZETIDIN-1-YL]ETHAN-1-OL

(71) Applicant: AskAt Inc., Aichi (JP)

(72) Inventors: Yukari Inami, Aichi (JP); Yoshiyuki Okumura, Aichi (JP); Tracy Walker, Craigavon (GB)

(73) Assignee: AskAt Inc., Aichi (JP)

( * ) Notice: Subject to any disclaimer, the term of this patent is extended or adjusted under 35 U.S.C. 154(b) by 141 days.

This patent is subject to a terminal disclaimer.

(21) Appl. No.: 18/595,742

(22) Filed: Mar. 5, 2024

(65) Prior Publication Data

US 2024/0352004 A1 Oct. 24, 2024

Related U.S. Application Data

(63) Continuation of application No. 18/035,195, filed as application No. PCT/JP2021/041552 on Nov. 11, 2021, now Pat. No. 11,964,963.

(60) Provisional application No. 63/112,893, filed on Nov. 12, 2020.

(51) Int. Cl.
*C07D 403/12* (2006.01)

(52) U.S. Cl.
CPC ........ *C07D 403/12* (2013.01); *C07B 2200/13* (2013.01)

(58) Field of Classification Search
CPC ...... A61P 1/04; A61P 1/08; A61P 1/12; A61P 1/16; A61P 11/00; A61P 13/12; A61P 17/00; A61P 19/02; A61P 19/10; A61P 25/00; A61P 25/08; A61P 27/06; A61P 29/00; A61P 3/10; A61P 35/02; A61P 37/08; A61P 43/00; A61P 9/00; A61P 1/02; A61P 1/10; A61P 11/02; A61P 11/06; A61P 17/06; A61P 25/04; A61P 9/10; A61P 1/00; C07B 2200/13; C07D 403/12; A61K 31/4184; C07C 309/04; C07C 57/145
See application file for complete search history.

(56) References Cited

U.S. PATENT DOCUMENTS

| | | | |
|---|---|---|---|
| 8,653,063 | B2 | 2/2014 | Ando et al. |
| 2011/0281840 | A1 | 11/2011 | Ando et al. |

FOREIGN PATENT DOCUMENTS

| | | |
|---|---|---|
| JP | 2012-515712 | 7/2012 |

OTHER PUBLICATIONS

International Search Report mailed Jan. 11, 2022 in International (PCT) Application No. PCT/JP2021/041552, pp. 1-4.

(Continued)

*Primary Examiner* — Sarah Pihonak
*Assistant Examiner* — Padmaja S Rao
(74) *Attorney, Agent, or Firm* — Wenderoth, Lind & Ponack, L.L.P.

(57) ABSTRACT

A salt of 2-[3-({1-[2-(dimethylamino)ethyl]-2-(2,2-dimethylpropyl)-1H-1,3-benzodiazol-5-yl}sulfonyl)azetidin-1-yl] ethan-1-ol with an acid, wherein the acid is selected from the group consisting of hydrochloric acid (HCl), maleic acid, and methanesulfonic acid; a crystalline form of the salt; a pharmaceutical composition comprising the salt; a pharmaceutical composition comprising the crystalline form; a method for preventing or treating a disorder or condition comprising administering the salt; and a process for preparing a pharmaceutically acceptable salt.

16 Claims, 104 Drawing Sheets

(56) References Cited

OTHER PUBLICATIONS

Iwata, Y., et al., "Identification of a highly potent and selective CB2 agonist, RQ-00202730, for the treatment of irritable bowel syndrome", Bioorganic & Medicinal Chemistry Letters, 2015, vol. 25, No. 2, pp. 236-240.
Hira Yama, N., "Yuki Kagobutsu Kessho Sakusei Handbook (Handbook of Organic Compound Crystal Production) Principles and Know-How-", Maruzen Co., Ltd., 2008, ISBN 978-4-621-07991-1, pp. 57-58 (with partial English translation).
Wermuth, C. G., Saishin Soyaku Kagaku (The Practice of Medicinal Chemistry), Second Volume Technomix Corporation, 1999, ISBN 4-924746-80-0, pp. 347-348 (with partial English translation).
Goutopoulos, A. et al., "From cannabis to cannabinergics: new therapeutic opportunities", Pharmacology & Therapeutics, 2002, vol. 95, pp. 103-117.
Wright, K.L., et al., "Cannabinoid $CB_2$ receptors in the gastrointestinal tract: a regulatory system in states of inflammation", British Journal of Pharmacology, 2008, vol. 153, pp. 263-270.
Aizpurua-Olaizola, O., et al., "Targeting the endocannabinoid system: future therapeutic strategies", Drug Discovery Today, 2017, vol. 22, No. 1, pp. 105-110.
Tanaka, M., et al., "Endocannabinoid Modulation of Microglial Phenotypes in Neuropathology", Frontiers in Neurology, 2020, vol. 11, Article 87, pp. 1-17.
Matsuda, L.A., et al., "Structure of a cannabinoid receptor and functional expression of the cloned cDNA", Nature, 1990, vol. 346, pp. 561-564.
C.M., et al., "Molecular cloning of a human cannabinoid receptor which is also expressed in testis", Biochem. J. 1991, vol. 279, pp. 129-134.
Munro, S., et al., "Molecular characterization of a peripheral receptor for cannabinoids", Nature, 1993, vol. 365, pp. 61-65.
Pacher, P., et al., "The Endocannabinoid System as an Emerging Target of Pharmacotherapy", Pharmacol Rev., 2006, vol. 58, No. 3, pp. 389-462.
Cabral, GA, et al., "CB2 receptors in the brain: role in central immune function", British Journal of Pharmacology, 2008, vol. 153, pp. 240-251.
Howlett, A.C. et al., "International Union of Pharmacology. XXVII. Classification of Cannabinoid Receptors", Pharmacological Reviews, 2002, vol. 54, No. 2, pp. 161-202.
Chung, Y.C., et al., "CB2 receptor activation prevents glial-derived neurotoxic mediator production, BBB leakage and peripheral immune cell infiltration and rescues dopamine neurons in the MPTP model of Parkinson's disease", Experimental & Molecular Medicine, 2016, vol. 48, pp. 1-10.
Cheng, Y., et al., "Targeting cannabinoid agonists for inflammatory and neuropathic pain", Expert Opin. Investig. Drugs, 2007, vol. 16, No. 7, pp. 951-965.
Hohmann, A.G., et al., "Selective Activation of Cannabinoid $CB_2$ Receptors Suppresses Hyperalgesia Evoked by Intradermal Capsaicin", The Journal of Pharmacology and Experimental Therapeutics, 2004, vol. 308, No. 2, pp. 446-453.
Ibrahim, M.M., et al., "Activation of $CB_2$ cannabinoid receptors by AM1241 inhibits experimental neuropathic pain: Pain inhibition by receptors not present in the CNS", PNAS, 2003, vol. 100, No. 18, pp. 10529-10533.
Mathison, R., et al., "Effects of cannabinoid receptor-2 activation on accelerated gastrointestinal transit in lipopolysaccharide-treated rats", British Journal of Pharmacology, 2004, vol. 142, pp. 1247-1254.
Pacher, P., et al., "Is lipid signaling through cannabinoid 2 receptors part of a protective system?", Prog. Lipid Res., 2011, vol. 50, No. 2, pp. 193-211.
Mario van der Stelt et al., "Discovery and Optimization of 1-(4-(Pyridin-2-yl)benzyl)-imidazolidine-2,4-dione Derivatives as a Novel Class of Selective Cannabinoid CB2 Receptor Agonists", Journal of Medicinal Chemistry, 2011, vol. 54, pp. 7350-7362.
Guindon, J., et al., "Cannabinoid CB2 receptors: a therapeutic target for the treatment of inflammatory and neuropathic Pain", British Journal of Pharmacology, 2008, vol. 153, pp. 319-334.
Kusakabe, K., et al., "Selective CB2 agonists with anti-pruritic activity: Discovery of potent and orally available bicyclic 2-pyridones", Bioorganic & Medicinal Chemistry, 2013, vol. 21, pp. 3154-3163.
Mukhopadhyay, P., et al., "Cannabinoid-2 receptor limits inflammation, oxidative/nitrosative stress and cell death in nephropathy", Free Radic Biol Med., 2010, vol. 48, No. 3, pp. 457-467.
Gruden, G., et al., "Role of the endocannabinoid system in diabetes and diabetic complications", British Journal of Pharmacology, 2015, vol. 173, pp. 1116-1127.
Julien, B., et al., "Antifibrogenic Role of the Cannabinoid Receptor CB2 in the Liver", Gastroenterology, 2005, vol. 128, pp. 742-755.
Bátkai, S., et al., "Cannabinoid-2 receptor mediates protection against hepatic ischemia/reperfusion injury", FASEB J., 2007, vol. 21, No. 8, pp. 1788-1800.
Rajesh, M., et al., "Pivotal Advance: Cannabinoid-2 receptor agonist HU-308 protects against hepatic ischemia/reperfusion injury by attenuating oxidative stress, inflammatory response, and apoptosis", J. Leukoc Biol., 2007, vol. 82, No. 6, pp. 1382-1389.
Horváth, B., et al., "A new cannabinoid $CB_2$ receptor agonist HU-910 attenuates oxidative stress, inflammation and cell death associated with hepatic ischaemia/reperfusion injury", British Journal of Pharmacology, 2012, vol. 165, pp. 2462-2478.
Montecucco, F., et al., "$CB_2$ cannabinoid receptor activation is cardioprotective in a mouse model of ischemia/reperfusion", Journal of Molecular and Cellular Cardiology, 2009, vol. 46, pp. 612-620.
Balbach, S., et al., "Pharmaceutical evaluation of early development candidates 'the 100 mg-approach'", International Journal of Pharmaceutics, 2004, vol. 275, pp. 1-12.
International Preliminary Report of Patentability (Chapter II) from the International Preliminary Examination Authority mailed Aug. 30, 2022 in International (PCT) Application No. PCT/JP2021/041552, pp. 1-13.
Written Opinion of the International Searching Authority mailed Jan. 11, 2022 in International (PCT) Application No. PCT/JP2021/041552, pp. 1-5.
Reply to the Written Opinion of the International Searching Authority under PCT Article 34 filed Jun. 20, 2022 in International (PCT) Application No. PCT/JP2021/041552, pp. 1-7.
"Polymorphism in Pharmaceutical Solids", David J.W. Grant, Chapter 1, pp. 1-10, and J. Keith Guillory, Chapter 5, pp. 183-226 (1999).
P. Heinrich Stahl., "Preparation of Water-Soluble Compounds Through Salt Formation", The Practice of Medicinal Chemistry, $2^{nd}$ Ed., pp. 601-615 (2003).
Shah et al., "Approaches for Improving Bioavailability of Poorly Soluble Drugs," pp. 62-67, in Pharmaceutical Dosage Forms: Tablets, edited by Larry L. Augsburger, Stephen W. Hoag, $3^{rd}$ Ed., vol. 2 (2008).
Delia A. Haynes et al., "Occurrence of Pharmaceutically Acceptable Anions and Cations in the Cambridge Structural Database", Journal of Pharmaceutical Sciences, vol. 94, No. 10, pp. 2111-2120 (Oct. 2005).
Stephen M. Berge et al. "Pharmaceutical Salts", Journal of Pharmaceutical Sciences, vol. 66, No. 1, pp. 1-19, 1977.
Richard J. Bastin et al., "Salt Selection and Optimisation Procedures for Pharmaceutical New Chemical Entities", Organic Process Research & Development, vol. 4, pp. 427-435, 2000.

FILENAME: C:\PROGRAM FILES\PYRISID...\JADE_003254.D6D
DATA COLLECTED: 11/SEP/2019 12:26:25
OPERATOR ID: CAOIMHIN ARNOTT
SAMPLE ID: CAT-0001E-003-01
SAMPLE WEIGHT: 2.219 mg
COMMENT: PROJECT:2662A0006C

CAT-0001E-003-01
2662A0006C

PEAK = 103.23 °C
ONSET = 100.67 °C
AREA = 189.929 mJ
DELTA H = 85.5922 J/g

11/SEP/2019 16:54:19

HEAT FLOW ENDO UP (mW)

TEMPERATURE (°C)

1) HOLD FOR 1.0 MIN AT 30.00°C
2) HEAT FROM 30.00°C TO 150.00°C AT 10.00°C/MIN

CAT-0001E-021-01

PEAK = 201.88 °C

PEAK = 220.62 °C

ONSET = 205.15 °C
AREA = -256.002 mJ
DELTA H = -101.0270 J/g

ONSET = 192.46 °C
AREA = 68.036 mJ
DELTA H = 26.8494 J/g

TEMPERATURE (°C)

HEAT FLOW ENDO UP (mW)

FILENAME: C:\PROGRAM FILES\PYRISID...\JADE_003362.D6D
DATA COLLECTED: 15/APR/2020 18:59:11
OPERATOR ID: CAOIMHIN ARNOTT
SAMPLE ID: TW-0012E-021
SAMPLE WEIGHT: 2.399 mg
COMMENT: 2662A0015C

TW-0012E-021
2662A0015C

ONSET = 190.84 °C

AREA = 151.293 mJ
DELTA H = 63.0651 J/g

PEAK = 197.38 °C

TEMPERATURE (°C)

HEAT FLOW ENDO DOWN (mW)

15/APR/2020 19:31:50

1) HOLD FOR 1.0 MIN AT 30.00 °C    2) HEAT FROM 30.00 °C TO 220.00 °C AT 10.00 °C/MIN

FIG. 102

Appendix Table A: Classifications of the diseases related to CB2 receptors

| Class of Disorders* | Indications |
|---|---|
| **Pain** | inflammatory pain, nociceptive pain, neuropathic pain, fibromyalgia, chronic pain, visceral pain, migraine, cluster headache, cancer related pain, complex regional pain syndrome, neuralgias (e.g. trigeminal neuralgia) |
| **Neurological & Neurodegenerative** | multiple sclerosis, Alzheimer's disease, Parkinson's disease, amyotrophic lateral sclerosis, epilepsy, diabetes neuropathy, human immunodeficiency virus (HIV) polyneuropathy, psychiatric diseases, psychosis, autistic spectrum disorder |
| **Gastrointestinal** | irritable bowel syndrome (IBS), inflammatory bowel disease (IBD), ulcerative colitis, Crohn's disease, gastroesophageal reflux disease (GERD), constipation, diarrhoea, functional gastrointestinal disorder |
| **Immune & Inflammatory** | arthritis, rheumatoid arthritis, osteoarthritis, atherosclerosis, psoriatic arthritis disease, spondylitides, asthma, allergy, psoriasis, dermatitis, seasonal allergic rhinitis, systemic lupus erythematosus (SLE), acute allograft rejection, gingivitis, encephalitis |
| **Oncology** | cutaneous T cell lymphoma, pancreatic cancer |
| **Fibrotic** | systemic fibrosis, systemic sclerosis (SSc), vasculitis, liver fibrosis, lung fibrosis, kidney fibrosis, keloids, hypertrophic scars |
| **Lung** | acute respiratory distress syndrome (ARDS), reversible airway obstruction, adult respiratory disease syndrome, chronic obstructive pulmonary disease (COPD), cryptogenic fibrosing alveolitis, bronchitis |
| **Eye** | glaucoma, age-related macular degeneration (AMD), geographic atrophy, diabetic retinopathy, uveitis, retinal vein occlusion, retinopathy of prematurity, ocular ischemic syndrome |
| **Kidney** | glomerulonephritis, renal ischemia, nephritis, diabetic nephropathy, chronic allograft nephropathy, |
| **Liver** | hepatitis, acute liver failure, liver cirrhosis, non-alcoholic steatohepatitis (NASH) |
| **Cardiocirculatory** | myocardial infarction, cerebral ischemia, ischemia-reperfusion injury, heart failure, stroke, myocardial ischemia, cardiomyopathy, transient ischemic attack |
| **Metabolic** | diabetes, osteoporosis, regulation of bone mass, non-alcoholic fatty liver (NAFL) |
| **Psychiatric** | attention-deficit hyperactivity disorder (ADHD), anxiety, autistic spectrum disorder, depression, insomnia/sleep disorders, obsessive compulsive disorder (OCD), post-traumatic stress disorder (PTSD), Tourette's syndrome |
| **Others** | malaria, pyrexia |

* *Some disorders, despite being localised in certain organs/tissues, may have complex aetiology and potentially classified in different groups.*

STABLE SALT AND CRYSTAL FORMS OF 2-[3-({1-[2-(DIMETHYLAMINO)ETHYL]-2-(2,2-DIMETHYLPROPYL)-1H-1,3-BENZODIAZOL-5-YL}SULFONYL)AZETIDIN-1-YL]ETHAN-1-OL

CROSS REFERENCE TO RELATED APPLICATIONS

This application is a continuation of U.S. application Ser. No. 18/035,195 filed May 3, 2023, which is a national stage entry under 35 U.S.C. § 371 of international application no. PCT/JP2021/041552 filed Nov. 11, 2021, which claims the benefit of U.S. Provisional Application No. 63/112,893 filed Nov. 12, 2020, each of which is incorporated by reference herein in its entirety.

TECHNICAL FIELD

This invention relates to novel salts and crystal forms of 2-[3-({1-[2-(dimethylamino)ethyl]-2-(2,2-dimethylpropyl)-1H-1,3-benzodiazol-5-yl}sulfonyl)azetidin-1-yl]ethan-1-ol, which is a selective CB2 receptor agonist, wherein the compound may be called Compound A through the present specification.

BACKGROUND ART

Classical cannabinoids such as the marijuana derived cannabinoid (CB) delta$^9$-tetrahydro-cannabinol, (delta$^9$-THC) produce their pharmacological effects via interaction with specific cannabinoid receptors in the body. The cannabinoid receptors are members of the endocannabinoid system and are involved in a variety of physiological processes including appetite, pain-sensation, mood, and memory ({NPL 1} Goutopoulos A. et al., Pharmacol. Ther. 2002, 95:103-117; {NPL 2} Wright, K. L. et al., Br. J. Pharmacol. 2008, 153:263-270; and {NPL 3} Aizpurua-Olaizola, O. et al., Drug Discovery Today 2017, 22:105-110), as well playing an important role in the regulation of inflammatory and immune-responses ({NPL 4} Tanaka M. et al., Front. Neurol. 2020, 11:87). These receptors belong to the rhodopsin family of G protein-coupled receptors (GPCRs). There are currently two known subtypes, termed Cannabinoid Receptor 1 (CB1) and Cannabinoid Receptor 2 (CB2) ({NPL 5} Matsuda, L. A. et al., Nature 1990, 346: 561-564; Gerard, C. M. et al., Biochem. J. 1991, 279:129-134). CB1 is expressed most abundantly in the neurons of the central nervous system (CNS), but is also present at lower concentrations in a variety of peripheral tissues and cells ({NPL 5}). In contrast, CB2 is expressed predominantly, although not exclusively, in non-neural tissues, e.g. in hematopoietic cells, endothelial cells, osteoblasts, osteoclasts, the endocrine pancreas, and cancerous cell lines ({NPL 6} Munro, S. et al., Nature 1993, 365:61-65 and {NPL 7} Pacher, P. et al., Pharmacol. Rev. 2006, 58:389-462). CB2 is also widely distributed in the brain where it is found primarily on microglia and not neurons ({NPL 8} Cabral, G. A. et al., Br. J. Pharmacol. 2008, 153:240-51). As such, CB1 is believed to be primarily responsible for mediating the psychotropic effects of cannabinoids on the body, whereas CB2 is unrelated to cannabinoid psychoactivity and believed to be primarily responsible for most of their non-neural effects represented by cannabinoid-induced immune modulation ({NPL 9} Howlett, A. C. et al., Pharmacol. Rev. 2002, 54:161-202; and {NPL 10} Chung, Y. C. et al., Exp. Mol. Med. 2016, 48: e205). There is a considerable interest in the development of selective CB2 receptor agonists since it is believed high selectivity for CB2 may offer avenues for harnessing the beneficial effect of CB receptor agonists while avoiding the central adverse events seen with cannabinoid structures ({NPL 11} Expert Opin. Investig. Drugs 2007, 16:951-965).

In general, CB2 receptor agonists could be beneficial for the treatment of a variety of indications in different therapeutic areas including chronic and acute pain (e.g. inflammatory pain, nociceptive pain, neuropathic pain, fibromyalgia, chronic low back pain, visceral pain, complex regional pain syndrome, neuralgias); immunological and inflammatory disorders also with a pain component (e.g. arthritis, rheumatoid arthritis, osteoarthritis, atherosclerosis, Crohn's disease, ulcerative colitis, asthma, allergy, psoriasis, dermatitis, seasonal allergic rhinitis, systemic lupus erythematosus); gastrointestinal disorders, including irritable bowel syndrome (IBS), gastroesophageal reflux disease (GERD), constipation, diarrhea, functional gastrointestinal disorder), oncology (e.g. cutaneous T cell lymphoma, pancreatic cancer); neurodegenerative disorders, such as multiple sclerosis, Alzheimer's disease, Parkinson's disease, amyotrophic lateral sclerosis; fibrotic disorders of heterogeneous aethiology (systemic fibrosis, systemic sclerosis vasculitis liver fibrosis, lung fibrosis, kidney fibrosis); lung disorders (e.g. acute respiratory distress syndrome (ARDS), reversible airway obstruction, adult respiratory disease syndrome, chronic obstructive pulmonary disease or COPD), and many metabolic and multi-aethiology disorders including diabetes, glaucoma, age-related macular degeneration, diabetic retinopathy, uveitis, retinal vein occlusion, retinopathy of prematurity, ocular ischemic syndrome, geographic atrophy, osteoporosis, regulation of bone mass, glomerulonephritis, renal ischemia, nephritis, hepatitis, acute liver failure, chronic allograft nephropathy, diabetic nephropathy, liver cirrhosis or tumors, myocardial infarction, cerebral ischemia, ischemia-reperfusion injury, heart failure, stroke, myocardial ischemia, cardiomyopathy, transient ischemic attack, cryptogenic fibrosing alveolitis, bronchitis, thermal injury, burn injury, hypertrophic scars, keloids, gingivitis, pyrexia, psychiatric diseases, psychosis, malaria, encephalitis, and acute allograft rejection ({NPL 12} Hohmann, A. G. et al., J. Pharmacol. Exp. Ther. 2004, 308:446-453; {NPL 13} Ibrahim, M. M. et al., Proc. Natl. Acad. Sci. USA 2003, 100: 10529-10533; {NPL 14} Mathison, R. et al., Br. J. Pharmacol. 2004, 142:1247-1254; {NPL 15} Pacher, P. et al., Prog. Lipid Res. 2011, 50:193-211; {NPL 16} Van Der Stelt, M. et al., J. Med. Chem. 2011, 54:7350-7362; {NPL 17} Guindon, J. et al., Br. J. Pharmacol. 2008, 153:319-334; {NPL 18} Kusakabe, K. et al., Bioorg. Med. Chem. 2013, 21:3154-3163; {NPL 19} Mukhopadhyay, P. et al., Free Radic. Biol. Med. 2010, 48:457-467; {NPL 20} Gruden, G. et al., Br. J. Pharmacol. 2015, 173:1116-1127; {NPL 21} Julien, B. et al., Gastroenterology 2005, 128; 742-755; {NPL 22} Batkai, S. et al., FASEB J. 2007, 21:1788-1800; {NPL 23} Rajesh, M. et al., J. Leukoc. Biol. 2007, 82:1382-1389; {NPL 24} Horvath, B. et al., Br. J. Pharmacol. 2012, 165:2462-2478; and {NPL 25} Montecucco, F. et al., J. Mol. Cell. Cardiol. 2009, 46:612-620). The classifications of the diseases described above are shown in Appendix Table A.

Accordingly, small-molecule compounds that have selective CB2 receptor agonistic activity are particularly desirable as a means to treat or prevent disease states associated with CB2 stimulation. One such small-molecule is 2-[3-({1-[2-(dimethylamino)ethyl]-2-(2,2-dimethylpropyl)-1H-1,3-benzodiazol-5-yl}sulfonyl)azetidin-1-yl]ethan-1-ol, which has the chemical structure:

{Chem.1}

Compound A

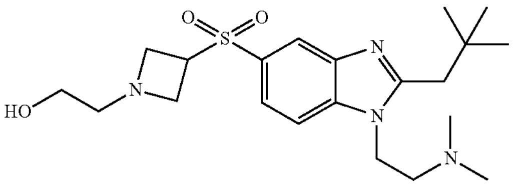

2-[3-({1-[2-(dimethylamino)ethyl]-2-(2,2-dimethylpropyl)-1H-1,3-benzodiazol-5-yl}sulfonyl)azetidin-1-yl]ethan-1-ol (Compound A), its preparation, and its use as a medicament for the treatment of conditions or diseases mediated by CB2 receptor activity are described in the {PL1} U.S. Pat. No. 8,653,063. Compound A is exemplified therein in free base form and the synthesis is also described in the experimental part as Example 23. Furthermore, the in vitro agonistic activities for human CB1 and CB2, in vivo and in vitro pharmacokinetic parameters, and in vivo efficacy of Compound A are described in the {NPL 26} Iwata, Y. et al., Bioorg. Med. Chem. Lett. 2015, 25, 236, as Compound 40. The present invention relates to a novel salt and crystalline solid form of the said salt of Compound A that demonstrate improved properties for use in a pharmaceutical dosage form, particularly for oral solid dosage forms.

Based on a chemical structure, it had not been possible so far to predict with any degree of certainty whether a compound would crystallize under any condition, how many crystalline solid forms of the compound may exist, or the solid-state structure of any of those forms. Due to the many factors influencing the rate and mechanism of crystallization, identifying a robust and reproducible process enabling consistent results in obtaining good quality and stable crystals requires a long and rigorous process of optimization. A key characteristic of any crystalline drug is the polymorphic behavior of such a material. In general, the different physical properties exhibited by different solid forms of a pharmaceutical compound can affect important pharmaceutical parameters such as storage, compressibility, density (important in formulation and product manufacturing), and dissolution rates (important in determining bioavailability). Stability differences may result from changes in chemical reactivity (e.g., differential hydrolysis or oxidation, such that a formulation comprising a certain polymorph can discolor more rapidly than a formulation comprising a different polymorph), mechanical changes (e.g., tablets can crumble on storage as a kinetically favored crystalline form converts to thermodynamically more stable crystalline form), or both (e.g., tablets of one polymorph can be more susceptible to breakdown at high humidity). Solubility differences between polymorphs may, in extreme situations, result in transitions to crystalline forms that lack potency. In addition, the physical properties of a crystalline form may also be important in pharmaceutical processing. For example, a particular crystalline form may form solvates more readily or may be more difficult to filter and wash free of impurities than other crystalline forms (i.e., particle shape and size distribution might be different between one crystalline form relative to other forms). These variety of characteristics are almost impossible to be speculated or expected before finding facts.

In general, the ideal physical form of a drug product cannot be defined a priori because different physical forms provide different advantages. Thus, it is important to seek a variety of unique drug forms, e.g., salts, polymorphs, non-crystalline forms, which may be used in various formulations. The selection of a drug form for a specific formulation, route of administration, or therapeutic application requires consideration of a variety of properties, with a different degree of priority or acceptability parameters based on a particular application. Specifically, a drug form used in solid oral dosage forms including tablets and capsules must be sufficiently stable, must retain its crystal polymorph form during the solid manufacturing process, and must not degrade during a normal shelf-life storage. Moreover, low melting point forms are regarded as undesirable as formulation issues such as exudation and spots due to melting of the drug during the different stage of manufacturing may occur. With regard to general solid formulation development, the melting point should not be below 80° C. and should preferably exceed 120° C. ({NPL 27} Stefan Balbach, Pharmaceutical evaluation of early development candidates "the 100 mg-approach", International Journal of Pharmaceutics 275 (2004) 1-12).

Different crystalline solid forms of the same compound often possess different solid-state properties such as melting point, solubility, dissolution rate, hygroscopicity, powder flow, mechanical properties, chemical stability, and physical stability. These solid-state properties may offer advantages in filtration, drying, dosage form manufacturing unit operations and eventually improve in vivo performance in terms of DMPK and efficacy parameters. Thus, once different crystalline solid forms of the same compound have been identified, the optimum crystalline solid form under any given set of processing and manufacturing conditions may be determined as well as the different solid-state properties of each crystalline solid form. However, only limited crystalline solid forms of a compound are suitable for use as active pharmaceutical ingredients (APIs). Therefore, the identification of the form with the desirable properties becomes an essential, but also time consuming and challenging component of drug development.

Polymorphs of a molecule can be obtained by a number of methods which are not entirely predictable a priori and therefore can constitute an important component of innovation, and consequently, of the originality of an invention. Such methods include, but are not limited to, melt recrystallization, melt cooling, solvent recrystallization, desolvation, rapid evaporation, rapid cooling, slow cooling, vapor diffusion and sublimation. Polymorphs can be detected, identified, classified and characterized using well-known techniques such as, but not limited to, differential scanning calorimetry (DSC), thermogravimetry (TGA), X-ray powder diffractometry (XRPD), single crystal X-ray diffractometry, solid state nuclear magnetic resonance (NMR), infrared (IR) spectroscopy, Raman spectroscopy, and hot-stage optical microscopy.

Citation List

Patent Literature

{PL1} U.S. Pat. No. 8,653,063

Non Patent Literature

{NPL 1} Goutopoulos A. et al., Pharmacol. Ther. 2002, 95:103-117

{NPL 2} Wright, K. L. et al., Br. J. Pharmacol. 2008, 153:263-270

{NPL 3} Aizpurua-Olaizola, O. et al., Drug Discovery Today 2017, 22:105-110
{NPL 4} Tanaka M. et al., Front. Neurol. 2020, 11:87
{NPL 5} Matsuda, L. A. et al., Nature 1990, 346:561-564; Gerard, C. M. et al., Biochem. J. 1991, 279:129-134
{NPL 6} Munro, S. et al., Nature 1993, 365:61-65
{NPL 7} Pacher, P. et al., Pharmacol. Rev. 2006, 58:389-462
{NPL 8} Cabral, G. A. et al., Br. J. Pharmacol. 2008, 153:240-51
{NPL 9} Howlett, A. C. et al., Pharmacol. Rev. 2002, 54:161-202
{NPL 10} Chung, Y. C. et al., Exp. Mol. Med. 2016, 48: e205
{NPL 11} Expert Opin. Investig. Drugs 2007, 16:951-965
{NPL 12} Hohmann, A. G. et al., J. Pharmacol. Exp. Ther. 2004, 308:446-453
{NPL 13} Ibrahim, M. M. et al., Proc. Natl. Acad. Sci. USA 2003, 100:10529-10533
{NPL 14} Mathison, R. et al., Br. J. Pharmacol. 2004, 142:1247-1254
{NPL 15} Pacher, P. et al., Prog. Lipid Res. 2011, 50:193-211
{NPL 16} Van Der Stelt, M. et al., J. Med. Chem. 2011, 54:7350-7362
{NPL 17} Guindon, J. et al., Br. J. Pharmacol. 2008, 153:319-334
{NPL 18} Kusakabe, K. et al., Bioorg. Med. Chem. 2013, 21:3154-3163
{NPL 19} Mukhopadhyay, P. et al., Free Radic. Biol. Med. 2010, 48:457-467
{NPL 20} Gruden, G. et al., Br. J. Pharmacol. 2015, 173: 1116-1127
{NPL 21} Julien, B. et al., Gastroenterology 2005, 128; 742-755
{NPL 22} Batkai, S. et al., FASEB J. 2007, 21:1788-1800
{NPL 23} Rajesh, M. et al., J. Leukoc. Biol. 2007, 82:1382-1389
{NPL 24} Horvath, B. et al., Br. J. Pharmacol. 2012, 165:2462-2478
{NPL 25} Montecucco, F. et al., J. Mol. Cell. Cardiol. 2009, 46: 612-620
{NPL 26} Iwata, Y. et al., Bioorg. Med. Chem. Lett. 2015, 25:236-240
{NPL 27} Stefan Balbach, Pharmaceutical evaluation of early development candidates "the 100 mg-approach", International Journal of Pharmaceutics 275 (2004) 1-12

SUMMARY OF INVENTION

Technical Problem

Compound A is disclosed in PL 1 and NPL 26 as a potent selective CB2 receptor agonist, which is useful in the treatment or alleviation of pain (i.e. chronic regional pain syndrome, trigeminal neuralgia, and other neuralgias) and inflammation, and also of gastrointestinal (GI) disorders, such as irritable bowel syndrome (IBS), inflammatory bowel disease (IBD), and colitis.

The previously known methods for preparation, described in PL 1 and NPL 26, have produced a free base of Compound A as a grease or solids, which are not crystalline and not amenable to drug development and formulation.

Therefore, the present invention aims to identify and produce a pharmaceutically acceptable form of Compound A and/or a salt of Compound A capable of enabling stable and effective pharmaceutical compositions, particularly those in solid dosage form. Important criteria to be satisfied are, inter alia, that the selected salt should be crystalline, non-deliquescent, and possess solid-state stability and properties, be of suitable melting point and have acceptable solubility characteristics.

Solution to Problem

Thus, the invention provides:

[1] A salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol with an acid, wherein the acid is selected from the group consisting of hydrochloric acid (HCl), maleic acid, and methanesulfonic acid.

[2] The salt according to [1], wherein the acid is hydrochloric acid (HCl).

[3] A crystalline form of the HCl salt of 2-[3-({1-[2-(dimethylamino)ethyl]-2-(2,2-dimethylpropyl)-$^{1}$H-1,3-benzodiazol-5-yl}sulfonyl)azetidin-1-yl]ethan-1-ol.

[4] The HCl salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol according to [2], wherein said salt is in crystalline form Pattern 2 and said Pattern 2 is characterized by at least one of the following:

(i) a powder X-ray diffraction (XRPD) pattern comprising peaks, in terms of 2-Theta, at 5.9, 6.6, 8.9, 11.8, 13.2, 14.5, 15.6, 16.0, 17.4, 18.3, 19.5, 20.2, 22.0, 26.6, and 27.0 degrees 2-Theta+/−0.2 degrees 2-Theta;

(ii) an XRPD pattern substantially and coinciding with the pattern shown by FIG. 1.

[5] The HCl salt according to any one of [2] to [4], having a melting endotherm at onset 191° C. in differential scanning calorimetry (DSC) or at onset 192° C. in thermogravimetry/differential thermal analysis (TG/DTA).

[6] The HCl salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol according to [3], wherein Pattern 2 of said salt is least 90 weight % based on weight of said salt.

[7] The HCl salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol according to [2], wherein said salt is in crystalline form Pattern 1 and said Pattern 1 is characterized by at least one of the following:

(i) a powder X-ray diffraction (XRPD) pattern comprising peaks, in terms of 2-Theta, at 6.6, 13.2, 15.6, 16.0, 17.2, 17.4, 17.9, 18.9, 20.1, 22.1, 23.4, 26.6, and 27.0 degrees 2-Theta+/−0.2 degrees 2-Theta;

(ii) an XRPD pattern substantially in accordance with the pattern shown by FIG. 4.

[8] The HCl salt according to [7], having a melting endotherm at onset 192° C. in differential scanning calorimetry (DSC) or at onset 200° C. in thermogravimetry/differential thermal analysis (TG/DTA).

[9] The HCl salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol according to claim 5, wherein Pattern 1 of said salt is least 90 weight % based on weight of said salt.

[10] A pharmaceutical composition comprising the salt according to [1].

[11] A method for preventing or treating a disorder or condition selected from pain, inflammatory pain, nociceptive pain, neuropathic pain, fibromyalgia, chronic pain, visceral pain, migraine, cluster headache, cancer related pain, complex regional pain syndrome, neuralgias (e.g. trigeminal neuralgia), multiple sclerosis, Alzheimer's disease, Parkinson's disease, amyotrophic lateral sclerosis, epilepsy, diabetes neuropathy, human immunodeficiency virus (HIV) polyneuropathy, psychiatric diseases, psychosis, autistic spectrum disorder, irritable bowel syndrome (IBS), inflammatory bowel disease (IBD), ulcerative colitis, Crohn's disease, gastroesophageal reflux disease (GERD), constipation, diarrhoea, functional gastrointestinal disorder, arthritis, rheumatoid arthritis, osteoarthritis, atherosclerosis, psoriatic arthritis disease, spondylitides, asthma, allergy, psoriasis, dermatitis, seasonal allergic rhinitis, systemic lupus erythematosus (SLE), acute allograft rejection, gingivitis, encephalitis, cutaneous T cell lymphoma, pancreatic cancer, systemic fibrosis, systemic sclerosis (SSc), vasculitis liver fibrosis, lung fibrosis, kidney fibrosis, keloids, hypertrophic scars, acute respiratory distress syndrome (ARDS), reversible airway obstruction, adult respiratory disease syndrome, chronic obstructive pulmonary disease (COPD), cryptogenic fibrosing alveolitis, bronchitis, glaucoma, age-related macular degeneration (AMD) and geographic atrophy, diabetic retinopathy, uveitis, retinal vein occlusion, retinopathy of prematurity, ocular ischemic syndrome, glomerulonephritis, renal ischemia, nephritis, diabetic nephropathy, chronic allograft nephropathy, hepatitis, acute liver failure, liver cirrhosis, non-alcoholic steatohepatitis (NASH), myocardial infarction, cerebral ischemia, ischemia-reperfusion injury, heart failure, stroke, myocardial ischemia, cardiomyopathy, transient ischemic attack, diabetes, osteoporosis, regulation of bone mass, non-alcoholic fatty liver (NAFL), attention-deficit hyperactivity disorder (ADHD), anxiety, autistic spectrum disorder, depression, insomnia/sleep disorders, obsessive compulsive disorder (OCD), post-traumatic stress disorder (PTSD), Tourette's syndrome, malaria, and pyrexia, comprising administering to a subject suffering from said disease or condition an effective amount of the salt according to [1].

[12] The method according to [11], wherein the disease is pain.

[13] The method according to [11], wherein the disease is inflammation.

[14] The method according to [11], wherein the disease is irritable bowel syndrome (IBS).

[15] The method according to [11], wherein the disease is inflammatory bowel disease (IBD).

[16] The method according to [11], wherein the disease is colitis.

[17] A process of producing an HCl salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol, comprising dissolving 2-[3-({1-[2-(dimethylamino)ethyl]-2-(2,2-dimethylpropyl)-1H-1,3-benzodiazol-5-yl}sulfonyl)azetidin-1-yl]ethan-1-ol in a suitable solvent.

[18] The process according to [17], wherein the suitable solvent is selected from the group consisting of acetone, acetonitrile, 1-butanol, cyclohexane, dichloromethane, diisopropyl ether, dimethylacetamide, dimethyl sulfoxide, dioxane, ethanol, ethyl acetate, heptane, isopropyl acetate, methyl tert-butyl ether, methyl ethyl ketone, methyl isobutyl ketone, methanol, 2-propanol, toluene, tetrahydrofuran, water and the mixture of the solvents thereof.

In consideration of all the above an exhaustive and careful study of Compound A and/or salts of Compound A has led to the novel and unforeseen discovery that certain salts of Compound A meet the foregoing requirements and have advantages with regard to the ability to prepare solid dosage forms over the corresponding free base or other salts. Particularly, novel and "essentially pure" (here from meant as greater than or equal to 95% by weight purity) crystalline polymorph forms of the hydrochloride (HCl salt) of Compound A have the best characters as the API. More preferably, the final product will be 98% by weight purity and optimally greater than or equal to 99% by weight purity.

In one embodiment, the invention is directed to a salt comprising Compound A:

{Chem.2}

Compound A

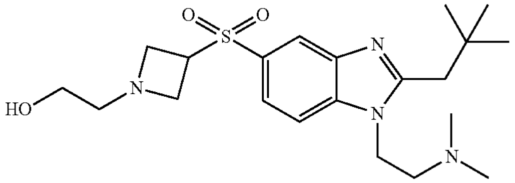

and an acid, wherein the acid is selected from the group consisting of acetic acid, L-ascorbic acid, L-aspartic acid, benzenesulfonic acid, citric acid, ethane-1,2-disulfonic acid (edisilic acid, EDSA), fumaric acid, 2,5-dihydroxybenzoic acid (gentisic acid), D-gluconic acid, D-glucuronic acid, L-glutamic acid, glutaric acid, glycolic acid, hippuric acid, hydrochloric acid (HCl), L-lactic acid, maleic acid, L-malic acid, methanesulfonic acid (MSA), phosphoric acid, p-toluenesulfonic acid (p-TSA), succinic acid, sulfuric acid ($H_2SO_4$), and L-tartaric acid.

In a preferred embodiment, the acid is selected from the group consisting of acetic acid, ethane-1,2-disulfonic acid (edisilic acid, EDSA), fumaric acid, glutaric acid, glycolic acid, hydrochloric acid (HCl), L-lactic acid, maleic acid, methanesulfonic acid (MSA), succinic acid, and sulfuric acid ($H_2SO_4$).

In another preferred embodiment, the acid is selected from the group consisting of glycolic acid, hydrochloric acid (HCl), L-lactic acid, maleic acid, and methanesulfonic acid (MSA). In one embodiment, the salt is the hydrochloric acid (HCl) salt, the maleic acid salt, or the methanesulfonic acid (MSA) salt. It is contemplated that the hydrochloric acid (HCl) salt of Compound A could be formed by protonating one or more nitrogen atoms of Compound A. In one embodiment, the nitrogen atom of the dimethylamino group ($-NMe_2$) of Compound A is protonated ($-NHMe_2^+$) to form the salt.

In one preferred embodiment, the hydrochloric acid (HCl) salt of Compound A is represented by the formula below:

{Chem. 3}

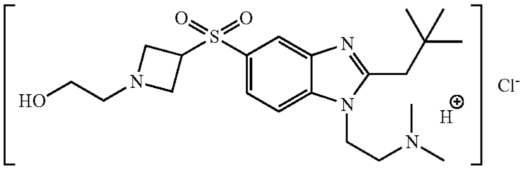

HCl Salt (Hydrochloric Acid) of Compound A

In another embodiment, the present invention provides essentially pure, crystalline, HCl salt of Compound A polymorph form Pattern 2, which is characterized by an X-ray powder diffraction (XRPD) pattern having approximate characteristic peak locations of 5.9, 6.6, 8.9, 11.8, 13.2, 14.5, 15.6, 16.0, 17.4, 18.3, 19.5, 20.2, 22.0, 26.6, and 27.0 degrees 2-Theta. In the invention, it is contemplated that the approximate characteristic peaks will have a deviation of up to about +/−0.2 degrees 2-Theta. The XRPD pattern of Pattern 2 is approximate to the pattern shown by FIG. 1. HCl salt of Compound A polymorph form Pattern 2 is further characterized by differential scanning calorimetry (DSC) in which it exhibits an endothermic thermal event at about 191° C. The DSC pattern of Pattern 2 is approximate to the pattern shown by FIG. 2. HCl salt of Compound A particularly polymorph form Pattern 2 is yet further characterized by thermogravimetry/differential thermal analysis (TG/DTA) in which it exhibits an endothermic thermal event at about 192° C. The TG/DTA pattern of Pattern 2 is approximate to the pattern shown by FIG. 3. This crystalline polymorph of the HCl salt of Compound A, polymorph form Pattern 2 provides for a reproducible form of Compound A suitable for use in preparing pharmaceutical formulations.

In still another embodiment, the present invention provides essentially pure and crystalline HCl salt of Compound A polymorph form Pattern 1, which is characterized by an XRPD pattern having approximate characteristic peak locations of 6.6, 13.2, 15.6, 16.0, 17.2, 17.4, 17.9, 18.9, 20.1, 22.1, 23.4, 26.6, and 27.0 degrees 2-Theta+/−0.2 degrees 2-Theta. The XRPD pattern of Pattern 1 is the pattern shown by FIG. 4. HCl salt of Compound A polymorph form Pattern 1 is further characterized by TG/DTA in which it exhibits an endothermic thermal event at about 200° C. HCl salt of Compound A polymorph form Pattern 1 is further characterized by differential scanning calorimetry (DSC) in which it exhibits an endothermic thermal event at about 192° C. The DSC pattern of Pattern 1 is approximate to the pattern shown by FIG. 5. The TG/DTA pattern of Pattern 1 is approximate to the pattern shown by FIG. 6. This crystalline polymorph of the HCl salt of Compound A, particularly polymorph form Pattern 1 also provides for a reproducible form of Compound A suitable for use in preparing pharmaceutical formulations.

In yet another embodiment, the present invention provides essentially pure and crystalline HCl salt of Compound A polymorph form Pattern 3 and polymorph form Pattern 4. It will be appreciated that these crystal forms are not to be regarded only as synthetic intermediates that can be further processed to HCl salt of Compound A polymorph form Pattern 2 and polymorph form Pattern 1, but they also have the same therapeutic properties. However, HCl salt of Compound A polymorph form Pattern 3 and polymorph form Pattern 4 are not as suitable as polymorph form Pattern 2 and polymorph form Pattern 1 for use in preparing pharmaceutical formulations, principally because the former crystal forms are less stable as compared with the latter. HCl salt of Compound A polymorph form Pattern 3 and polymorph form Pattern 4 are characterized by PXRD, as detailed in Table 1-1:

TABLE 1-1

| Form | PXRD peaks at 2-Theta° +/− 0.2 | FIG. |
|---|---|---|
| Pattern 3 | 5.6, 6.7, 16.6, 17.1, 18.8, 19.9, 24.0, 25.9, 26.8 | FIG. 7 |

TABLE 1-1-continued

| Form | PXRD peaks at 2-Theta° +/− 0.2 | FIG. |
|---|---|---|
| Pattern 4 | 6.2, 7.0, 8.2, 16.6, 18.6, 19.3, 19.8, 20.4, 23.3, 24.4, 24.7 | FIG. 8 |

In a further embodiment, the present invention provides a pharmaceutical composition for preventing or treating conditions or diseases mediated by CB2 receptor activity in a mammal comprising a pharmaceutically acceptable carrier and a therapeutically effective amount of the HCl salt of Compound A having a crystalline polymorph form, polymorph form Pattern 2 or polymorph form Pattern 1.

In a yet further embodiment, the present invention provides a method for treating a disorder or condition using a selective CB2 receptor agonist, particularly for the curative, prophylactic, or palliative treatment including administration of a therapeutically effective amount of HCl salt of Compound A polymorph form Pattern 2 and polymorph form Pattern 1 to a mammal, including a human, in need of such treatment.

In an alternative embodiment, the present invention provides a method for preparing an HCl salt of Compound A having a crystalline polymorph form, particularly polymorph form Pattern 2 or polymorph form Pattern 1. The methods typically include suspending Compound A in a solvent or a mixture of solvents, contacting HCl (hydrochloric acid or hydrogen chloride gas) with Compound A to provide a mixture, heating the mixture, cooling the mixture, and isolating the HCl salt.

BRIEF DESCRIPTION OF DRAWINGS

FIG. 102 provides an Appendix Table A which provides the classifications of diseases related to CB2 receptors.

DETAILED DESCRIPTION OF THE INVENTION

Figure 1:
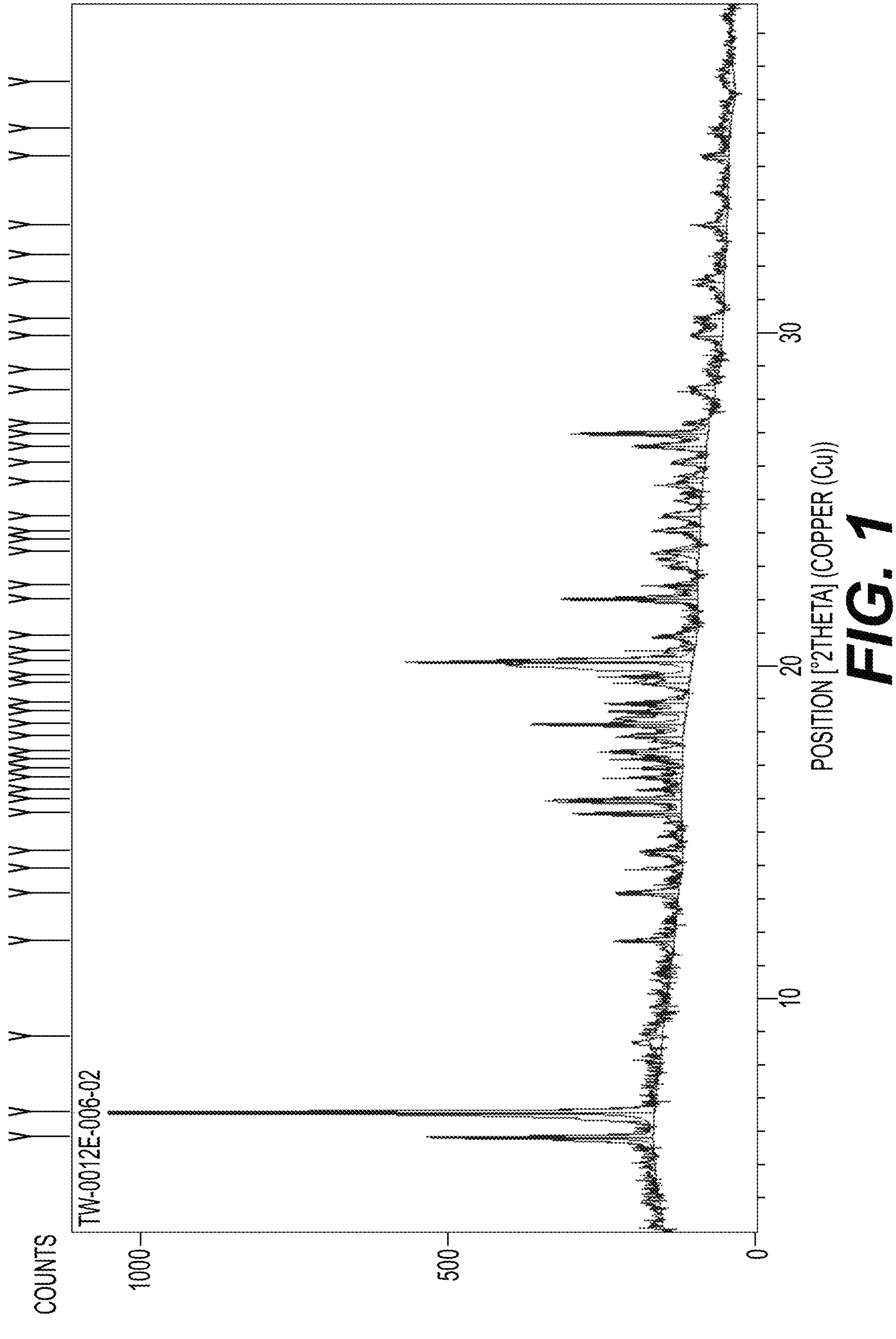
FIG. 1 provides an X-ray powder diffraction (XRPD) pattern of the hydrochloride (HCl salt) of Compound A polymorph form Pattern 2.
Figure 2:
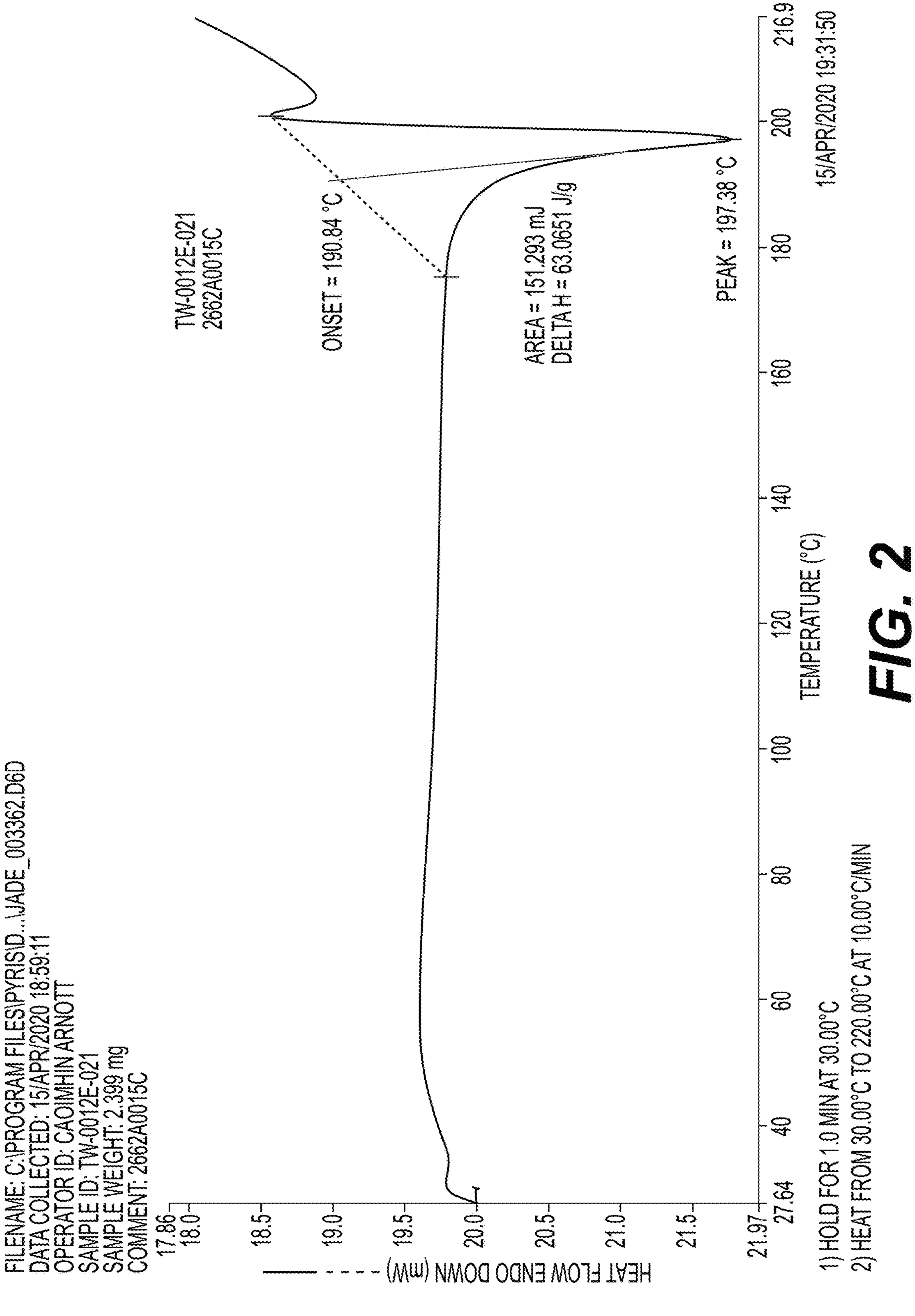
FIG. 2 provides a differential scanning calorimetry (DSC) pattern of the hydrochloride (HCl salt) of Compound A polymorph form Pattern 2.
Figure 3:
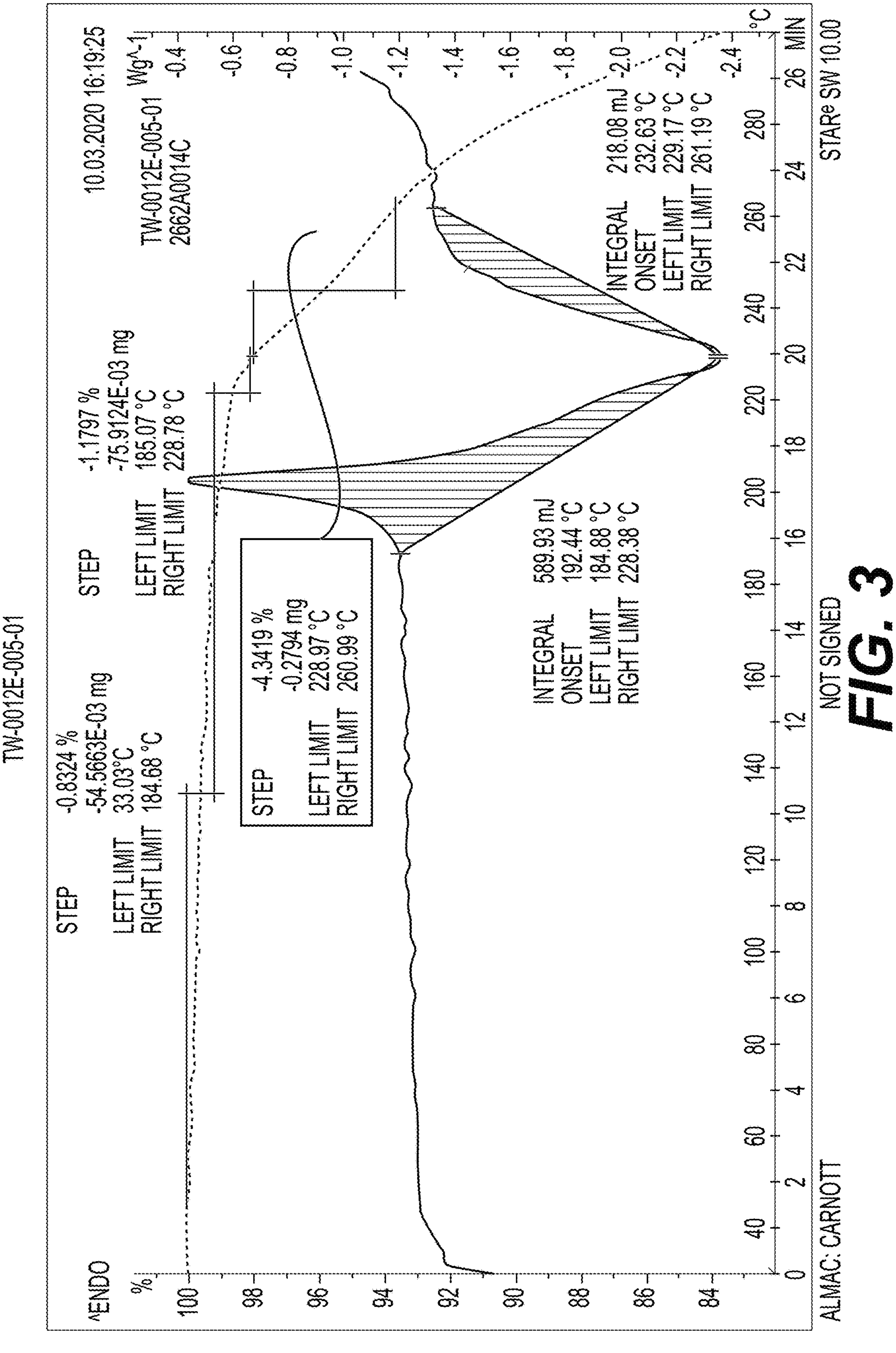
FIG. 3 provides a thermogravimetry/differential thermal analysis (TG/DTA) pattern of the hydrochloride (HCl salt) of Compound A polymorph form Pattern 2.
Figure 4:
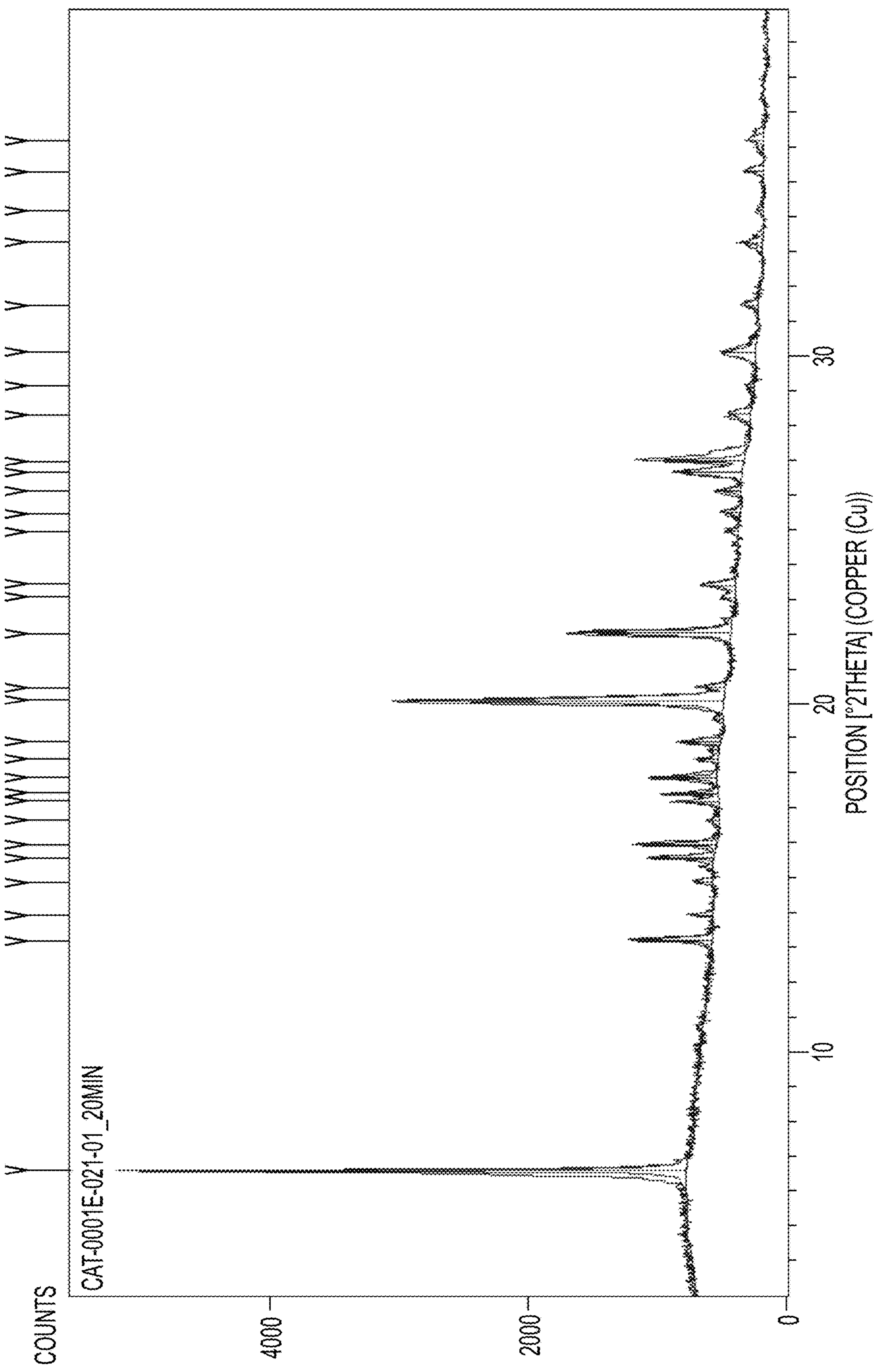
FIG. 4 provides an X-ray powder diffraction (XRPD) pattern of the hydrochloride (HCl salt) of Compound A polymorph form Pattern 1.
Figure 5:
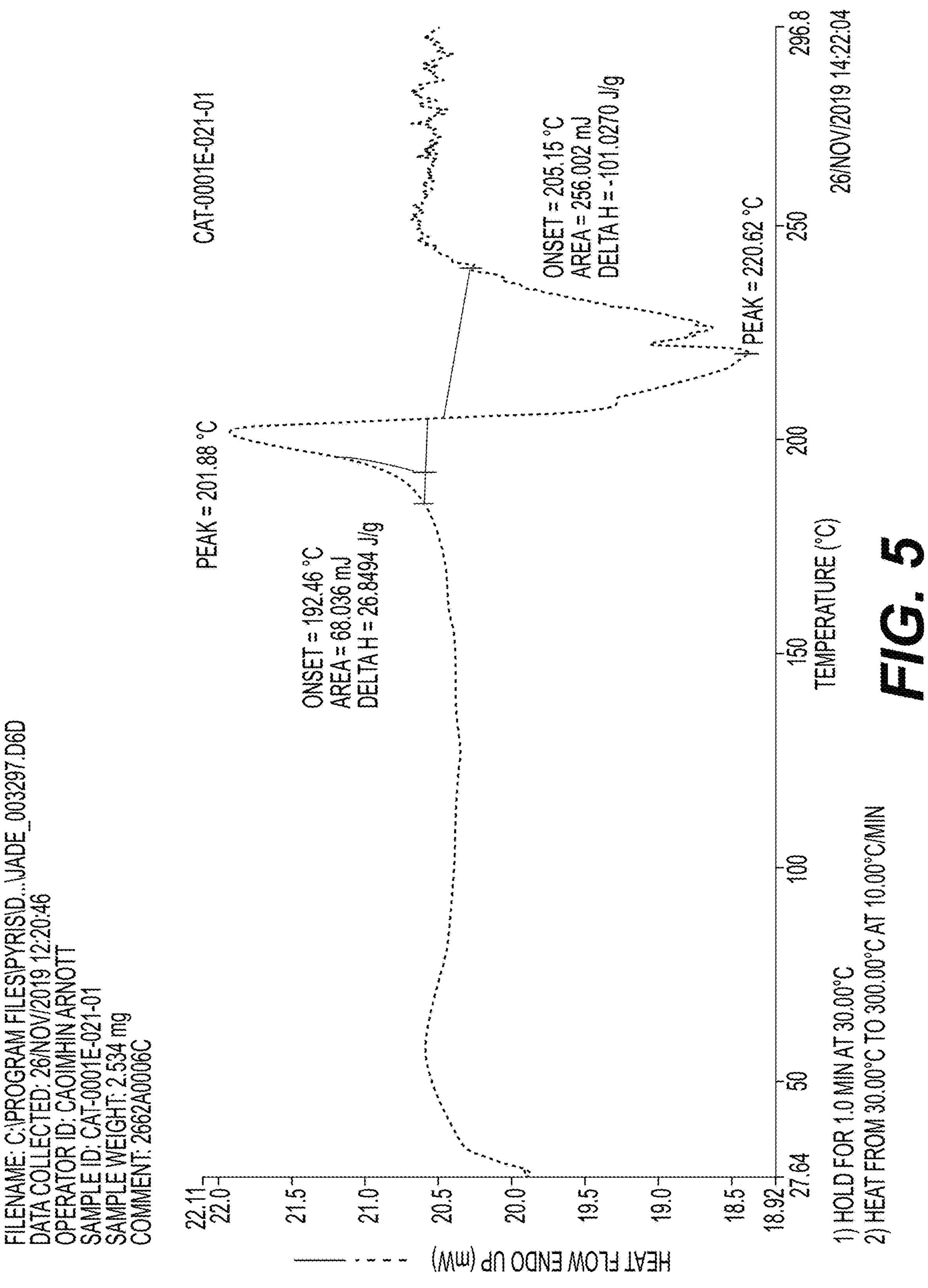
FIG. 5 provides a differential scanning calorimetry (DSC) pattern of the hydrochloride (HCl salt) of Compound A polymorph form Pattern 1.
Figure 6:
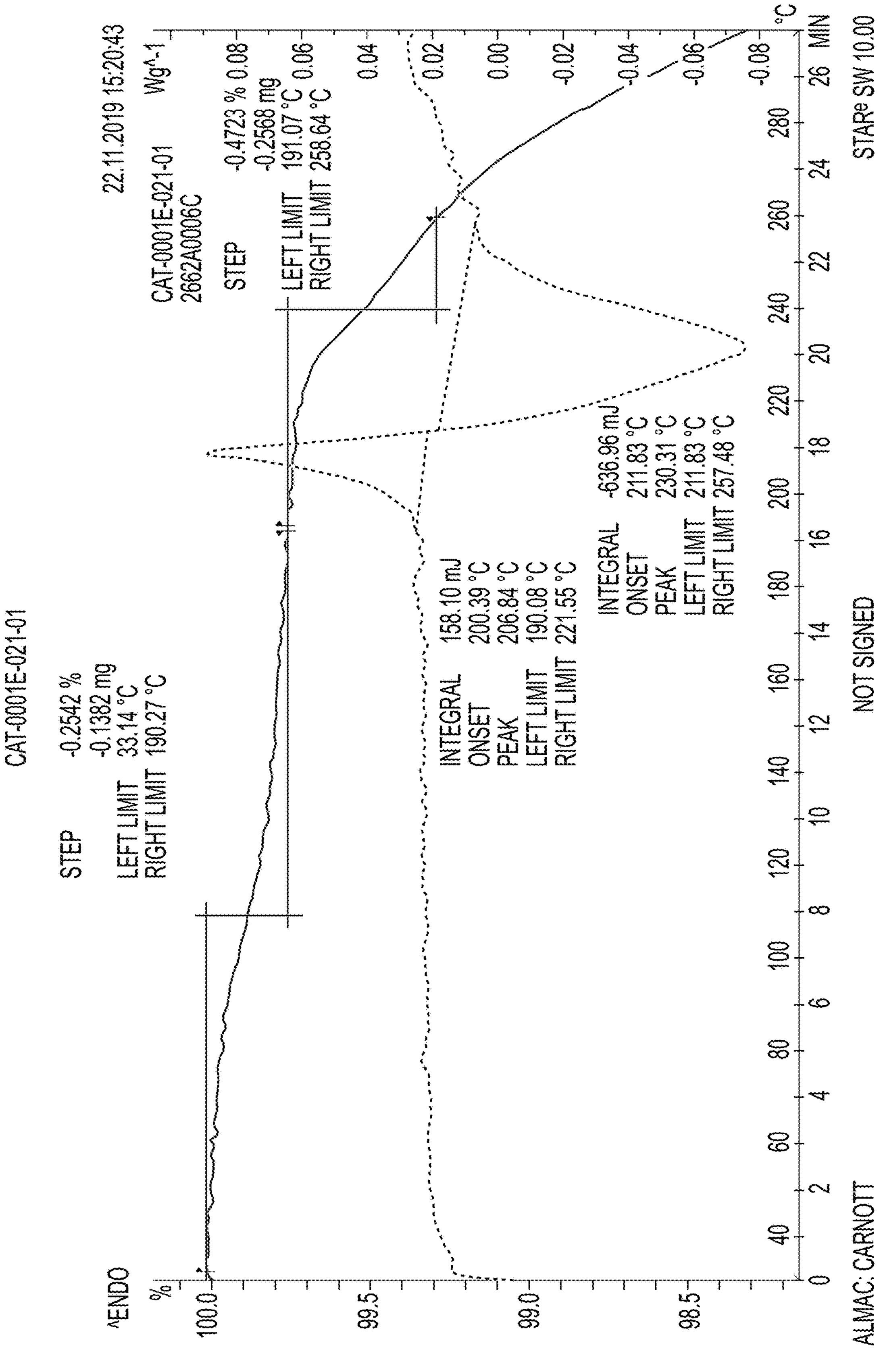
FIG. 6 provides a thermogravimetry/differential thermal analysis (TG/DTA) pattern of the hydrochloride (HCl salt) of Compound A polymorph form Pattern 1.
Figure 7:
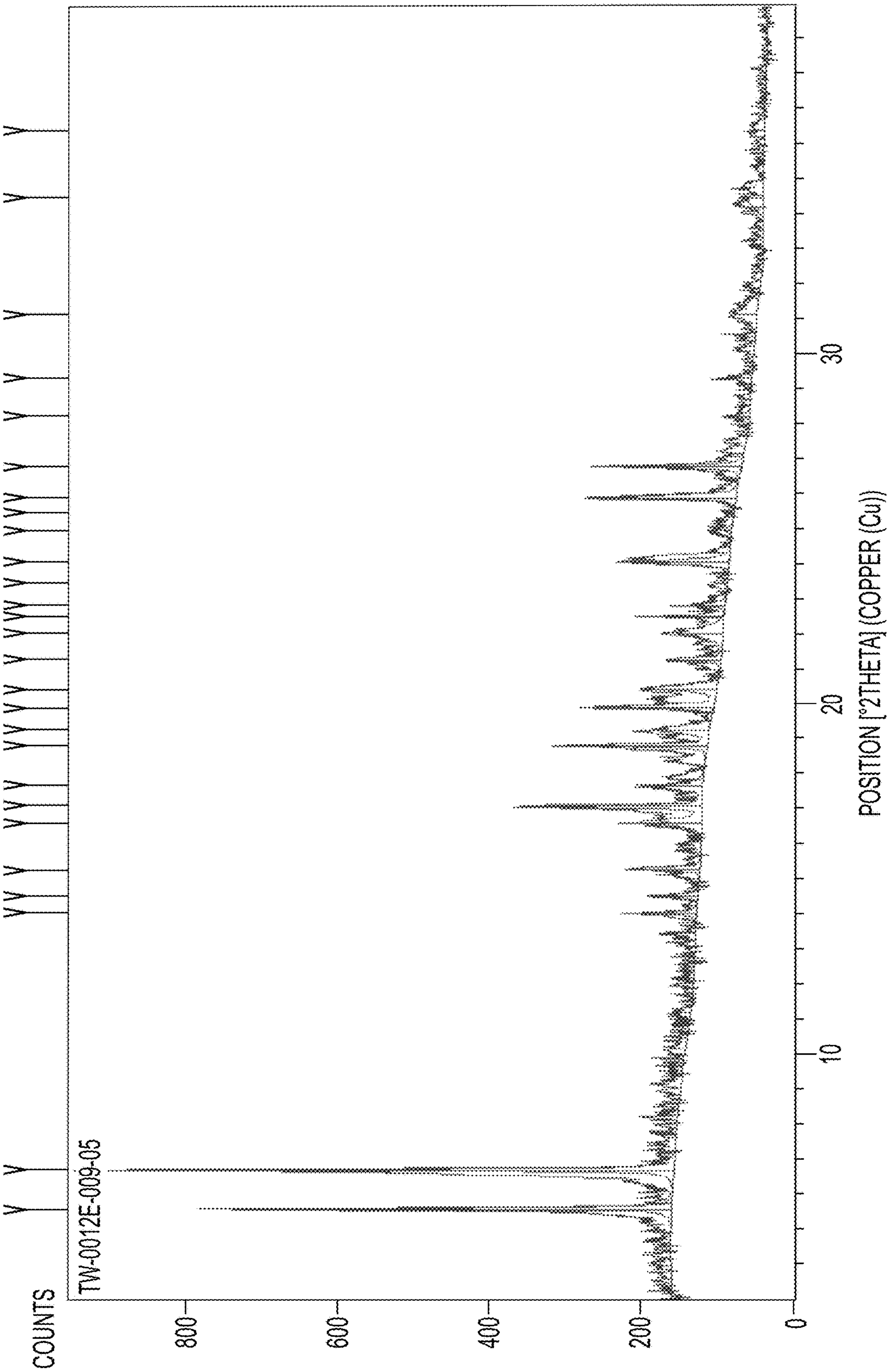
FIG. 7 provides an X-ray powder diffraction (XRPD) pattern of the hydrochloride (HCl salt) of Compound A polymorph form Pattern 3.
Figure 8:
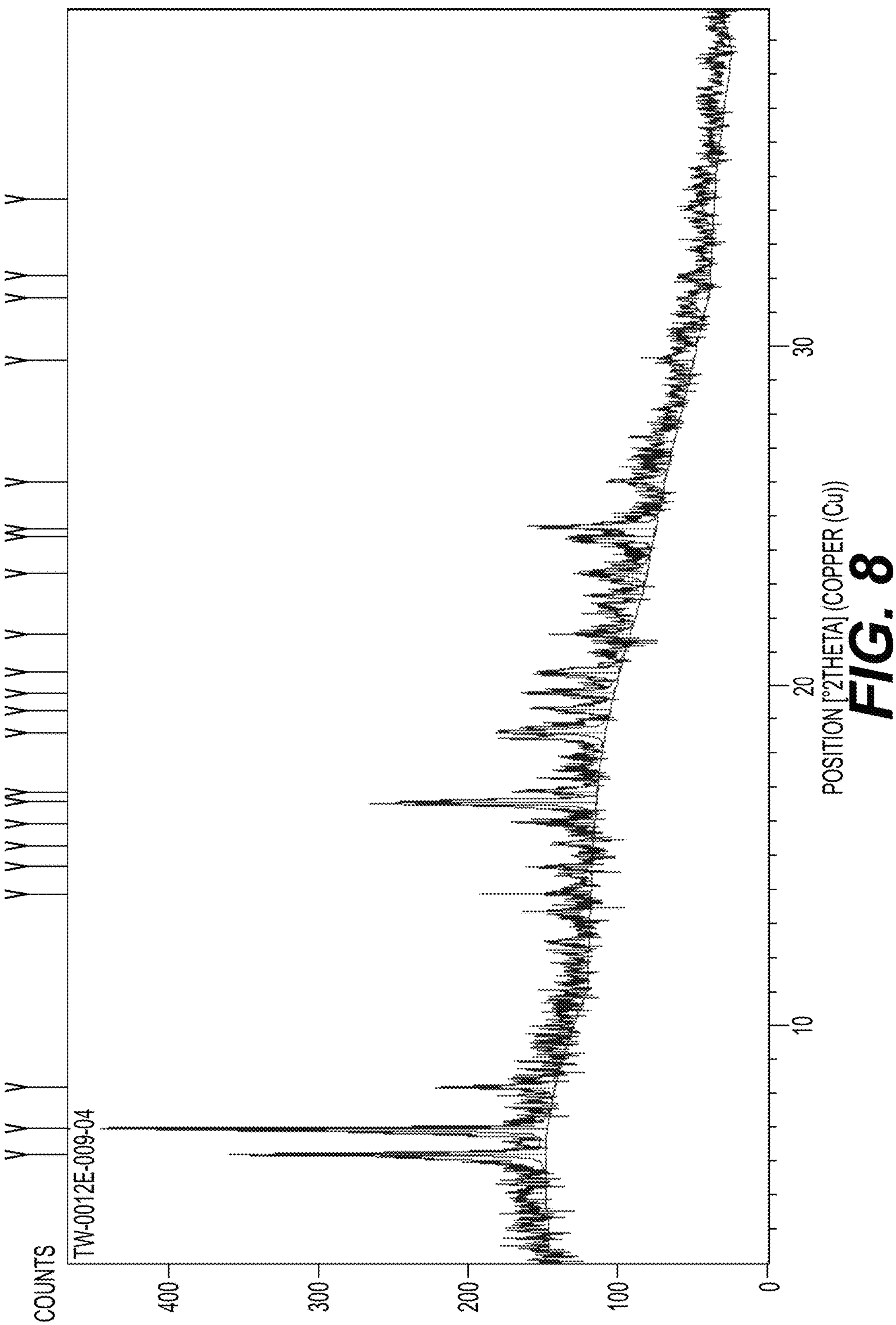
FIG. 8 provides an X-ray powder diffraction (XRPD) pattern of the hydrochloride (HCl salt) of Compound A polymorph form Pattern 4.

PL1 and NPL 26 describe a series of 5-sulfonylbenzimidazoles as potent and selective CB2 receptor agonists. The free base of Compound A is specifically described therein as a non-crystalline form (grease or low-melting solids) and it is unsuitable for the preparation of pharmaceutical compositions, particularly solid dosage forms. Therefore, we set to identify innovative and original approaches to establish whether we could identify, and robustly and consistently isolate salts showing good properties in terms of crystallinity, chemical and physical stability, and not deliquescent in standard temperature and pressure (STP) and humidity.

By generating different typologies of salts (e.g. hydrochloride (HCl salt), maleate, and mesylate), we were successful in discovering that the HCl salt (hydrochloride) of Compound A in particular exhibits excellent crystallinity, purity, high melting point, good chemical and physical stability, non-deliquescent, and high aqueous solubility. The hydrochloride of Compound A of the present invention is useful for the treatment of CB2 receptor mediated diseases in mammals.

Definition

The present invention may be understood more readily by reference to the following detailed description of the embodiments of the invention and the Examples included herein. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

As used herein, unless otherwise indicated, the term "treat" or "treating" means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

As used herein, the term "preventing" means the prophylactic treatment of a patient in need thereof. The prophylactic treatment can be accomplished by providing an appropriate dose of a therapeutic agent to a subject at risk of suffering from an ailment, thereby substantially averting onset of the ailment. It is to be understood that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass "preventing" as defined herein.

The term "therapeutically effective amount" means that amount of a salt of this invention, typically delivered as a pharmaceutical composition, that is sufficient to effect treatment, as defined herein, when administered to a subject in need of such treatment. The therapeutically effective amount will vary depending upon the subject and disease condition being treated, the weight and age of the subject, the severity of the disease condition, the particular compound chosen, the dosing regimen to be followed, timing of administration, the manner of administration, and the like, all of which can be determined readily by one of ordinary skill in the art.

As used herein, the term "condition" refers to a disease state for which the compounds, salts, compositions, and methods of the present invention are being used against.

The term "about" as used herein means having a value falling within an accepted standard of error of the mean, when considered by one of ordinary skill in the art, for example +/−20%, preferably +/−10% or more preferably +/−5% of the mean.

As used herein, the term "approximate to" means that variability typical for a particular method is taken into consideration. For example, with reference to X-ray diffraction peak positions, the term "approximate to" means that typical variability in peak position and intensity are taken into consideration. One skilled in the art will appreciate that the peak positions (2-Theta) will show some variability, typically as much as +/−0.2 degrees. Further, one skilled in the art will appreciate that relative peak intensities will show inter-apparatus variability as well as variability due to degree of crystallinity, preferred orientation, prepared sample surface, and other factors known to those skilled in the art and should be taken as qualitative measures only. Similarly, in DSC or TG/DTA measurements there is a certain degree of variability in actual measured onset and peak temperatures, typically as much as +/−1%, which is dependent on rate of heating, crystal shape and purity, and a number of measurement parameters. NMR chemical shift (ppm from TMS) values show variability, typically as much as +/−0.2 ppm.

The term "crystalline" or "crystal" as used herein, means having a regularly repeating arrangement of molecules or external face planes. Crystalline forms or crystal forms may differ with respect to thermodynamic stability, physical parameters, X-ray structure, and preparation processes.

As used herein, the term "polymorph" means the crystalline form of a substance that is distinct from another crystalline form but that shares the same chemical formula.

The invention described herein suitably may be practiced in the absence of any element(s) not specifically disclosed herein. Thus, for example, in each instance herein any of the terms "comprising", "consisting essentially of", and "consisting of" may be replaced with either of the other two terms.

Pharmaceutical Compositions

The pharmaceutical compositions of the present invention can be used for preventing or treating a subject suffering from conditions or diseases, wherein the conditions or diseases are mediated by CB2 receptor activity. Such conditions or diseases include but are not limited to, but for example, pain, inflammatory pain, nociceptive pain, neuropathic pain, fibromyalgia, chronic pain, visceral pain, migraine, cluster headache, cancer related pain, complex regional pain syndrome, neuralgias (e.g. trigeminal neuralgia), multiple sclerosis, Alzheimer's disease, Parkinson's disease, amyotrophic lateral sclerosis, epilepsy, diabetes neuropathy, human immunodeficiency virus (HIV) polyneuropathy, psychiatric diseases, psychosis, autistic spectrum disorder, irritable bowel syndrome (IBS), inflammatory bowel disease (IBD), ulcerative colitis, Crohn's disease, gastroesophageal reflux disease (GERD), constipation, diarrhoea, functional gastrointestinal disorder, arthritis, rheumatoid arthritis, osteoarthritis, atherosclerosis, psoriatic arthritis disease, spondylitides, asthma, allergy, psoriasis, dermatitis, seasonal allergic rhinitis, systemic lupus erythematosus (SLE), acute allograft rejection, gingivitis, encephalitis, cutaneous T cell lymphoma, pancreatic cancer, systemic fibrosis, systemic sclerosis (SSc), vasculitis liver fibrosis, lung fibrosis, kidney fibrosis, keloids, hypertrophic scars, acute respiratory distress syndrome (ARDS), reversible airway obstruction, adult respiratory disease syndrome, chronic obstructive pulmonary disease (COPD), cryptogenic fibrosing alveolitis, bronchitis, glaucoma, age-related macular degeneration (AMD) and geographic atrophy, diabetic retinopathy, uveitis, retinal vein occlusion, retinopathy of prematurity, ocular ischemic syndrome, glomerulonephritis, renal ischemia, nephritis, diabetic nephropathy, chronic allograft nephropathy, hepatitis, acute liver failure, liver cirrhosis, non-alcoholic steatohepatitis (NASH), myocardial infarction, cerebral ischemia, ischemia-reperfusion injury, heart failure, stroke, myocardial ischemia, cardiomyopathy, transient ischemic attack, diabetes, osteoporosis, regulation of bone mass, non-alcoholic fatty liver (NAFL), attention-deficit hyperactivity disorder (ADHD), anxiety, autistic spectrum disorder, depression, insomnia/sleep disorders, obsessive compulsive disorder (OCD), post-traumatic stress disorder (PTSD), Tourette's syndrome, malaria, and pyrexia.

The pharmaceutical compositions of the present invention are comprised of a pharmaceutically acceptable excipient, diluent, or carrier and a therapeutically acceptable amount of the salt of Compound A, wherein the salt is selected from the group consisting of acetic acid salt, L-ascorbic acid salt, L-aspartic acid salt, benzenesulfonic acid salt, citric acid salt, ethane-1,2-disulfonic acid (edisilic acid, EDSA) salt, fumaric acid salt, 2,5-dihydroxybenzoic acid (gentisic acid) salt, D-gluconic acid salt, D-glucuronic acid salt, L-glutamic acid salt, glutaric acid salt, glycolic acid salt, hippuric acid salt, hydrochloric acid (HCl) salt, L-lactic acid salt, maleic acid salt, L-malic acid salt, methanesulfonic acid (MSA) salt, phosphoric acid salt, p-toluenesulfonic acid (p-TSA) salt, succinic acid salt, sulfuric acid ($H_2SO_4$) salt, and L-tartaric acid salt. In the preferred embodiment, the pharmaceutical compositions of the present invention are comprised of a pharmaceutically acceptable excipient, diluent, or carrier and a therapeutically acceptable amount of the salt of Compound A, wherein the salt is selected from the group consisting of HCl salt, maleic acid salt, and methanesulfonic acid (MSA) salt. In the more preferred embodiment, the pharmaceutical compositions of the present invention are comprised of a pharmaceutically acceptable excipient, diluent, or carrier and a therapeutically acceptable amount of the HCl salt of Compound A having a crystalline polymorph form, Polymorph Form Pattern 2 or Polymorph Pattern 1 is exemplified.

Thus, the compound of the invention may be administered alone, but will generally be administered in admixture with a suitable pharmaceutical excipient, diluent, or carrier selected with regard to the intended route of administration and standard pharmaceutical practice.

For example, the compound of the invention may be administered orally in the form of optionally flavored and/or colored tablets, capsules, pills, powders, granules, elixirs, solutions, or suspensions suitable for immediate, delayed, or controlled release applications. The compound may also be administered systemically; by parenteral injection as a sterile solution, suspension, or emulsion; by rectal administration as a suppository; or by inhalation as an aerosol or as inhaled micronized powder or nanoparticles. Topical administration may be achieved as an ointment, cream, gel, liquid solution, or emulsion suppository.

Such tablets may contain excipients, such as microcrystalline cellulose, lactose, sodium citrate, calcium carbonate, dibasic calcium phosphate, or glycine, disintegrants, such as starch (preferably corn, potato, or tapioca starch), sodium starch glycollate, croscarmellose sodium or certain complex silicates, and granulation binders such as polyvinylpyrrolidone, hydroxypropylmethylcellulose (HPMC), hydroxypropylcellulose (HPC), sucrose, gelatin, or acacia. Additionally, lubricating agents, such as magnesium stearate, stearic acid, glyceryl behenate, or talc may be included.

Solid compositions of a similar type may also be employed as fillers in gelatin capsules. Preferred excipients in this regard include lactose, starch, a cellulose, milk sugar, or a high molecular weight polyethylene glycol. For aqueous suspensions and/or elixirs, the compound may be combined with various sweetening or flavoring agents, coloring matter, or dyes, with emulsifying and/or suspending agents and with diluents, such as water, ethanol, propylene glycol, or glycerin, or combinations thereof.

The compound may also be administered parenterally, for example, intravenously, intra-arterially, intraperitoneally, intrathecally, intraventricularly, intrasternally, intracranially, intramuscularly, or subcutaneously, or it may be administered by infusion techniques. It is best used in the form of a sterile aqueous solution which may contain other substances, for example, enough salts or glucose to make the solution isotonic with blood. If necessary, the aqueous solutions may be suitably buffered, preferably to a pH of from 3 to 9. The preparation of suitable parenteral formulations under sterile conditions is readily accomplished by standard pharmaceutical techniques well known to those skilled in the art.

For oral and parenteral administration to human patients, the daily dosage level of the compound of the invention will usually be from 0.01 to 20 mg/kg (in single or divided doses). Thus, tablets, capsules, or pills of the compound of the invention may contain from 0.5 to 500 mg of active compound for administration either singly or two or more at a time as appropriate. The physician in any event will determine the actual dosage which will be most suitable for any individual patient and it may vary with the age, weight, and response of the particular patient. The above dosages are exemplary of the average case. There can, of course, be individual instances where higher or lower dosage ranges are merited, and such are within the scope of this invention.

The compound of the invention may also be administered intranasally or by inhalation and is conveniently delivered in the form of a dry powder inhaler or an aerosol spray presentation from a pressurized container, pump, spray, or nebuliser using a suitable propellant, for example, dichlorodifluoromethane, trichlorofluoromethane, dichlorotetrafluoroethane, a hydrofluoroalkane, such as 1,1,1,2-tetrafluoroethane (norflurane, HFA-134a) or 1,1,1,2,3,3,3-heptafluoropropane (apaflurane, HFC-227ea), carbon dioxide, or other suitable gas. In the case of a pressurized aerosol, the dosage unit may be determined by providing a valve to deliver a metered amount. The pressurized container, pump, spray, or nebuliser may contain a solution or suspension of the active compound, for example, by using a mixture of ethanol and the propellant as the solvent, which may additionally contain a lubricant, for example, sorbitan trioleate. Capsules and cartridges (made, for example, from gelatin) for use in an inhaler or insufflator may be formulated to contain a powder mix of the compound and a suitable powder base such as lactose or starch.

Aerosol or dry powder formulations are preferably arranged so that each metered dose or 'puff' contains from 25 μg to 50 mg of the compound of the invention for delivery to the patient. The overall daily dose with an aerosol will be in the range of from 100 μg to 100 mg which may be administered in a single dose or, more usually, in divided doses throughout the day.

Alternatively, the compound of the invention may be administered in the form of a suppository or pessary or it may be applied topically in the form of a lotion, solution, cream, ointment, or dusting powder. The compound may also be administered transdermally, for example, by means of a skin patch, or by the ocular route.

For ocular administration, the compound of the invention may be formulated as micronized suspensions in isotonic and pH-adjusted sterile saline or, preferably, as solutions in isotonic and pH-adjusted sterile saline, optionally in combination with a preservative, such as a benzylalkonium chloride. Alternatively, it may be formulated in an ointment, such as petrolatum.

For topical application to the skin, the compound of the invention may be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, or water. Alternatively, it may be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol, or water.

Particularly preferred compositions in accordance with the invention include conventional, controlled release, and fast dispersion dosage forms such as tablets, capsules, pills, powders, or granules, all of which may readily be prepared by conventional means using the polymorph form of the invention.

Finally, the invention also provides for the use of the salt of Compound A, polymorph forms of the invention for the manufacture of a medicament for the curative, prophylactic, or palliative treatment of a medical disease or condition for which an agonist of CB2 receptors is indicated and for a method of curative, prophylactic or palliative treatment of a disease or medical condition for which an agonist of CB2 receptors is indicated which comprises the administration of a therapeutically effective amount of the salt of Compound A polymorph forms of the invention, wherein the salt is selected from the group consisting of acetic acid salt, L-ascorbic acid salt, L-aspartic acid salt, benzenesulfonic acid salt, citric acid salt, ethane-1,2-disulfonic acid (edisilic acid, EDSA) salt, fumaric acid salt, 2,5-dihydroxybenzoic acid (gentisic acid) salt, D-gluconic acid salt, D-glucuronic acid salt, L-glutamic acid salt, glutaric acid salt, glycolic acid salt, hippuric acid salt, hydrochloric acid (HCl) salt, L-lactic acid salt, maleic acid salt, L-malic acid salt, methanesulfonic acid (MSA) salt, phosphoric acid salt, p-toluenesulfonic acid (p-TSA) salt, succinic acid salt, sulfuric acid ($H_2SO_4$) salt, and L-tartaric acid salt. In the preferred embodiment, the salt is selected from the group consisting of HCl salt, maleic acid salt, and methanesulfonic acid (MSA) salt.

In the more preferred embodiment, the salt is HCl salt of Compound A polymorph forms of the invention, which is for the manufacture of a medicament for the curative, prophylactic, or palliative treatment of a medical disease or condition for which an agonist of CB2 receptors is indicated and for a method of curative, prophylactic or palliative treatment of a medical disease or condition for which an agonist of CB2 receptors is indicated which comprises the administration of a therapeutically effective amount of the HCl salt of Compound A polymorph forms of the invention.

Such diseases or conditions include pain, inflammatory pain, nociceptive pain, neuropathic pain, fibromyalgia, chronic pain, visceral pain, migraine, cluster headache, cancer related pain, complex regional pain syndrome, neuralgias (e.g. trigeminal neuralgia), multiple sclerosis, Alzheimer's disease, Parkinson's disease, amyotrophic lateral sclerosis, epilepsy, diabetes neuropathy, human immunodeficiency virus (HIV) polyneuropathy, psychiatric diseases, psychosis, autistic spectrum disorder, irritable bowel syndrome (IBS), inflammatory bowel disease (IBD), ulcerative colitis, Crohn's disease, gastroesophageal reflux disease (GERD), constipation, diarrhoea, functional gastrointestinal disorder, arthritis, rheumatoid arthritis, osteoarthritis, atherosclerosis, psoriatic arthritis disease, spondylitides, asthma, allergy, psoriasis, dermatitis, seasonal allergic rhinitis, systemic lupus erythematosus (SLE), acute allograft rejection, gingivitis, encephalitis, cutaneous T cell lymphoma, pancreatic cancer, systemic fibrosis, systemic sclerosis (SSc), vasculitis liver fibrosis, lung fibrosis, kidney fibrosis, keloids, hypertrophic scars, acute respiratory distress syndrome (ARDS), reversible airway obstruction, adult respiratory disease syndrome, chronic obstructive pulmonary disease (COPD), cryptogenic fibrosing alveolitis, bronchitis, glaucoma, age-related macular degeneration (AMD) and geographic atrophy, diabetic retinopathy, uveitis, retinal vein occlusion, retinopathy of prematurity, ocular ischemic syndrome, glomerulonephritis, renal ischemia, nephritis, diabetic nephropathy, chronic allograft nephropathy, hepatitis, acute liver failure, liver cirrhosis, non-alcoholic steatohepatitis (NASH), myocardial infarction, cerebral ischemia, ischemia-reperfusion injury, heart failure, stroke, myocardial ischemia, cardiomyopathy, transient ischemic attack, diabetes, osteoporosis, regulation of bone mass, non-alcoholic fatty liver (NAFL), attention-deficit hyperactivity disorder (ADHD), anxiety, autistic spectrum disorder, depression, insomnia/sleep disorders, obsessive compulsive disorder (OCD), post-traumatic stress disorder (PTSD), Tourette's syndrome, malaria, and pyrexia.

Combination Therapies

The salts of the present invention may also optionally be combined with another pharmacologically active compound, or with two or more other pharmacologically active compounds. For example, the salts of the present invention, as defined above, may be administered simultaneously, sequentially, or separately in combination with one or more agents selected from: analgesic compounds such as: acetaminophen; and NSAIDs, for example aspirin, choline and magnesium salicylates, choline salicylate, celecoxib, diclofenac potassium or sodium, diflunisal, etodolac, flurbiprofen, ibuprofen, indomethacin, ketoprofen, magnesium salicylate, meclofenamate sodium, mefenamic acid, meloxicam, nabumetone, naltrexone, naproxen, naproxen sodium, oxaprozin, piroxicam, salsalate, sodium salicylate, sulindac, tolmetin sodium or valdecoxib; gastrointestinal anti-inflammatory agents, for example 5-aminosalicylates (5-ASA), mesalamine, sulfasalazine and vedolizumab; immunosuppressive agents, for example azathioprine; purine antagonists, for example 6-mercaptopurine; oral corticosteroid therapeutics, for example prednisone, budesonide, or equivalent steroids; anti-inflammatory agents, for example anti-TNF-a agents, for example infliximab, adalimumab, ustekinumab, and certolizumab pegol; probiotics, for example Culturelle, *Saccharomyces boulardii*; antibiotics used for the treatment of Crohn's Disease, for example ciprofloxacin and metronidazole; antidiarrheals, for example loperamide and diphenoxylate with atropine; and the pharmaceutically acceptable salts and solvates thereof.

The present invention extends to a combination comprising the salts of Compound A and one or more therapeutic agents, such as those listed above, for simultaneous, separate or sequential use in the curative, prophylactic, or palliative treatment of conditions or diseases, wherein the conditions or diseases are mediated by CB2 receptor activity. Such conditions or diseases are not limited to, but for example, pain, inflammatory pain, nociceptive pain, neuropathic pain, fibromyalgia, chronic pain, visceral pain, migraine, cluster headache, cancer related pain, complex regional pain syndrome, neuralgias (e.g. trigeminal neuralgia), multiple sclerosis, Alzheimer's disease, Parkinson's disease, amyotrophic lateral sclerosis, epilepsy, diabetes neuropathy, human immunodeficiency virus (HIV) polyneuropathy, psychiatric diseases, psychosis, autistic spectrum disorder, irritable bowel syndrome (IBS), inflammatory bowel disease (IBD), ulcerative colitis, Crohn's disease, gastroesophageal reflux disease (GERD), constipation, diarrhoea, functional gastrointestinal disorder, arthritis, rheumatoid arthritis, osteoarthritis, atherosclerosis, psoriatic arthritis disease, spondylitides, asthma, allergy, psoriasis, dermatitis, seasonal allergic rhinitis, systemic lupus erythematosus (SLE), acute allograft rejection, gingivitis, encephalitis, cutaneous T cell lymphoma, pancreatic cancer, systemic fibrosis, systemic sclerosis (SSc), vasculitis liver fibrosis, lung fibrosis, kidney fibrosis, keloids, hypertrophic scars, acute respiratory distress syndrome (ARDS), reversible airway obstruction, adult respiratory disease syndrome, chronic obstructive pulmonary disease (COPD), cryptogenic fibrosing alveolitis, bronchitis, glaucoma, age-related macular degeneration (AMD) and geographic atrophy, diabetic retinopathy, uveitis, retinal vein occlusion, retinopathy of prematurity, ocular ischemic syndrome, glomerulonephritis, renal ischemia, nephritis, diabetic nephropathy, chronic allograft nephropathy, hepatitis, acute liver failure, liver cirrhosis, non-alcoholic steatohepatitis (NASH), myocardial infarction, cerebral ischemia, ischemia-reperfusion injury, heart failure, stroke, myocardial ischemia, cardiomyopathy, transient ischemic attack, diabetes, osteoporosis, regulation of bone mass, non-alcoholic fatty liver (NAFL), attention-deficit hyperactivity disorder (ADHD), anxiety, autistic spectrum disorder, depression, insomnia/sleep disorders, obsessive compulsive disorder (OCD), post-traumatic stress disorder (PTSD), Tourette's syndrome, malaria, and pyrexia. Preferably, the conditions or diseases mediated by CB2 receptor activity is for example, pain and inflammation, gastrointestinal (GI) disorders, such as irritable bowel syndrome (IBS), inflammatory bowel disease (IBD), and colitis. In the preferred embodiment, the salt of Compound A is selected from the group consisting of acetic acid salt, L-ascorbic acid salt, L-aspartic acid salt, benzenesulfonic acid salt, citric acid salt, ethane-1,2-disulfonic acid (edisilic acid, EDSA) salt, fumaric acid salt, 2,5-dihydroxybenzoic acid (gentisic acid) salt, D-gluconic acid salt, D-glucuronic acid salt, L-glutamic acid salt, glutaric acid salt, glycolic acid salt, hippuric acid salt, hydrochloric acid (HCl) salt, L-lactic acid salt, maleic acid salt, L-malic acid salt, methanesulfonic acid (MSA) salt, phosphoric acid salt, p-toluenesulfonic acid (p-TSA) salt, succinic acid salt, sulfuric acid ($H_2SO_4$) salt, and L-tartaric acid salt. In the preferred embodiment, the salt is selected from the group consisting of HCl salt, maleic acid salt, and methanesulfonic acid (MSA) salt. In the preferred embodiment, the salt is selected from the group consisting of HCl salt, maleic acid salt, and methanesulfonic acid (MSA) salt. In the more preferred embodiment, the salt of Compound A is HCl salt.

Preparation Method

The invention also provides a method for preparing a pharmaceutically acceptable salt of Compound A. In general, the method includes:

(a) suspending the free base of Compound A in a single solvent or mixture of solvents;

(b) contacting HCl (hydrochloric acid or hydrogen chloride gas), maleic acid, or methanesulfonic acid with Compound A to provide a mixture;

(c) heating the mixture at the temperature of from 20° C. to 100° C.;

(d) cooling the mixture at the temperature of from −20° C. to 40° C.;

(e) and isolating the salt.

In some embodiments of the method for preparing the salt, the mixture is cooled, and the salt is precipitated out of the solution.

In some embodiments of the method for preparing the salt, the mixture is heated and refluxed prior to cooling.

In some embodiments of the method of preparing the salt, the isolating step further includes filtering the mixture.

In some embodiments, the solvent used in the method of preparing the salt is an organic solvent miscible with water.

In other embodiments of the invention, the solvent used in the method of preparing the salt is selected from the group consisting of acetone, acetonitrile, 1-butanol, cyclohexane, dichloromethane, diisopropyl ether, dimethylacetamide, dimethyl sulfoxide, dioxane, ethanol, ethyl acetate, heptane, isopropyl acetate, methyl tert-butyl ether, methyl ethyl ketone, methyl isobutyl ketone, methanol, 2-propanol, toluene, tetrahydrofuran, water, and combinations of these.

The salt of Compound A having a kinetically favored crystalline form will be converted to a thermodynamically more stable crystalline form under appropriate conditions.

Compound A can be prepared according to the procedure described in Bioorg. Med. Chem. Lett. 2015, 25, 236 (NPL 26) as Compound 40 on a gram scale (<100 g). A smaller scale preparation is also set forth in U.S. Pat. No. 8,653,063 (PL 1) as Example 23.

EXAMPLES

The present invention is explained in more detail in the following by referring to Reference Example and Examples, which are not to be construed as limitative but just typical examples.

Abbreviations

The following abbreviations are used in the Examples:

AAT-730:2-[3-({1-[2-(dimethylamino)ethyl]-2-(2,2-dimethylpropyl)-1H-1,3-benzodiazol-5-yl}sulfonyl)azetidin-1-yl]ethan-1-ol (Compound A)
µL: microliter
µM: micromolar
$^1$H NMR: proton nuclear magnetic resonance spectroscopy
ACN: acetonitrile
API: active pharmaceutical ingredient, i.e. AAT-730
aq.: aqueous
Aw: water activity
DCM: dichloromethane
DIPE: diisopropyl ether
DMAc: N,N-dimethylacetamide
DMSO: dimethyl sulfoxide
DMSO-$d_6$: dimethyl sulfoxide-$d_6$
DSC: differential scanning calorimetry
EDSA: ethane-1,2-disulfonic acid
eq.: equivalent
EtOAc: ethyl acetate
EtOH: ethanol
evap: evaporation
g: gram
$H_2SO_4$: sulfuric acid
HCl: hydrochloric acid
HPLC: high performance liquid chromatography
IPA: isopropyl alcohol, 2-propanol
i-PrOAc: isopropyl acetate
IR: infrared
KF: karl fischer
kg: kilogram
L: liter
M: molar
MEK: methyl ethyl ketone
MeOH: methanol
MeOH-$d_4$: methanol-$d_4$ ($CD_3OD$)
mg: milligram
MHz: megahertz
MIBK: methyl isobutyl ketone
min: minute
mL: milliliter
mm: millimeter
MSA: methanesulfonic acid
MTBE: methyl tert-butyl ether
N/A: not available
$N_2$: nitrogen
No.: number
pH: power of hydrogen, potential of hydrogen, hydrogen-ion exponent
$pK_a$: acid dissociation constant, acidity constant
PO: preferred orientation
pptn: precipitation
PS: peak shifting
PSD: position sensitive detector
PTFE: polytetrafluoroethylene
p-TSA: p-toluenesulfonic acid
RH: relative humidity
rpm: revolutions per minute
T, Temp: temperature
TFA: trifluoroacetic acid
TG/DTA: thermogravimetric differential thermal analysis
TGA: thermal gravimetric analysis
THF: tetrahydrofuran
UV: ultraviolet
XRPD: X-ray powder diffraction Experimental Techniques X-Ray Powder Diffraction (XRPD)

XRPD analyses were performed using a Panalytical Xpert Pro diffractometer equipped with a Cu X-ray tube and a Pixcel detector system. The isothermal samples were analyzed in transmission mode and held between low density polyethylene films. The default XRPD program was used (range 3-40 degrees 2-Theta, step size 0.013 degree, counting time 22 sec, at most 5 min run time). XRPD patterns were sorted using HighScore Plus 2.2c software.

Differential Scanning Calorimetry (DSC)

DSC analyses were carried out on a Perkin Elmer Jade Differential Scanning calorimeter. Accurately weighed samples were placed in crimped aluminum pans. Each sample was heated under nitrogen at a rate of 10° C./minute to a maximum of 150° C. Temperatures were reported at the transition onset to the nearest 0.01 degree. Note that DSC traces within this report may contain automated peak integrations which calculate Delta H (ΔH) of fusion. Where multiple thermal events are observed at similar temperatures, these Delta H values are prone to significant error.

Thermogravimetric Differential Thermal Analysis (TG/DTA)

Thermogravimetric analyses were carried out on a Mettler Toledo TGA/DSC1 STARe instrument. Samples were accurately weighed in an aluminum sample pan on an analytical balance and inserted into the TG furnace. The heat flow signal was stabilized for one minute at 30° C., prior to heating to 300° C. in a stream of nitrogen at a rate of 10° C./minute.

$^1$H Nuclear Magnetic Resonance Spectroscopy ($^1$H NMR)

$^1$H NMR analysis was carried out on a Bruker 400 or 500 MHz instrument in $CD_3OD$ (MeOH-$d_4$) or DMSO-$d_6$. Instrumental parameters are listed on the relevant spectrum plots.

Optical and Hot Stage Microscopy

Microscopy analyses were carried out using an Olympus BX51 stereomicroscope with crosspolarized light and a 1st order red compensator plate. Photomicrographic images were captured using a ColorView IIIu digital camera and SynchronizIR basic V5.0 imaging software with objective lens magnification of ×10. Hot stage microscopy analyses were performed using a Linkam hot stage accessory. Solid samples were heated using pre-set temperature programs which included the selected ramp rate, final temperature and interval hold times if required for individual samples.

Volumetric Karl Fischer (KF) Analysis for Water Content

Volumetric KF analysis was performed using a Mettler Toledo V30 KF titrator. A weighed amount of solid sample was added directly to the KF cell. The solution was stirred, and the water content of the sample was then determined by automatic titration against standard KF reagent titrant.

Reference Example, Preparation of AAT-730 (Compound A)

2-[3-({1-[2-(dimethylamino)ethyl]-2-(2,2-dimethylpropyl)-1H-1,3-benzodiazol-5-yl}sulfonyl)azetidin-1-yl]ethan-1-ol (AAT-730) was prepared according to the procedure described in the Non Patent Literature 25 (Bioorg. Med. Chem. Lett. 2015, 25:236-240). The solid reaction product was further purified by the following preparative HPLC procedure.

The solids (22.8 g) were dissolved in 10% ACN containing 0.1% TFA in water (460 mL) and purified by HPLC using ODS silica (Daiso SP-120-40/60 ODS-B, 110×1000 mm, 10 L volume, OSAKA SODA CO., LTD., Osaka, Japan), gradient elution with 0.1% TFA/ACN system (ascending mode of ACN from 9% to 15%) at a flow rate of 200 mL/min, and UV detection at 220 nm. The collected fractions (24 L) were evaporated to remove ACN under 30° C. Then, to the concentrated aqueous mixture was added 0.5% aq. Ammonia (2 L) and chloroform (1 L), and the organic layer was separated. The aqueous layer was extracted with chloroform (1 L). The combined organic layers were washed with water and brine, dried with sodium sulfate, and concentrated to give a residue. The residue was dried under reduced pressure at room temperature overnight to afford 12.4 g of AAT-730 (Lot No. 033-190725-1) as a colorless oil.

The product (12.4 g) was recrystallized from a mixture of isopropyl acetate (15 mL) and n-heptane (30 mL) to provide 10.79 g of AAT-730 (Lot No. 33-13) as white solids.

Example 1, Free Base Form of AAT-730 (Compound A)

Free base form of AAT-730 was characterized by XRPD, polarized light microscopy, TG/DTA, DSC, and $^1$H NMR. The stability was also tested at a range of elevated relative humidity conditions for 7 days. The solubility of AAT-730 free base was estimated in various solvent systems.

Example 1-1, Characterization of AAT-730 (Compound A)

Figure 9:
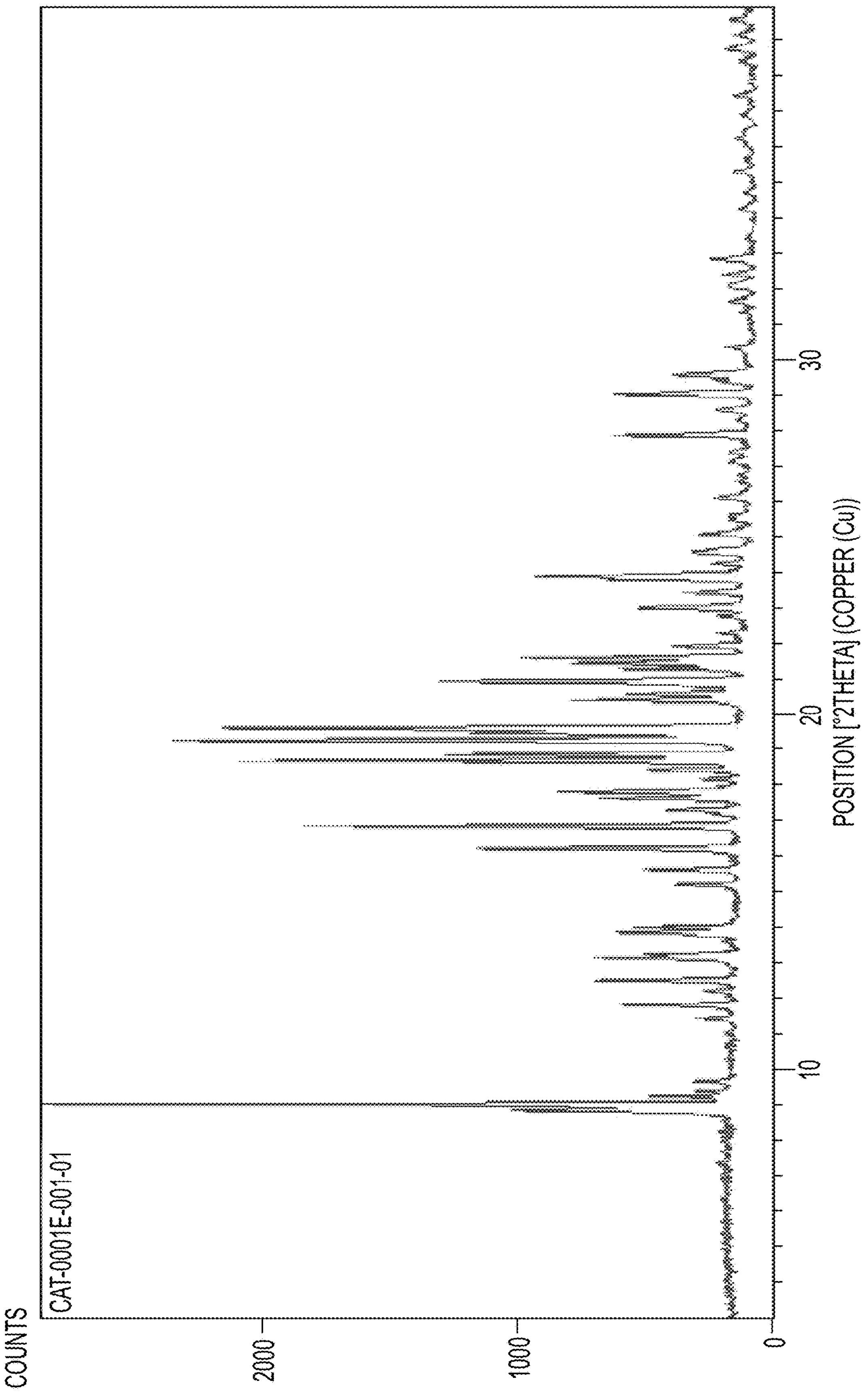
FIG. 9 provides an XRPD pattern of AAT-730 (Lot No. 33-13).

The XRPD pattern obtained for AAT-730 is shown in FIG. 9. The XRPD pattern is indicative of a crystalline material.

Figure 10:
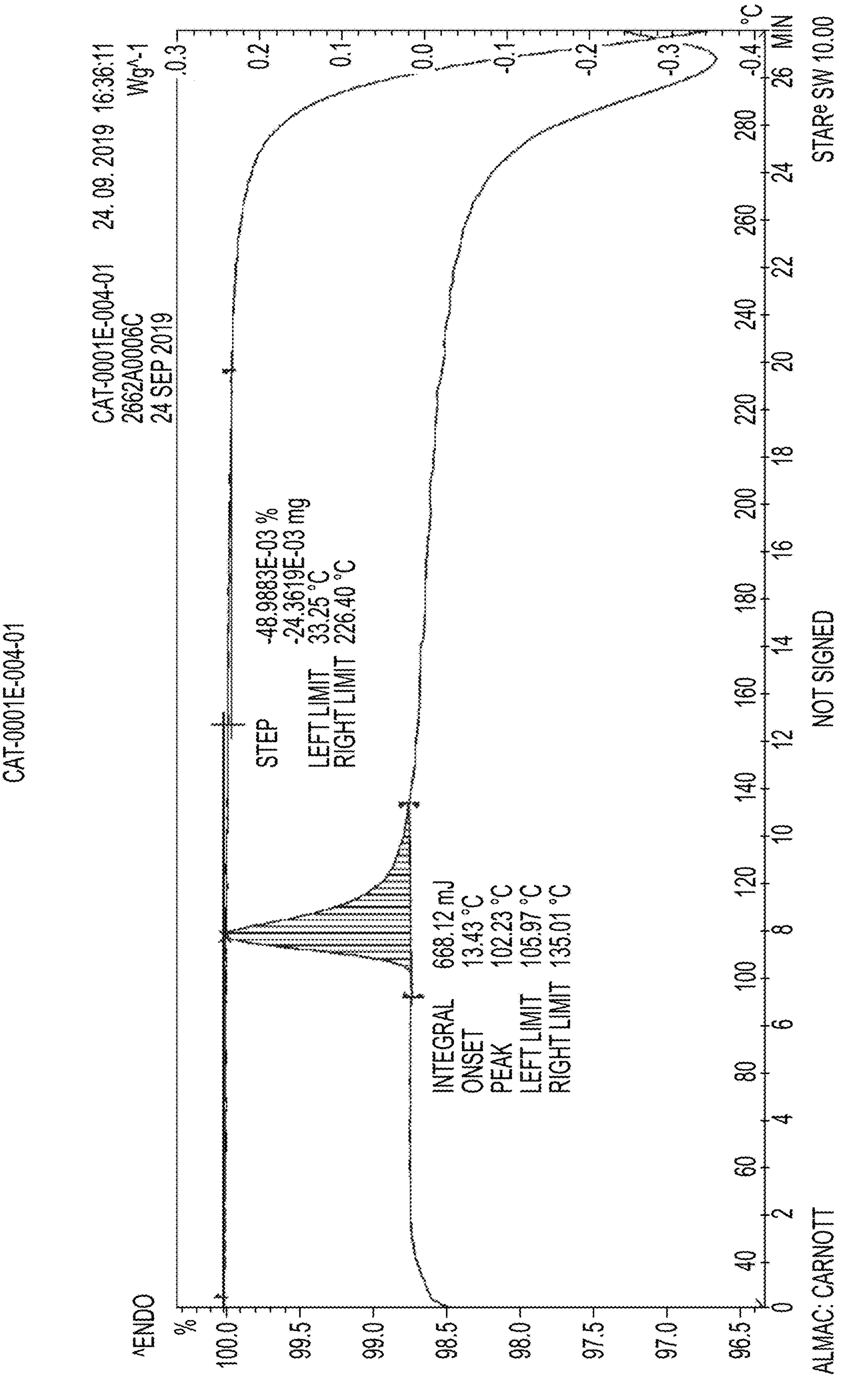
FIG. 10 provides a TG/DTA thermogram for AAT-730 analyzed from 30-300° C. at 10° C. per minute.

Thermogravimetric/Differential Thermal Analysis (TG/DTA) was performed to determine the thermal profile and associated % weight changes of AAT-730 (FIG. 10).

Weight loss of 0.05% was noted from 30° C. to 225° C. suggesting minimal moisture or solvent content, indicating AAT-730 to be an anhydrous material. A second weight loss at temperatures greater than approximately 250° C. may correspond to the initiation of decomposition of the material. A melting endotherm was observed at onset temperature 102.23° C.

Figure 11:
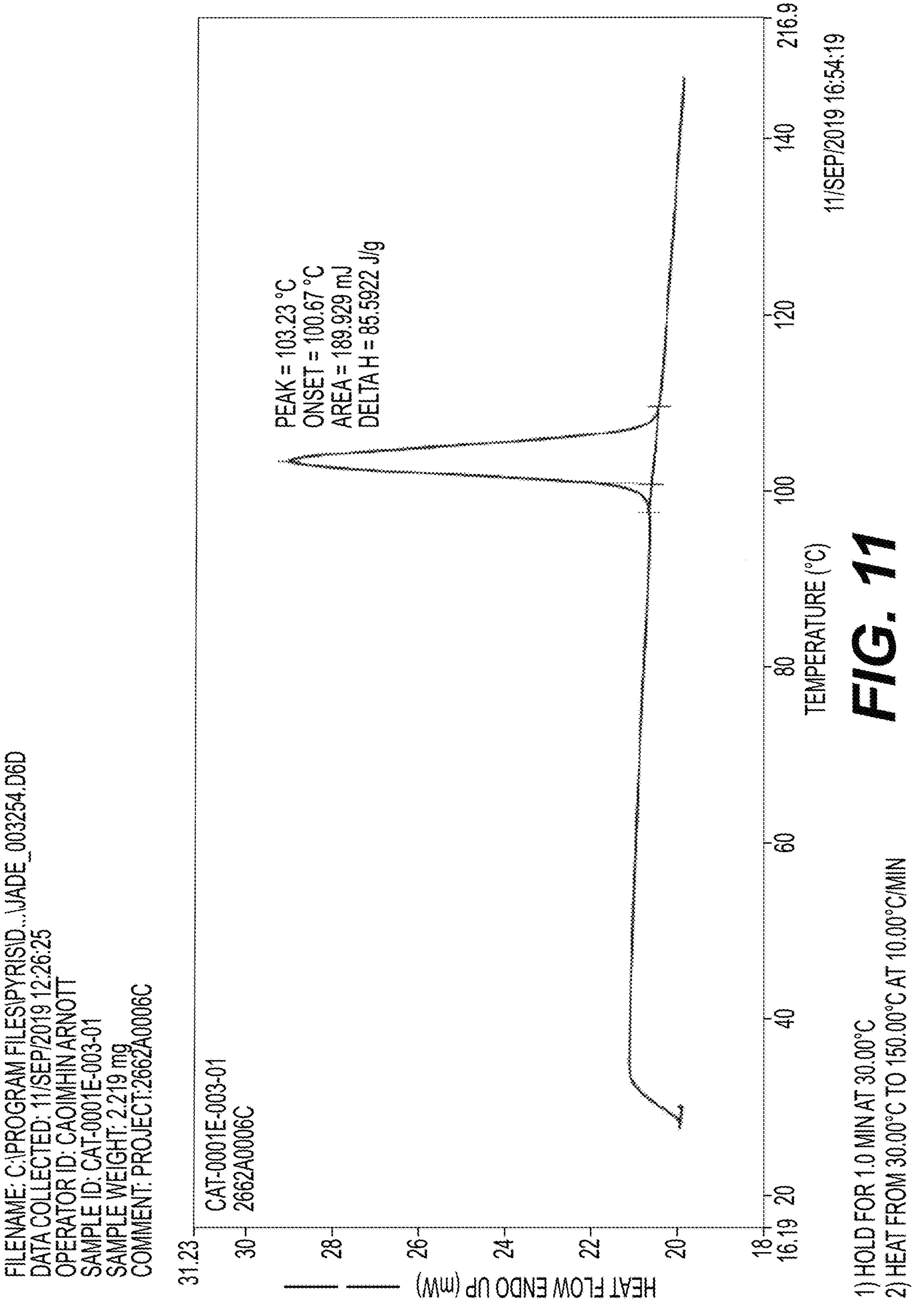
FIG. 11 provides a DSC thermogram for AAT-730 analyzed from 30-150° C. at 10° C. per minute.

The DSC thermogram obtained for AAT-730 at 10° C./min is shown in FIG. 11 and the melting onset is 100.67° C.

Figure 12:
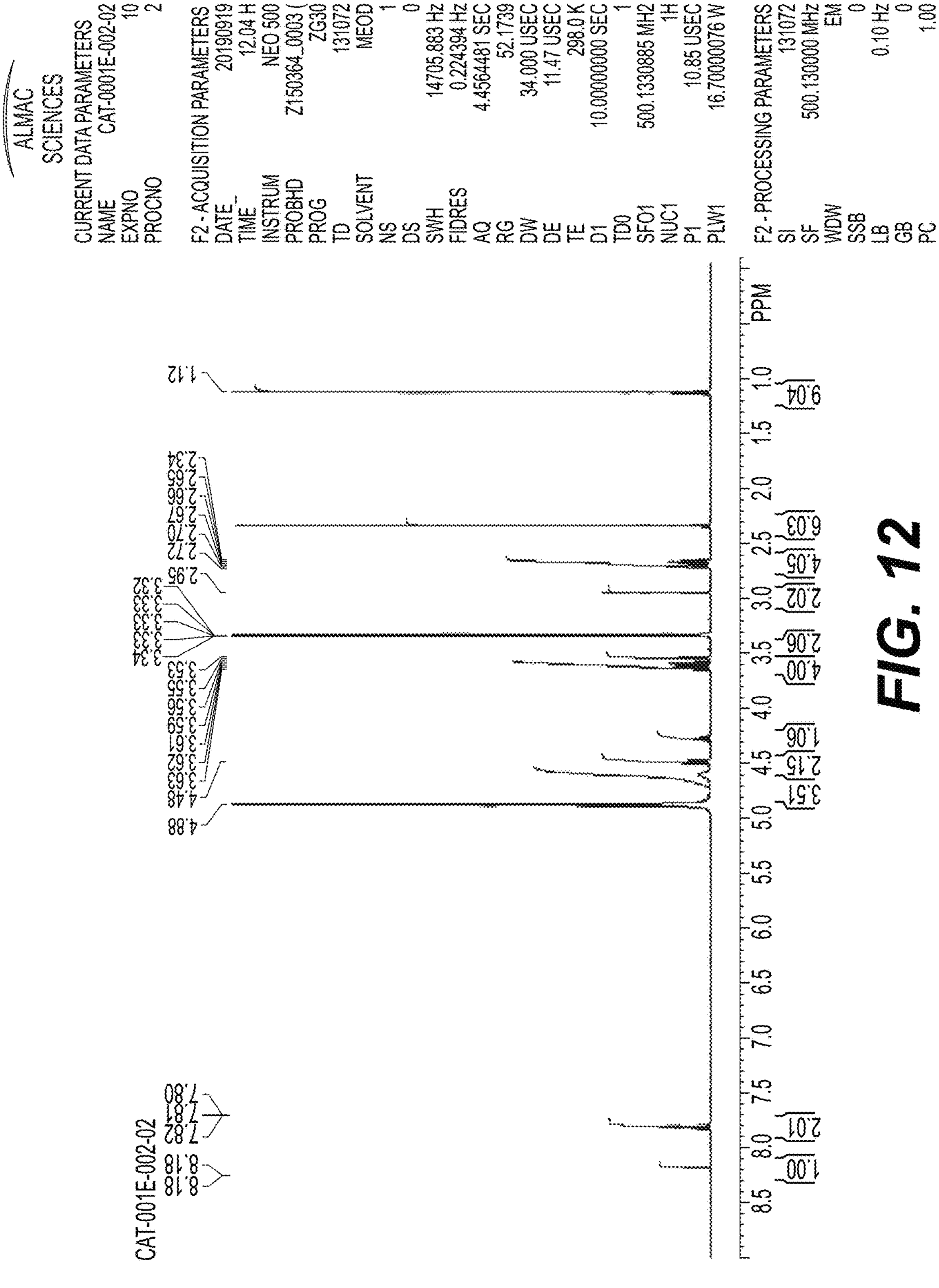
FIG. 12 provides a $^{1}H$ NMR spectrum of AAT-730 (analyzed in $CD_3OD$).
Figure 13:
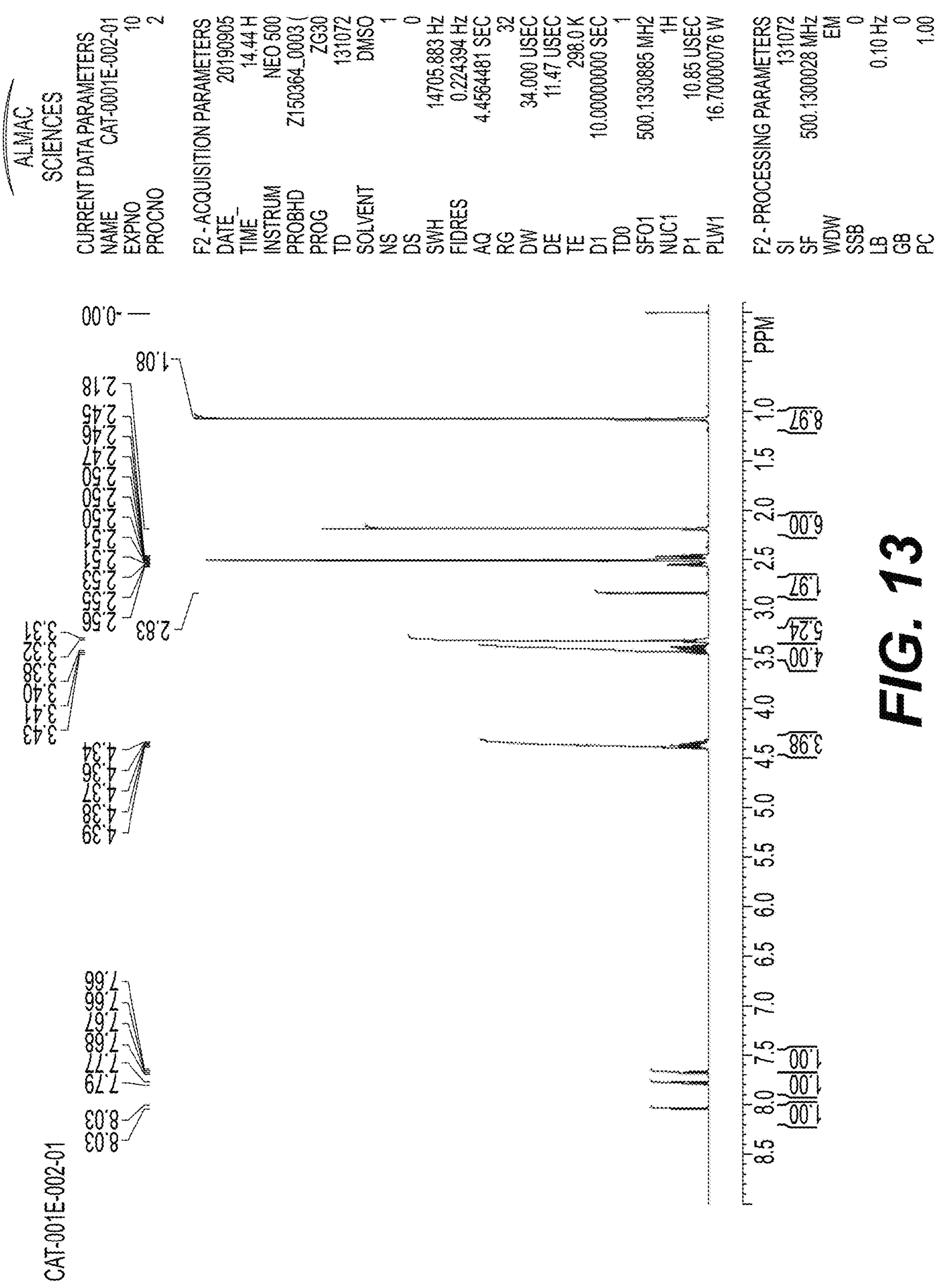
FIG. 13 provides a $^{1}H$ NMR spectrum of AAT-730 (analyzed in DMSO-$d_6$).

The $^1$H NMR spectrum of AAT-730 analyzed (FIG. 12 and FIG. 13) conformed to the molecular structure and solvent was not detected.

Figure 14:
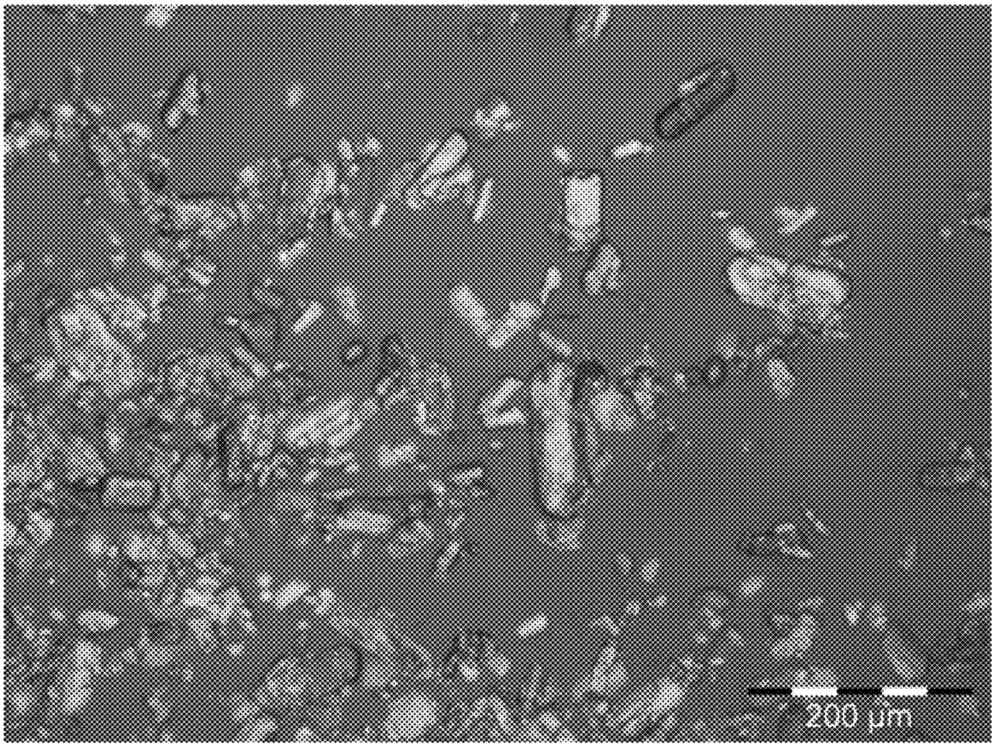
FIG. 14 provides a photomicrograph of AAT-730.

Polarized light microscopy of AAT-730 showed that the material is composed of crystalline particles of varying particle size distribution. The crystal habit appears to be laths, as shown in the photomicrograph (FIG. 14).

Figure 15:
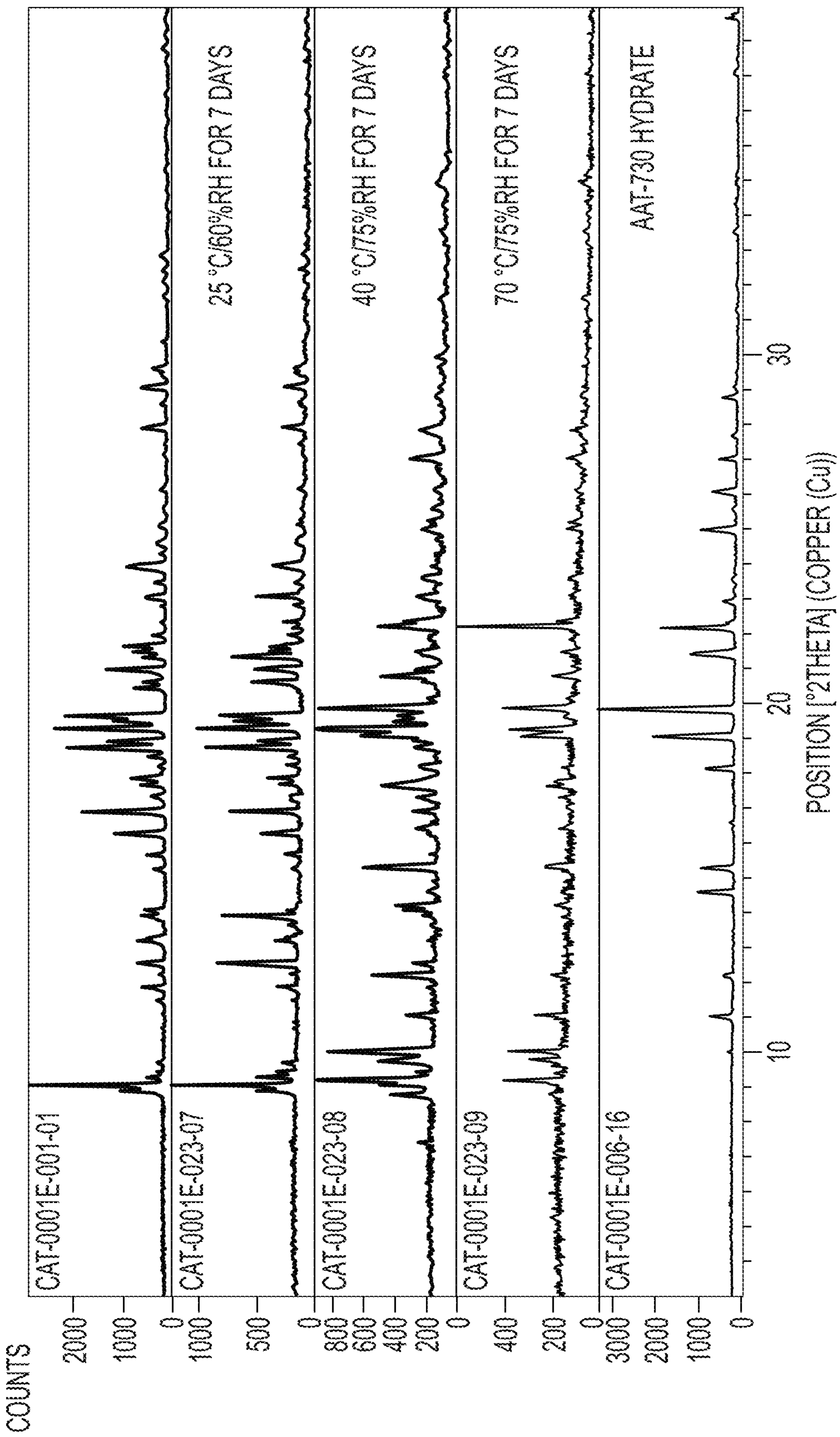
FIG. 15 provides an XRPD analysis of AAT-730 free base samples after elevated relative humidity and temperature stressing.
Figure 16:
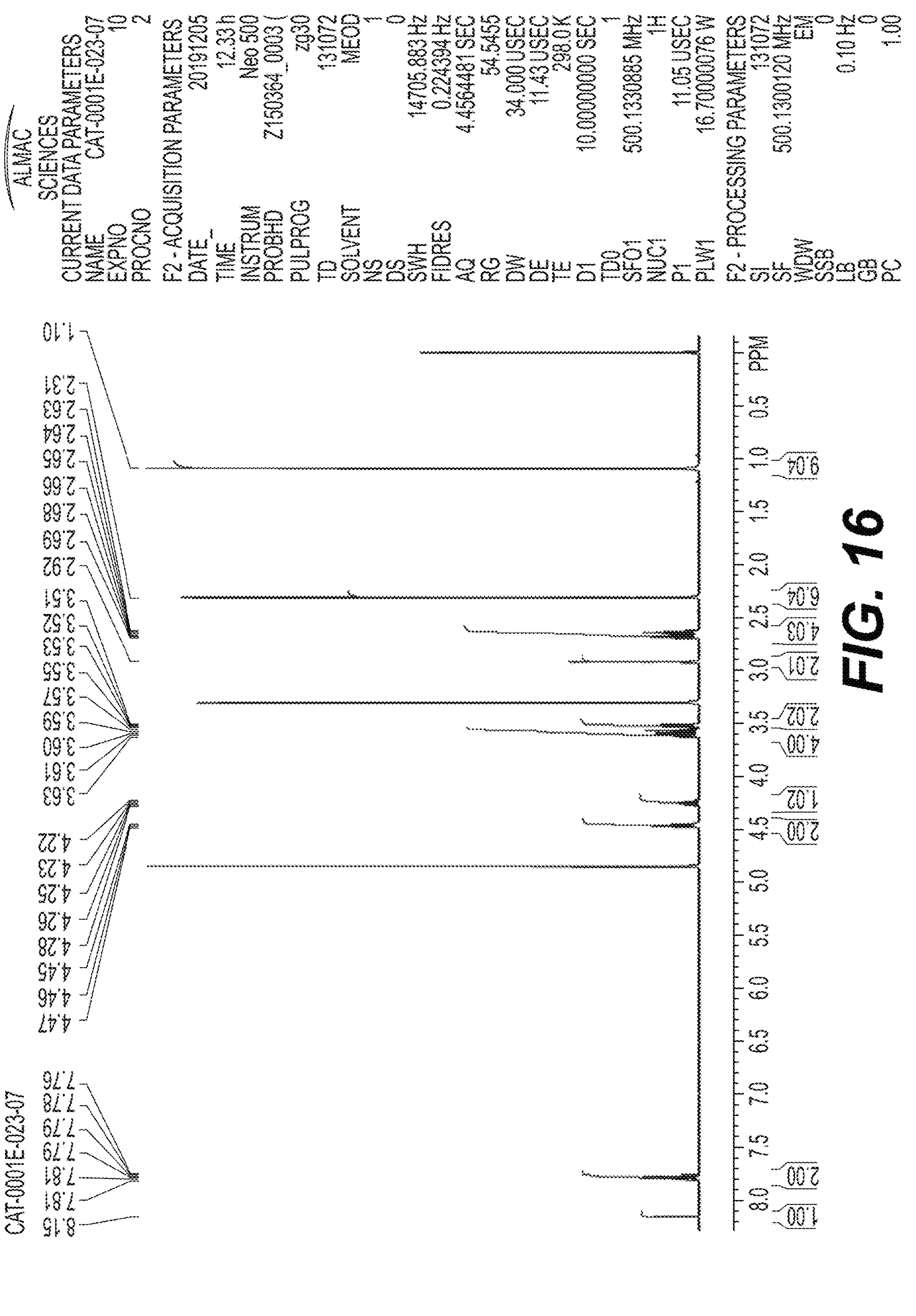
FIG. 16 provides a $^{1}H$ NMR spectrum of AAT-730 free base after 1 week at 25° C./60% RH.
Figure 17:
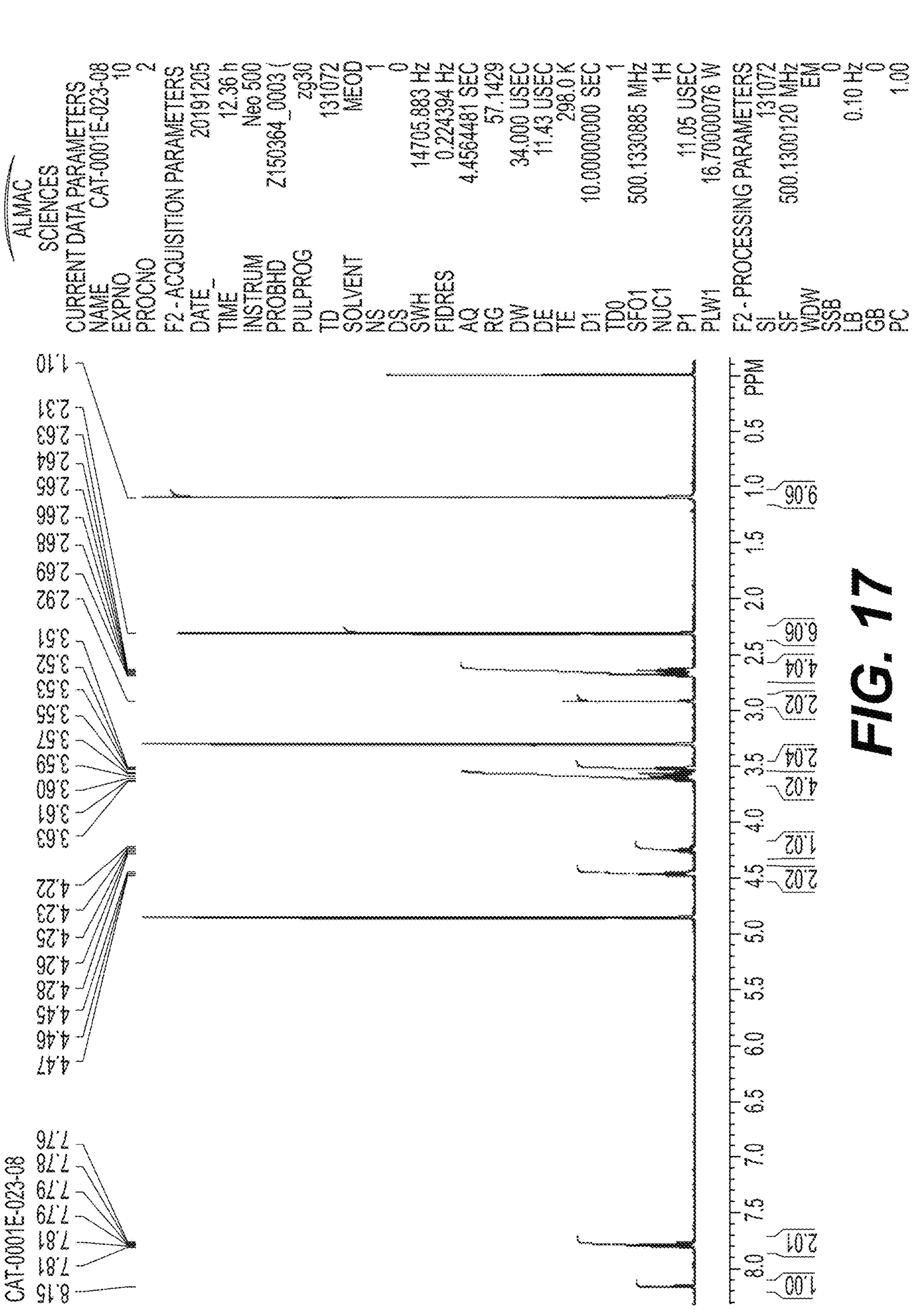
FIG. 17 provides a $^{1}H$ NMR spectrum of AAT-730 free base after 1 week at 40° C./75% RH.
Figure 18:
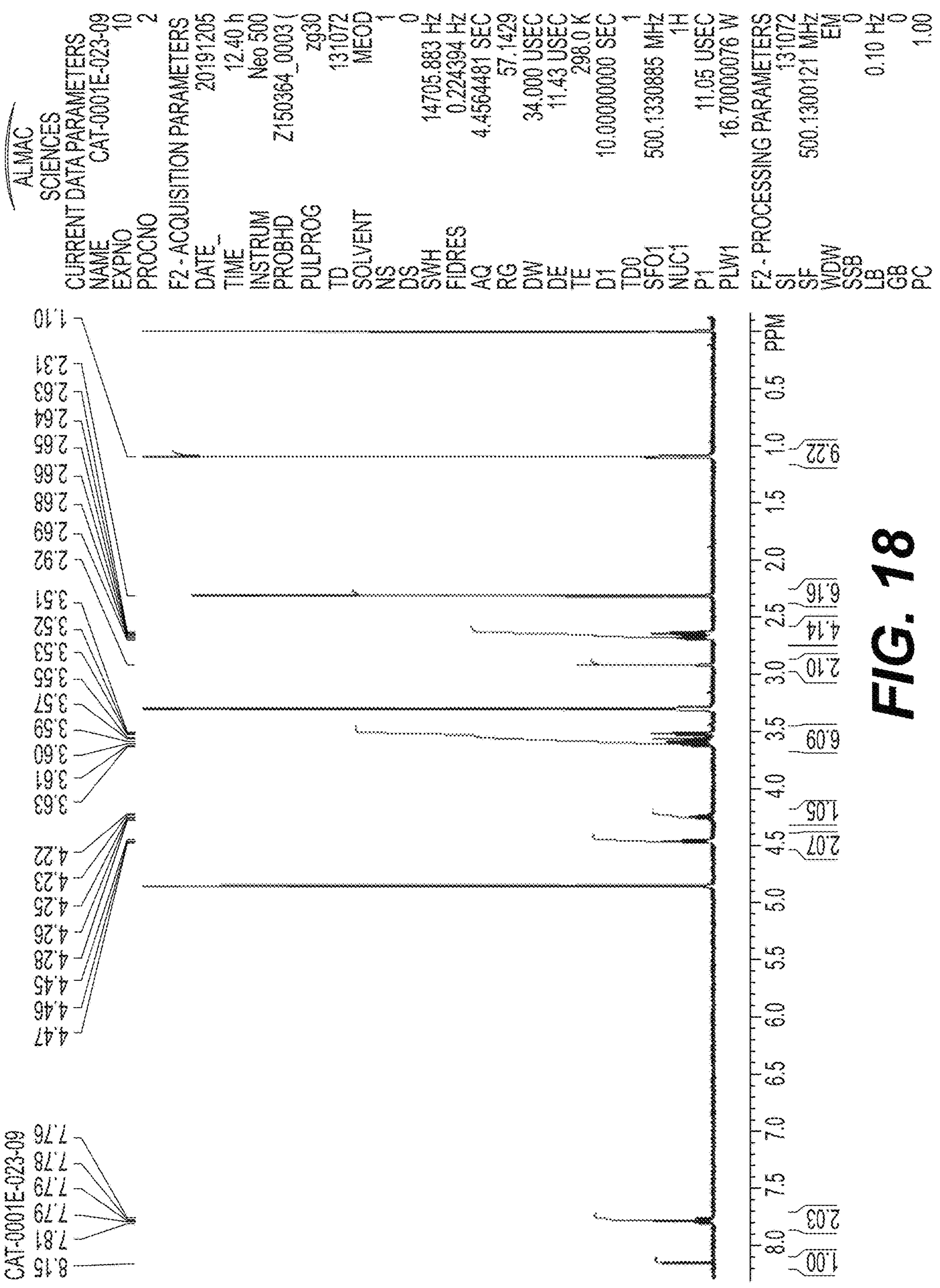
FIG. 18 provides a $^{1}H$ NMR spectrum of AAT-730 free base after 1 week at 70° C./75% RH.

AAT-730 free base was stressed at elevated relative humidity and temperature as shown in Table 1-2. XRPD analysis of the post-stressed samples (FIG. 15) showed a change in form to the hydrate at 40° C./75% RH and at 70° C./75% RH. The material remained as an anhydrate at 25° C./60% RH. $^1$H NMR analysis (FIG. 16, FIG. 17, and FIG. 18) showed no change.

Table of Humidity Stressing Experiments

TABLE 1-2

| Sample No. (CAT-0001E-) | Conditions |
|---|---|
| 023-07 | 25° C./60% RH |
| 023-08 | 40° C./75% RH |
| 023-09 | 70° C./75% RH |

Conclusions from Characterization

1) XRPD analysis indicated that AAT-730 was a crystalline material and polarized light microscopy concurred with this.
2) TG/DTA data showed negligible weight loss from 30-225° C., suggesting minimal moisture or residual solvent content, and shows that AAT-730 remains thermally stable up to 250° C.
3) Heat rate studies by DSC indicated a melting onset of 100.7° C.
4) $^1$H NMR spectroscopy conformed to molecular structure and no solvent was detected.
5) XRPD and $^1$H NMR analyses of AAT-730 free base samples after elevated relative humidity and temperature stressing suggested that the anhydrate had converted to a hydrate at 40° C./75% RH and 70° C./75% RH.

Example 1-2, Solubility Estimation

Aliquots of the test solvent were added to an accurately weighed sample (at most 25 mg) of AAT-730 at ambient temperature. The aliquot volumes were typically 20-200 μL. Complete dissolution of the test material was determined by visual inspection. The solubility was estimated from these experiments based on the total solvent used to provide complete dissolution. It should be noted that the actual solubility may be greater than that calculated because of the use of solvent aliquots that were too large or due to a slow rate of dissolution.

If dissolution did not occur after the last aliquot of solvent was added (typically at most 40 volumes of solvent), the sample was subjected to two cycles of the following temperature cycling regime on the Clarity crystallization station:

Heating from 20° C. to within 3° C. of solvent boiling point (or 100° C., whichever was lower) at 0.5° C./minute.

Cooling to 20° C. at 0.2° C./minute.

Stirring speed 800 rpm.

From the infrared (IR) transmission data of the sample vials, dissolution and precipitation events were recorded as the point of complete transmission of IR and the onset of turbidity by IR respectively.

(Note: IR probe was not functioning correctly throughout; did not give the dissolution temperature of MIBK)

Samples were held at ambient temperature for at least 18 hours to maximize the chance of precipitation. Any recoverable solids were analyzed by XRPD. The solubility values for AAT-730 were expressed as a range and rounded to the nearest whole number.

Estimated Solubility of AAT-730 (Compound A)

The solubility of AAT-730 was estimated in 20 solvent systems using the aliquot addition method. These included 4 aqueous/organic mixtures at compositions. AAT-730 had a solubility of >25 mg/mL in 11 of the solvents and 4 of the aqueous mixtures at ambient temperature. The solubility data obtained is shown in Table 1-3. AAT-730 had an aqueous solubility of approximately 367-514 mg/mL.

Solubility Estimates of AAT-730 at 20° C.

TABLE 1-3

| Solvent | Acronym | Solubility range (mg/ML) |
|---|---|---|
| acetone | — | 118-157 |
| acetonitrile | ACN | 145-164 |
| anisole | — | 58-60 |
| cyclohexane | — | <24 |
| dichloromethane | DCM | 360-504 |
| dimethyl sulfoxide | DMSO | 242-303 |
| dioxane | — | 117-129 |
| ethanol | EtOH | 213-256 |
| ethyl acetate | EtOAc | 27-28 |
| methanol | MeOH | >510 |
| methyl isobutyl ketone | MIBK | <26 |
| methyl tert-butyl ether | MTBE | <26 |
| 2-propanol, isopropyl alcohol | IPA | 81-87 |
| tetrahydrofuran | THF | 246-492 |
| toluene | — | <25 |
| water | — | 367-514 |
| acetone/water (50/50, $A_w$ at most 0.91) | — | 618-1235 |
| EtOH/water (96/4, $A_w$ at most 0.25) | — | 313-417 |
| MeOH/water (84/16, $A_w$ at most 0.44) | — | 638-1275 |
| THF/water (96/4, $A_w$ at most 0.74) | — | 410-615 |

Conclusions from Solvent Screening

AAT-730 had a solubility greater than or equal to 25 mg/mL in 15 of the solvents and aqueous mixtures tested. It had an aqueous solubility of approximately 367-514 mg/mL.

Example 2, Polymorph Screening of AAT-730 (Compound A) Freebase

A focused polymorph screen has been performed on AAT-730 freebase, the objective of which was to investigate the polymorphic landscape of AAT-730 free base. The approach was to generate solids under a wide and diverse range of nucleation conditions, designed to mimic the process conditions and solvents used during development and formulation. The starting material used in this study was AAT-730 (Lot No. 33-13).

All solids from the crystallization experiments were analyzed by XRPD and the resulting patterns compared to that exhibited by the starting material. Novel XRPD patterns were assigned an alphabetical descriptor in order of discovery (Pattern A, Pattern B etc.). Where sufficient material was available, further analysis (e.g. $^1H$ NMR or TGA) was conducted on solids with novel XRPD patterns to allow tentative assignment of the novel pattern as a polymorph, solvate, hydrate, degradant or mixture thereof.

Polymorph Screening Methods of Example 2

Method 2-1, Slow Evaporation

A solution of AAT-730 was prepared in each solvent and filtered through a 0.2 μm PTFE filter. The filtered solution was evaporated in a fume hood at ambient temperature in a vial covered with perforated aluminum foil. High boiling solvents (boiling point>100° C.) were evaporated under a flow of nitrogen. The resulting solids were analyzed by XRPD.

Method 2-2, Crash Precipitation

AAT-730 (20 mg) was dissolved in solvent (100-400 μL) and added into a vial containing antisolvent (2.5-10 volumes) at ambient temperature and the mixture stirred overnight. In some cases, an oil was generated, and the samples were heated up to 40° C. and/or further anti-solvent was added. Where precipitation was not observed overnight, samples were cooled to 5° C. to encourage precipitation.

Method 2-3, Slurry Experiments

Sufficient AAT-730 (Lot No. 33-13 or gels from previous experiments) was added to a given solvent until undissolved solids remained at the desired temperature (5, 20, or 40° C.). The vial was sealed, and the slurry was maintained at the selected temperature and agitated by magnetic stirring for 4-7 days or approximately 2 hours for gels. Solids were isolated by centrifugation and air dried prior to analysis by XRPD.

Method 2-4, Slow Cooling

AAT-730 (Lot No. 33-13, at most 20 mg) and solvent (100-1000 μL) were added to a vial and stirred to form an almost saturated solution at 60° C. (the solvent was added in aliquots). The solutions were cooled without agitation at 0.2° C./min to a final temperature of 5° C. Experiments that precipitated solids were filtered and air dried before analysis by XRPD.

Method 2-5, Vapor Stress

Approximately 20 mg of amorphous AAT-730 was prepared by melt quench as detailed in Example 2-1. Each vial was placed unsealed inside a larger sealed vessel containing 500 μL of the selected solvent. After up to 7 days, the samples were removed and analyzed by XRPD.

Method 2-6, Humidity Stress

Approximately 20 mg of amorphous AAT-730 was prepared by melt quench as detailed in Example 2-1. Each vial was placed unsealed inside the following relative humidity chambers (sealed cabinets with relative humidity conditions controlled by super-saturated salt solutions) for 7 days prior to analysis by XRPD:

Chamber 1-23% RH

Chamber 2-59% RH

Chamber 3-76% RH

Chamber 4-98% RH

Method 2-7, Temperature Cycling

The test solvent (100 μL) was added to a sample of AAT-730 (at most 20 mg) at ambient temperature and 10 cycles of the following temperature program was performed using the Clarity crystallization station:

Heating from 20° C. to 60-80° C. at 1° C./min (depending on boiling point of solvent)

Cooling to 20° C. at 1° C./min

Stirring speed-600 rpm

Method 2-8, Sonication of Pastes

AAT-730 (at most 20 mg) was added to a vial with 10 μL of the selected solvent to form a paste. The mixture was sonicated at 50% intensity using a Cole-Parmer 130 Watt ultrasonic processor using a pulsed program (3 cycles-30 seconds on and 30 seconds off). In cases where the solids dissolved at ambient temperature, the sample was left uncapped to evaporate. The wet pastes recovered from these experiments were analyzed using XRPD.

Method 2-9, Thermal Stressing

Approximately 20 mg of various forms of AAT-730 was added to a vial, flushed with nitrogen, sealed and placed into a heater block at 40, 60, or 80° C. for varying times prior to analysis by XRPD.

Method 2-10, Vapor Diffusion

A solution of AAT-730 was prepared and the vial was placed unsealed inside larger vials, which contained an aliquot of anti-solvent. The larger vials were sealed and left undisturbed under ambient conditions for up to 7 days. Solids were isolated by centrifugation and air dried prior to analysis by XRPD. Cyclohexane (500 μL) was added to vials which contained solutions, and these were stirred for 16 hours prior to isolation of solids and analysis by XRPD.

Example 2-1, Generation of Amorphous AAT-730 (Compound a, Melt Quench)

Amorphous AAT-730 was generated from melt quench for screening. AAT-730 (20 mg) was added to a HPLC vial and flushed with $N_2$. This was heated to 120° C. for up to 5 minutes and was quickly immersed in a liquid nitrogen/acetone mixture to form amorphous AAT-730. The resulting amorphous material was confirmed visually by microscopy.

Example 2-2, Slow Evaporation

Slow evaporation of AAT-730 solutions were conducted as described in Method 2-1. The results are shown in Table 2-1. Solids were isolated from four evaporation experiments. Pattern A material was isolated from DCM and EtOAc and Pattern C material was isolated from acetone. Pattern B material was isolated from water, although some amorphous content was noted. All other experiments afforded gels and were slurried in cyclohexane (Table 2-3). Unique materials were further characterized and are discussed further in Examples 2-11 to 2-14.

Screening Results from Slow Evaporation Experiments

TABLE 2-1

| Sample (TW-0011E-) | Solvent | Result | XRPD |
|---|---|---|---|
| 001-01 | acetone | solid | Pattern C |
| 001-02 | ACN | gel | N/A |
| 001-03 | DCM | solid | Pattern A (PO) |
| 001-04 | EtOH | gel | N/A |
| 001-05 | EtOAc | solid | Pattern A |
| 001-06 | MeOH | gel | N/A |
| 001-07 | IPA | gel | N/A |
| 001-08 | water | solid | Pattern B + amorphous (minor) |
| 001-09 | THF | gel | N/A |

PO = preferred orientation

Example 2-3, Crash Precipitation Experiments

Crash precipitation experiments were carried out as detailed in Method 2-2. Solvents and chemically diverse anti-solvents were selected, and the results are shown in Table 2-2. In four cases, precipitation was not observed. Experiments which afforded solids were confirmed as Pattern A, Pattern B and Pattern C material by XRPD and these are discussed further in Examples 2-11 to 2-14.

Precipitation of Saturated AAT-730 Solutions with Anti-Solvents

TABLE 2-2

| Sample No. (TW-0011E-) | Solvent | Anti-solvent | Result | XRPD |
|---|---|---|---|---|
| 003-01 | acetone | cyclohexane | solid | Pattern C |
| 003-02 | EtOAc | cyclohexane | solid | Pattern B |
| 003-03 | EtOH | cyclohexane | solution | N/A |
| 003-04 | THF | cyclohexane | solid | Pattern A |
| 003-05 | water | toluene | solid | Pattern B |
| 003-06 | acetone | MTBE | solution | N/A |
| 003-07 | ACN | MTBE | solution | N/A |
| 003-08 | dioxane | MTBE | solid | Pattern B |
| 003-09 | DCM | MTBE | solid | Pattern C |
| 003-10 | EtOH | MTBE | solution | N/A |

Example 2-4, Slurry Experiments

Suspensions of AAT-730 in various solvents were held at 5, 20 and 40° C. for 5-7 days prior to isolation and analysis by XRPD (Table 2-3) as detailed in Method 2-3. Pattern B and Pattern C materials were isolated from a range of solvents and temperatures in pure form with Pattern B+C also isolated from a few experiments. A unique form, Pattern D was isolated from the recycling of a gel in cyclohexane however, this was isolated as a mixture with Pattern A material. No further analysis was performed on this mixture.

Screening Results from Slurry Experiments

TABLE 2-3

| Sample No (TW-0011E-) | Input material | Solvent | Temp (° C.) | Result | XRPD |
|---|---|---|---|---|---|
| 002-01 | Lot No. 33-13 | acetone | 5 | solution | N/A |
| 002-02 | Lot No. 33-13 | ACN/cyclohexane (20/80) | 5 | solution | N/A |
| 002-03 | Lot No. 33-13 | EtOAc | 5 | solid | Pattern B |
| 002-04 | Lot No. 33-13 | MIBK | 5 | solid | Pattern B + C |
| 002-05 | Lot No. 33-13 | MTBE | 5 | solid | Pattern C + B |
| 002-06 | Lot No. 33-13 | IPA | 5 | solid | Pattern C |
| 002-07 | Lot No. 33-13 | toluene | 5 | solid | Pattern C |
| 013-01 | Lot No. 33-13 | MeOH/water (84/16, $A_w$ at most 0.44) | 5 | solution | N/A |
| 013-02 | Lot No. 33-13 | THF/water (96/4, $A_w$ at most 0.74) | 5 | solid | Pattern B |
| 013-03 | Lot No. 33-13 | acetone/water (20/1, $A_w$ at most 0.6) | 5 | solid | Pattern B |
| 005-01 | Lot No. 33-13 | EtOAc | 20 | solid | Pattern B |
| 005-02 | Lot No. 33-13 | acetone/cyclohexane (20/80) | 20 | solid | Pattern C |
| 005-03 | Lot No. 33-13 | IPA/cyclohexane (20/80) | 20 | solid | Pattern C |
| 005-04 | Lot No. 33-13 | ACN/cyclohexane (10/90) | 20 | solid | Pattern C |
| 005-05 | Lot No. 33-13 | dioxane/cyclohexane (10/90) | 20 | solid | Pattern C + B |
| 004-01 | Lot No. 33-13 | cyclohexane | 40 | solid | Pattern C |
| 004-02 | Lot No. 33-13 | MTBE | 40 | solid | Pattern C |
| 004-03 | Lot No. 33-13 | MIBK | 40 | solid | Pattern C |
| 004-04 | Lot No. 33-13 | toluene | 40 | solid | Pattern C |
| 012-01 | 001-02 | cyclohexane | 40 | solid | Pattern B |
| 012-02 | 001-04 | cyclohexane | 40 | solid | Pattern B + C |
| 012-03 | 001-06 | cyclohexane | 40 | solid | Pattern B + C |
| 012-04 | 001-07 | cyclohexane | 40 | solid | Pattern B + C |
| 012-05 | 001-09 | cyclohexane | 40 | solid | Pattern D + A |

Example 2-5, Slow Cooling

The slow increase in supersaturation allows more stable forms to nucleate. A sub-ambient final temperature also probes for stable solvates at temperatures typically accessed during cooling crystallization at plant scale. Experiments were carried out as detailed in Method 2-4. Table 2-4 shows the screening results from slow cooling experiments. Pattern C material was isolated from most experiments. A mixture of Pattern C+A with preferred orientation was isolated from EtOAc. Crystallization was not observed from an experiment with MIBK.

Screening Results from Slow Cooling Experiments

TABLE 2-4

| Sample No. (TW-0011E-) | Solvent | Result | XRPD |
|---|---|---|---|
| 006-01 | acetone | solid | Pattern C (PO) |
| 006-02 | EtOAc | solid | Pattern C + A (PO) |
| 006-03 | MIBK | solution | N/A |
| 006-04 | MTBE | solid | Pattern C |
| 006-05 | toluene | solid | Pattern C |

PO = preferred orientation

Example 2-6, Vapor and Humidity Stress

X-ray amorphous material generated from melt quench was exposed to air saturated in solvent vapor and various controlled humidity conditions for up to 7 days before analysis by XRPD as detailed in Method 2-5 and Method 2-6. The results are shown in Table 2-5. As amorphous material has lost long range order, it is in a high energy state. Exposure to vapor plasticizes the solid, allowing limited molecular mobility and is therefore an excellent method of generating metastable solvates and hydrates. Several mixtures of forms were isolated from these experiments (Patterns A+B, A+C and B+C). Phase pure Pattern C material was isolated from the majority of these stress experiments. Pattern B material was isolated from stressing at 98% relative humidity. Pattern A material was isolated from three experiments but with some amorphous content present from stressing in cyclohexane, with peak shifting from stressing in MTBE and with an extra peak present from stressing in toluene.

Results from Vapor Stressing and Humidity Experiments

TABLE 2-5

| Sample No. (TW-0011E-) | Solvent | Result | XRPD |
|---|---|---|---|
| 008-01 | acetone | solid | Pattern C (PO) |
| 008-02 | ACN | solid | Pattern C (PO) |
| 008-03 | cyclohexane | solid | Pattern A (slight amorphous character) |
| 008-04 | DCM | solid | Pattern C + A + peak at 6.56 |
| 008-05 | EtOH | gel | Pattern A + B |
| 008-06 | EtOAc | solid | Pattern C |
| 008-07 | MIBK | solid | Pattern C (PO) |

TABLE 2-5-continued

| Sample No. (TW-0011E-) | Solvent | Result | XRPD |
|---|---|---|---|
| 008-08 | MTBE | solid | Pattern A (PS) |
| 008-09 | IPA | solid (after cyclohexane added) | Pattern B + C |
| 008-10 | THF | solid | Pattern C |
| 008-11 | toluene | solid | Pattern A + peak at 7.33 |
| 009-01 | 23% RH stress | gel (solid after cyclohexane added) | Pattern B + C |
| 009-02 | 59% RH stress | solid | Pattern C |
| 009-03 | 75% RH stress | solid | Pattern C |
| 009-04 | 98% RH stress | gel (solid after cyclohexane added) | Pattern B |

PO = preferred orientation,
PS = peak shifting

Example 2-7, Temperature Cycling

Samples were subjected to the temperature cycling program outlined in Method 2-7 and the results are shown in Table 2-6. Pattern C material was isolated from most experiments. A mixture of Pattern A+C was isolated from cycling IPA.

Screening Results from Temperature Cycling Experiments

TABLE 2-6

| Sample No. (TW-0011E-) | Solvent | Result | XRPD |
|---|---|---|---|
| 010-01 | anisole | solid | Pattern C |
| 010-02 | cyclohexane | solid | Pattern C |
| 010-03 | EtOAc | solid | Pattern B + C |
| 010-04 | MIBK | solid | Pattern C |
| 010-05 | MTBE | solid | Pattern C |
| 010-06 | IPA | solid | Pattern A + C |
| 010-07 | toluene | solid | Pattern C |

Example 2-8, Sonication

Sonication experiments were carried out as detailed in Method 2-8. The results are shown in Table 2-7. Most experiments afforded Pattern C material. Pattern B material was isolated from an experiment with water. A mixture of forms, Pattern A+C was isolated from an experiment with MTBE. Solutions were isolated from four experiments and no further work was performed on these samples.

Screening Results from Sonication Experiments

TABLE 2-7

| Sample No. (TW-0011E-) | Solvent | Result | XRPD |
|---|---|---|---|
| 011-01 | acetone | solid | Pattern C |
| 011-02 | ACN | solid | Pattern C |
| 011-03 | anisole | solid | Pattern C |
| 011-04 | DCM | solid | Pattern C |
| 011-05 | dioxane | solution | N/A |
| 011-06 | EtOH | solution | N/A |
| 011-07 | EtOAc | solid | Pattern C |
| 011-08 | MeOH | solution | N/A |
| 011-09 | MIBK | solid | Pattern C |
| 011-10 | MTBE | solid | Pattern A + C |
| 011-11 | IPA | solution | N/A |
| 011-12 | toluene | solid | Pattern C |
| 011-13 | water | solid | Pattern B |

Example 2-9, Thermal Stress

AAT-730 was thermally stressed at 40 or 60° C. for several days in a sealed vial and analyzed by XRPD as detailed in Method 2-9. The results are shown in Table 2-8. AAT-730 (Lot No. 33-13), Pattern A (isolated during screening) and Pattern B were physically unstable to stressing at the temperatures tested. Pattern C remained physically stable to stressing at 40° C. Pattern B material was also stressed at 80° C.

Screening Results from Thermal Stress Experiments

TABLE 2-8

| Input | Sample No. (TW-0011E-) | Temp (° C.) | Result | XRPD | Comments/Time |
|---|---|---|---|---|---|
| Lot No. 33-13 | 014-01 | 40 | solid | Pattern A + Pattern C | increase in the amount of Pattern C |
| Lot No. 33-13 | 014-02 | 60 | solid | Pattern A + Pattern C | — |
| Pattern B | 014-03 | 40 | solid | Pattern C | — |
| Pattern C | 014-04 | 40 | solid | Pattern C | — |
| Pattern A | 014-05 | 40 | solid | Pattern A + Pattern C | — |
| Pattern B | 014-06 | 60 | solid | Pattern A | — |
| Pattern B | 016-01 | 80 | solid | Pattern A (very weak sample) | 20 minutes |
| Pattern B | 016-02 | 80 | solid | Pattern A (disordered/ weak sample) | 120 minutes |

Example 2-10, Vapor Diffusion

Vapor diffusion experiments were carried out as detailed in Method 2-10. The results are shown in Table 2-9. No novel patterns were isolated.

Screening Results from Vapor Diffusion Experiments

TABLE 2-9

| Sample No. (TW-0011E-) | Solvent | Anti-solvent | Result | XRPD |
|---|---|---|---|---|
| 015-01 | acetone | cyclohexane | solid | Pattern C |
| 015-02 | EtOH | cyclohexane | solid (after trituration) | Pattern B + C |
| 015-03 | EtOAc | cyclohexane | solid | Pattern C |
| 015-04 | IPA | cyclohexane | solid (after trituration) | Pattern B |
| 015-05 | THF | cyclohexane | solid | Pattern A |

Conclusions from Polymorph Screening

Approximately 100 experiments were carried out using solvent and non-solvent based techniques. Four crystalline solids (Table 2-10) were observed during this study, including AAT-730 (Lot No. 33-13). Amorphous material was also generated from melt quench of AAT-730.

Summary of the Physical Forms Observed During this Study

TABLE 2-10

| Pattern | Comment |
|---|---|
| A | Novel polymorph, suspected anhydrate |
| B | Novel polymorph, suspected monohydrate |
| C | Novel polymorph, suspected anhydrate |
| D | Unique pattern, only isolated as a mixture with Pattern A |
| Amorphous | Isolated by melt quench up to 130° C. |

Figure 19:
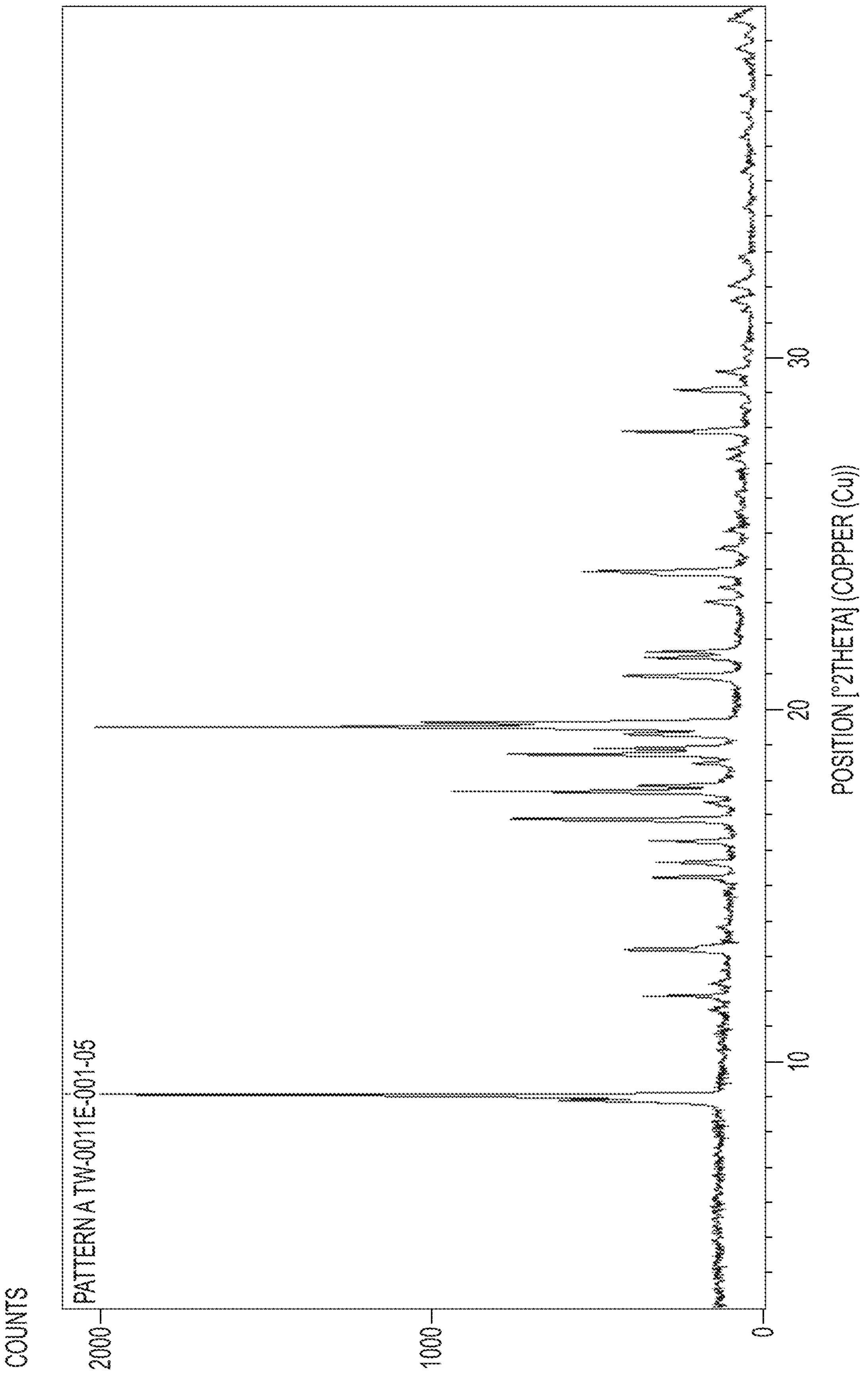
FIG. 19 provides an XRPD trace of AAT-730 Pattern A material.
Figure 20:
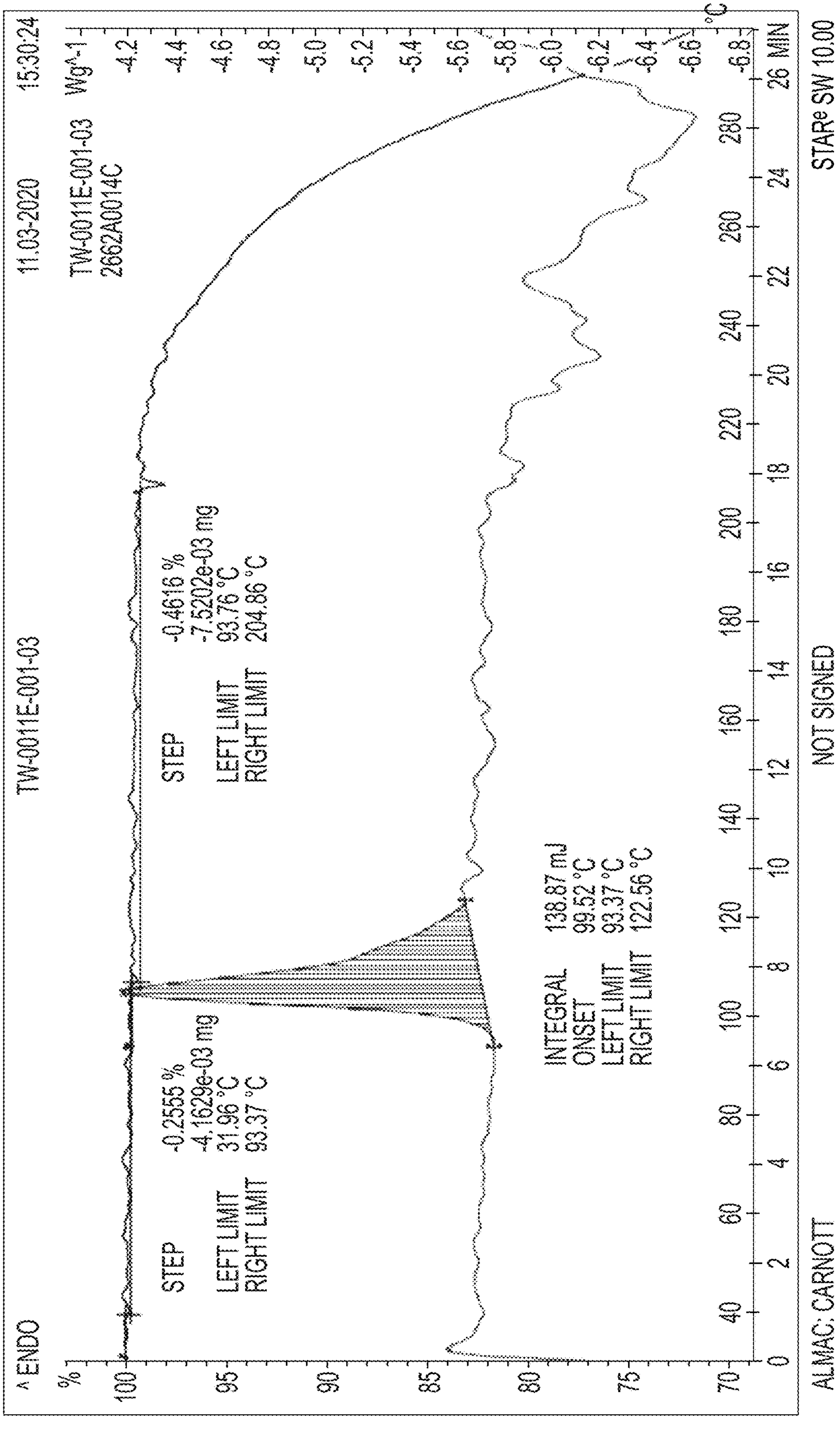
FIG. 20 provides a TG/DTA thermogram of AAT-730 Pattern A analyzed from 30 to 300° C. at 10° C. per minute.

Example 2-11, Preparation and Characterization of AAT-730 (Compound A), Pattern A AAT-730 Pattern A material was isolated from a range of screening experiments, as shown in Table 2-11. Pattern A material is a crystalline solid and the XRPD diffractogram is shown in FIG. 19. TG/DTA analysis (FIG. 20) suggests that Pattern A material is an anhydrate with a melting onset up to 99.5° C. Thermally stressing Pattern A material at 40° C. gave a mixture of Pattern A+Pattern C suggesting that Pattern A is thermally unstable and converts to Pattern C.

Screening Experiments which Yielded Pattern a Solids

TABLE 2-11

| Input | Sample No. (TW-0011E-) | Solvent | Antisolvent | Screen method | Result | XRPD |
|---|---|---|---|---|---|---|
| Lot No. 33-13 | 001-03 | DCM | none | slow evap | solid | Pattern A |
| Lot No. 33-13 | 001-05 | EtOAc | none | slow evap | solid | Pattern A |
| Lot No. 33-13 | 003-04 | THF | cyclohexane | crash pptn | solid | Pattern A |
| amorphous | 008-03 | cyclohexane | none | vapor stress | solid | Pattern A (slight amorphous character) |
| amorphous | 008-08 | MTBE | none | vapor stress | solid | Pattern A (PS) |
| Pattern B | 014-06 | N/A | N/A | thermal stress (60° C.) | solid | Pattern A |
| Lot No. 33-13 | 015-05 | THF | cyclohexane | vapor diffusion | solid | Pattern A |
| Pattern B | 016-02 | N/A | N/A | thermal stress (80° C.) | solid | Pattern A |

PS = peak shifting

Figure 21:
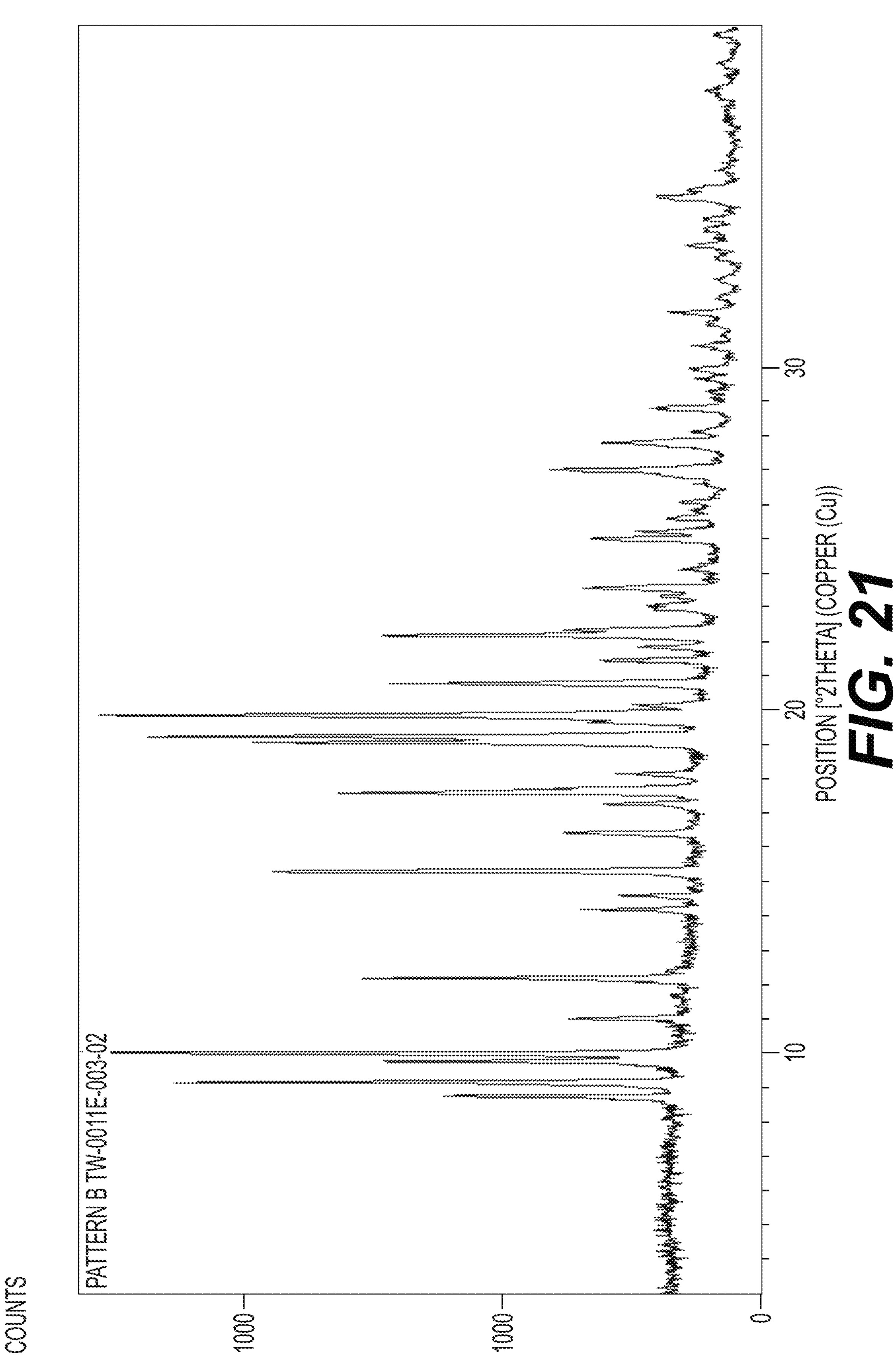
FIG. 21 provides an XRPD trace of AAT-730 Pattern B material.
Figure 22:
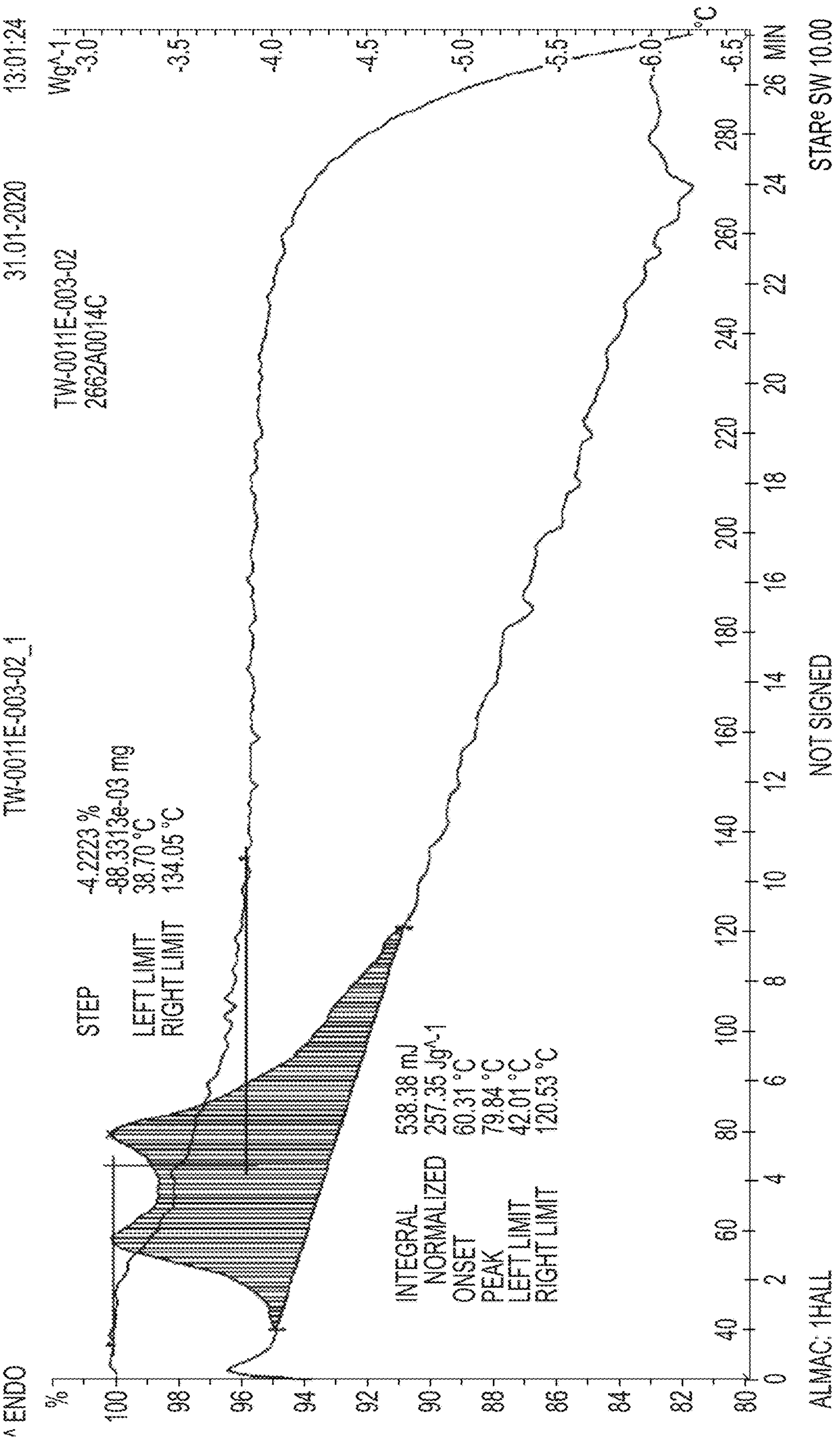
FIG. 22 provides a TG/DTA thermogram of AAT-730 Pattern B solids analyzed from 30 to 300° C. at 10° C. per minute.
Figure 23:
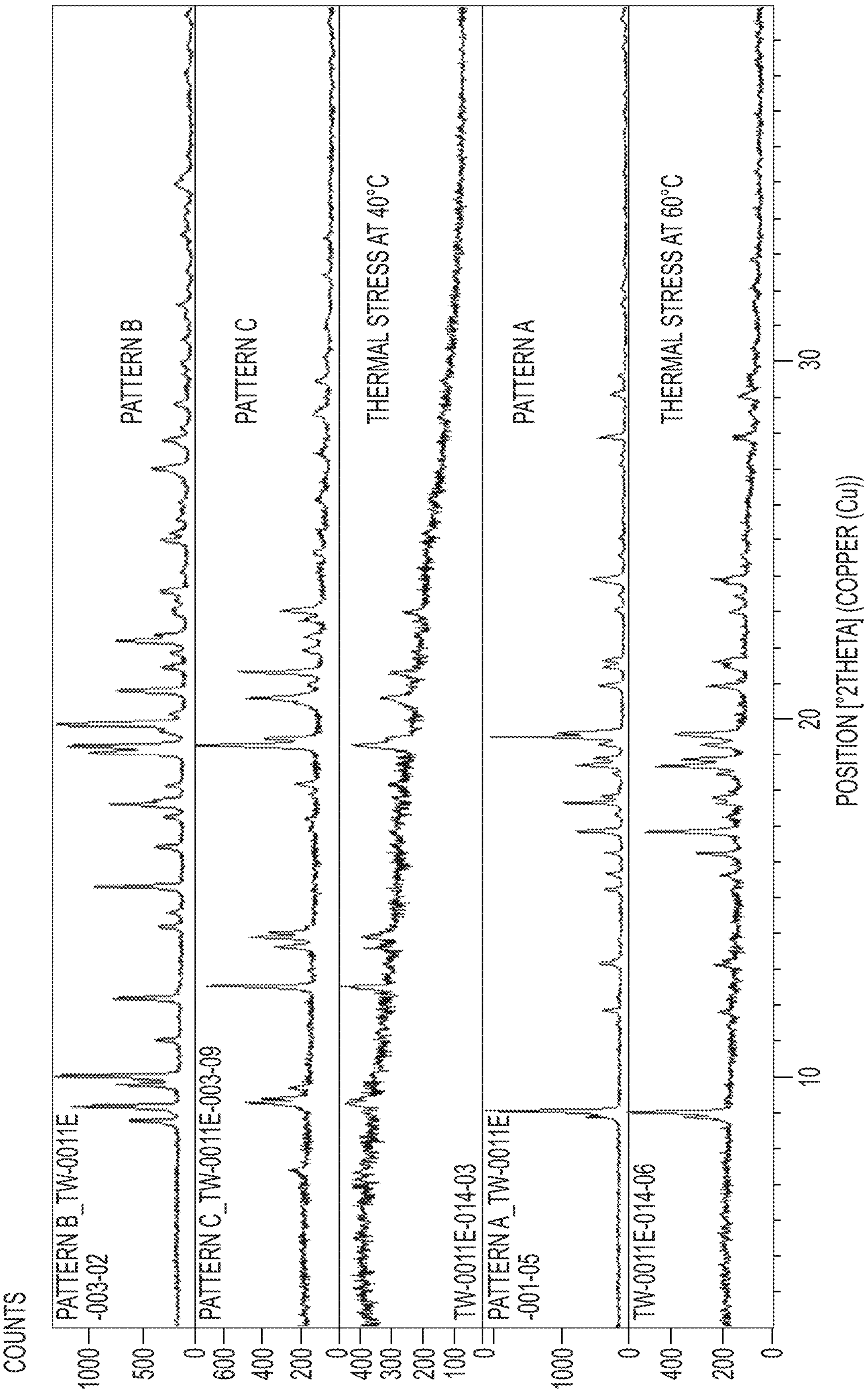
FIG. 23 provides an XRPD overlay illustrating thermal stressing of Pattern B material.

Example 2-12, Preparation and Characterization of AAT-730 (Compound A) Pattern B AAT-730 Pattern B material was isolated from a range of experiments using various solvents and techniques as shown in Table 2-12. The XRPD trace is shown in FIG. 21 and the material was crystalline. TG/DTA (FIG. 22) showed a weight loss of at most 4.2% w/w between approximately 40 and 120° C. which corresponded to at most 1 mole of water, suggesting Pattern B was a monohydrate. Pattern B material was physically unstable to stressing at 40 and 60° C., converting to Pattern C and Pattern A respectively as shown in FIG. 23.

Screening Experiments which Yielded Pattern B Solids

TABLE 2-12

| Input | Sample No. (TW-0011E-) | Solvent | Antisolvent | Screen method | Result | XRPD |
|---|---|---|---|---|---|---|
| Lot No. 33-13 | 001-08 | water | none | slow evap | solid | Pattern B |
| Lot No. 33-13 | 002-03 | EtOAc | none | slurry (5° C.) | solid | Pattern B |
| Lot No. 33-13 | 003-02 | EtOAc | cyclohexane | crash pptn | solid | Pattern B |
| Lot No. 33-13 | 003-05 | water | toluene | crash pptn | solid | Pattern B |
| Lot No. 33-13 | 003-08 | dioxane | MTBE | crash pptn | solid | Pattern B |
| Lot No. 33-13 | 005-01 | EtOAc | none | slurry (20° C.) | solid | Pattern B |
| amorphous | 009-04 | none | none | 98% RH stress | gel | Pattern B |
| Lot No. 33-13 | 011-13 | water | none | sonication | solid | Pattern B |
| gel (001-02) | 012-01 | cyclohexane | none | slurry (40° C.) | solid | Pattern B |
| Lot No. 33-13 | 013-03 | Acetone/water, $A_w$ at most 0.6 | none | slurry (5° C.) | solid | Pattern B |

Figure 24:
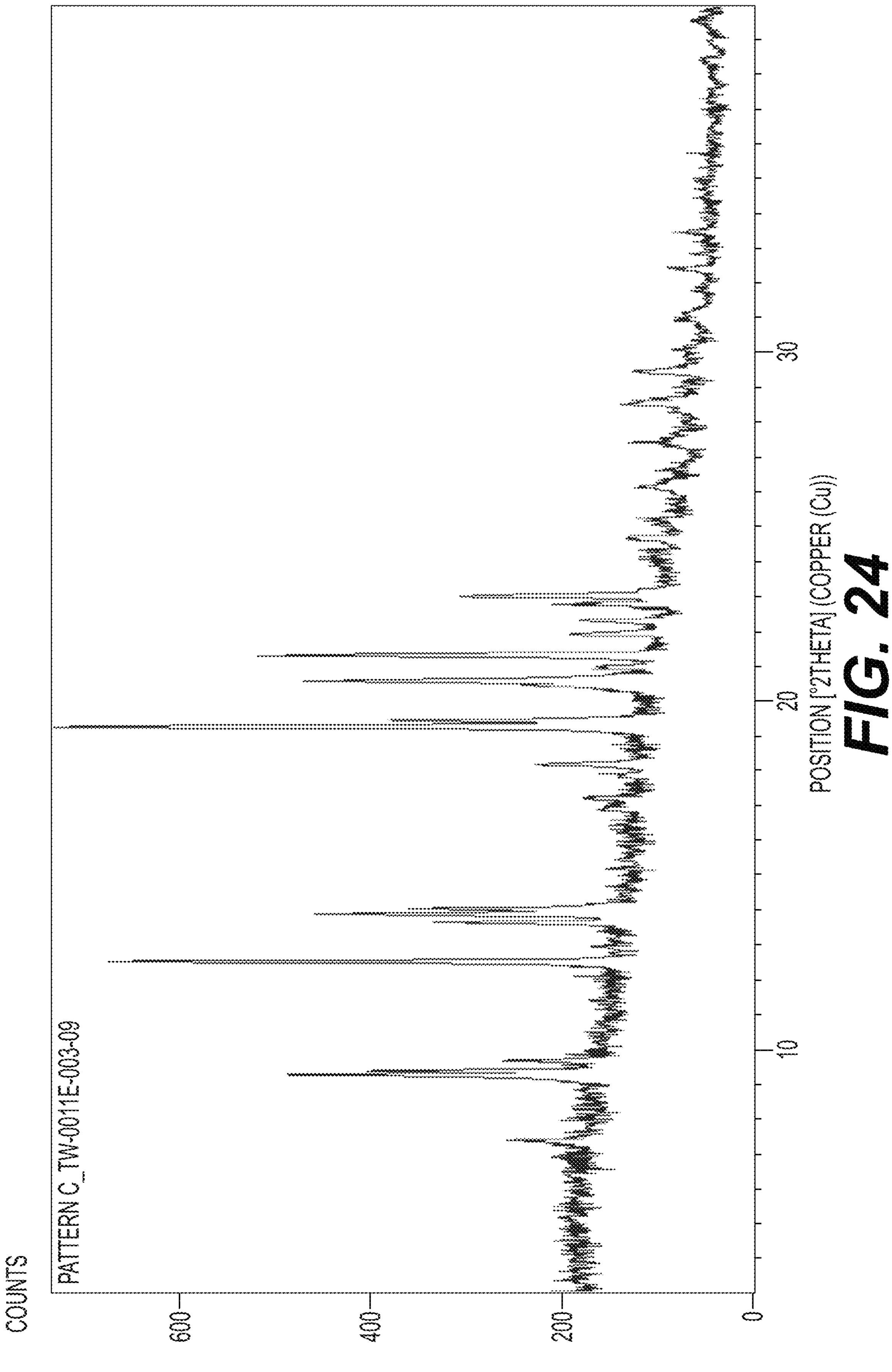
FIG. 24 provides an XRPD trace of AAT-730 Pattern C material.
Figure 25:
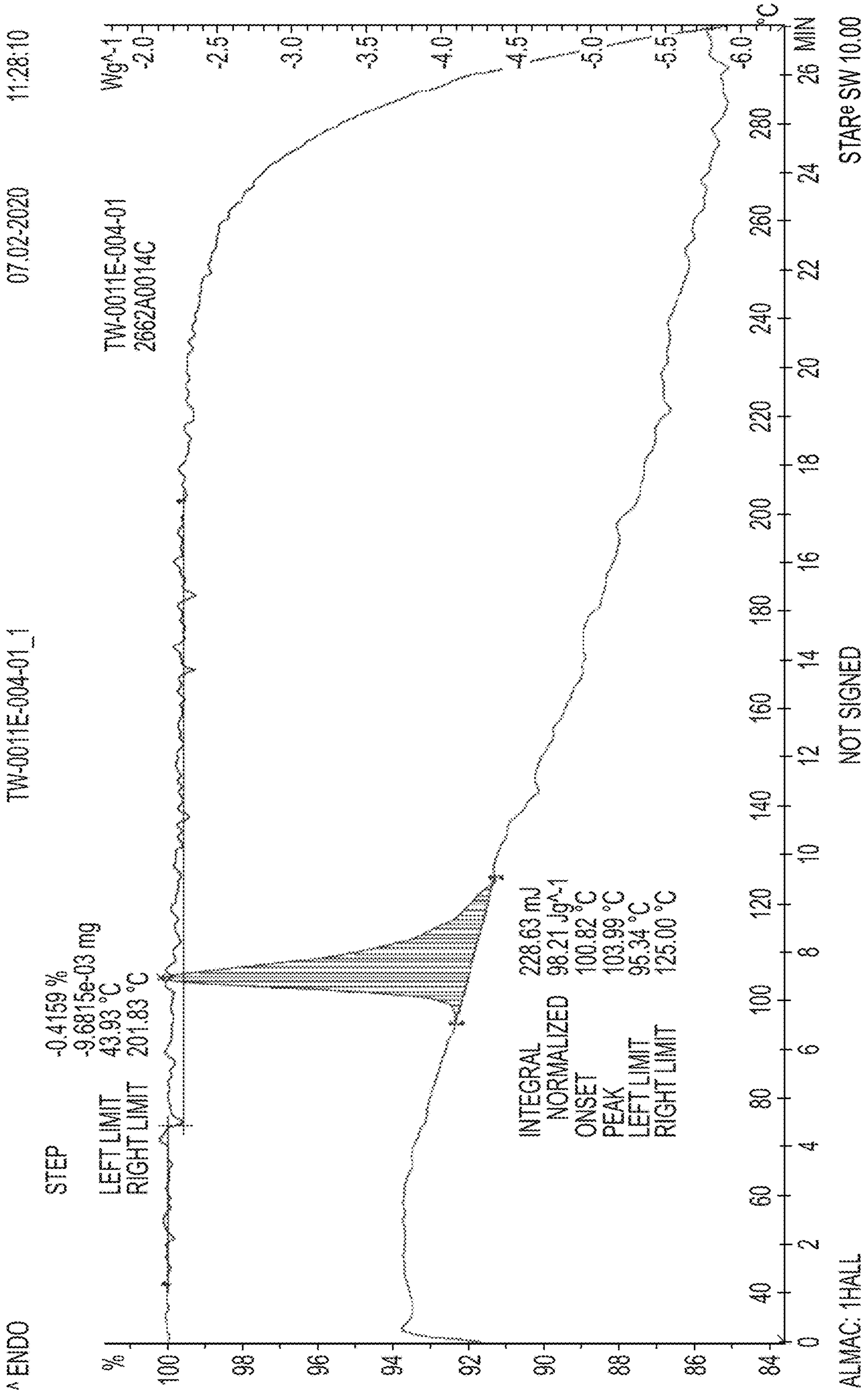
FIG. 25 provides a TG/DTA thermogram of AAT-730 Pattern C solids analyzed from 30 to 300° C. at 10° C. per minute.
Figure 26:
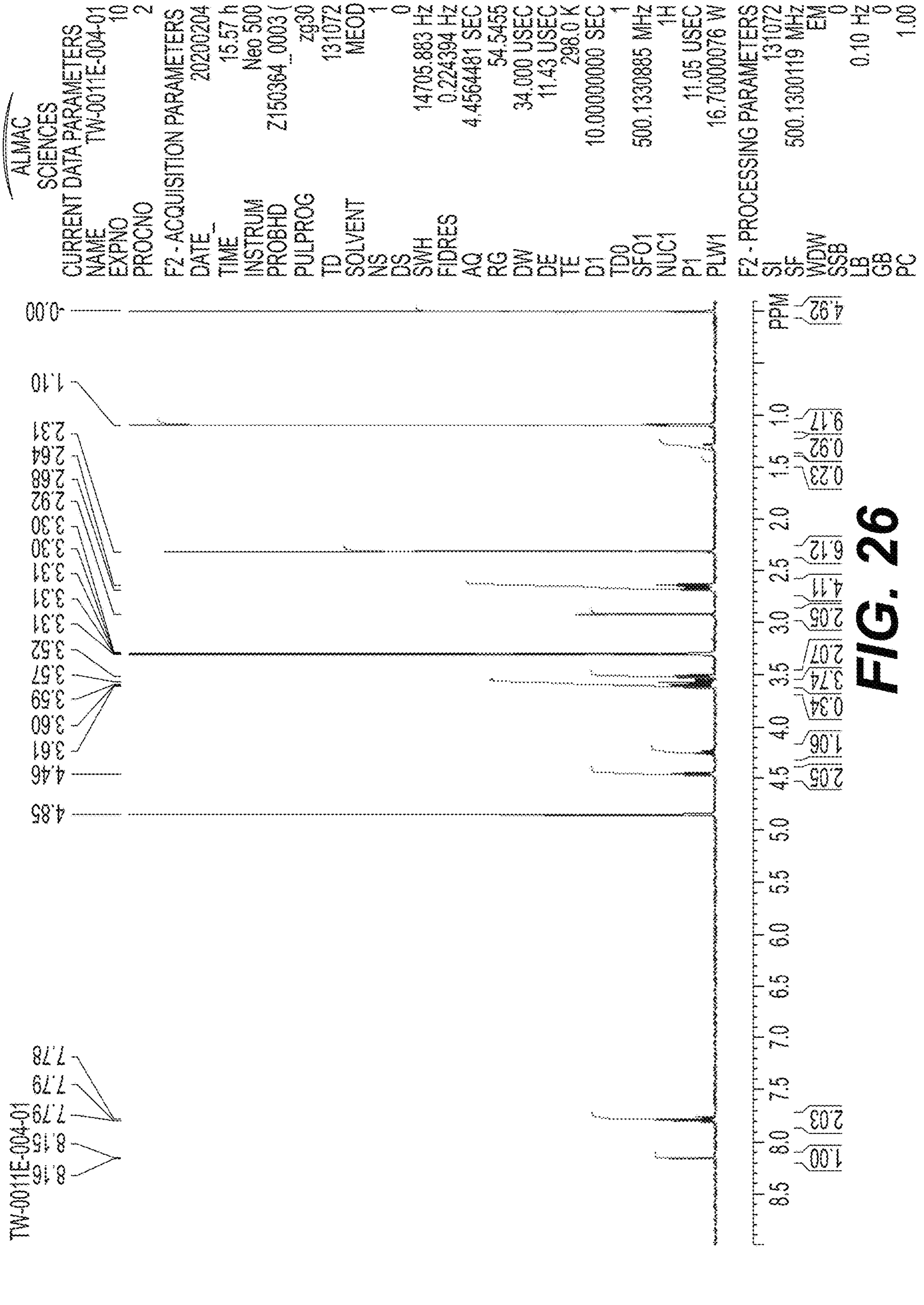
FIG. 26 provides a $^{1}H$ NMR spectrum of AAT-730 Pattern C material analyzed in $CD_3OD$.

Example 2-13, Preparation and Characterization of AAT-730 (Compound A) Pattern C AAT-730 Pattern C material was isolated from a range of experiments using various solvents and techniques as shown in Table 2-13. The XRPD trace is shown in FIG. 24 and the material was crystalline. Pattern C solids were analyzed by $^1H$ NMR (FIG. 25) and TG/DTA (FIG. 26) analyses. TG/DTA analysis showed at most 0.4% weight loss between approximately 30 and 200° C. which was likely due to a small amount of residual solvent. The $^1H$ NMR spectrum concurred with the molecular structure and a small amount of cyclohexane was present in the spectrum suggesting Pattern C material was an anhydrate with a very similar melting point to Pattern A material. The melting onset of Pattern C material, determined by TG/DTA is up to 100.8° C.

Screening Experiments which Yielded Pattern C Solids

TABLE 2-13

| Input | Sample No. (TW0011E-) | Solvent | Anti-solvent | Screen method | XRPD |
|---|---|---|---|---|---|
| Lot No. 33-13 | 001-01 | acetone | none | slow evap | Pattern C |
| Lot No. 33-13 | 002-06 | IPA | none | slurry (5° C.) | Pattern C |
| Lot No. 33-13 | 002-07 | toluene | none | slurry (5° C.) | Pattern C |
| Lot No. 33-13 | 003-01 | acetone | cyclohexane | crash pptn | Pattern C |
| Lot No. 33-13 | 003-09 | DCM | MTBE | crash pptn | Pattern C |
| Lot No. 33-13 | 004-01 | cyclohexane | none | slurry (40° C.) | Pattern C |
| Lot No. 33-13 | 004-02 | MTBE | none | slurry (40° C.) | Pattern C |
| Lot No. 33-13 | 004-03 | MIBK | none | slurry (40° C.) | Pattern C |
| Lot No. 33-13 | 004-04 | toluene | none | slurry (40° C.) | Pattern C |
| Lot No. 33-13 | 005-02 | acetone/cyclohexane (20/80) | none | slurry (20° C.) | Pattern C |
| Lot No. 33-13 | 005-03 | IPA/cyclohexane (20/80) | none | slurry (20° C.) | Pattern C |
| Lot No. 33-13 | 005-04 | ACN/cyclohexane (10/90) | none | slurry (20° C.) | Pattern C |
| Lot No. 33-13 | 006-01 | acetone | none | slow cool | Pattern C |
| Lot No. 33-13 | 006-05 | toluene | none | slow cool | Pattern C |

TABLE 2-13-continued

| Input | Sample No. (TW0011E-) | Solvent | Anti-solvent | Screen method | XRPD |
|---|---|---|---|---|---|
| amorphous | 008-01 | acetone | none | vapor stress | Pattern C (PO) |
| amorphous | 008-02 | ACN | none | vapor stress | Pattern C (PO) |
| amorphous | 008-06 | EtOAc | none | vapor stress | Pattern C |
| amorphous | 008-07 | MIBK | none | vapor stress | Pattern C (PO) |
| amorphous | 009-02 | none | none | 59% RH stress | Pattern C |
| amorphous | 009-03 | none | none | 75% RH stress | Pattern C |
| Lot No. 33-13 | 010-02 | cyclohexane | none | temp cycle | Pattern C |
| Lot No. 33-13 | 010-04 | MIBK | none | temp cycle | Pattern C |
| Lot No. 33-13 | 010-05 | MTBE | none | temp cycle | Pattern C |
| Lot No. 33-13 | 010-07 | toluene | none | temp cycle | Pattern C |
| Lot No. 33-13 | 011-01 | acetone | none | somication | Pattern C |
| Lot No. 33-13 | 011-02 | ACN | none | sonication | Pattern C |
| Lot No. 33-13 | 011-03 | anisole | none | sonication | Pattern C |
| Lot No. 33-13 | 011-04 | DCM | none | sonication | Pattern C |
| Lot No. 33-13 | 011-07 | EtOAc | none | sonication | Pattern C |
| Lot No. 33-13 | 011-09 | MIBK | none | sonication | Pattern C |
| Lot No. 33-13 | 011-12 | toluene | none | sonication | Pattern C |
| Pattern C | 014-04 | none | none | thermal stress 40° C. | Pattern C |

PO = preferred orientation

Figure 27:
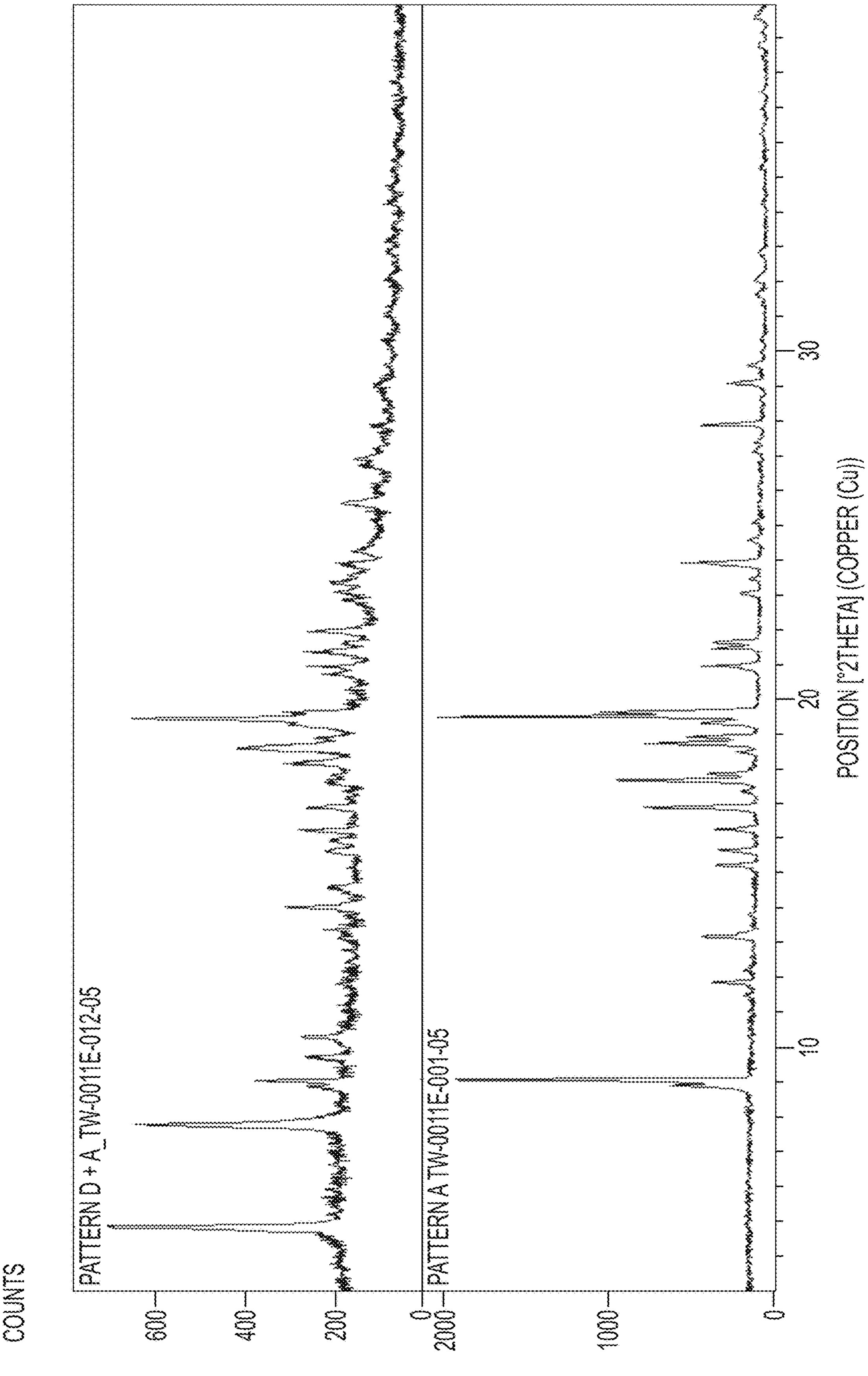
FIG. 27 provides an XRPD trace of Pattern D+A mixture (Top) and Pattern A (Bottom).

Example 2-14, Preparation and Characterization of AAT-730 (Compound A) Pattern D Pattern D material was isolated from one slurry experiment (40° C.) in cyclohexane as a mixture with Pattern A. The diffractogram is shown in FIG. 27 and was crystalline. As Pattern D was isolated as a mixture, no further analysis was performed.

Conclusions

1) XRPD analysis indicated that AAT-730 (Lot No. 33-13) was a mixture of two crystalline forms, Pattern A and Pattern C.
2) Approximately 100 experiments were carried out using solvent and non-solvent based techniques. Four crystalline XRPD patterns (Table 2-10) were observed during this study, including AAT-730 (Lot No. 33-13). Amorphous material was also generated from melt quench of AAT-730.
3) Patterns A and C materials appear to be crystalline anhydrates with similar melting points. Pattern C appears to be the most stable of these forms as it was isolated from most of the slurry experiments starting with AAT-730 (Lot No. 33-13).
4) AAT-730 Pattern B material is a monohydrate which dehydrates on heating to either Pattern A or Pattern C material.

Example 3, Salt Screening

The starting material used in this study was AAT-730 (Lot No. 33-13). Table 3-1 shows details of the materials and reagents used in the salt screen. The list has been chosen based on the following factors:

$pK_a$—AAT-730 has $pK_a$ values of 7.1 and 2.1, and the counterions were chosen with a $pK_a$ difference of >2 $pK_a$ units for salt formation.

Acids which are pharmaceutically acceptable, generally Class 1 but some Class 2 salt formers have also been included as these may give good salt properties and have been used previously in marketed drugs.

At the screening stage, a range of different types of counterion: mineral acids, carboxylic acids, aromatic acids, mono, di and tri-acids, different carbon chain lengths, cyclic acids, chiral and non-chiral acids as the properties of the counterion affect the properties of the salts were chosen.

Generally a low molecular weight counterion is preferred, however, in this case the increase in molecular weight may be a benefit due to the low melting point of the API.

Details of Acids Used in Screening

TABLE 3-1

| Acid | MW | $pK_a$ | Class | ADI/GRAS* |
|---|---|---|---|---|
| acetic acid | 60.05 | 4.76 | 1 | No limit/yes |
| L-ascorbic acid | 176.13 | 4.17, 11.57 | 1 | No limit/yes |
| L-aspartic acid | 133.11 | 1.88, 3.65, 9.6 | 1 | No limit/yes |
| benzenesulfonic acid | 158.18 | 0.7 | 2 | |
| citric acid | 192.13 | 3.13, 4.76, 6.4 | 1 | No limit/yes |
| ethane-1,2-disulfonic acid (EDSA) | 190.2 | −2.06, −1.5 | 2 | |
| fumaric acid | 116.02 | 3.03, 4.38 | 1 | 6 mg/kg |
| 2,5-dihydroxybenzoic acid (gentisic acid) | 154.12 | 2.93 | 2 | |
| D-gluconic acid | 196.16 | 3.76 | 1 | No limit/yes |
| D-glucuronic acid | 194.14 | 3.18 | 1 | |
| L-glutamic acid | 147.13 | 2.19, 4.25, 9.67 | 1 | No limit/yes |
| glutaric acid | 132.12 | 4.34, 5.22 | 1 | |
| glycolic acid | 76.05 | 3.83 | 1 | |
| hippuric acid | 179.17 | 3.55 | 1 | |

TABLE 3-1-continued

| Acid | MW | $pK_a$ | Class | ADI/GRAS* |
|---|---|---|---|---|
| hydrochloric acid (HCl) | 36.46 | −6 | 1 | No limit/yes |
| L-lactic acid | 90.08 | 3.86 | 1 | |
| maleic acid | 116.08 | 1.92, 6.23 | 1 | |
| L-malic acid | 134.09 | 3.46, 5.1 | 1 | Acceptable/yes |
| methanesulfonic acid (MSA) | 96.1 | −1.2 | 2 | |
| phosphoric acid | 98.0 | 1.96, 7.12, 12.32 | 1 | 70 mg/kg/yes |
| p-toluenesulfonic acid (p-TSA) | 172.2 | −1.34 | 2 | |
| succinic acid | 118.09 | 4.21, 5.64 | 1 | No limit/yes |
| sulfuric acid ($H_2SO_4$) | 98.08 | −3, 1.92 | 1 | No limit/yes |
| L-tartaric acid | 150.09 | 3.02, 4.36 | 1 | 30 mg/kg/yes |

*ADI: Acceptable Daily Intake, GRAS: Generally Recognized As Safe

The salt screening approach was to generate salts from precipitation experiments with 24 acids and test the stability of any salts to elevated relative humidity. TG/DTA analysis was also carried out on any stable salts to determine the melting point.

All solids from the salt formation experiments were analyzed by XRPD and the resulting patterns compared to that exhibited by the starting material. Where sufficient material was available, further analysis (e.g. $^1H$ NMR or TGA) was conducted on solids with novel XRPD patterns to allow tentative assignment of the novel pattern as a salt.

Salt Screening Methods of Example 3

Experiments were carried out at a scale of at most 30 mg with 1:1, 1:0.5 and 1:2 stoichiometry (free base of AAT-730: salt former). Solutions of the free base in the chosen solvent were added to either solutions of the salt former, or if the salt was not soluble in the solvent, slurries of the salt formers. Any solids which precipitated were recovered and analyzed by XRPD analysis to determine if the solid was crystalline.

Method 3-1, Preparation of Stock Solution of AAT-730 (Compound A) in THF

AAT-730 (1.059 g) was added to a 5 mL volumetric flask, dissolved in THF and diluted to volume with THF. The concentration of the stock solution was up to 1 M.

Method 3-2, Preparation of Stock Solution of AAT-730 (Compound A) in THF/Water

AAT-730 (1.058 g) was added to a 5 mL volumetric flask, dissolved in THF/water (9/1) and diluted to volume with THF/water (9/1). The concentration of the stock solution was up to 1 M.

Method 3-3, Precipitation Experiments

The required acid (1 molar equivalent) was added to each HPLC vial and the API stock solution (containing 30 mg of API) was added. The mixtures were stirred at 300 rpm (ambient temperature) for up to 16 hours. Any solids which precipitated were isolated by centrifugation, solvent decanted and solids dried with thin strips of filter paper prior to analysis by XRPD. Any solutions were evaporated to dryness and solids analyzed by XRPD. Gels were either triturated or temperature cycled in MTBE.

Method 3-4, Slurry/Precipitation Experiments

API (30 mg), acid co-former (1 mol. eq.) and ethanol (300 μL) were added to HPLC vials and stirred at 40° C. for up to 16 hours. Solids were recovered by centrifugation, solvent decanted and dried with thin strips of filter paper prior to analysis by XRPD. Solutions were evaporated to dryness.

Method 3-5, Trituration of Gels in MTBE or EtOAc

Gels isolated from the screening experiments were triturated in either MTBE or EtOAc to induce precipitation. MTBE or EtOAc (200 μL) was added to the gel and stirred at 40° C. for up to 3 hours prior to cooling to ambient and stirring for up to 48 hours. Any solids were isolated by centrifugation, solvent decanted and solids dried with thin strips of filter paper prior to analysis by XRPD. Any solutions were evaporated to dryness.

Method 3-6, Temperature Cycling of Gels in MTBE

Gels isolated from screening experiments were temperature cycled in MTBE according to the following program:

Heating from 20° C. to 40° C. at 0.2° C./minute.

Cooling to 20° C. at 0.1° C./minute.

Stirring speed 400 rpm.

Solids were recovered by centrifugation, solvent decanted and solids dried with thin strips of filter paper prior to analysis by XRPD.

Method 3-7, Planetary Milling

AAT-730 (at most 30 mg), acid co-former (1 mol. eq.) and isopropyl acetate (i-PrOAc, 20 μL) were added to vials with 3 steel milling balls. The vials were sealed and the contents milled using a Fritsch Pulverisette 5 planetary mill (30 repetitions of 20 minutes milling at 400 rpm and 20 minutes pause). The resultant material was analyzed using XRPD.

Method 3-8, Humidity Stress of Possible Salts

Samples of the suspected salts were added to HPLC vials (if sufficient material was available the weight was recorded). The samples were place in a RH chamber at 40° C. The relative humidity of the chamber was controlled by a supersaturated salt solution. The samples were removed after 1 week and any deliquescence was recorded.

Method 3-9, Aqueous Solubility

Aliquots of the water were added to an accurately weighed sample (at most 5 mg) of AAT-730 at ambient temperature. The aliquot volumes were typically 10-20 μL. Complete dissolution of the test material was determined by visual inspection. The solubility was estimated from these experiments based on the total solvent used to provide complete dissolution.

Example 3-1, Precipitations Experiments in THF

Precipitation experiments in THF were carried out as described in Method 3-3 and the results are shown in Table 3-2. Most of the experiments yielded gels after evaporation. Solids/gels isolated from experiments with citric, L-malic and L-tartaric acids were amorphous by XRPD. These samples were triturated in MTBE to try to induce crystallization (Method 3-5 and Example 3-3). Solids isolated from the experiments with L-aspartic acid and L-glutamic acid were composed of acid co-former and salt formation had not occurred. Solids displaying novel XRPD patterns were isolated from the experiments with fumaric acid, EDSA, maleic acid and MSA and these are possible salts. These solids were further analyzed and are discussed in Examples 3.8 to 3.18.

Results from Salt Formation Experiments in THF

TABLE 3-2

| Acid | Sample No. (CAT-0001E-) | Screen method | Result | XRPD Result |
|---|---|---|---|---|
| acetic acid | 008-01 | precipitation | solution | N/A |
| L-ascorbic acid | 008-02 | precipitation → evap. | gel | N/A |
| L-aspartic acid | 008-03 | precipitation | haze | L-aspartic acid |
| benzenesulfonic acid | 008-04 | precipitation → evap. | gel | N/A |
| citric acid | 008-05 | precipitation → evap. | gel* | Amorphous |
| EDSA | 008-06 | precipitation | solid | AAT-730 EDSA salt |
| fumaric acid | 008-07 | precipitation | solid | AAT-730 fumarate |
| gentisic acid | 008-08 | precipitation → evap. | gel | N/A |
| D-gluconic acid | 008-09 | precipitation → evap. | gel | N/A |
| D-glucuronic acid | 008-10 | precipitation → evap. | gel | N/A |
| L-glutamic acid | 008-11 | precipitation | solid | L-glutamic acid |
| glutaric acid | 008-12 | precipitation → evap. | gel | N/A |
| glycolic acid | 008-13 | precipitation | solution | N/A |
| hippuric acid | 008-14 | precipitation | gel | N/A |
| HCl | 008-15 | precipitation | solution | N/A |
| L-lactic acid | 008-16 | precipitation | gel | N/A |
| maleic acid | 008-17 | precipitation | solid | AAT-730 maleate |
| L-malic acid | 008-18 | precipitation | gel* | Amorphous |
| MSA | 008-19 | precipitation | solid | AAT-730 MSA salt |
| phosphoric acid | 008-20 | precipitation → evap. | gel | N/A |
| p-TSA | 008-21 | precipitation → evap. | gel | N/A |
| succinic acid | 008-22 | precipitation → evap. | gel | N/A |
| $H_2SO_4$ | 008-23 | precipitation → evap. | gel | N/A |
| L-tartaric acid | 008-24 | precipitation | solid | Amorphous |

*these initially appeared to contain solids but on preparation of the XRPD sample were determined to be gels Example 3-2, Precipitation Experiments in THF/Water Precipitation experiments in THF/water were carried out as detailed in Method 3-3 and the results are shown in Table 3-3. Gels were isolated from almost all screening experiments and this may be due to the presence of water. As salt formation may have occurred these gels were temperature cycled in MTBE to try to induce crystallization (Method 3-6 and Example 3-4).

Solids displaying novel XRPD patterns were isolated from the experiments with L-lactic acid, maleic acid, MSA and succinic acid and these are possible salts. These were further analyzed and are discussed in Examples 3.8 to 3.18.

Results from Salt Formation Experiments in THF

TABLE 3-3

| Acid | Sample No. (CAT-0001E-) | Screen method | Result | XRPD Result |
|---|---|---|---|---|
| acetic acid | 009-01 | precipitation → evap. | gel | N/A |
| L-ascorbic acid | 009-02 | precipitation → evap. | gel | N/A |
| L-aspartic acid | 009-03 | precipitation → evap. | gel | N/A |
| benzenesulfonic acid | 009-04 | precipitation → evap. | gel | N/A |
| citric acid | 009-05 | precipitation → evap. | gel | N/A |
| EDSA | 009-06 | precipitation → evap. | gel | N/A |
| fumaric acid | 009-07 | precipitation → evap. | gel | N/A |
| gentisic acid | 009-08 | precipitation → evap. | gel | N/A |
| D-gluconic acid | 009-09 | precipitation → evap. | gel | N/A |
| D-glucuronic acid | 009-10 | precipitation → evap. | gel | N/A |
| L-glutamic acid | 009-11 | precipitation → evap. | gel | N/A |
| glutaric acid | 009-12 | precipitation → evap. | gel | N/A |
| glycolic acid | 009-13 | precipitation → evap. | gel | N/A |
| hippuric acid | 009-14 | precipitation → evap. | gel | N/A |
| HCl | 009-15 | precipitation → evap. | gel | N/A |
| L-lactic acid | 009-16 | precipitation → evap. | solid | AAT-730 L-lactate |
| maleic acid | 009-17 | precipitation | solid | AAT-730 maleate |
| L-malic acid | 009-18 | precipitation → evap. | gel | N/A |
| MSA | 009-19 | precipitation → evap. | solid | AAT-730 MSA salt |
| phosphoric acid | 009-20 | precipitation → evap. | gel | N/A |
| p-TSA | 009-21 | precipitation → evap. | gel | N/A |
| succinic acid | 009-22 | precipitation → evap. | solid | AAT-730 succinate |
| $H_2SO_4$ | 009-23 | precipitation → evap. | gel | N/A |
| L-tartaric acid | 009-24 | precipitation → evap. | gel | N/A |

Example 3-3, Trituration of Gels in MTBE

The gels isolated from the precipitation experiments in THF were triturated in MTBE as described in Method 3-5 and the results are shown in Table 3-4. Solids were isolated from glutaric acid, L-lactic acid, sulfuric acid and L-tartaric acid and these were analyzed by XRPD analysis. Solids displaying crystalline XRPD patterns were further analyzed (Examples 3.8 to 3.18). Gels or amorphous solids were isolated from the remaining experiments and as these could not be easily crystallized, they were not expected to be useful for further scale up and characterization within this project.

Screening Results from Temperature Cycling of Gels Isolated from THF

TABLE 3-4

| Acid | Sample No. (CAT-0001E-) | Screen method | Result | XRPD Result |
|---|---|---|---|---|
| acetic acid | 010-02 | trituration | gel | N/A |
| citric acid | 010-05 | trituration | solution | N/A |
| gentisic acid | 010-08 | trituration | gel | N/A |
| D-gluconic acid | 010-09 | trituration | gel | N/A |
| D-glucuronic acid | 010-10 | trituration | gel | N/A |
| glutaric acid | 010-12 | trituration | solid | AAT-730 glutarate |
| hippuric acid | 010-14 | trituration | gel | N/A |
| L-lactic acid | 010-16 | trituration | solid | AAT-730 L-lactate |
| L-malic acid | 010-18 | trituration | gel | N/A |
| phosphoric acid | 010-20 | trituration | gel | N/A |
| p-TSA | 010-21 | trituration | gel | N/A |
| succinic acid | 010-22 | trituration | gel | N/A |
| $H_2SO_4$ | 010-23 | trituration | solid | AAT-730 sulfate |
| L-tartaric acid | 010-24 | trituration | solid | amorphous |

Example 3-4, Temperature Cycling of Gels

The gels isolated from screening experiments in THF/water were temperature cycled in MTBE as shown in Method 3-6 and the results are shown in Table 3-5. Any solids with novel crystalline XRPD patterns were further analyzed and this is shown in Examples 3.8 to 3.18. Salt formation had not occurred with L-aspartic or L-glutamic acids. Gels or amorphous solids were isolated from the remaining experiments and as these could not be easily crystallized, they were not expected to be useful for further scale up and characterization within this project.

Screening Results from Temperature Cycling of Gels Isolated from THF/Water

TABLE 3-5

| Acid | Sample No. (CAT-0001E-) | Screen method | Result | XRPD Result |
|---|---|---|---|---|
| acetic acid | 011-01 | trituration | gel | AAT-730 acetate |
| L-ascorbic acid | 011-02 | trituration | gel | N/A |
| L-aspartic acid | 011-03 | trituration | solid | Free base Pattern A |
| benzenesulfonic acid | 011-04 | trituration | gel | N/A |
| citric acid | 011-05 | trituration | gel | N/A |
| EDSA | 011-06 | trituration | gel | N/A |
| fumaric acid | 011-07 | trituration | gel | N/A |
| gentisic acid | 011-08 | trituration | gel | N/A |
| D-gluconic acid | 011-09 | trituration | gel | N/A |
| D-glucuronic acid | 011-10 | trituration | gel | N/A |
| L-glutamic acid | 011-11 | trituration | solid | L-glutamic acid + API |
| glutaric acid | 011-12 | trituration | solid | AAT-730 glutarate |
| glycolic acid | 011-13 | trituration | solid | AAT-730 glycolate |
| hippuric acid | 011-14 | trituration | gel | N/A |
| HCl | 011-15 | trituration | solid | AAT-730 HCl salt |
| L-malic acid | 011-18 | trituration | gel | N/A |
| phosphoric acid | 011-20 | trituration | gel | N/A |
| p-TSA | 011-21 | trituration | gel | N/A |

TABLE 3-5-continued

| Acid | Sample No. (CAT-0001E-) | Screen method | Result | XRPD Result |
|---|---|---|---|---|
| $H_2SO_4$ | 011-23 | trituration | gel | N/A |
| L-tartaric acid | 011-24 | trituration | gel | N/A |

Example 3-5, Screening Experiments in Ethanol or Dioxane

Screening experiments were carried out in EtOH or dioxane as described in Method 3-3 and the results are shown in Table 3-6 and Table 3-7. These experiments were carried out using acid co-formers which had not resulted in crystalline salt formation from the precipitation reactions in THF or THF/water (Example 3-1 and Example 3-2). Dioxane was used for the experiments with sulfonic acids. Possible glycolate, HCl and L-lactate salts of AAT-730 were isolated. Experiments which yielded gels were triturated in EtOAc and the results are shown in Table 3-8, acetate and succinate salts were isolated. Any suspected salts which were isolated are further analyzed in Examples 3.8 to 3.18.

Results from Salt Formation Experiments in EtOH

TABLE 3-6

| Acid | Sample No. (CAT-0001E-) | Screen method | Result | XRPD Result |
|---|---|---|---|---|
| acetic acid | 012-01 | precipitation → evap. | gel | N/A |
| L-ascorbic acid | 012-02 | precipitation → evap. | gel | N/A |
| L-aspartic acid | 012-03 | precipitation → evap. | gel | L-aspartic acid |
| citric acid | 012-05 | precipitation → evap. | gel | N/A |
| gentisic acid | 012-08 | precipitation → evap. | gel | N/A |
| D-gluconic acid | 012-09 | precipitation → evap. | gel | N/A |
| D-glucuronic acid | 012-10 | precipitation → evap. | solid | IS* |
| L-glutamic acid | 012-11 | precipitation → evap. | solid | L-glutamic acid |
| glycolic acid | 012-13 | precipitation → evap. | solid | AAT-730 glycolate |
| hippuric acid | 012-14 | precipitation → evap. | gel | N/A |
| HCl | 012-15 | precipitation → evap. | solid | AAT-730 HCl salt |
| L-lactic acid | 012-16 | precipitation → evap. | solid | AAT-730 L-lactate |
| L-malic acid | 012-18 | precipitation → evap. | gel | N/A |
| phosphoric acid | 012-20 | precipitation → evap. | gel | N/A |
| succinic acid | 012-22 | precipitation → evap. | gel | N/A |
| L-tartaric acid | 012-24 | precipitation → evap. | gel | N/A |

*Insufficient sample for XRPD analysis

Results from Salt Formation Experiments in Dioxane

TABLE 3-7

| Acid | Sample No. (CAT-0001E-) | Screen method | Result | XRPD Result |
|---|---|---|---|---|
| benzenesulfonic acid | 013-04 | precipitation → evap. | gel | N/A |
| p-TSA | 013-21 | precipitation → evap. | gel | N/A |

Results from Trituration of Gels in EtOAc

TABLE 3-8

| Acid | Sample No. (CAT-0001E-) | Screen method | Result | XRPD Result |
|---|---|---|---|---|
| acetic acid | 015-01 | trituration | solid | AAT-730 acetate |
| L-ascorbic acid | 015-02 | trituration | gel | N/A |
| citric acid | 015-05 | trituration | gel | N/A |
| gentisic acid | 015-08 | trituration | gel | N/A |
| D-gluconic acid | 015-09 | trituration | gel | N/A |
| D-glucuronic acid | 015-10 | trituration | gel | N/A |

TABLE 3-8-continued

| Acid | Sample No. (CAT-0001E-) | Screen method | Result | XRPD Result |
|---|---|---|---|---|
| hippuric acid | 015-14 | trituration | gel | N/A |
| L-malic acid | 015-18 | trituration | gel | N/A |
| phosphoric acid | 015-20 | trituration | gel | N/A |
| succinic acid | 015-22 | trituration | solid | AAT-730 succinate |
| L-tartaric acid | 015-24 | trituration | gel | N/A |
| benzenesulfonic acid | 016-04 | trituration | gel | N/A |
| p-TSA | 016-21 | trituration | gel | N/A |

Example 3-6, Planetary Milling

Figure 28:
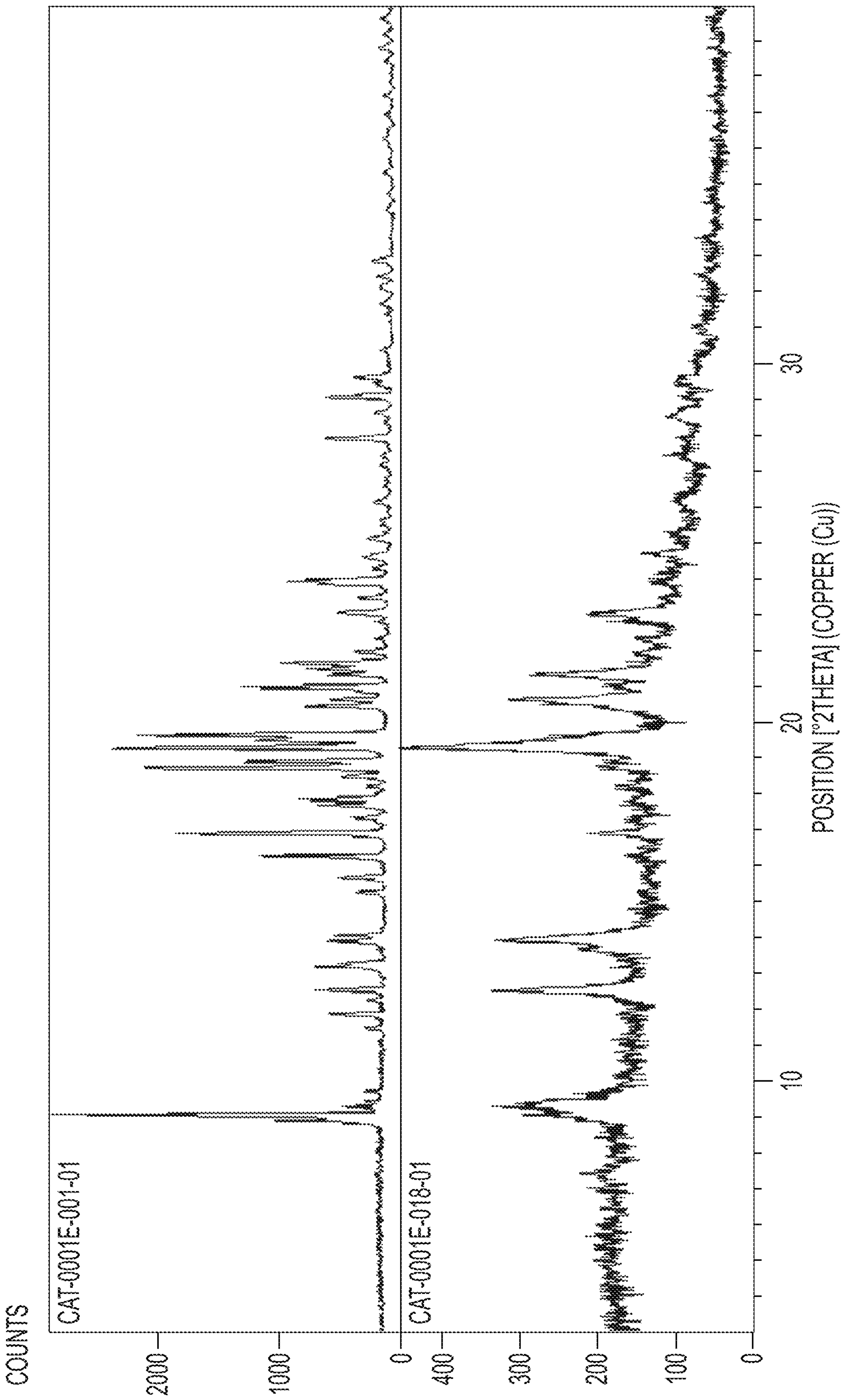
FIG. 28 provides an XRPD diffractogram showing (top) AAT-730 Lot. No. 33-13 and (bottom) typical diffractogram after planetary milling.

Screening experiments were carried out using the planetary mill (Method 3-7) and these results are shown in Table 3-9. This method was chosen to try to eliminate formation of gels as only a small amount of solvent was used. Salt formation was not observed by this technique and the milling appeared to cause AAT-730 to become slightly disordered as peak broadening was noted in the diffractogram (FIG. 28).
Results from Screening by Planetary Milling

TABLE 3-9

| Acid | Sample No. (CAT-0001E-) | Result | XRPD Result |
|---|---|---|---|
| acetic acid | 018-01 | solid | AAT-730 – disordered XRPD pattern |
| L-ascorbic acid | 018-02 | solid | AAT-730 – disordered XRPD pattern |
| L-aspartic acid | 018-03 | solid | AAT-730 (disordered) + L-aspartic acid |
| benzenesulfonic acid | 018-04 | gel | N/A |
| citric acid | 018-05 | solid | AAT-730 – disordered XRPD pattern |
| gentisic acid | 018-08 | gel | N/A |
| D-gluconic acid | 018-09 | gel | N/A |
| D-glucuronic acid | 018-10 | solid | AAT-730 (disordered) + D-glucuronic acid |
| L-glutamic acid | 018-11 | solid | AAT-730 – disordered XRPD pattern |
| hippuric acid | 018-14 | solid | AAT-730 (disordered) + hippuric acid + possible salt |
| L-malic acid | 018-18 | solid | AAT-730 – disordered XRPD pattern |
| phosphoric acid | 018-20 | solid | AAT-730 – disordered XRPD pattern |
| p-TSA | 018-21 | solution | N/A |
| L-tartaric acid | 018-24 | solid | AAT-730 – disordered XRPD pattern |

Example 3-7, Experiments with Altered Stoichiometry

Some of the acid co-formers had $pK_a$ values which were suitable for forming either hemi or bis-salts and experiments were carried out using these acids. The molar equivalents used are shown in Table 3-10. Crystalline solids were isolated from the experiments using 0.5 mol. eq. of EDSA but these appeared to be composed of polymorphs of the free base and salt formation hadn't occurred with 0.5 mol. eq. of EDSA. The EDSA salt formed with 2 mol. eq. of EDSA yielded solids with the same XRPD pattern as the mono-EDSA salt. Two different crystalline salts were isolated from the reactions with HCl and these may be the mono and bis-HCl salts, however stoichiometry cannot be determined by $^1H$ NMR. The salt formation with MSA yielded the bis-MSA salt and this is discussed in Example 3-16. The salt isolated with glutaric acid has the same XRPD pattern as the salt isolated with 1 mol. eq. of glutaric acid and is a mono-glutarate salt (Example 3-17). A solid was isolated from the experiment with 2 mol. eq. of sulfuric acid and this may be a sulfate.

Screening Experiments with Alternative Stoichiometry

TABLE 3-10

| Acid | Sample No. (CAT0001E-) | Solvent | Acid (mol. eq.) | Result | XRPD Result |
|---|---|---|---|---|---|
| EDSA | 019-01 | THF | 0.5 | solid | free base polymorph + free base Pattern A |
| EDSA | 019-01B | EtOH | 0.5 | solid | crystalline, not salt formation |
| EDSA | 019-01C | THF | 0.5 | solid | free base polymorph + free base Pattern A |
| $H_2SO_4$ | 019-02 | THF | 0.5 | haze | N/A |
| benzenesulfonic acid | 019-03 | THF | 2 | gel | N/A |
| EDSA | 019-04 | THF | 2 | solid | AAT-730 EDSA |
| HCl | 019-05 | THF | 2 | solid | AAT-730 HCl Pattern A** |
| HCl | 019-05B | EtOH | 2 | solid | AAT-730 HCl Pattern B |
| MSA | 019-06 | THF | 2 | solid | AAT-730 MSA Pattern B |
| p-TSA | 019-07 | THF | 2 | haze | N/A |
| $H_2SO_4$ | 019-08 | THF | 2 | haze | possible sulfate Pattern B |
| L-aspartic acid | 019-09 | THF | 0.5 | solid | API |
| citric acid | 019-10 | THF | 0.5 | solid | IS* |
| L-glutamic acid | 019-11 | THF | 0.5 | solid | API |
| glutaric acid | 019-12 | THF | 0.5 | solid | AAT-730 glutarate |
| L-malic acid | 019-13 | THF | 0.5 | gel | N/A |
| succinic acid | 019-14 | THF | 0.5 | solution | N/A |
| L-tartaric acid | 019-15 | THF | 0.5 | gel | N/A |

*IS = insufficient sample for XRPD analysis

**The XRPD pattern of AAT-730 HCl salt Pattern A is referred as to Pattern 1 in Examples 5 and 6.

Conclusions from Salt Screening

1) Approximately 175 salt screening experiments were carried out. Fourteen possible salts from 11 different salt formers were isolated as listed in Table 3-11.

2) These were stressed at 40° C./75% RH for 1 week and visually checked for deliquescence. Further analysis by $^1H$ NMR, TGA and aqueous solubility was carried out where sufficient material was available.

Summary of the Salts Observed During this Study

TABLE 3-11

| Salt | Pattern | Comment |
|---|---|---|
| acetate | A | crystalline solid, non-stoichiometric, gained at most 18.4% weight on stressing at 40° C. |
| EDSA salt | A | 1:1 salt, unstable to 40° C./75% RH stressing |
| fumarate | A | crystalline 1:1 salt, unstable to 40° C./75% RH stressing |
| glutarate | A | crystalline 1:1 salt, physically stable to 40° C./75% RH stressing, aqueous solubility approximately 163-245 mg/mL |
| glycolate | A | crystalline 1:1 salt, physically stable to 40° C./75% RH stressing, aqueous solubility approximately 179-238 mg/mL |
| HCl salt | A | crystalline 1:1 salt, physically stable to 40° C./75% RH stressing, aqueous solubility approximately 164-205 mg/mL |
| | B | crystalline salt (stoichiometry 1:2 AAT-730:HCl) physically stable to 40° C./75% RH stressing |
| L-lactate | A | crystalline 1:1 salt, physically stable to 40° C./75% RH stressing, aqueous solubility approximately 320-640 mg/mL |
| maleate | A | crystalline 1:1 salt, physically stable to 40° C./75% RH stressing, aqueous solubility approximately 280-560 mg/mL |
| MSA salt | A | crystalline 1:1 salt, physically stable to 40° C./75% RH stressing, aqueous solubility approximately 228-260 mg/mL |
| | B | crystalline salt (stoichiometry 1:2 AAT-730:MSA), unstable to 40° C./75% RH stressing |

TABLE 3-11-continued

| Salt | Pattern | Comment |
|---|---|---|
| sulfate | A | crystalline salt, stoichiometry of salt not determined, physically stable to 40° C./75% RH stressing, aqueous solubility up to approximately 500 mg/mL |
| | B | crystalline, possible salt, stoichiometry not determined, deliquesced on stressing at 40° C./75% RH |
| succinate | A | crystalline 1:1 salt, unstable to 40° C./75% RH stressing |

Example 3-8, Characterization of AAT-730 (Compound A) Acetate

Figure 29:
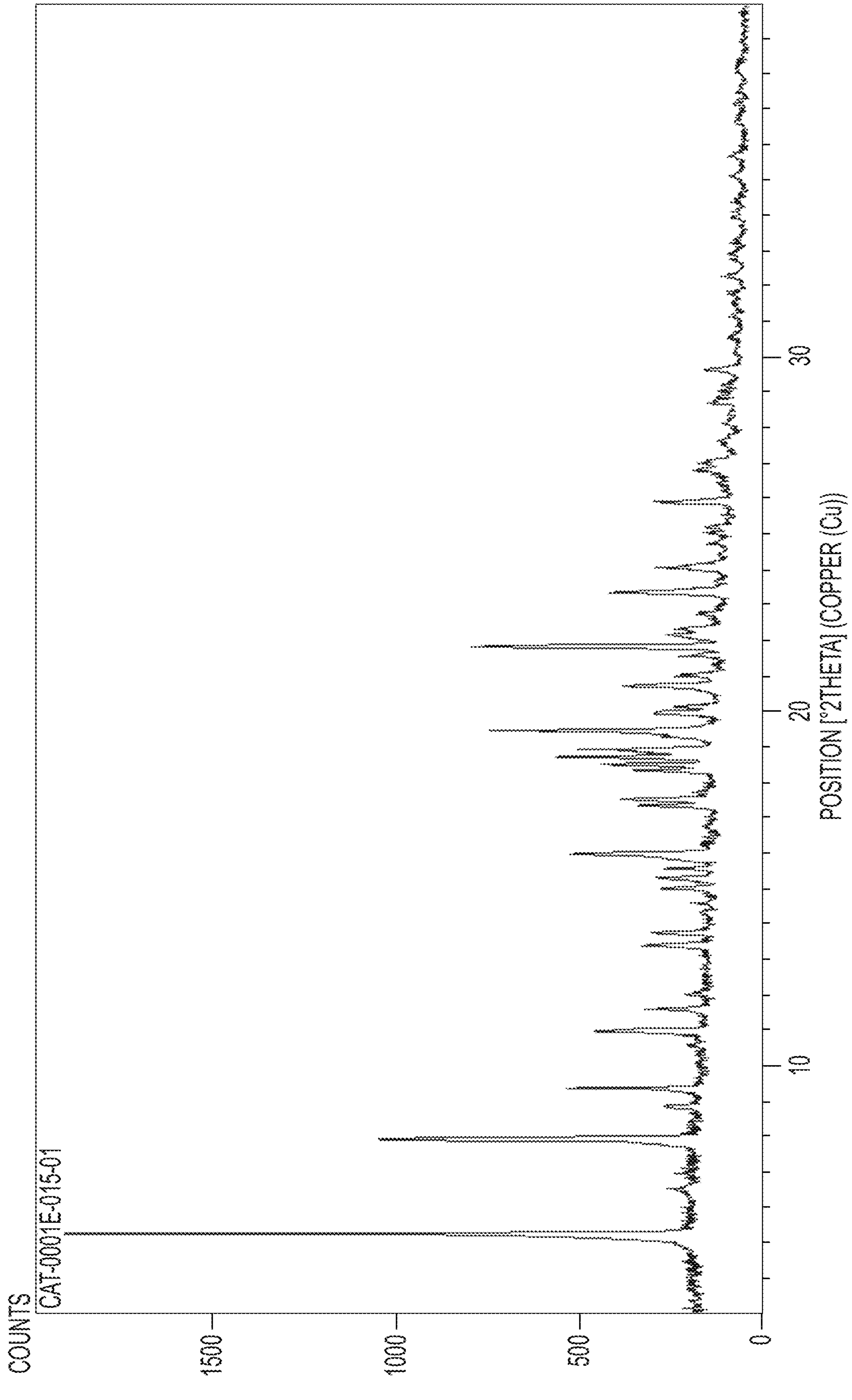
FIG. 29 provides an XRPD diffractogram of possible AAT-730 acetate.
Figure 30:
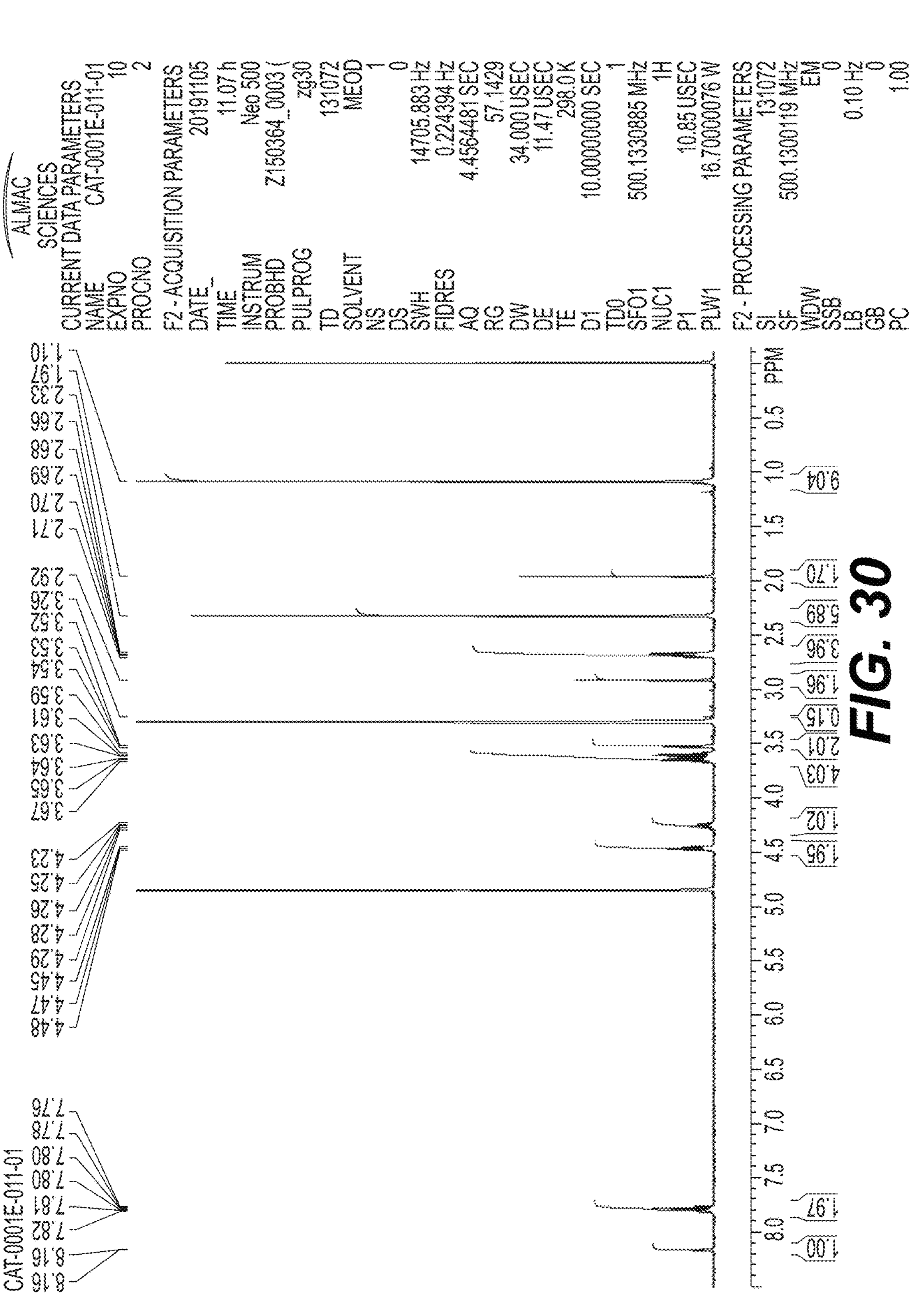
FIG. 30 provides a $^{1}H$ NMR spectrum of possible AAT-730 acetate.

A possible acetate (acetic acid salt) of AAT-730 was isolated after trituration in MTBE of the gel isolated from the reaction of AAT-730 and acetic acid in THF/water or from trituration in EtOAc after reaction in ethanol. The solids were analyzed by XRPD (FIG. 29) and $^1H$ NMR analyses (FIG. 30) and shown to be crystalline by XRPD analysis. The $^1H$ NMR spectrum suggested that the material was a non-stoichiometric salt. The salt gained at most 18% w/w on stressing at 40° C./75% RH.

Example 3-9, Characterization of AAT-730 (Compound A) EDSA Salt

Figure 31:
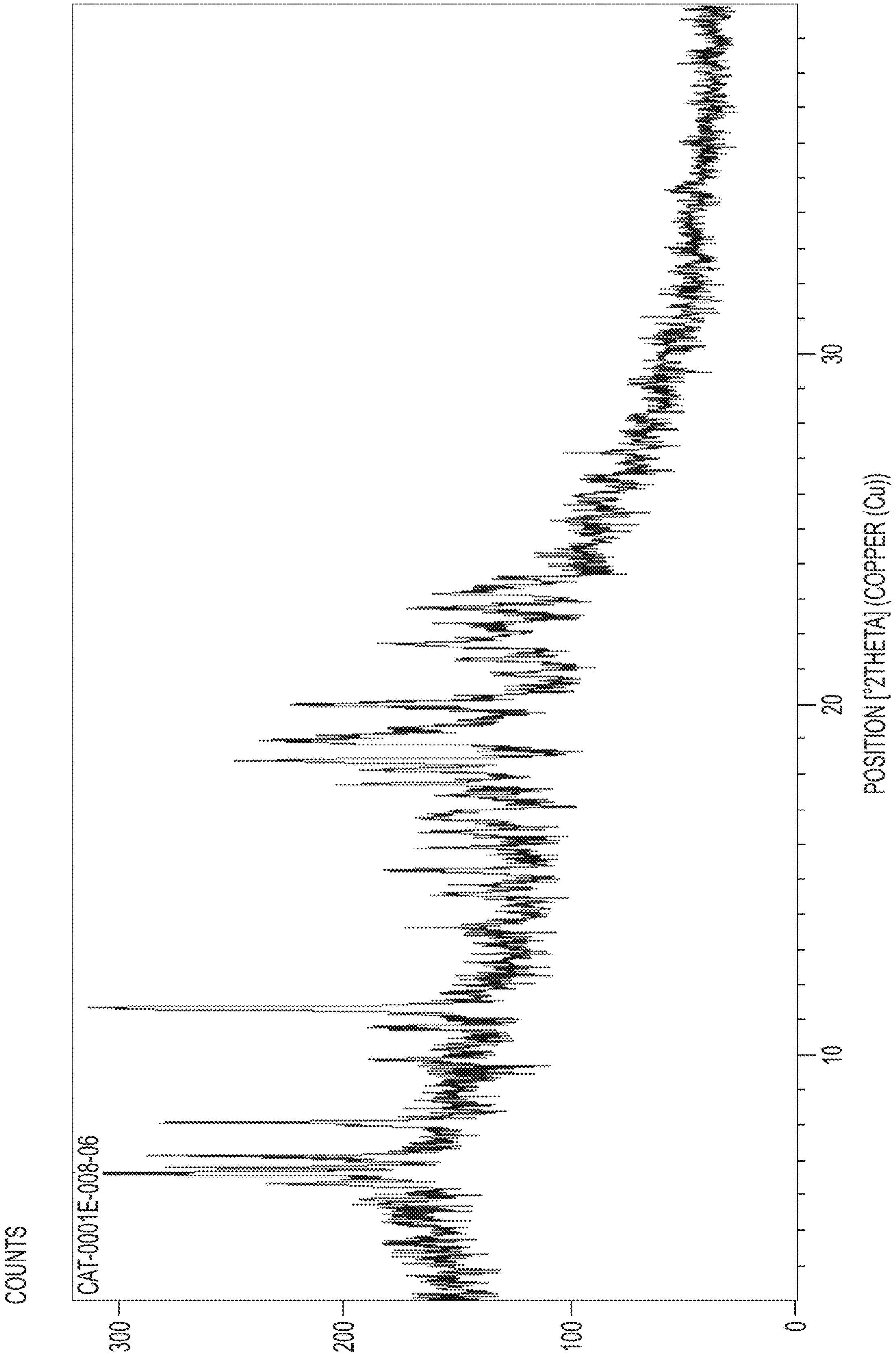
FIG. 31 provides an XRPD pattern of AAT-730 EDSA salt.
Figure 32:
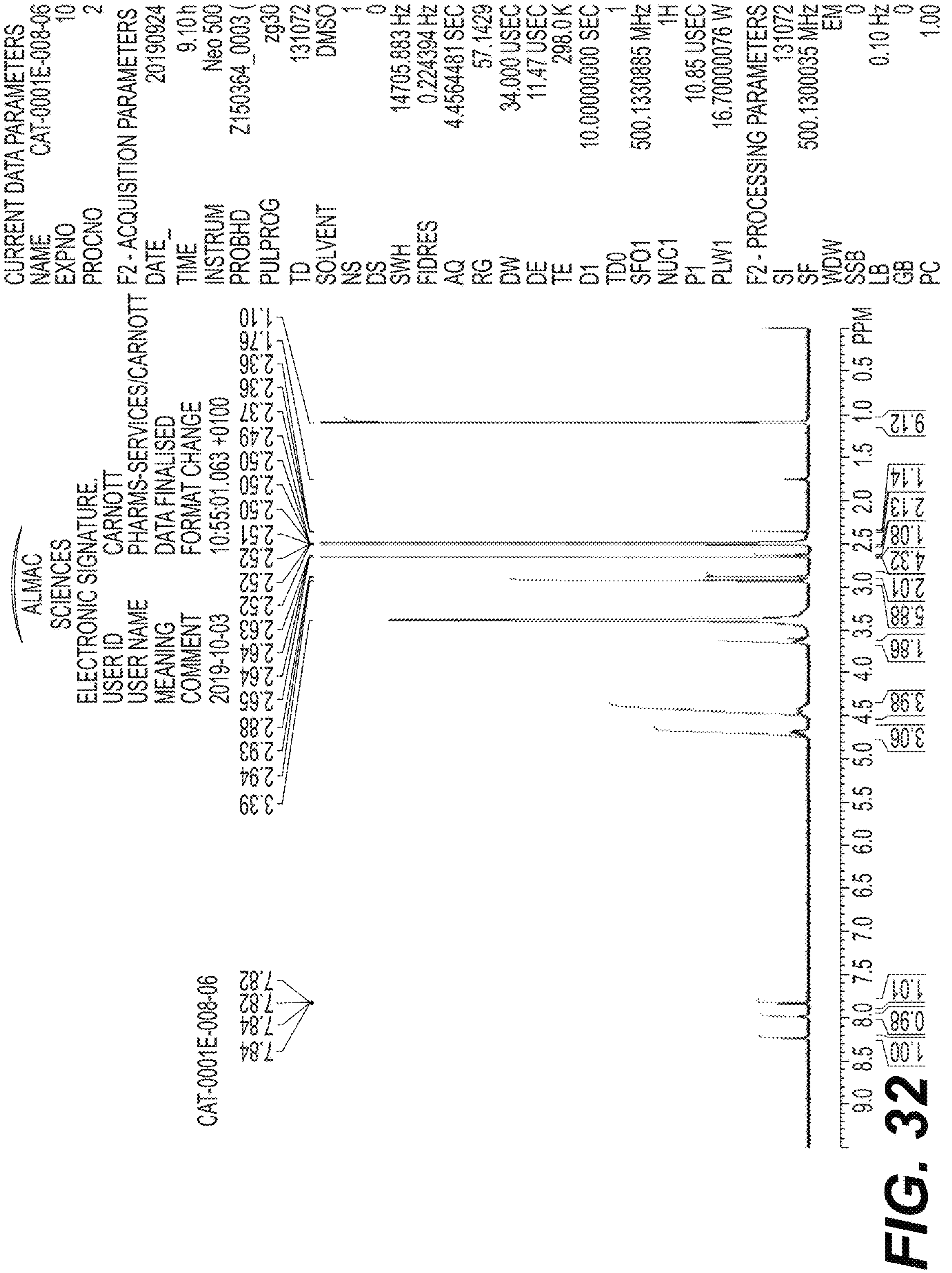
FIG. 32 provides a $^{1}H$ NMR spectrum of suspected AAT-730 EDSA salt.

AAT-730 mono-EDSA salt was isolated from a precipitation reaction of AAT-730 and EDSA (1 or 2 mol. eq.) in THF. The solids were isolated and analyzed by XRPD (FIG. 31). Although the sample was weak, the material was crystalline. $^1H$ NMR analysis (FIG. 32) confirmed a 1:1 ratio of API:acid. The salt deliquesced on stressing at 40° C./75% RH.

Figure 33:
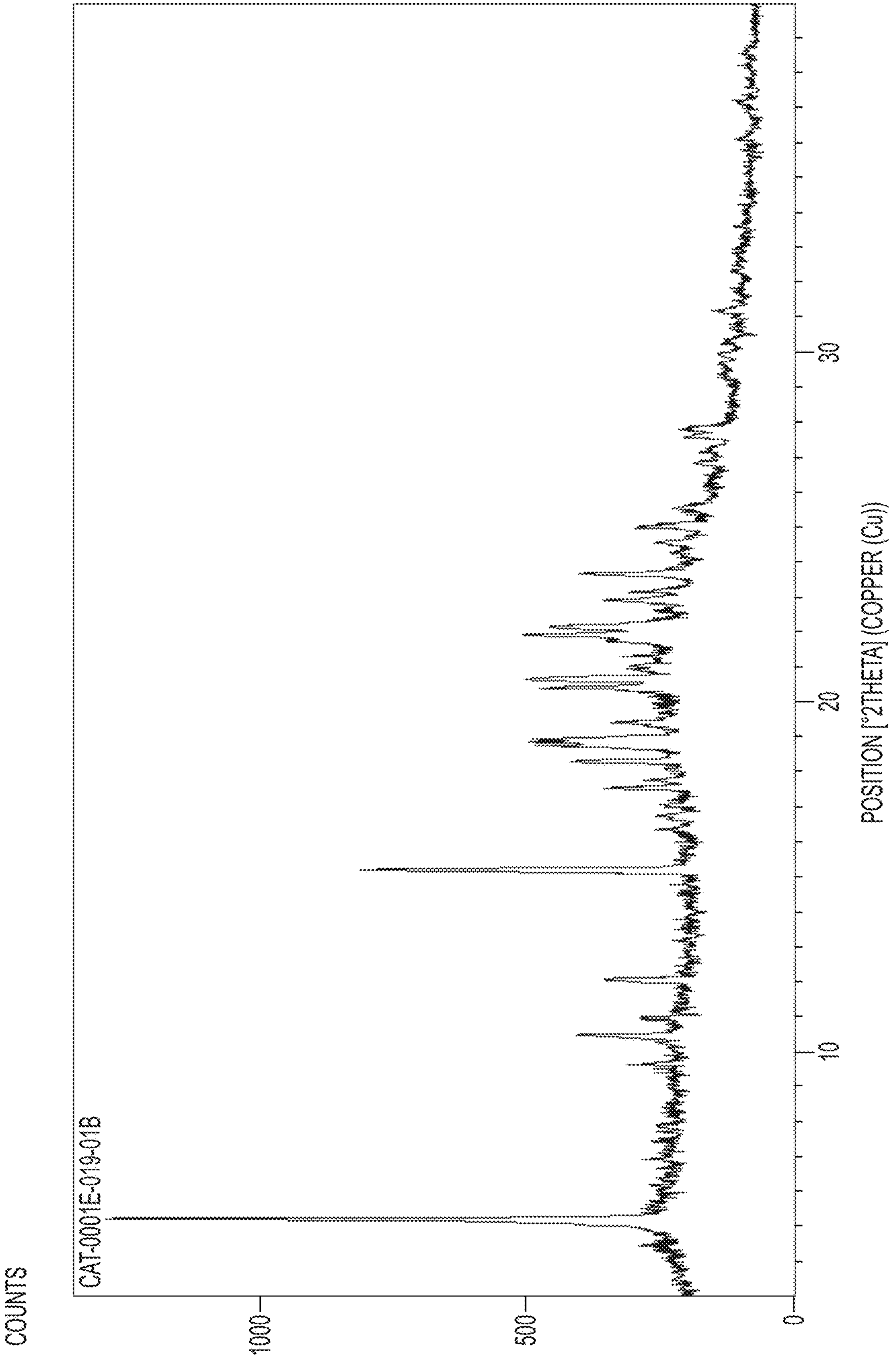
FIG. 33 provides an XRPD pattern of possible AAT-730 EDSA salt.
Figure 34:
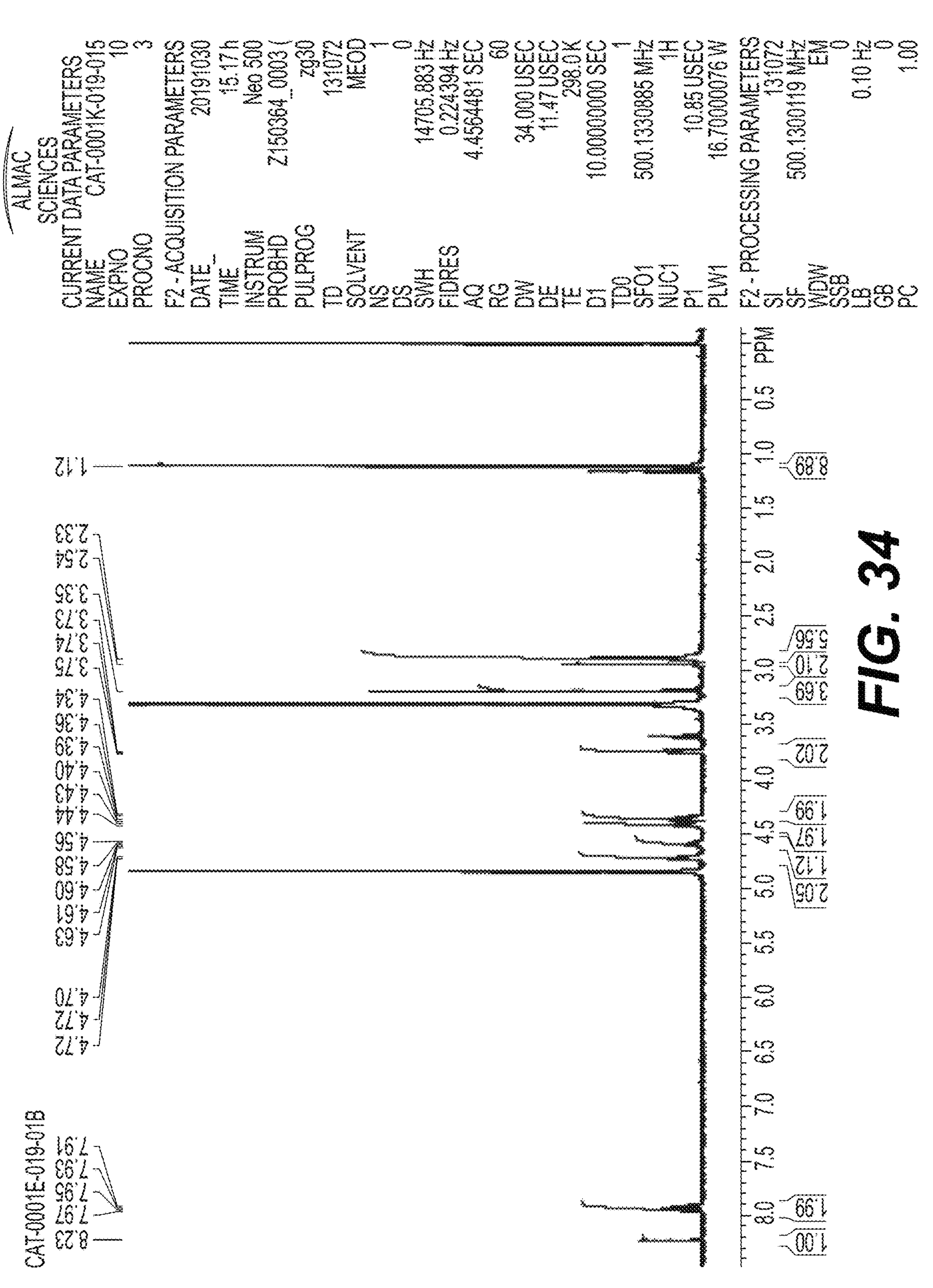
FIG. 34 provides a $^{1}H$ NMR spectrum of possible AAT-730 EDSA salt.

Solids isolated from the reaction of AAT-730 and EDSA (0.5 mol eq.) in EtOH yielded solids with a novel XRPD pattern (FIG. 33). This was labelled AAT-730 EDSA Pattern C. $^1H$ NMR (FIG. 34) analysis suggested that salt formation may not have occurred.

Example 3-10, Characterization of AAT-730 Fumarate

Figure 35:
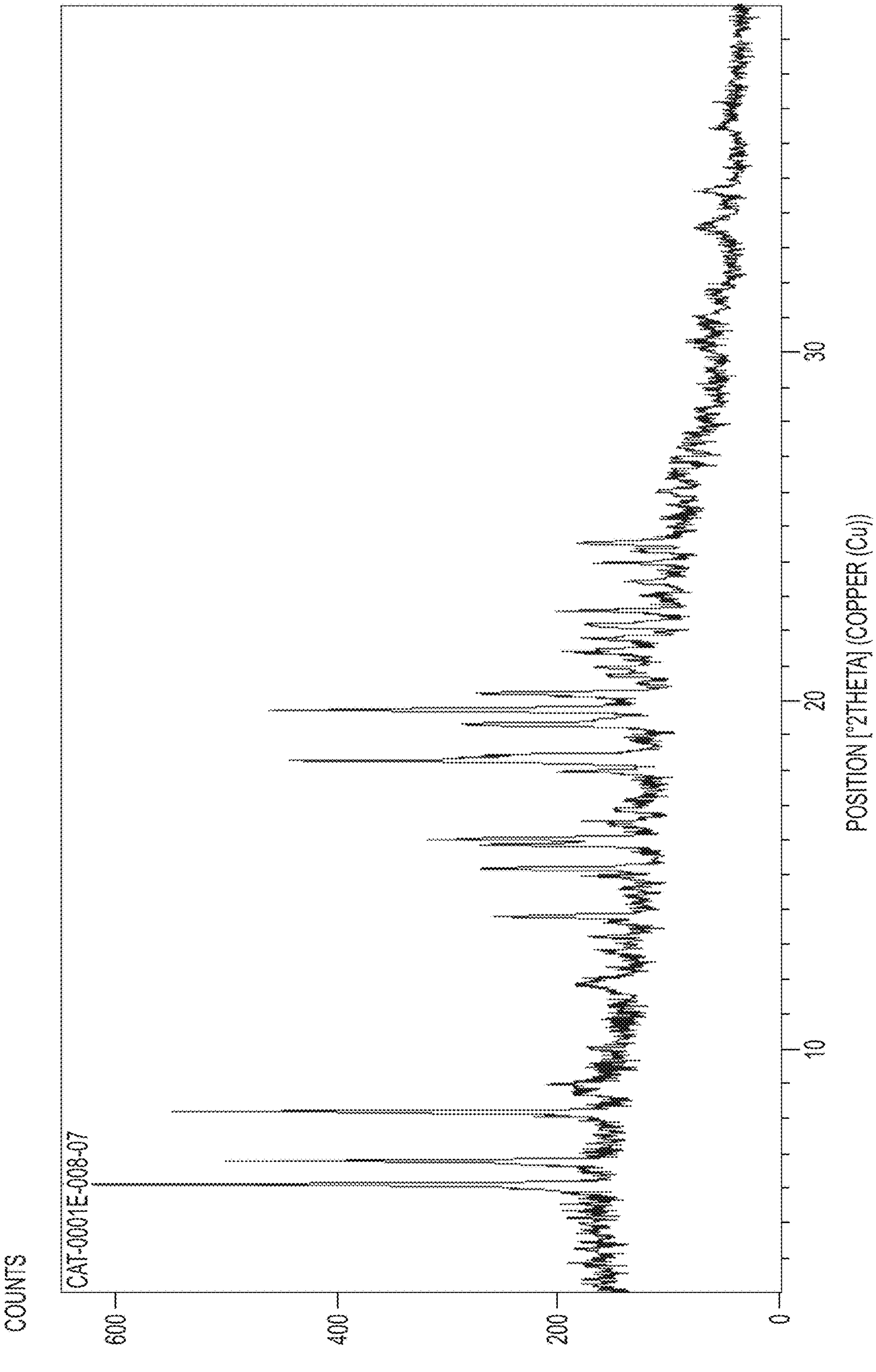
FIG. 35 provides an XRPD pattern of suspected AAT-730 fumarate.
Figure 36:
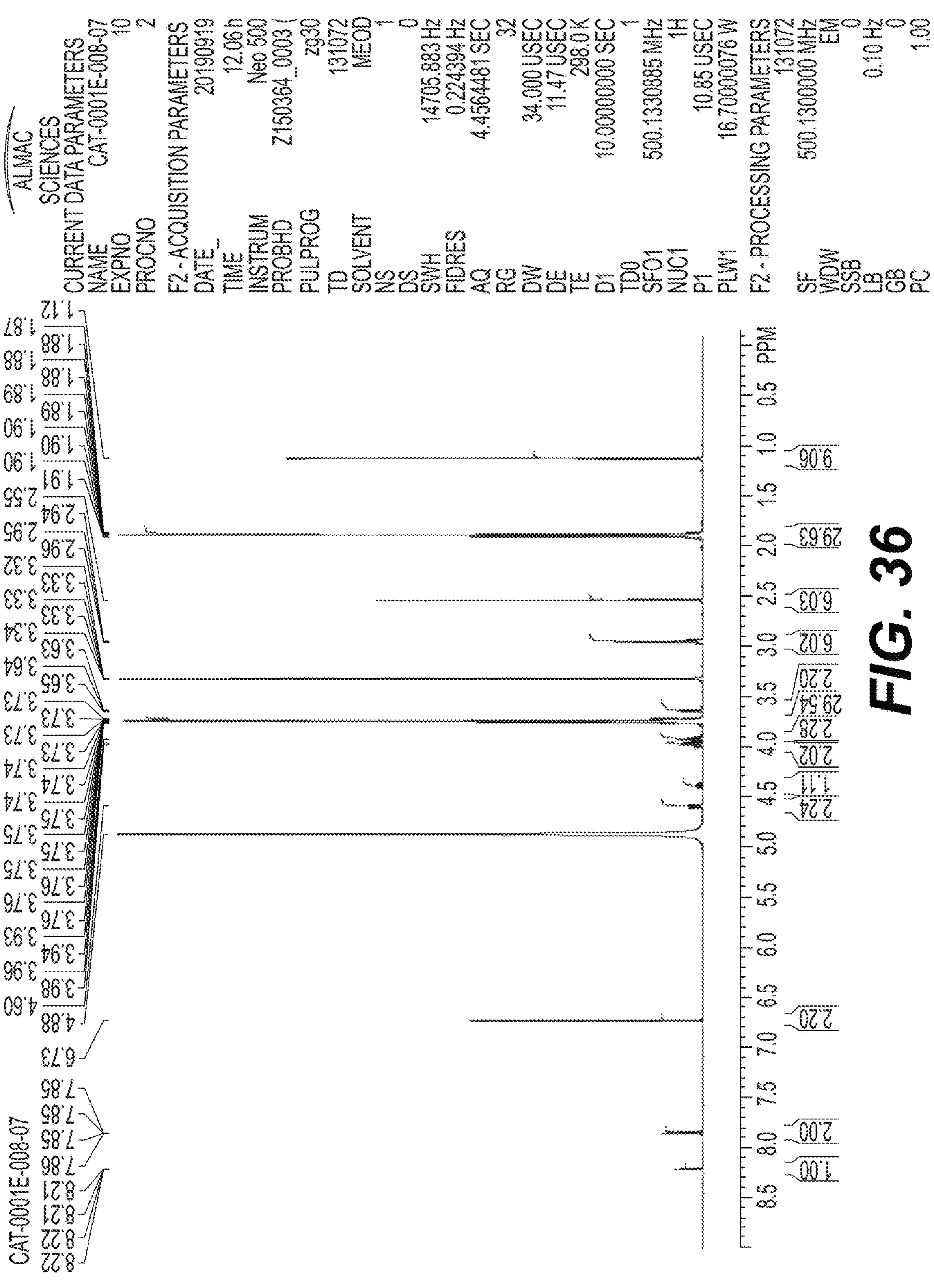
FIG. 36 provides a $^{1}H$ NMR spectrum of suspected AAT-730 fumarate.

Solids precipitated from the reaction of AAT-730 and fumaric acid in THF. XRPD analysis of the solids showed they were crystalline with a novel XRPD pattern (FIG. 35). The material was analyzed by $^1H$ NMR analysis (FIG. 36) which suggested formation of a mono-fumarate. The material was stressed at 40° C./75% RH for 7 days and the solid deliquesced.

Example 3-11, Characterization of AAT-730 (Compound A) Glutarate

Figure 37:
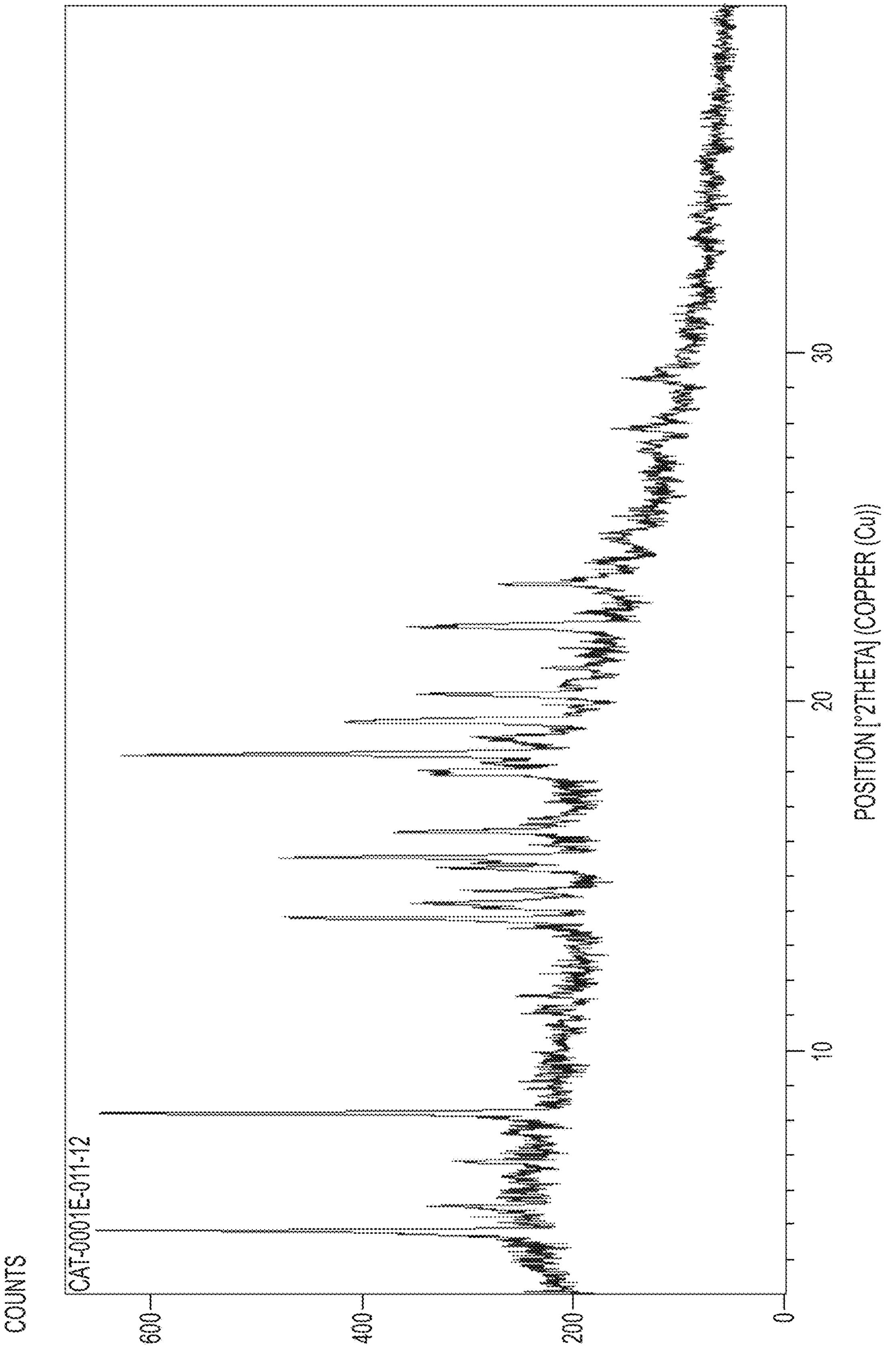
FIG. 37 provides an XRPD pattern of suspected AAT-730 glutarate.
Figure 38:
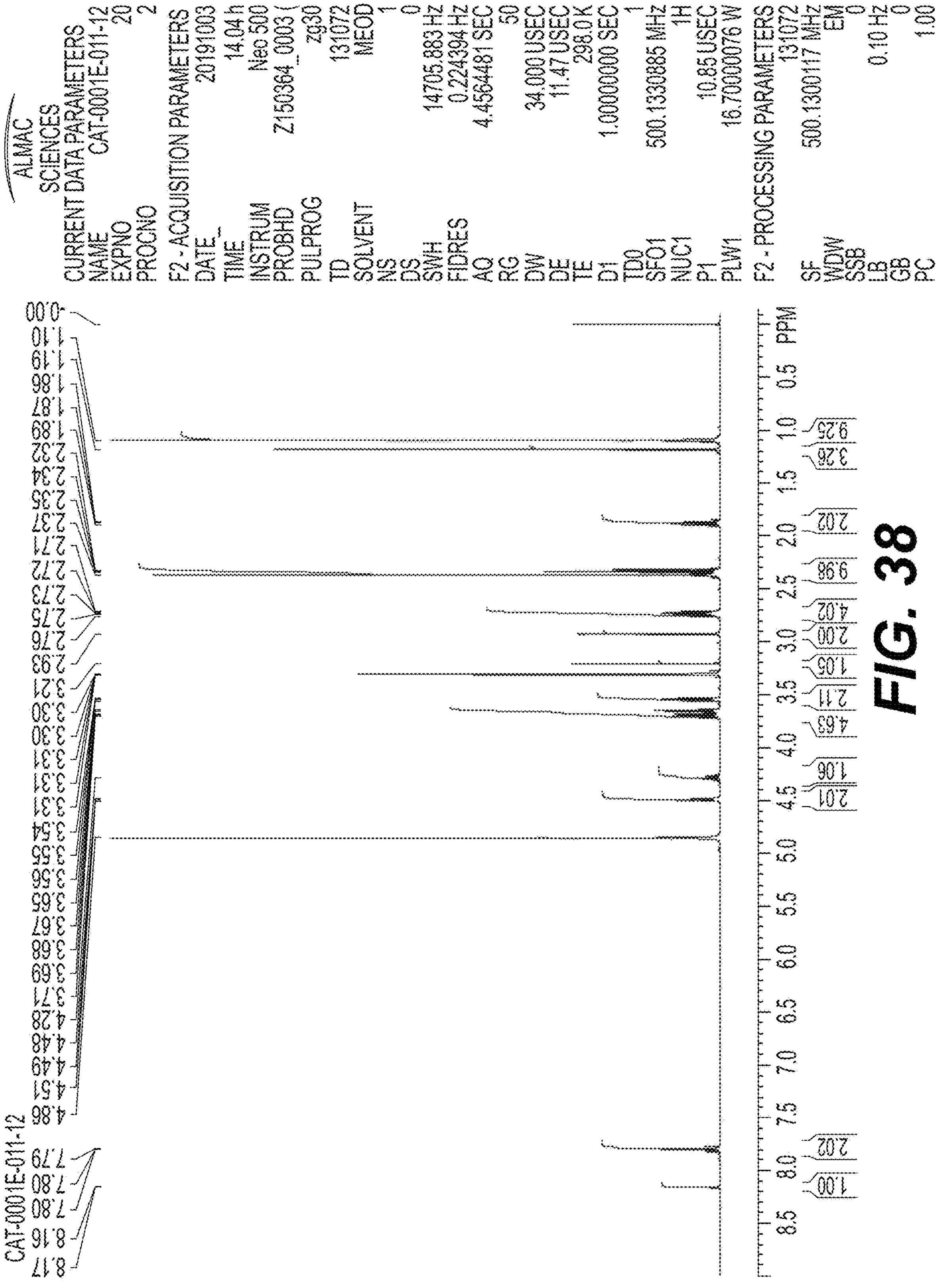
FIG. 38 provides a $^{1}H$ NMR spectrum of AAT-730 glutarate.
Figure 39:
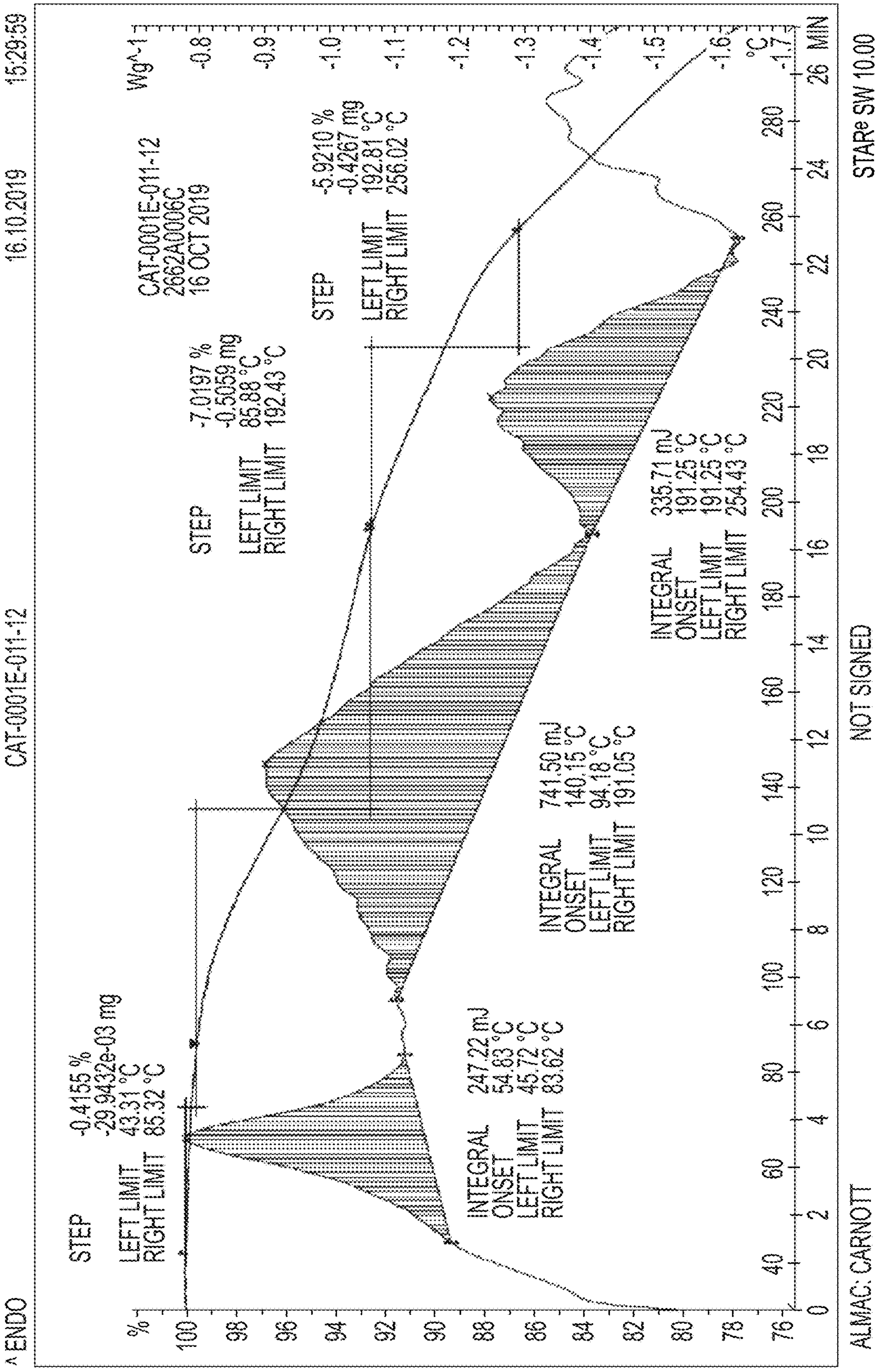
FIG. 39 provides a TG/DTA thermogram of suspected AAT-730 glutarate analyzed from 30 to 300° C. at 10° C. per minute.

AAT-730 glutarate (glutaric acid salt) was isolated from screening experiments of AAT-730 and glutaric acid in THF and THF/water. Gels were isolated from the experiments with 1 molar equivalent of acid and these were triturated/temperature cycled in MTBE to yield solids which were crystalline by XRPD (FIG. 37). Analysis by $^1H$ NMR (FIG. 38) showed formation of a mono-glutarate (at most 5.4% w/w of MTBE was also noted). The approximate aqueous solubility was 163-245 mg/mL. TG/DTA of the salt showed 3 endothermic events which may be due to either melting of the material or loss of solvent or acid on heating (FIG. 39).

Example 3-12, Characterization of AAT-730 (Compound A) Glycolate

Figure 40:
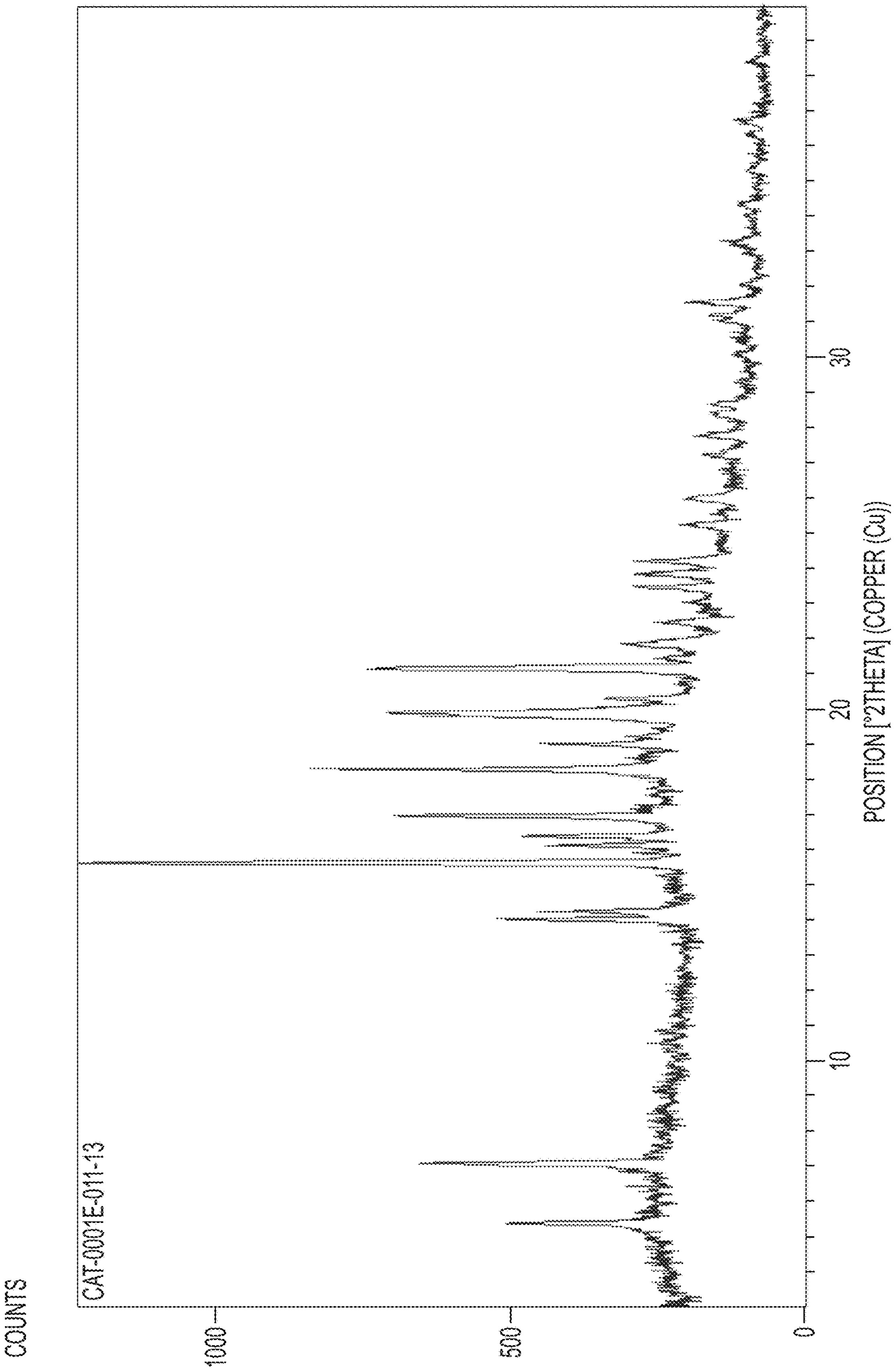
FIG. 40 provides an XRPD pattern of suspected AAT-730 glycolate.
Figure 41:
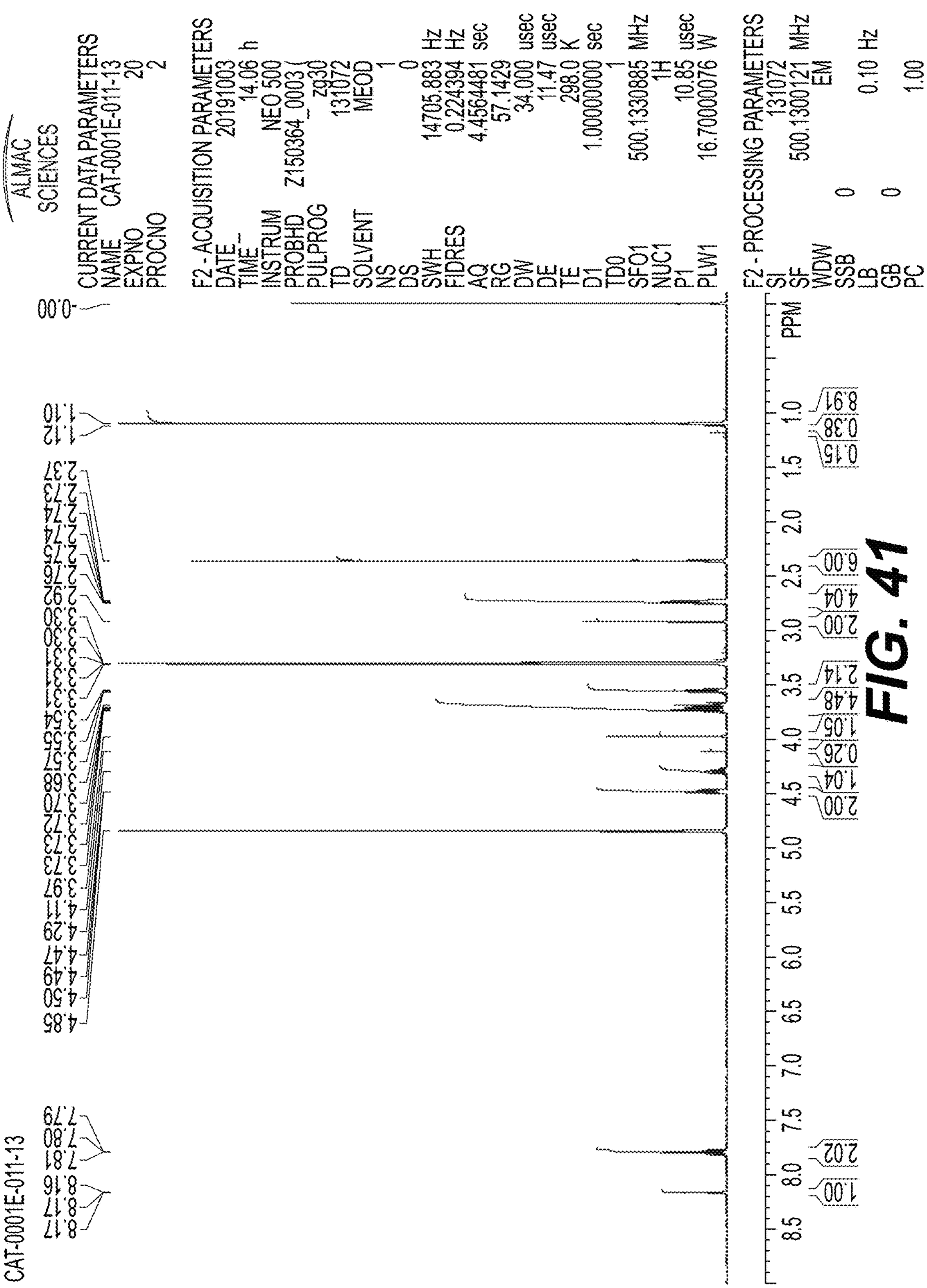
FIG. 41 provides a $^{1}H$ NMR spectrum of suspected AAT-730 glycolate.

A suspected salt was isolated from a screening experiment of AAT-730 and glycolic acid in EtOH and was analyzed by XRPD analysis (FIG. 40). The solid was crystalline and this was analyzed by $^1H$ NMR analysis (FIG. 41) which suggested formation of a mono-glycolate.

Figure 42:
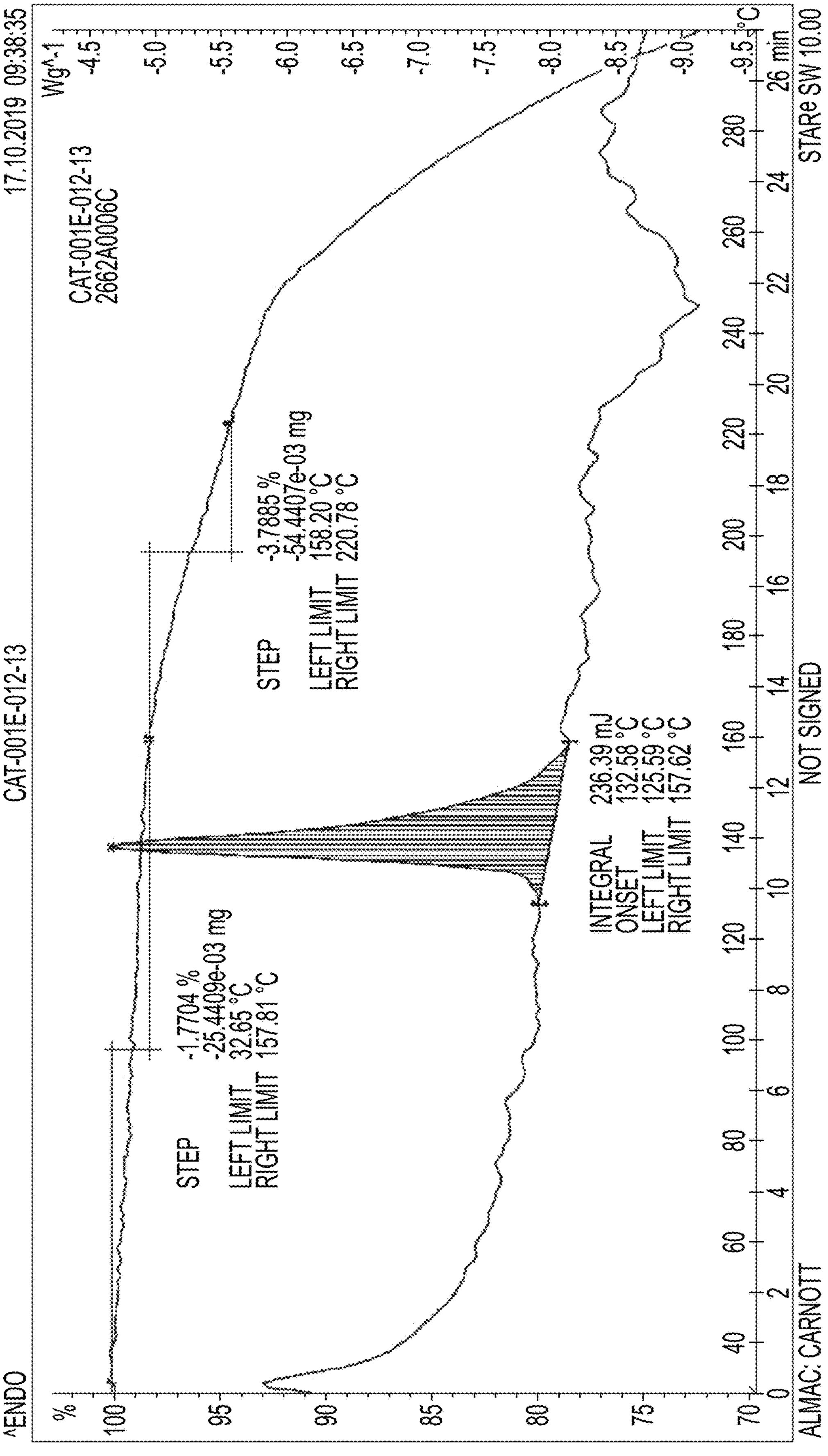
FIG. 42 provides a TG/DTA thermogram of suspected AAT-730 glycolate analyzed from 30 to 300° C. at 10° C. per minute.

TG/DTA analysis (FIG. 42) showed a small weight loss between 3° and 160° C. which is likely to be due to residual solvent. An endotherm at onset up to 133° C. is probably due to melting of the material. The material was physically stable to stressing at 40° C./75% RH for 1 week.

Example 3-13, Characterization of AAT-730 (Compound A) HCl Salt Pattern A

Figure 43:
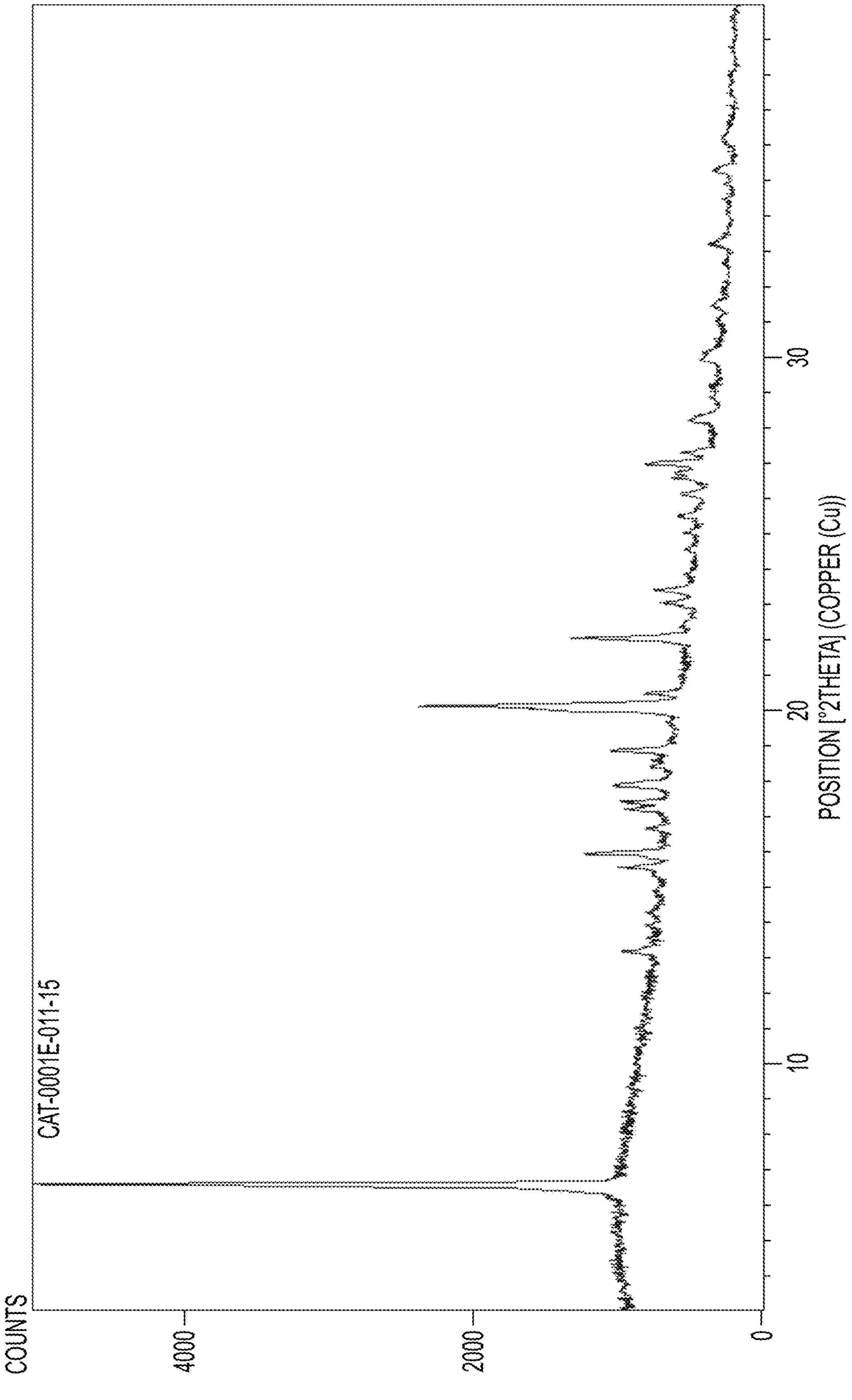
FIG. 43 provides an XRPD pattern of suspected AAT-730 HCl salt.
Figure 44:
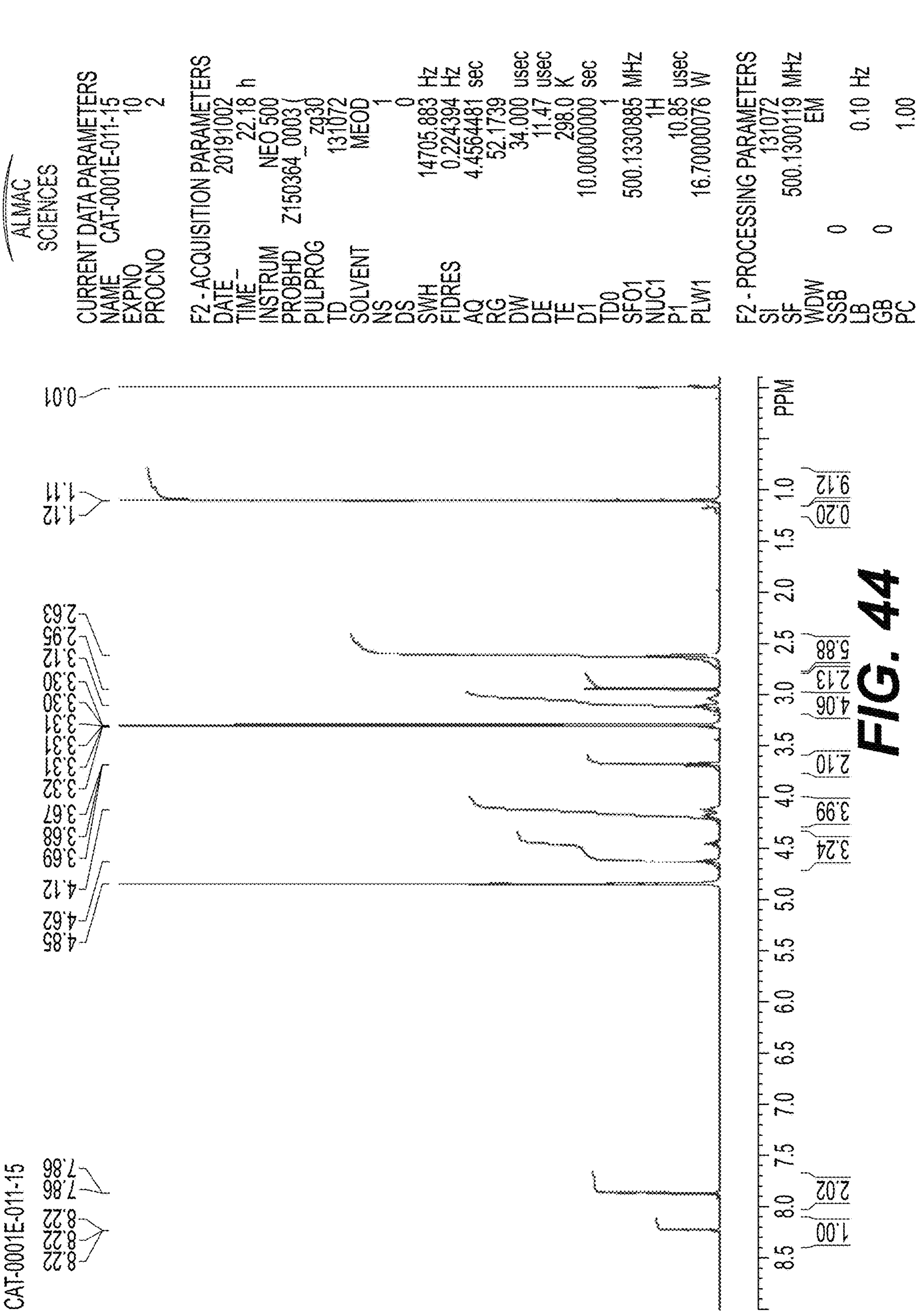
FIG. 44 provides a $^{1}H$ NMR spectrum of suspected AAT-730 HCl salt.
Figure 45:
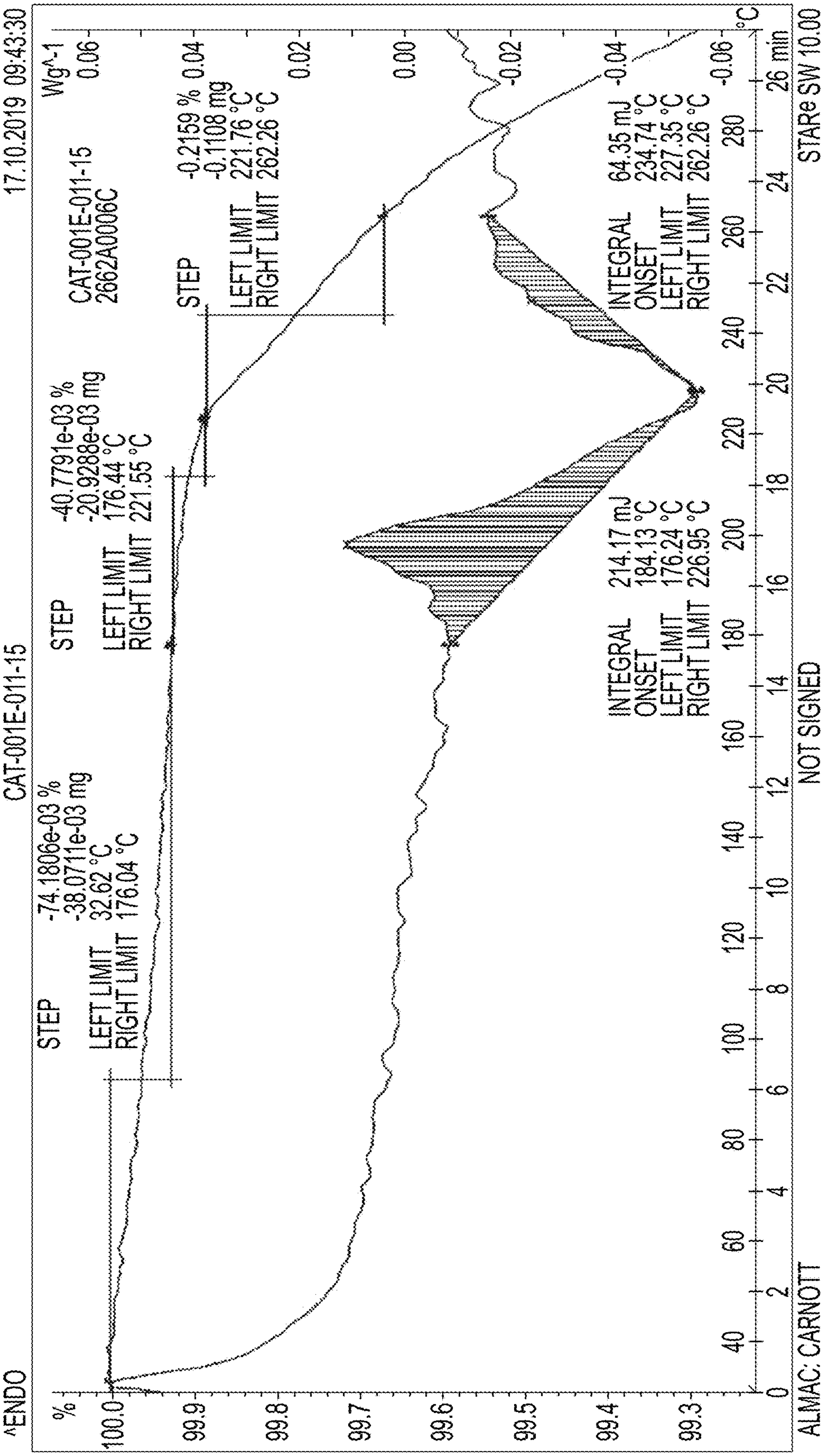
FIG. 45 provides a TG/DTA thermogram of suspected AAT-730 HCl salt analyzed from 30 to 300° C. at 10° C. per minute.

A suspected HCl salt was isolated from a precipitation experiment of AAT-730 and HCl (1 mol. eq.) in ethanol. The solids were analyzed by XRPD (FIG. 43), TG/DTA (FIG. 45) and $^1H$ NMR (FIG. 44) analyses. The XRPD diffractogram was consistent with a crystalline solid and the TG/DTA showed a possible melting endotherm at onset up to 184° C. No weight loss is observed which suggests an anhydrous material. A second endotherm at onset up to 234° C. may be due to melting of another crystalline form. The $^1H$ NMR spectrum shows peak shifting consistent with salt formation and the solids were stable to stressing at 40° C./75% RH. The solubility of the suspected salt was approximately 164-205 mg/mL.

Figure 46:
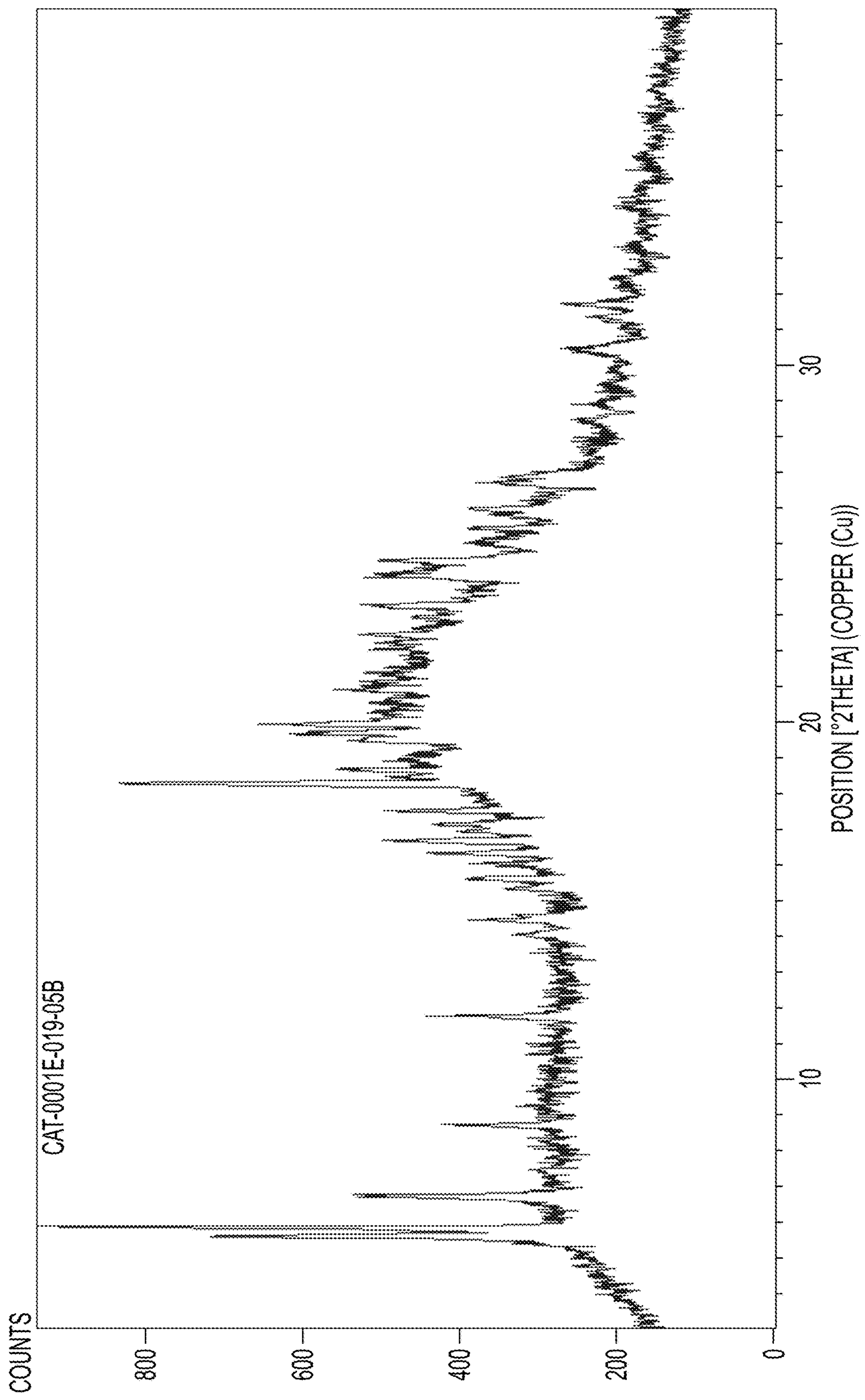
FIG. 46 provides an XRPD pattern of suspected AAT-730 HCl salt (2 mol. eq. of HCl).
Figure 47:
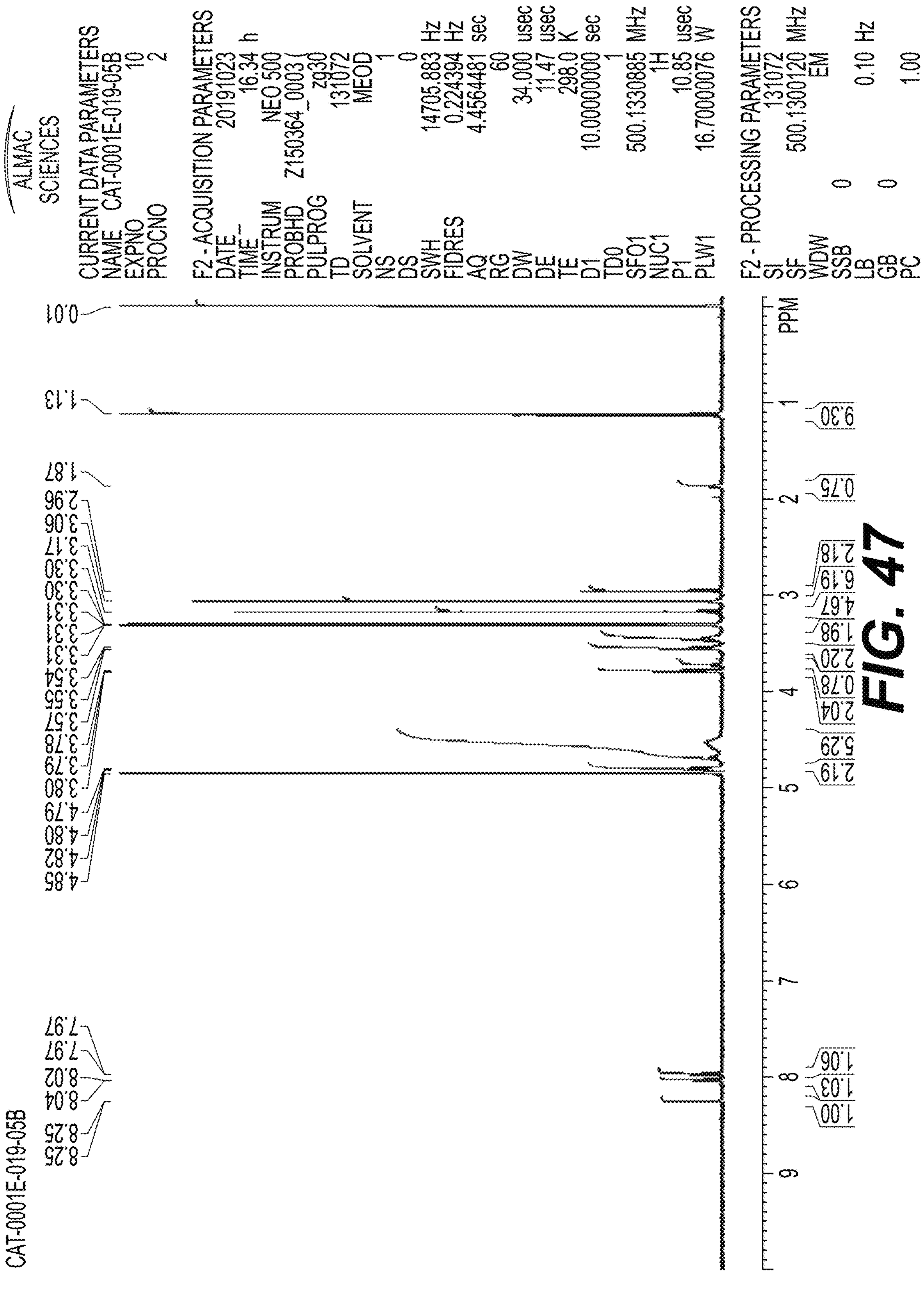
FIG. 47 provides a $^{1}H$ NMR spectrum of suspected AAT-730 HCl salt (2 mol. eq. of HCl).
Figure 48:
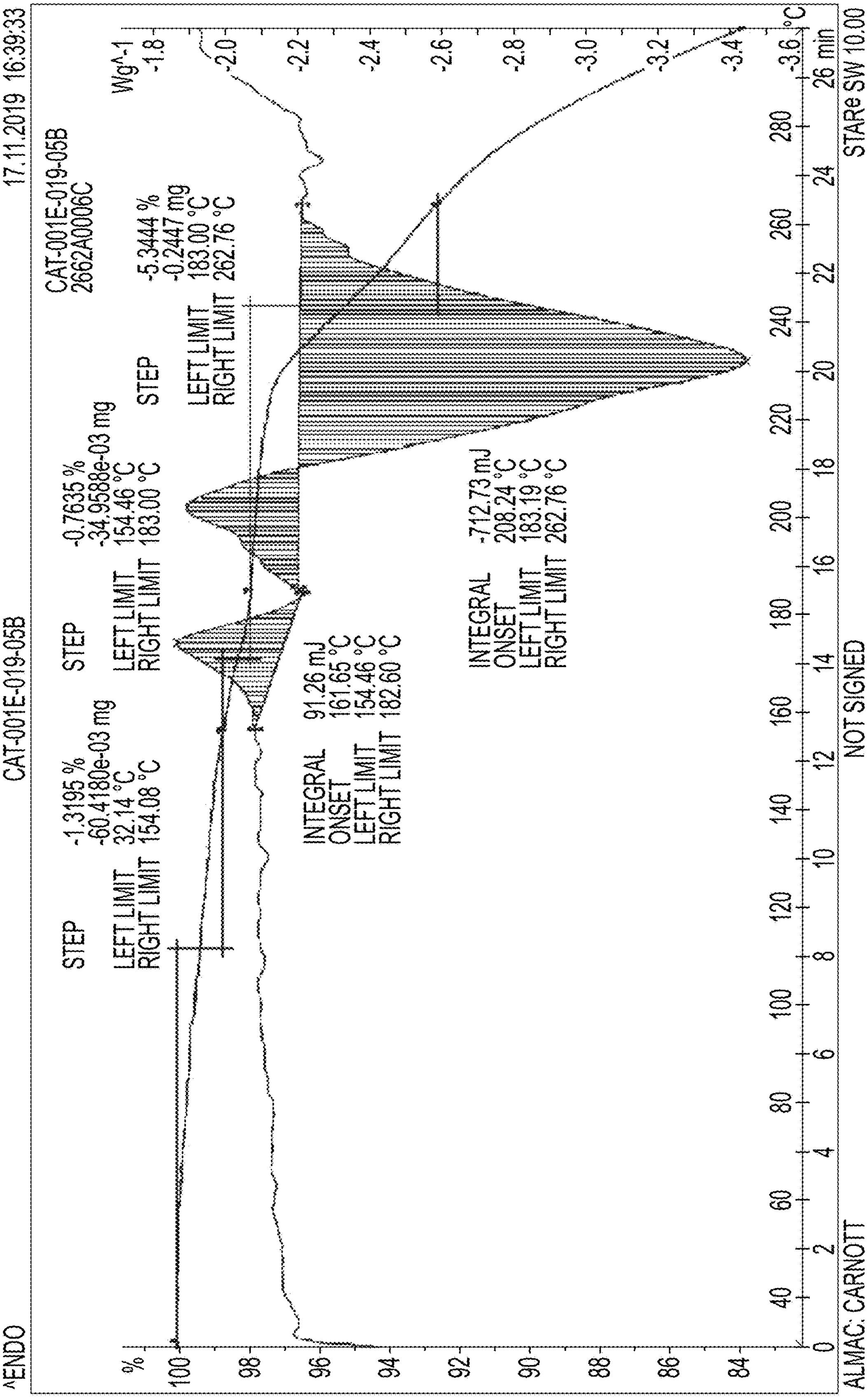
FIG. 48 provides a TG/DTA thermogram of suspected AAT-730 HCl salt analyzed from 30 to 300° C. at 10° C. per minute.

A second possible HCl salt (AAT-730 HCl salt Pattern B) was isolated from a screening experiment of AAT-730 with 2 moles of HCl in ethanol. This may be a 1:2 salt (API:acid), however stoichiometry cannot be determined by $^1H$ NMR analysis (FIG. 47). XRPD analysis (FIG. 46) showed that the material was crystalline with some amorphous content and $^1H$ NMR analysis showed peak shifting consistent with salt formation. TG/DTA analysis showed an endotherm at onset 161.6° C. and a second endotherm followed immediately by an exotherm (FIG. 48). The solids were stable to stressing at 40° C./75% RH for 1 week.

Example 3-14, Characterization of AAT-730 (Compound A) L-Lactate

Figure 49:
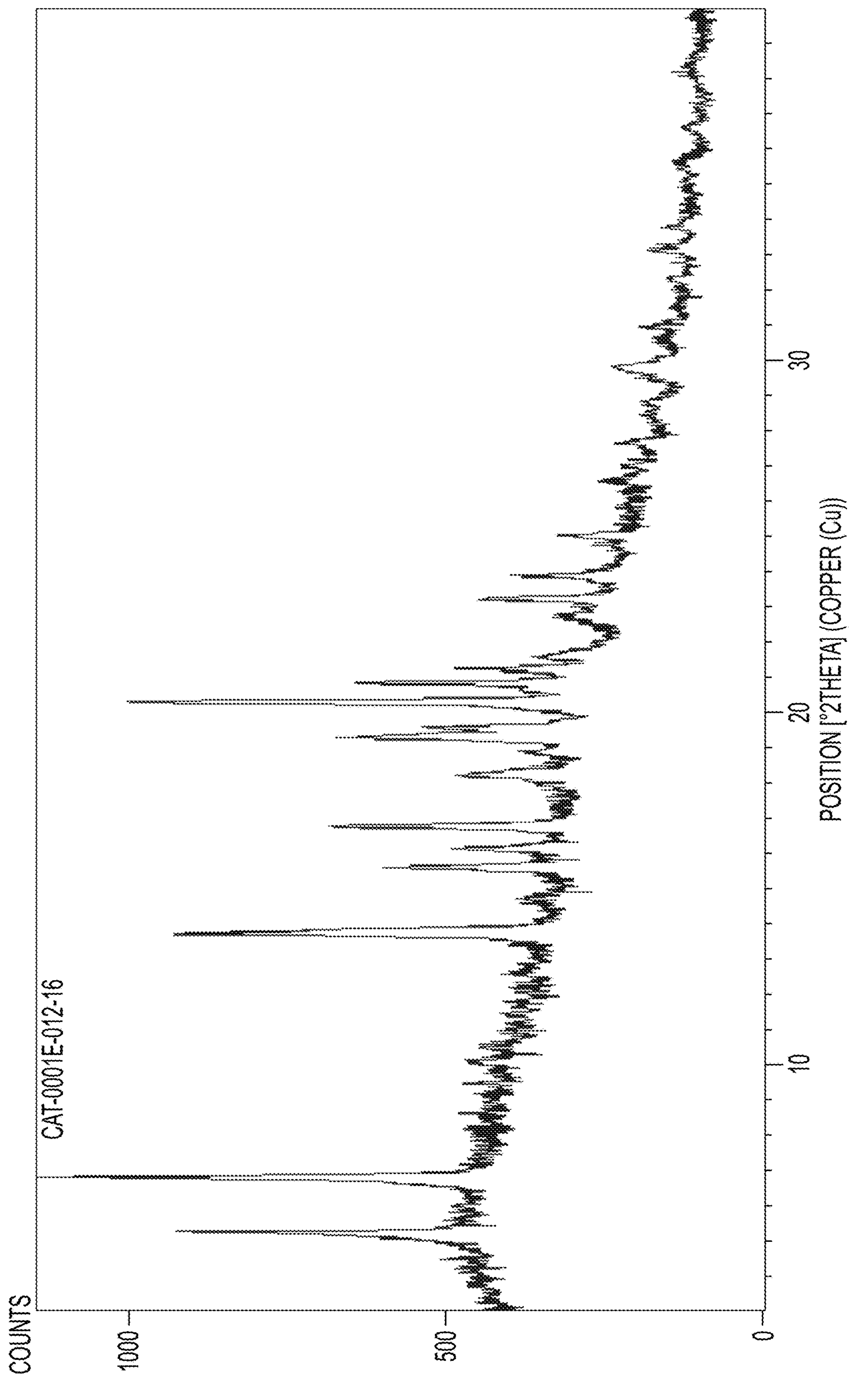
FIG. 49 provides an XRPD pattern of suspected AAT-730 L-lactate.
Figure 50:
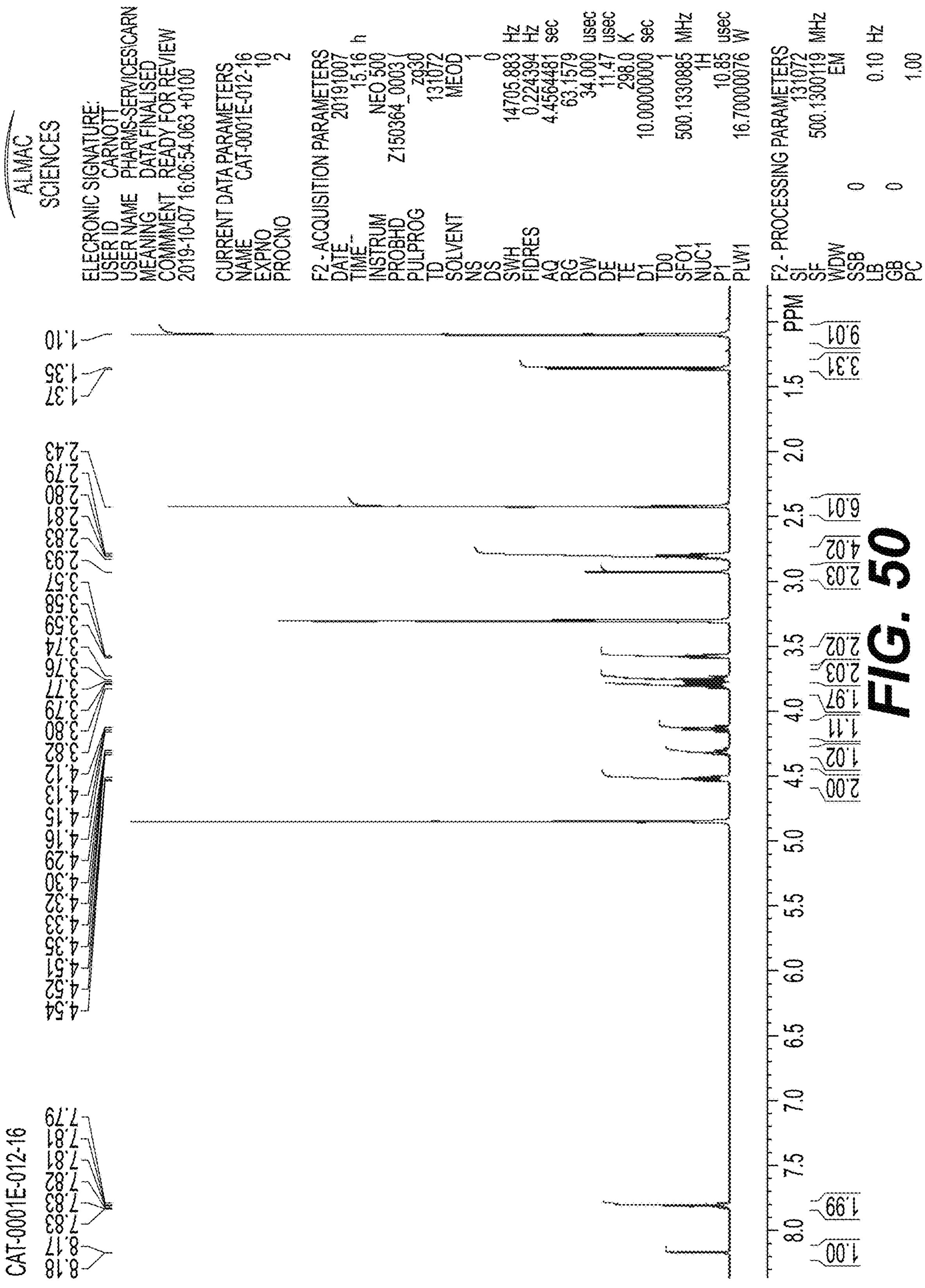
FIG. 50 provides a $^{1}H$ NMR spectrum of suspected AAT-730 L-lactate.
Figure 51:
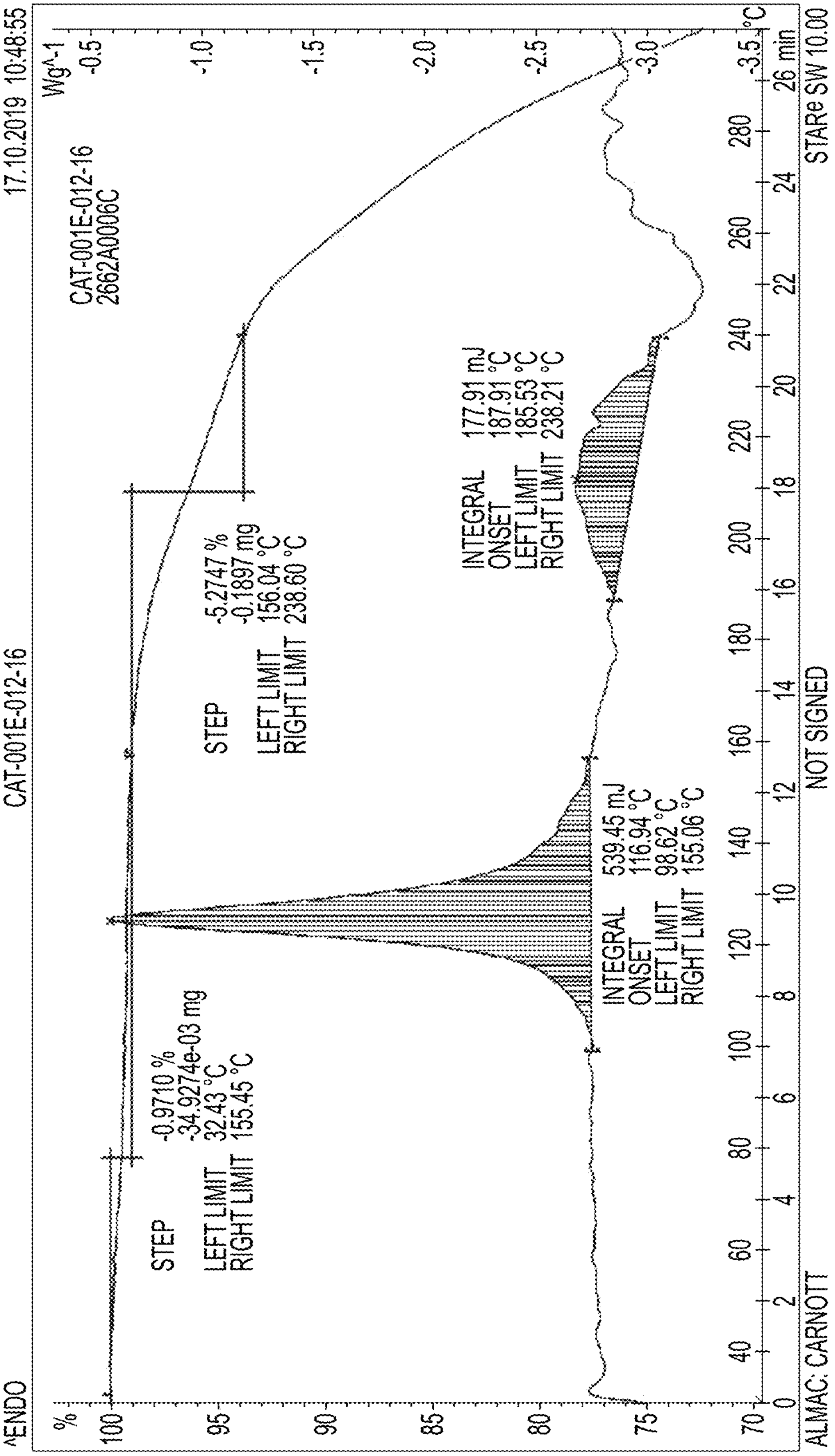
FIG. 51 provides a TG/DTA thermogram of suspected AAT-730 L-lactate analyzed from 30 to 300° C. at 10° C. per minute.

AAT-730 L-lactate (L-lactic acid salt) was isolated from a precipitation experiment of AAT-730 and L-lactic acid (1 mol. eq.) in either ethanol or THF/water. XRPD analysis (FIG. 49) showed that the material was composed of a crystalline solid. $^1H$ NMR analysis (FIG. 50) suggested formation of a mono-lactate salt. The TG/DTA thermogram (FIG. 51) showed a probable melting onset at up to 117° C. and minimal weight loss between 3° and 150° C. due to residual solvent. The material had a solubility of approximately 320-640 mg/mL in water and was stable to stressing at 40° C./75% RH for 1 week.

Example 3-15, Characterization of AAT-730 (Compound A) Maleate

Figure 52:
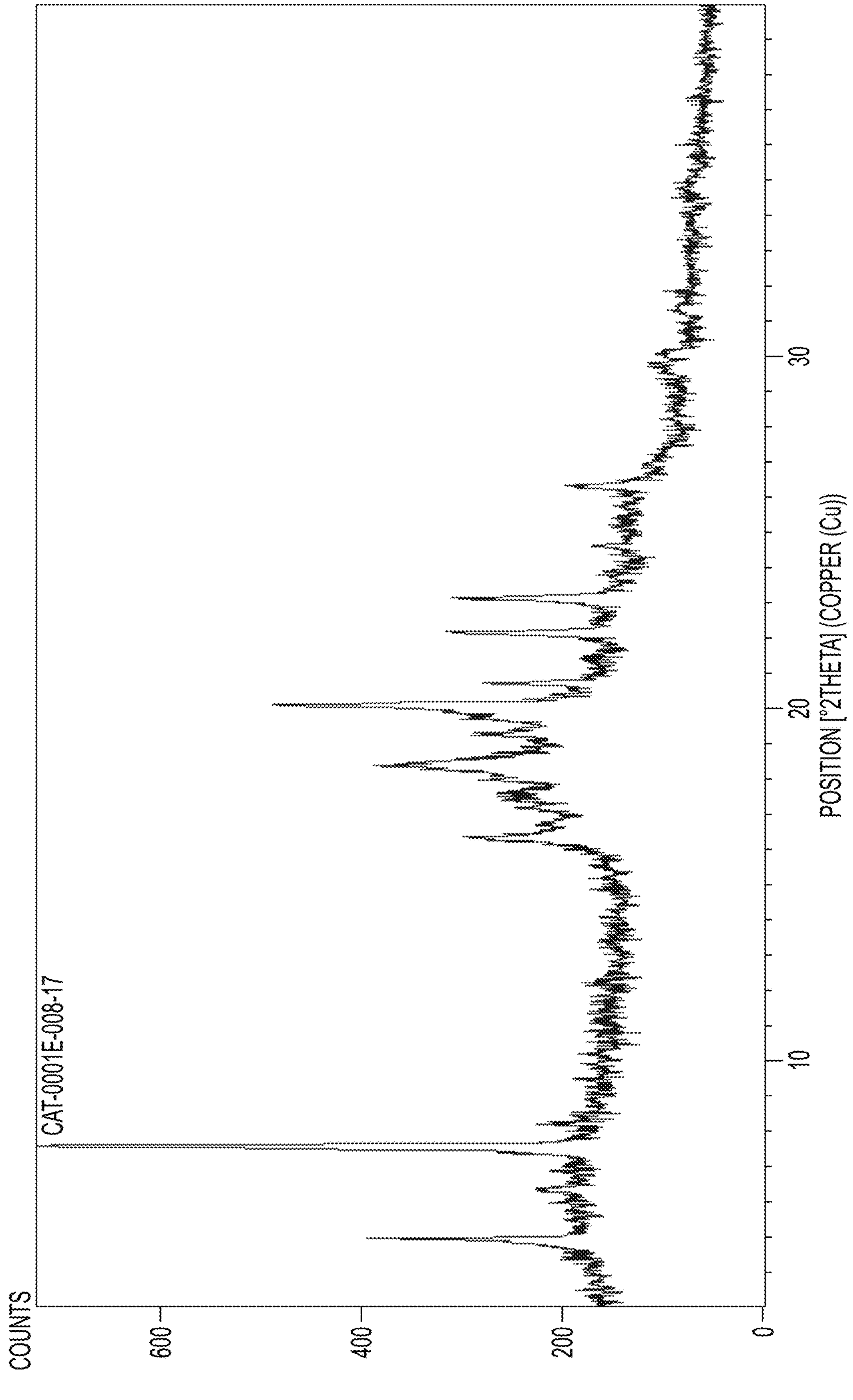
FIG. 52 provides an XRPD pattern of suspected AAT-730 maleate.
Figure 53:
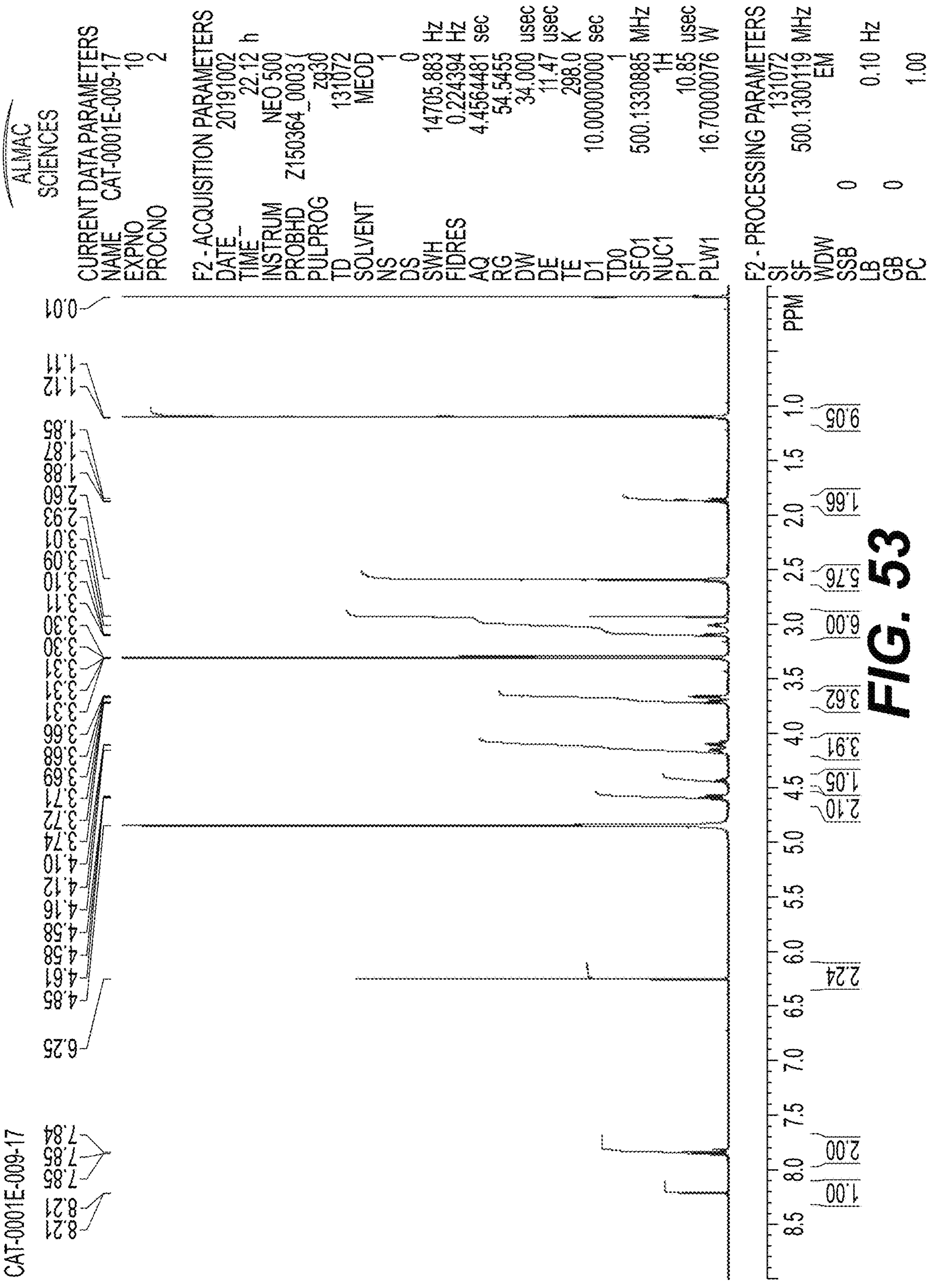
FIG. 53 provides a $^{1}H$ NMR spectrum of suspected AAT-730 maleate.
Figure 54:
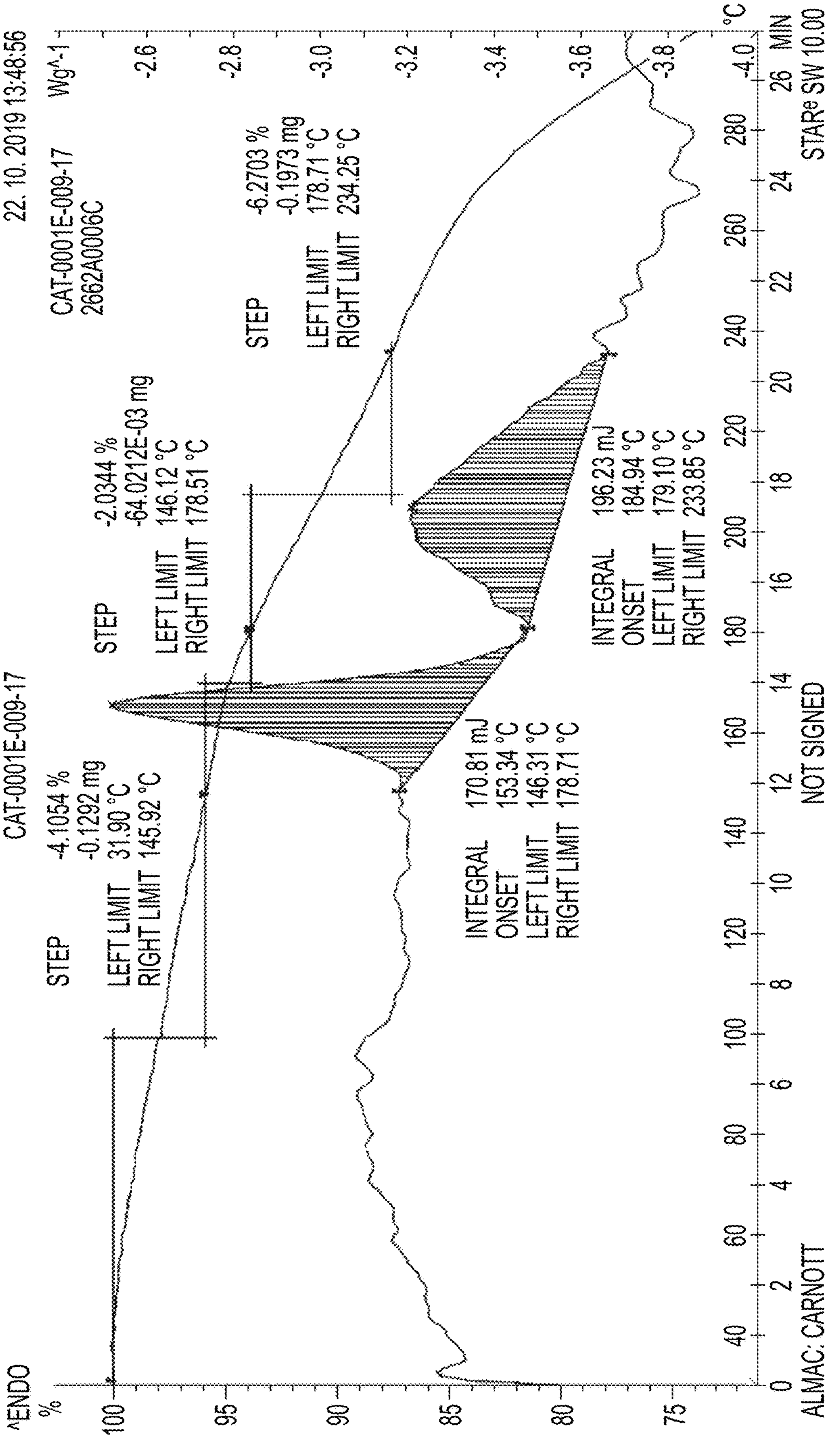
FIG. 54 provides a TG/DTA thermogram of suspected AAT-730 maleate analyzed from 30 to 300° C. at 10° C. per minute.

A suspected AAT-730 maleate (maleic acid salt) was isolated from precipitation experiments in THF and THF/water. The solid was crystalline by XRPD analysis (FIG. 52) and $^1H$ NMR analysis (FIG. 53) suggested formation of a mono-maleate. TG/DTA (FIG. 54) showed a probable melting endotherm at onset up to 153° C. Weight loss observed in the thermogram is likely to be due to residual THF which was also noted in the $^1H$ NMR spectrum. The salt had an aqueous solubility of approximately 280-560 mg/mL and it was stable to stressing at 40° C./75% RH for 1 week.

Example 3-16, Characterization of AAT-730 (Compound A) MSA Salt

Figure 55:
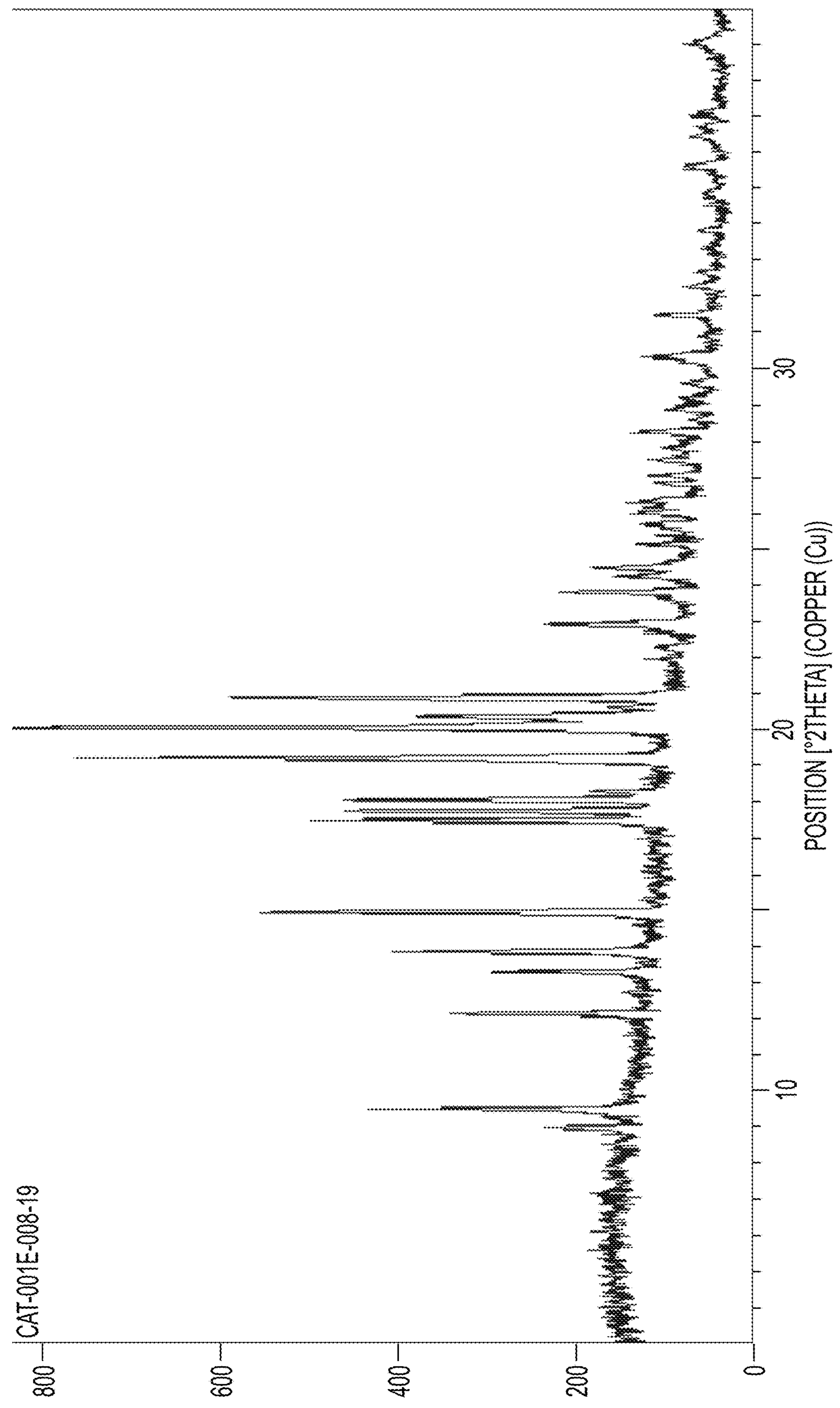
FIG. 55 provides an XRPD diffractogram of suspected AAT-730 MSA salt.
Figure 56:
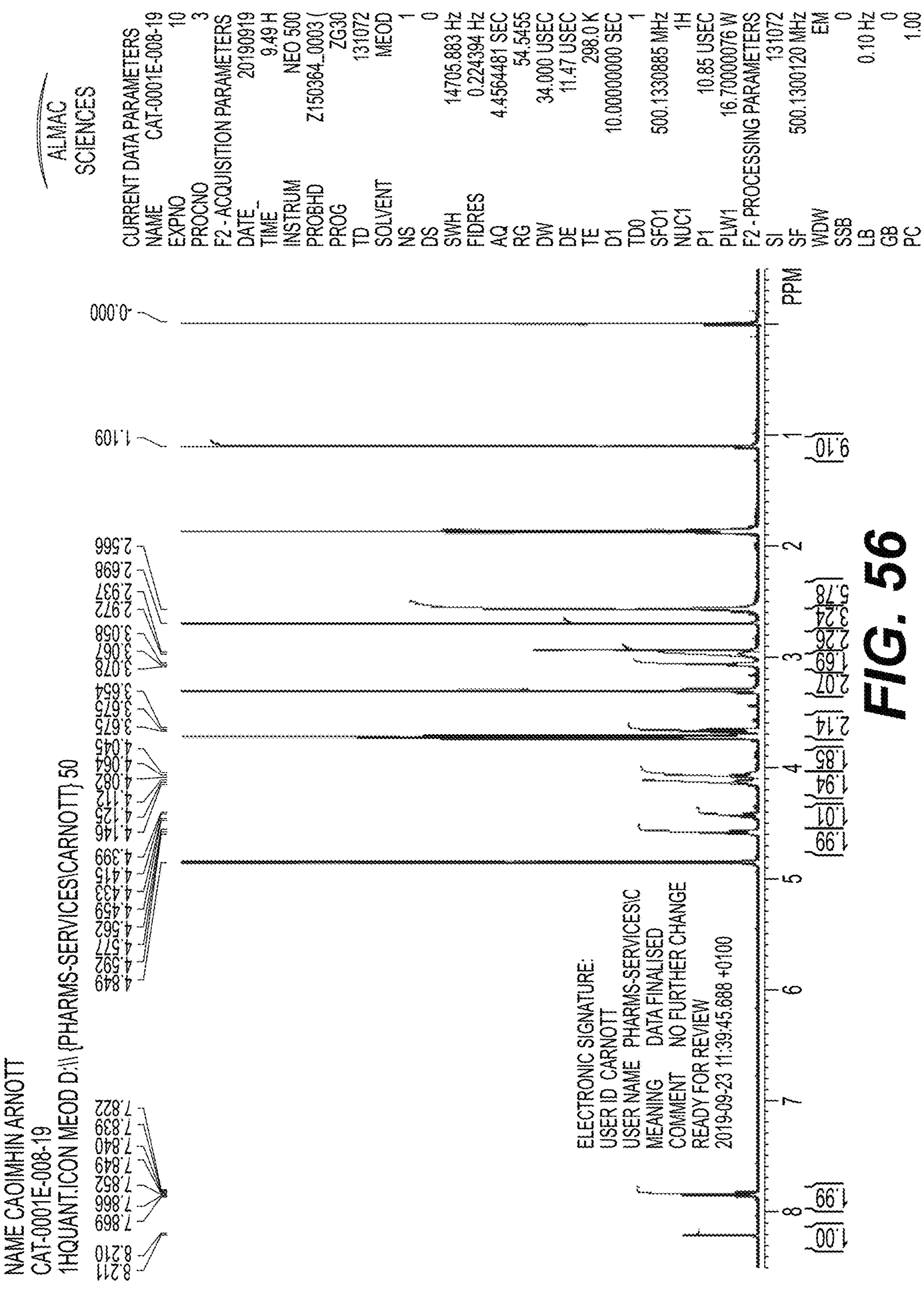
FIG. 56 provides a $^{1}H$ NMR spectrum of suspected AAT-730 MSA salt.
Figure 57:
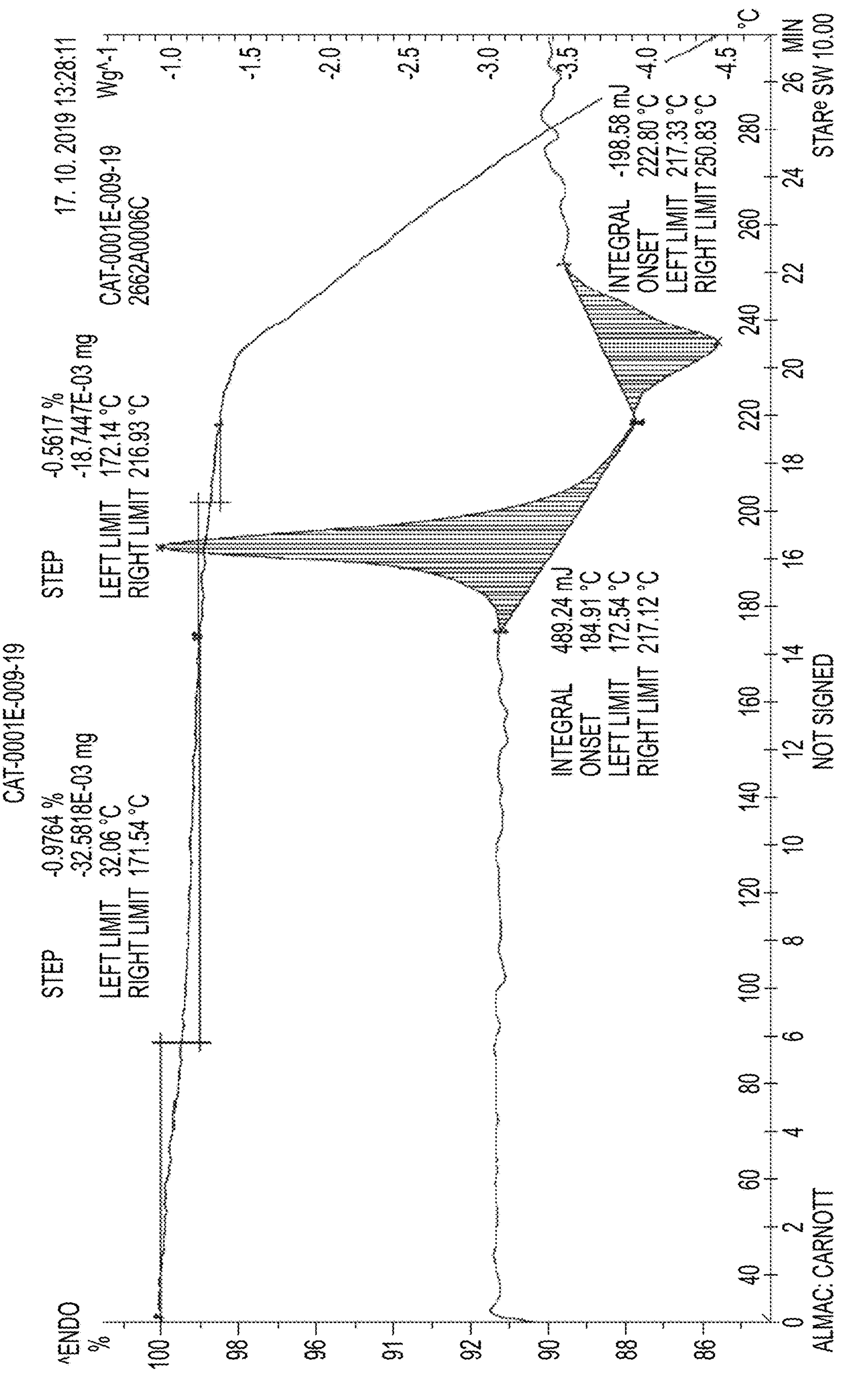
FIG. 57 provides a TG/DTA analysis of AAT-730 MSA salt analyzed from 30 to 300° C. at 10° C. per minute.

A suspected AAT-730 MSA salt was isolated from precipitation experiments in THF and THF/water. The solid was crystalline by XRPD analysis (FIG. 55) and $^1H$ NMR analysis (FIG. 56) suggested formation of a mono-MSA salt of AAT-730. TG/DTA analysis (FIG. 57) showed minimal weight loss between 3° and 150° C. suggesting an anhydrous form. A probable melting endotherm was observed at onset up to 155° C. An exotherm immediately after melting may be due to recrystallisation or decomposition. The salt had a solubility of approximately 228-260 mg/mL in water and was stable to stressing at 40° C./75% RH for 1 week.

Figure 58:
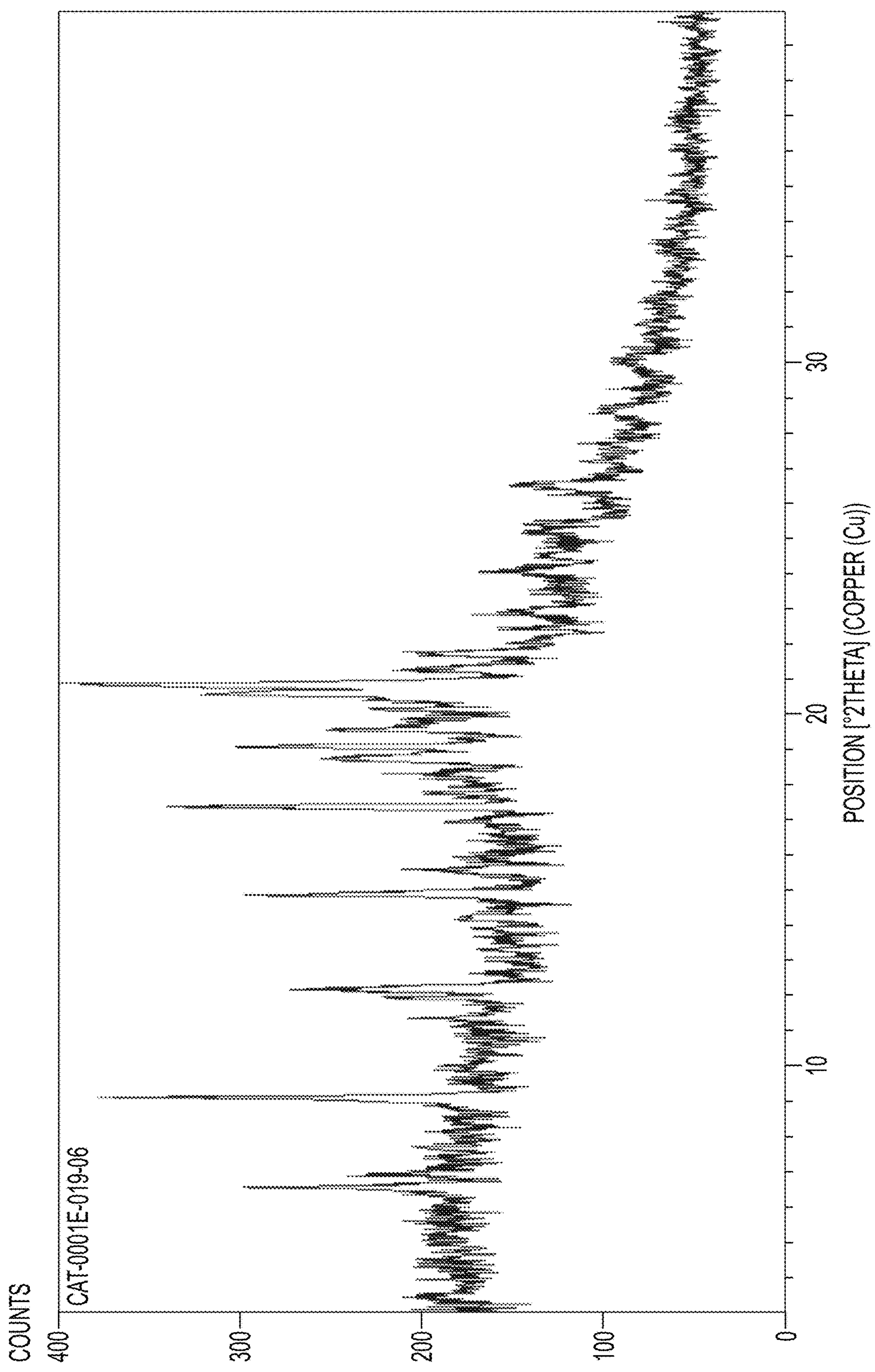
FIG. 58 provides an XRPD diffractogram of suspected AAT-730 MSA salt.
Figure 59:
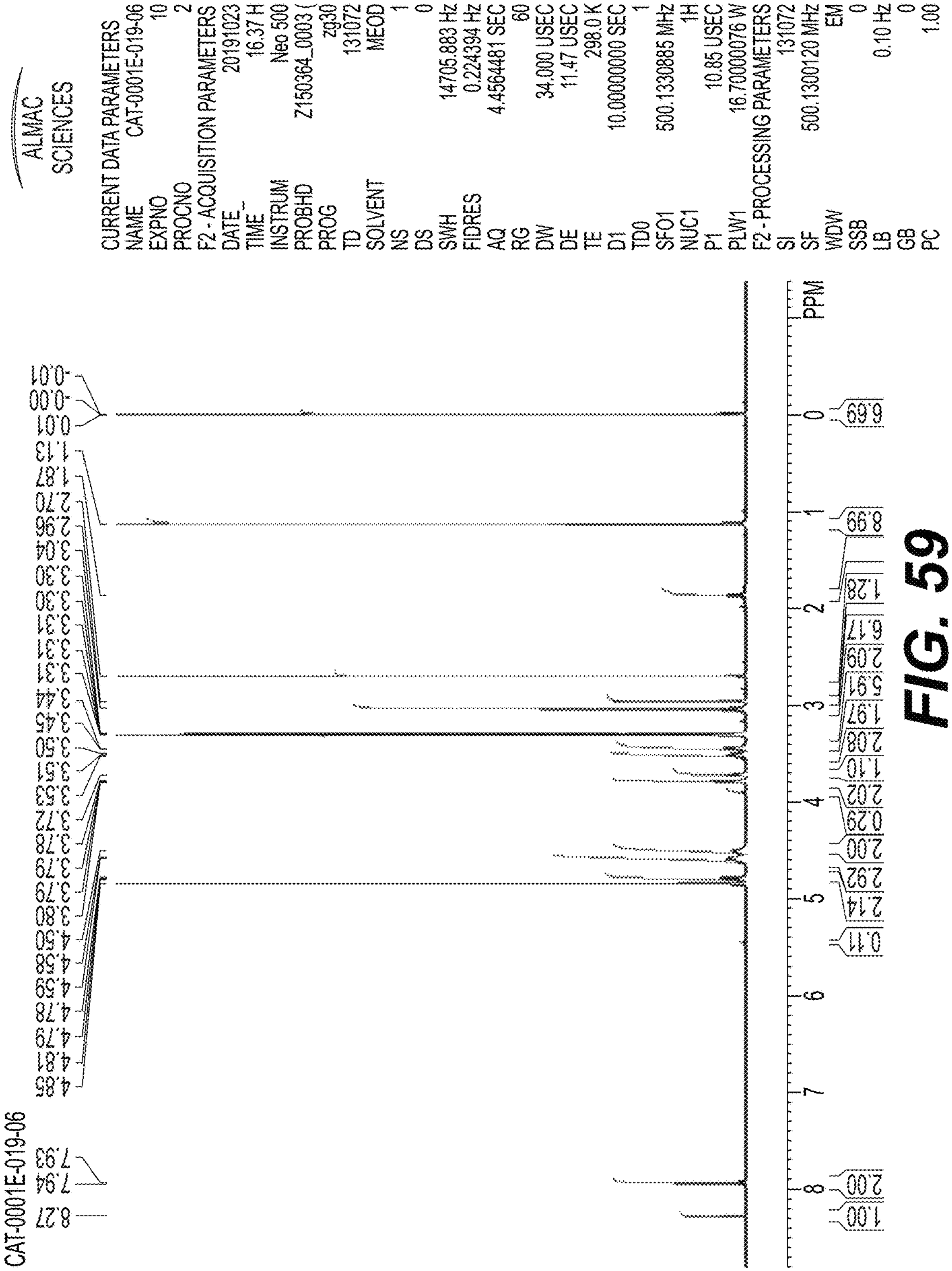
FIG. 59 provides a $^{1}H$ NMR spectrum of suspected AAT-730 MSA salt.

A second possible MSA salt was isolated from a screening experiment of AAT-730 with 2 moles of MSA in THF. $^1H$ NMR analysis (FIG. 59) suggests that this may be a 1:2 salt (API:acid). The material was crystalline by XRPD analysis (FIG. 58) and it deliquesced on stressing at 40° C./75% RH.

Example 3-17, Characterization of AAT-730 (Compound A) Succinate

Figure 60:
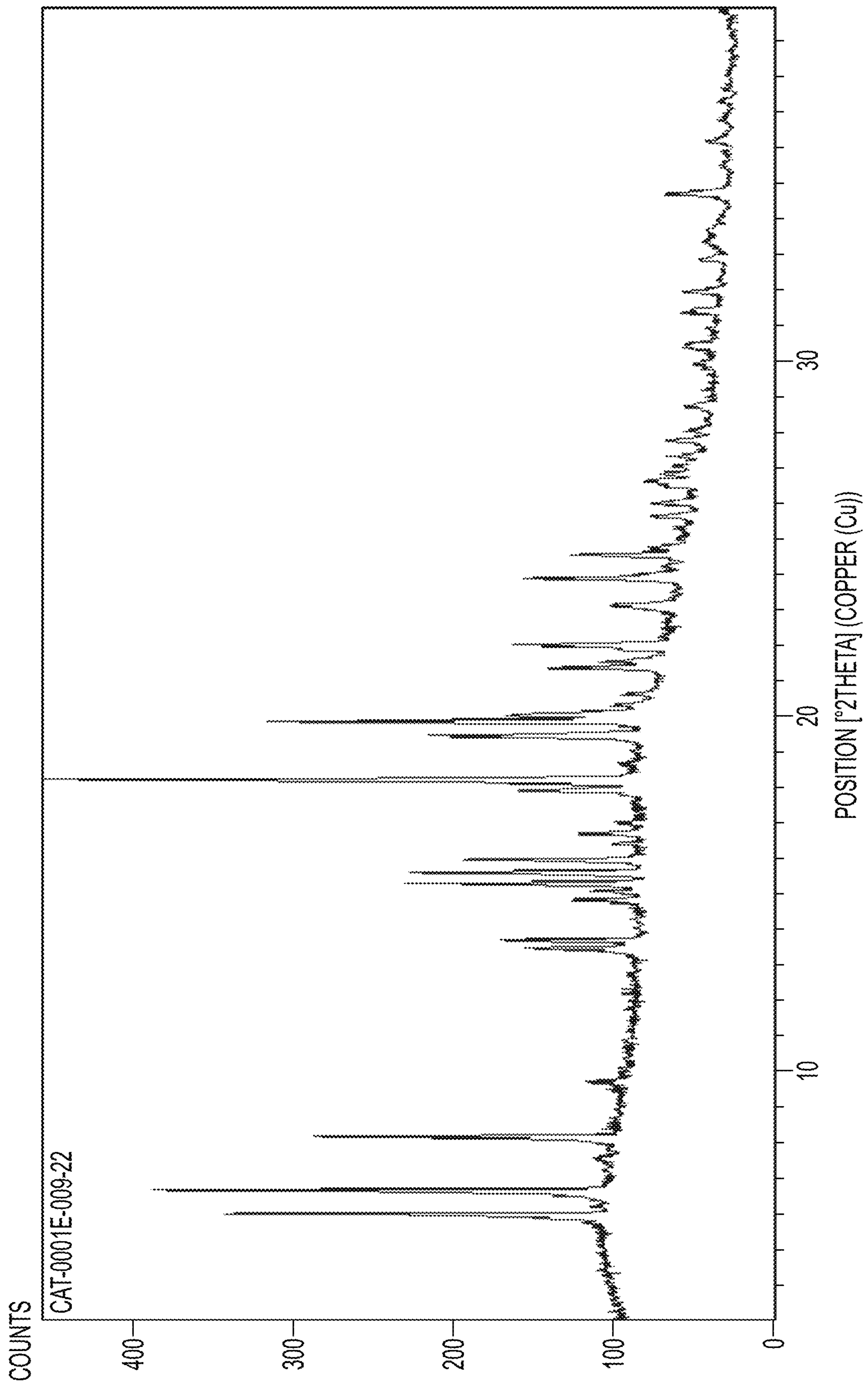
FIG. 60 provides an XRPD diffractogram of suspected AAT-730 succinate.
Figure 61:
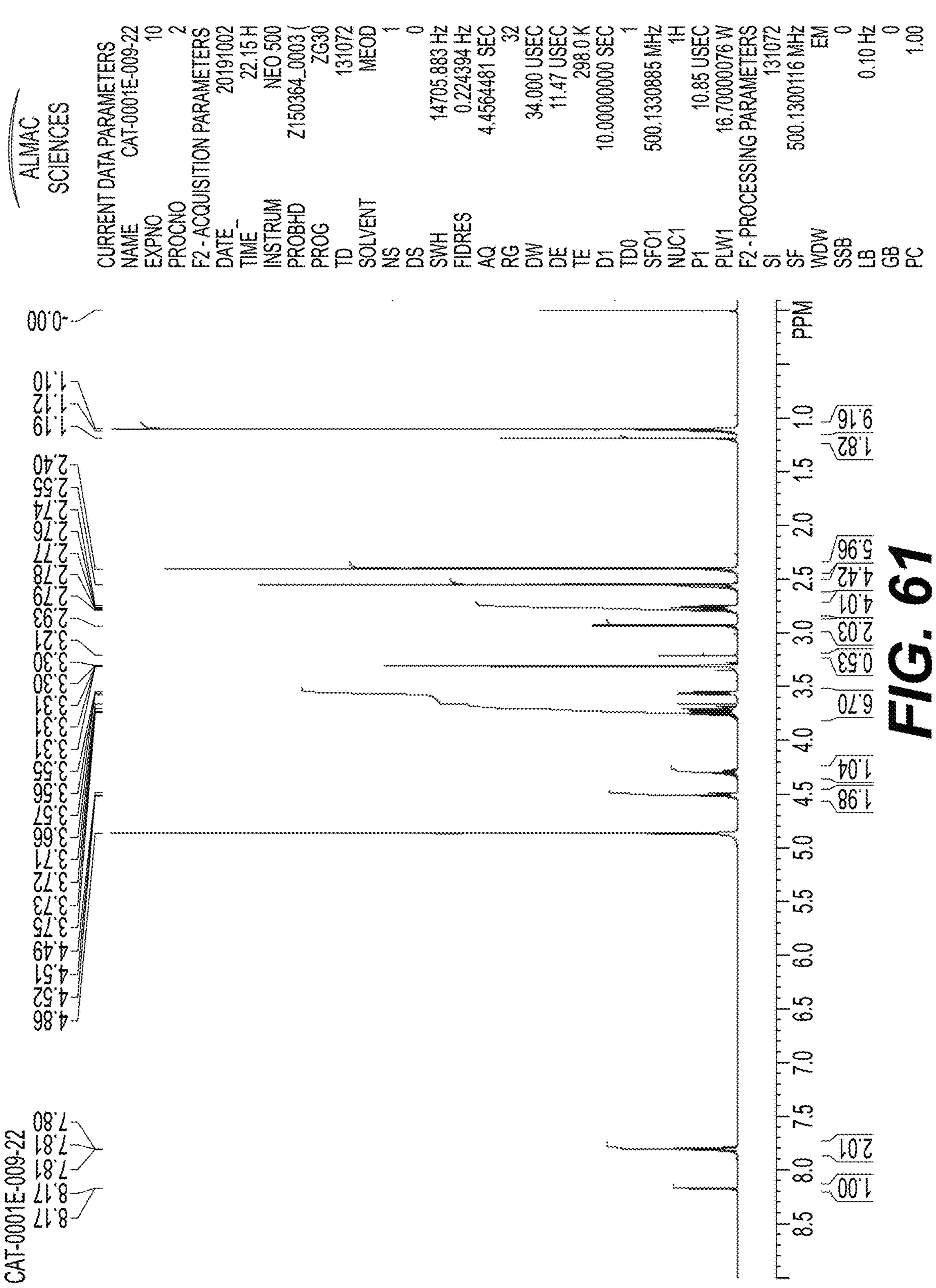
FIG. 61 provides a $^{1}H$ NMR analysis of suspected AAT-730 succinate.

The succinate (succinic acid salt) of AAT-730 was isolated from salt formation experiments in THF/water or ethanol to form gels which were then triturated in either MTBE or EtOAc to form a solid which was crystalline by XRPD analysis (FIG. 60). $^1H$ NMR analysis (FIG. 61) suggested formation of a mono-succinate which deliquesced on stressing at 40° C./75% RH.

Example 3-18, Characterization of AAT-730 (Compound A) Sulfate

Figure 62:
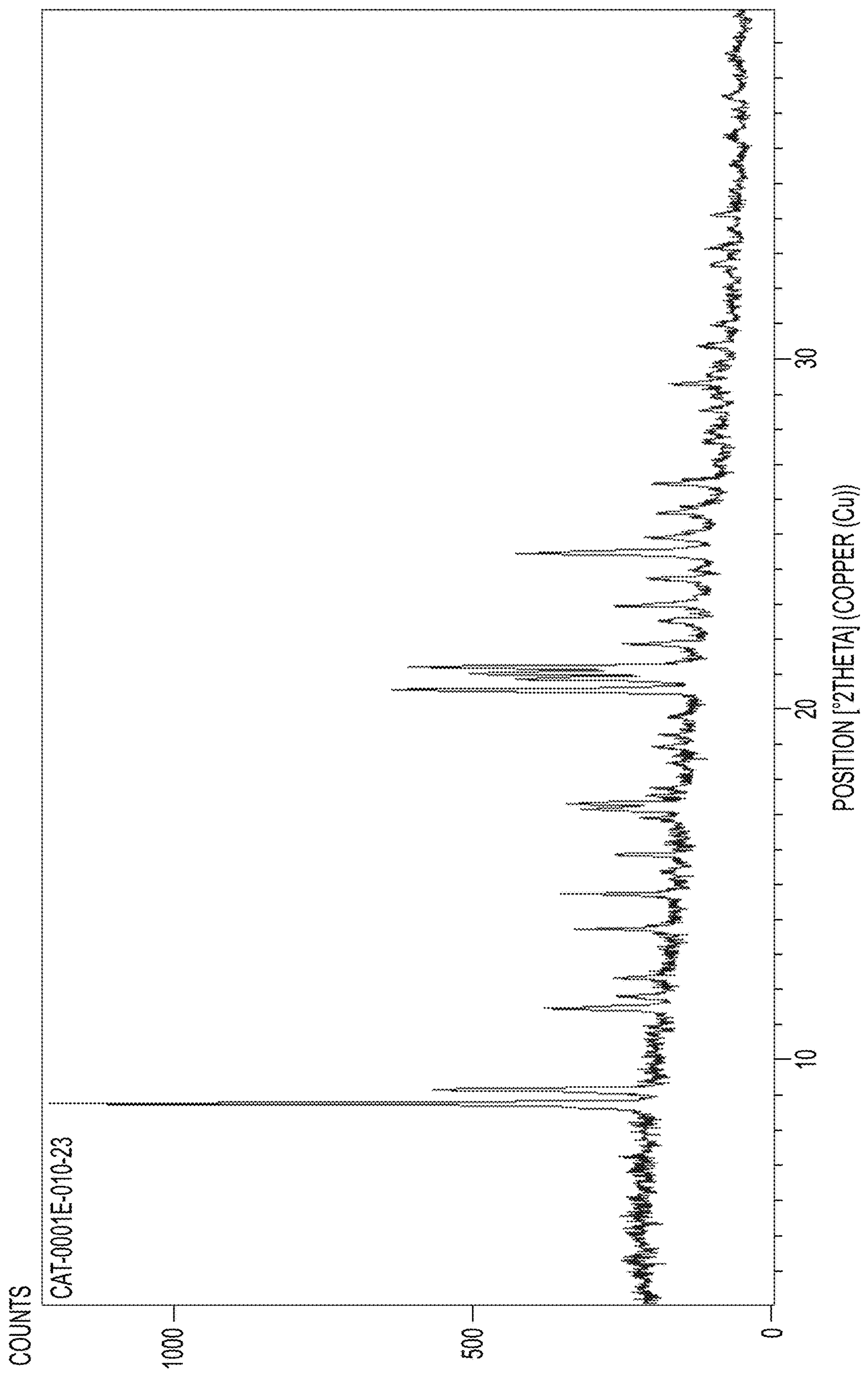
FIG. 62 provides an XRPD diffractogram of suspected AAT-730 sulfate.
Figure 63:
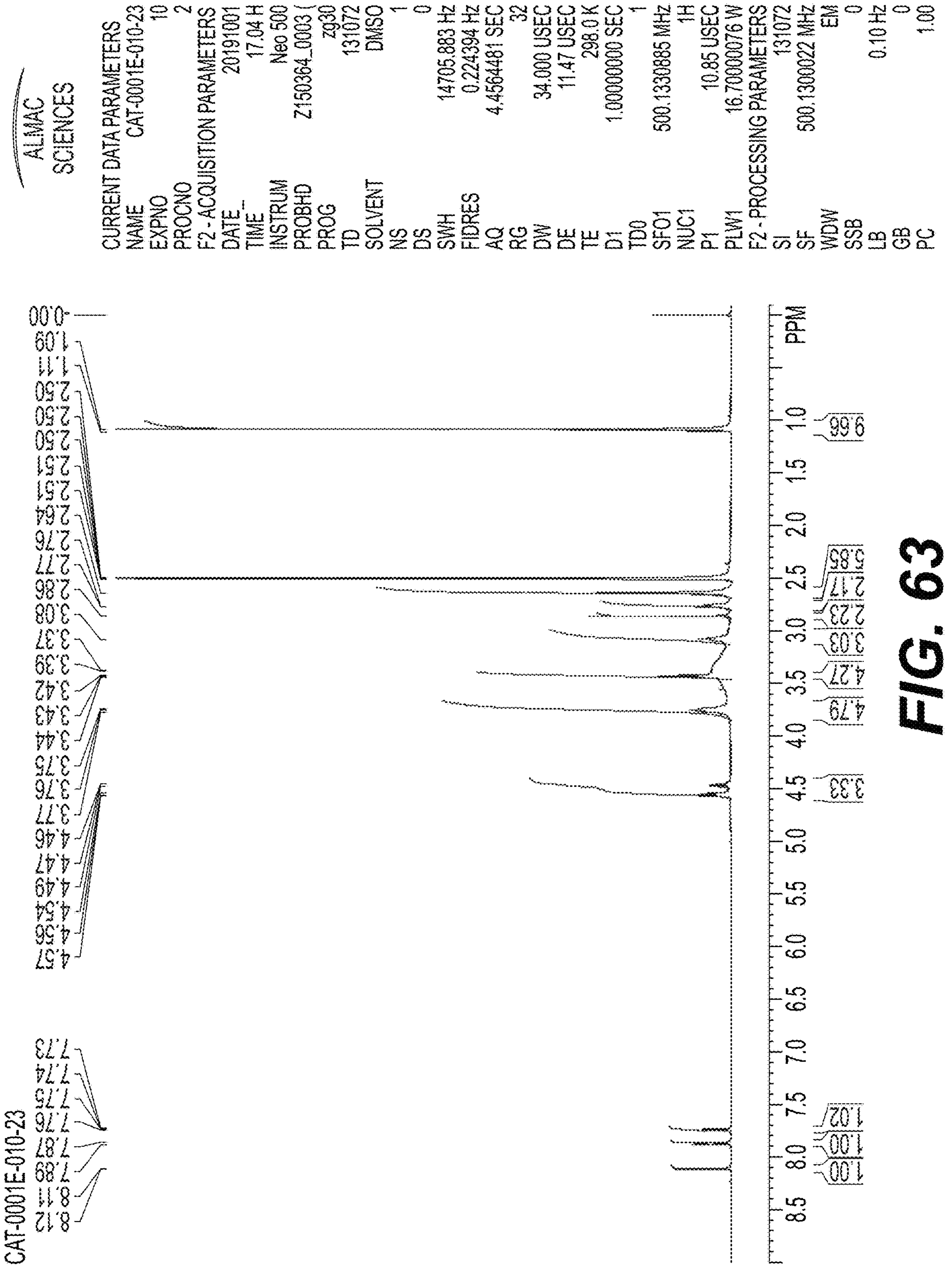
FIG. 63 provides a $^{1}H$ NMR analysis of suspected AAT-730 sulfate.

AAT-730 sulfate was isolated from a salt formation experiment in THF which was evaporated to yield a gel. The gel was triturated in MTBE to yield the salt as a solid which was crystalline by XRPD analysis (FIG. 62). $^1H$ NMR analysis suggested formation of a salt as peak shifting was observed in the $^1$H NMR spectrum (FIG. 63). Stoichiometry could not be determined by $^1$H NMR analysis and the solids did not deliquesce on stressing at 40° C./75% RH.

Figure 64:
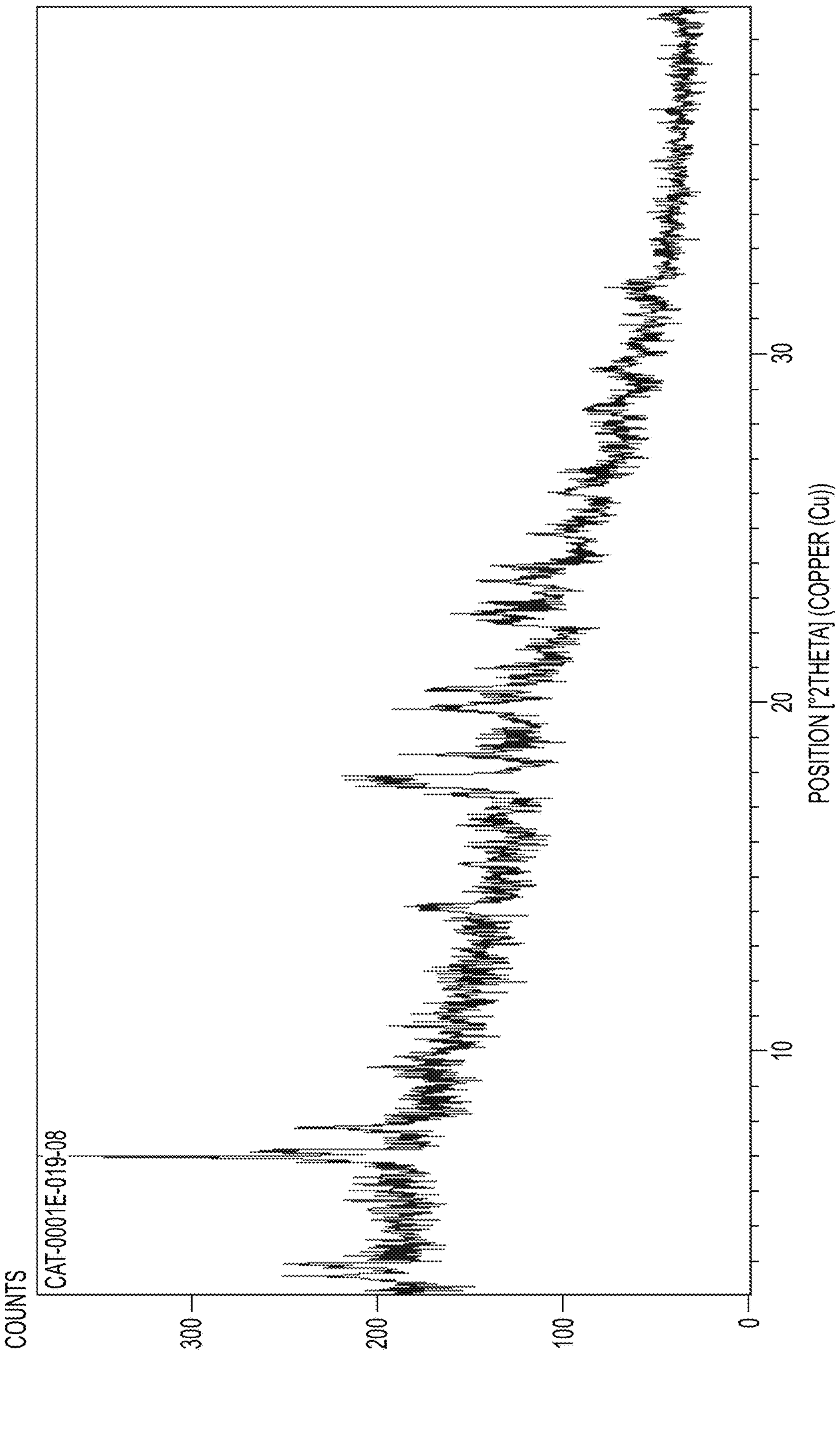
FIG. 64 provides an XRPD diffractogram of suspected AAT-730 sulfate (Pattern B).

Another possible sulfate was isolated from the screening experiment with 2 mol. eq. of $H_2SO_4$ and analyzed by XRPD (FIG. 64). This deliquesced on stressing at 40° C./75% RH.

Example 4, AAT-730 (Compound A) HCl Salt and Maleate

The preparation of the HCl salt and maleate (maleic acid salt) of AAT-730 was scaled up to 250 mg. Both salts were characterized using a range of techniques including XRPD, DSC, TG/DTA, $^1$H NMR, and microscopy. The stability was also tested at a range of elevated relative humidity conditions for 7 days. The solubility of AAT-730 HCl salt Pattern A was estimated in various solvent systems.

Method 4-1, Solubility Estimation Method

Aliquots of the test solvent were added to an accurately weighed sample (at most 20 mg) of AAT-730 HCl salt at ambient temperature. The aliquot volumes were typically 25-100 μL. Complete dissolution of the test material was determined by visual inspection. The solubility was estimated from these experiments based on the total solvent used to provide complete dissolution. It should be noted that the actual solubility may be greater than that calculated because of the use of solvent aliquots that were too large or due to a slow rate of dissolution.

If dissolution did not occur after the last aliquot of solvent was added (typically up to 50 volumes of solvent), the sample was subjected to two cycles of the following temperature cycling regime on the Clarity crystallization station:

Heating from 20° C. to within 3° C. of solvent boiling point (or 100° C., whichever was lower) at 0.5° C./minute.

Cooling to 20° C. at 0.2° C./minute.

Stirring speed 600 rpm.

From the infrared (IR) transmission data of the sample vials, dissolution and precipitation events were recorded as the point of complete transmission of IR and the onset of turbidity by IR respectively.

Samples were held at ambient temperature for 18 hours to maximize the chance of precipitation. Any recoverable solids were analyzed by XRPD. The solubility values for AAT-730 HCl salt were expressed as a range and rounded to the nearest whole number. From this data, the solvents were grouped in the following manner to guide the screening experiments:

Solvents (A): AAT-730 HCl salt was soluble in less than or equal to 50 volumes (greater than or equal to 20 mg/mL) at ambient temperature.

Soluble with heating (B): AAT-730 HCl salt was not soluble in 50 volumes at ambient but dissolved at higher temperatures. These solvents could be regarded as possible solvents for cooling crystallizations.

Anti-solvents (C): AAT-730 HCl salt was not soluble in 50 volumes at all temperatures studied.

Example 4-1, Preparation of AAT-730 (Compound A) HCl Salt Pattern a

AAT-730 (250 mg) and THF (1.25 mL) were stirred in a vial and a solution of HCl in dioxane (4 M, 177.5 μL) was added dropwise. This was stirred at 400 rpm for up to 16 hours. A gel had formed on the surface and a further portion of THF (1 mL) was added. The crust was broken with a pipette and the mixture instantly became cloudy and a thick white precipitate formed. The mixture was centrifuged, and the supernatant was removed. THF (at most 1 mL) was added and the mixture was agitated, centrifuged and solvent decanted. This was repeated and the solids were dried under $N_2$ overnight to yield the product as a white solid (185 mg, 68% yield).

Example 4-2, Characterization of AAT-730 (Compound A) HCl Salt Pattern a

Figure 65:
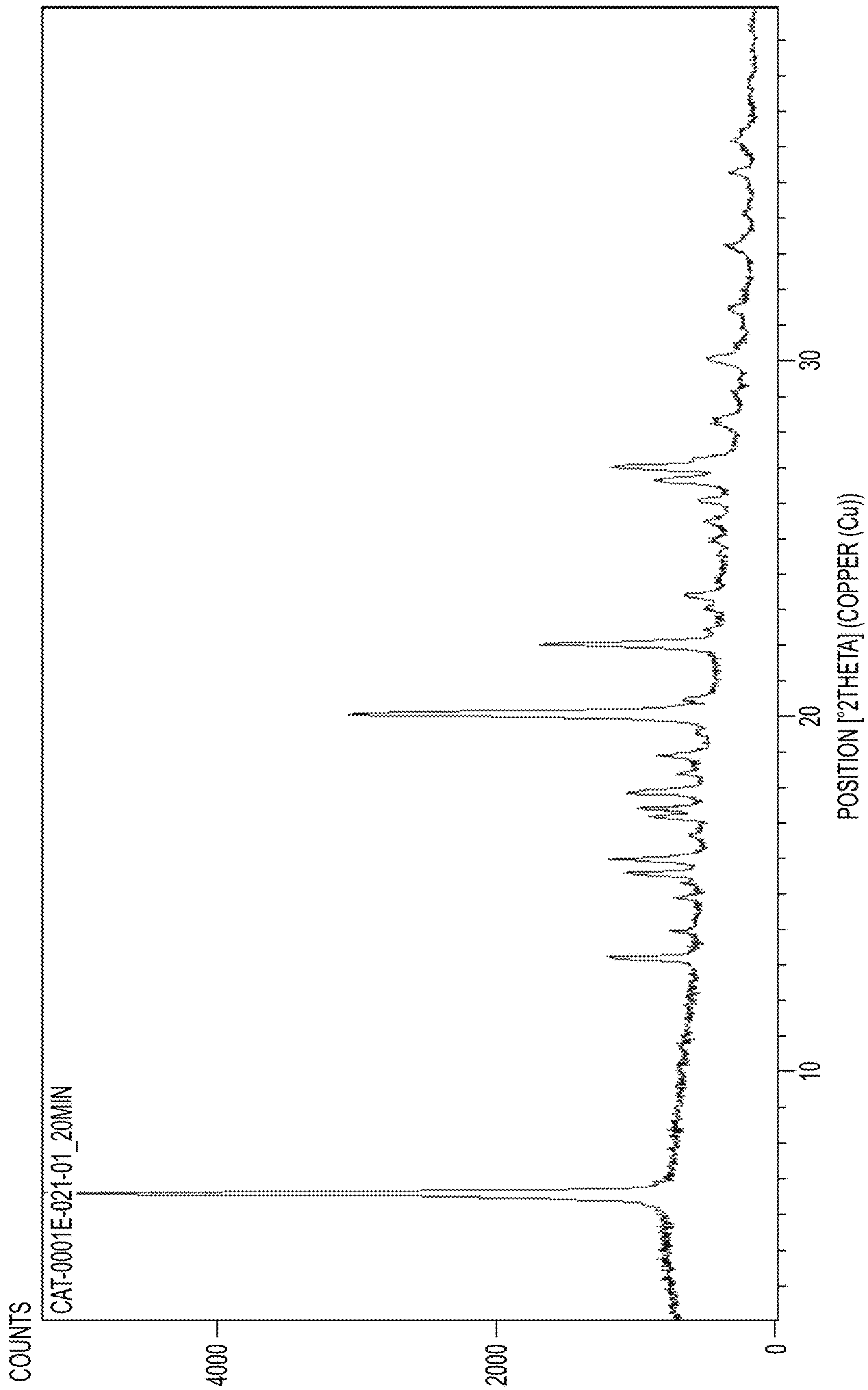
FIG. 65 provides an XRPD pattern of AAT-730 HCl salt Pattern A.

AAT-730 HCl salt Pattern A was prepared on at most 185 mg scale from a precipitation experiment of AAT-730 and HCl (1 mol. eq.) in THF. The solids were characterized, and the results are detailed below. The XRPD diffractogram (FIG. 65) was consistent with a crystalline solid and was composed of the same form as the previously prepared AAT-730 HCl salt Pattern A material.

Figure 66:
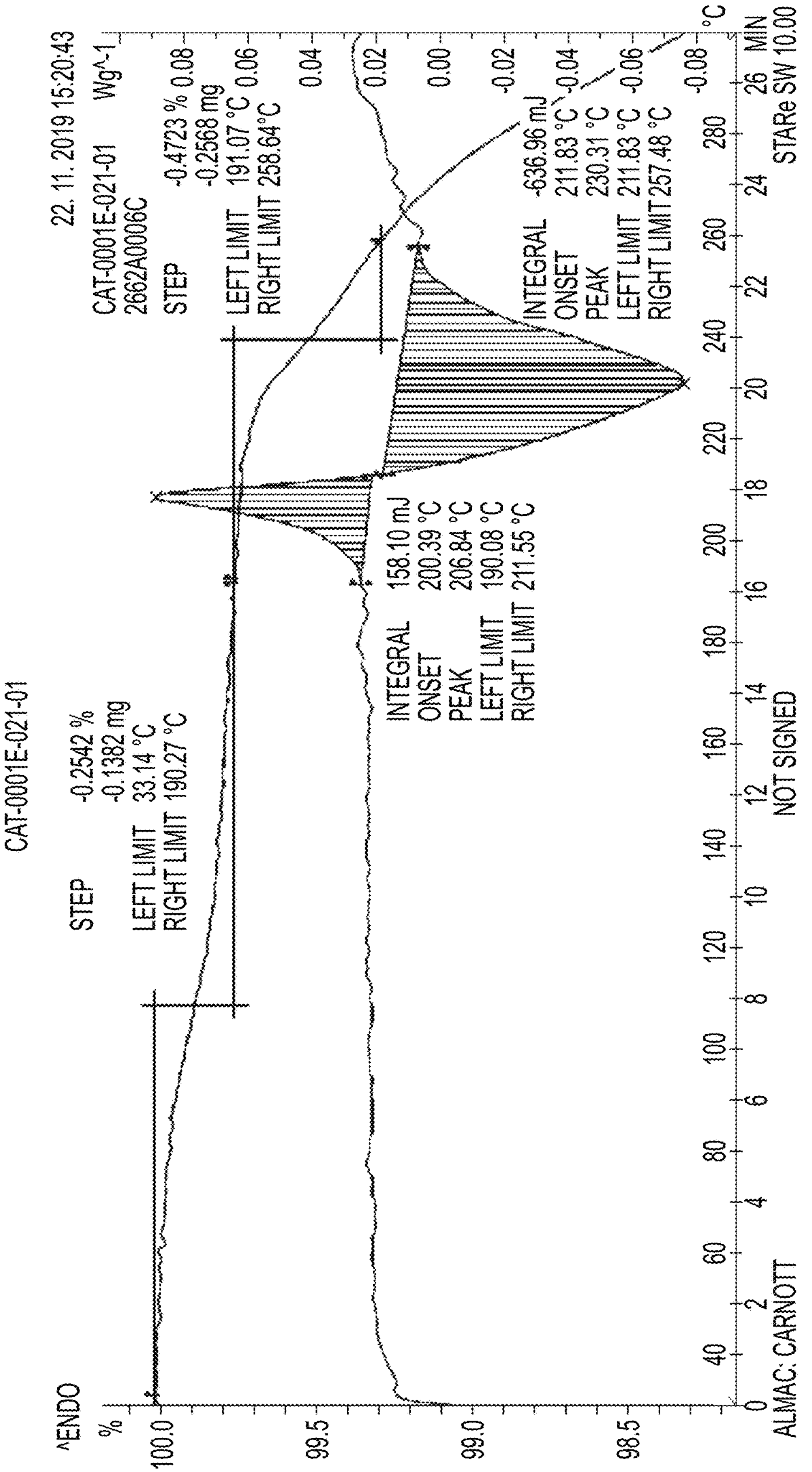
FIG. 66 provides a TG/DTA thermogram for AAT-730 HCl salt Pattern A analyzed from 30-300° C. at 10° C. per minute.

Thermogravimetric/Differential Thermal Analysis (TG/DTA) was performed to determine the thermal profile and associated % weight changes of AAT-730 HCl salt Pattern A (FIG. 66). The TG/DTA data showed a melting endotherm at onset up to 200° C. Weight loss of at most 0.25% w/w was observed between approximately 30 and 190° C. which suggests an anhydrous material with a small amount of residual solvent. An exotherm at onset up to 212° C. may be due to crystallization to another form or decomposition.

Figure 67:
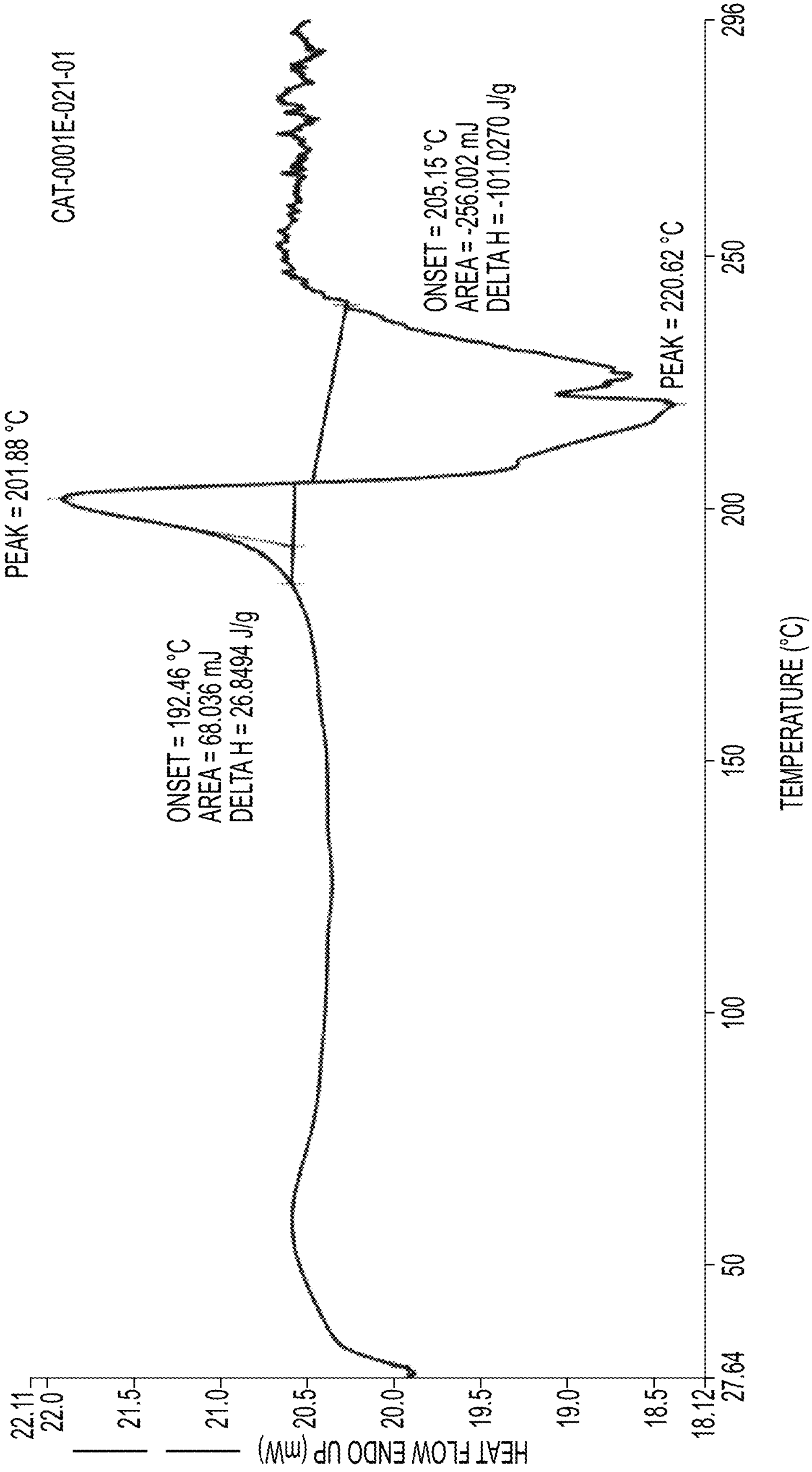
FIG. 67 provides a DSC thermogram for AAT-730 HCl salt Pattern A analyzed from 30-300° C. at 10° C. per minute.

The DSC thermogram obtained for AAT-730 HCl salt Pattern A at 10° C./min is shown in FIG. 67 and the melting onset is 192.46° C.

Figure 68:
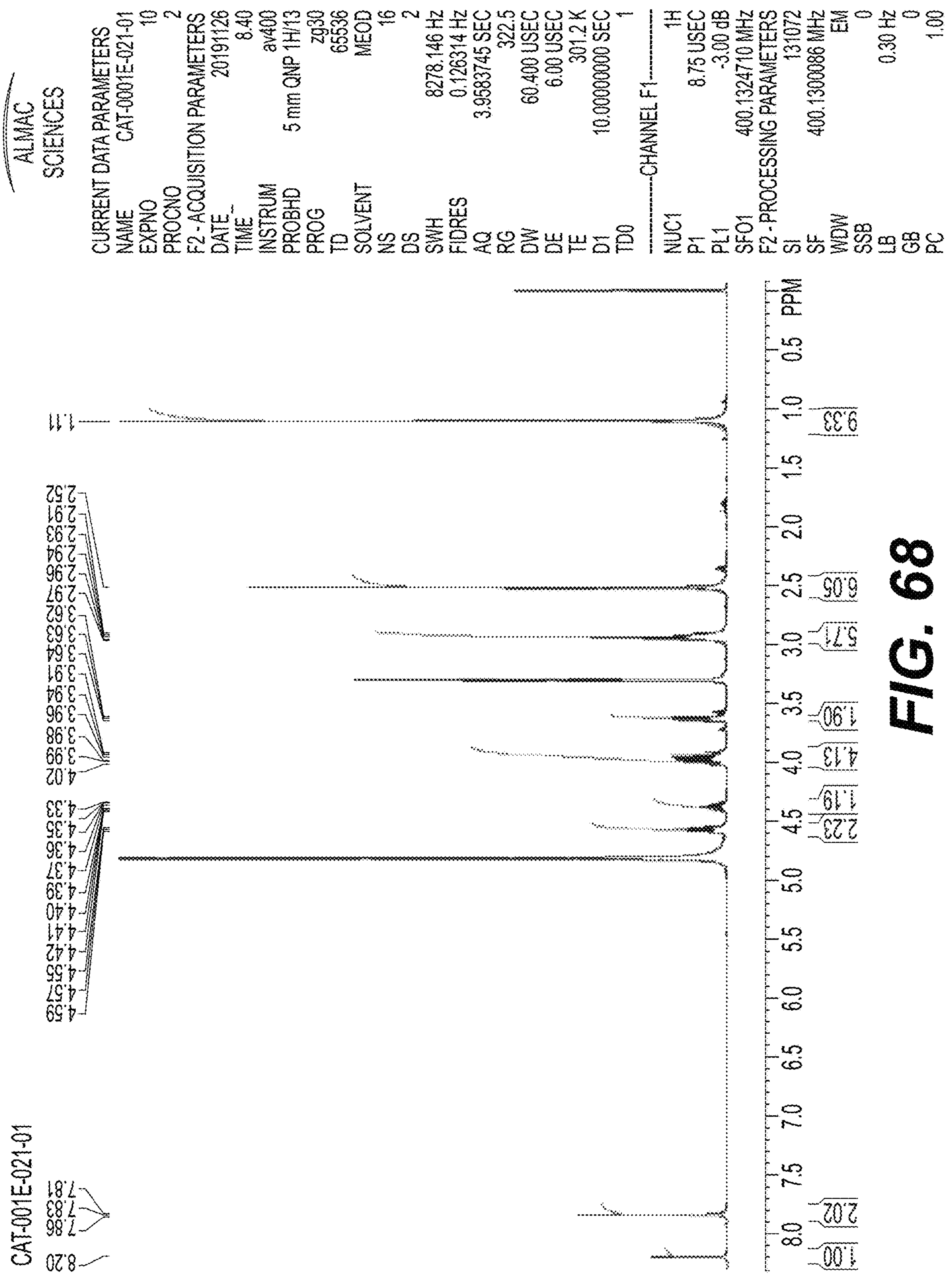
FIG. 68 provides a $^{1}H$ NMR spectrum of AAT-730 HCl salt (analyzed in $CD_3OD$).

The $^1$H NMR spectrum of AAT-730 HCl salt Pattern A analyzed in $CD_3OD$ (FIG. 68) conformed to the molecular structure and a small amount of residual THF was observed in the spectrum. This concurs with the TG/DTA data.

Figure 69:
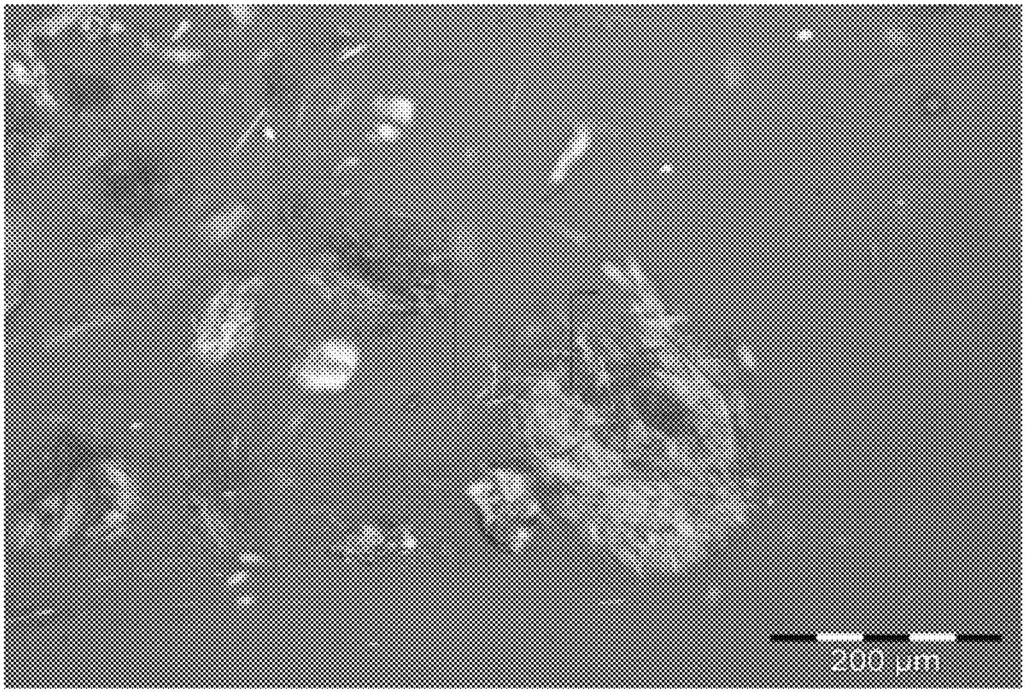
FIG. 69 provides a Photomicrograph of AAT-730 HCl salt.

Polarized light microscopy of AAT-730 HCl salt Pattern A solids (FIG. 69) showed that the material is composed of fine acicular particles and some aggregation and/or agglomeration is observed.

Figure 103:
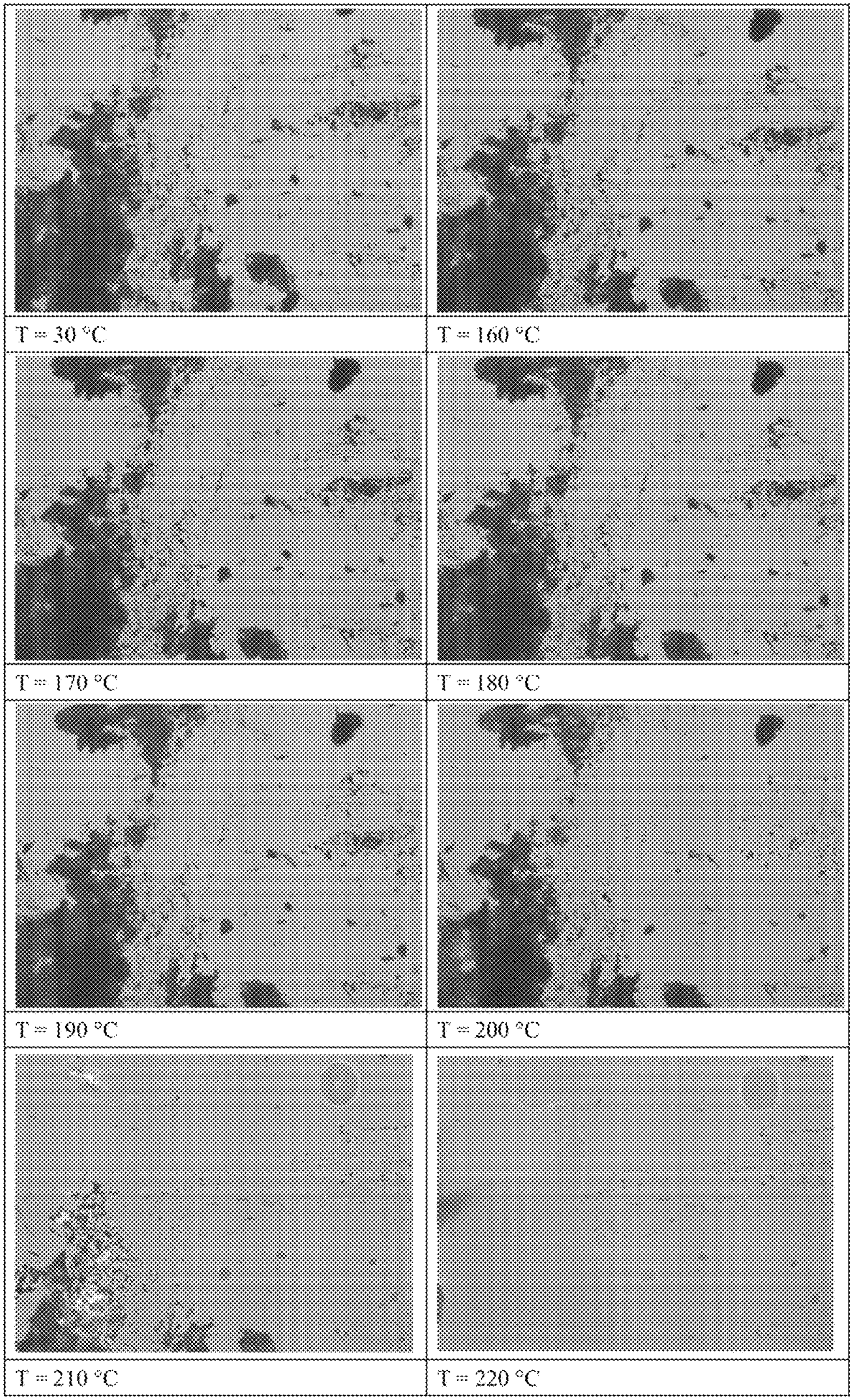
FIG. 103 provides hot-stage microscopy carried out using a Linkam hot-stage accessory and the photomicrographs of AAT-730 HCl salt Pattern A.

Hot-stage microscopy was carried out using a Linkam hot-stage accessory and the photomicrographs are shown in FIG. 103. The material remains mostly unchanged on heating until approximately 190° C. Between 190° C. and 200° C. some changes in the bulk density can be observed as the solids begin to melt. The bulk density has further reduced by 210° C. and the material has completely liquefied by 220° C.

Hot-stage photomicrographs of AAT-730 HCl salt Pattern A are shown in FIG. 103.

Example 4-3, Humidity Stress of AAT-730 (Compound A) HCl Salt

Sample of AAT-730 HCl salt was added to HPLC vials. The vials were placed, uncapped, into RH chambers as shown in Table 4-2.

The relative humidity of the chambers was controlled by supersaturated salt solutions. The samples were removed after 1 week and the XRPD patterns were acquired.

Figure 70:
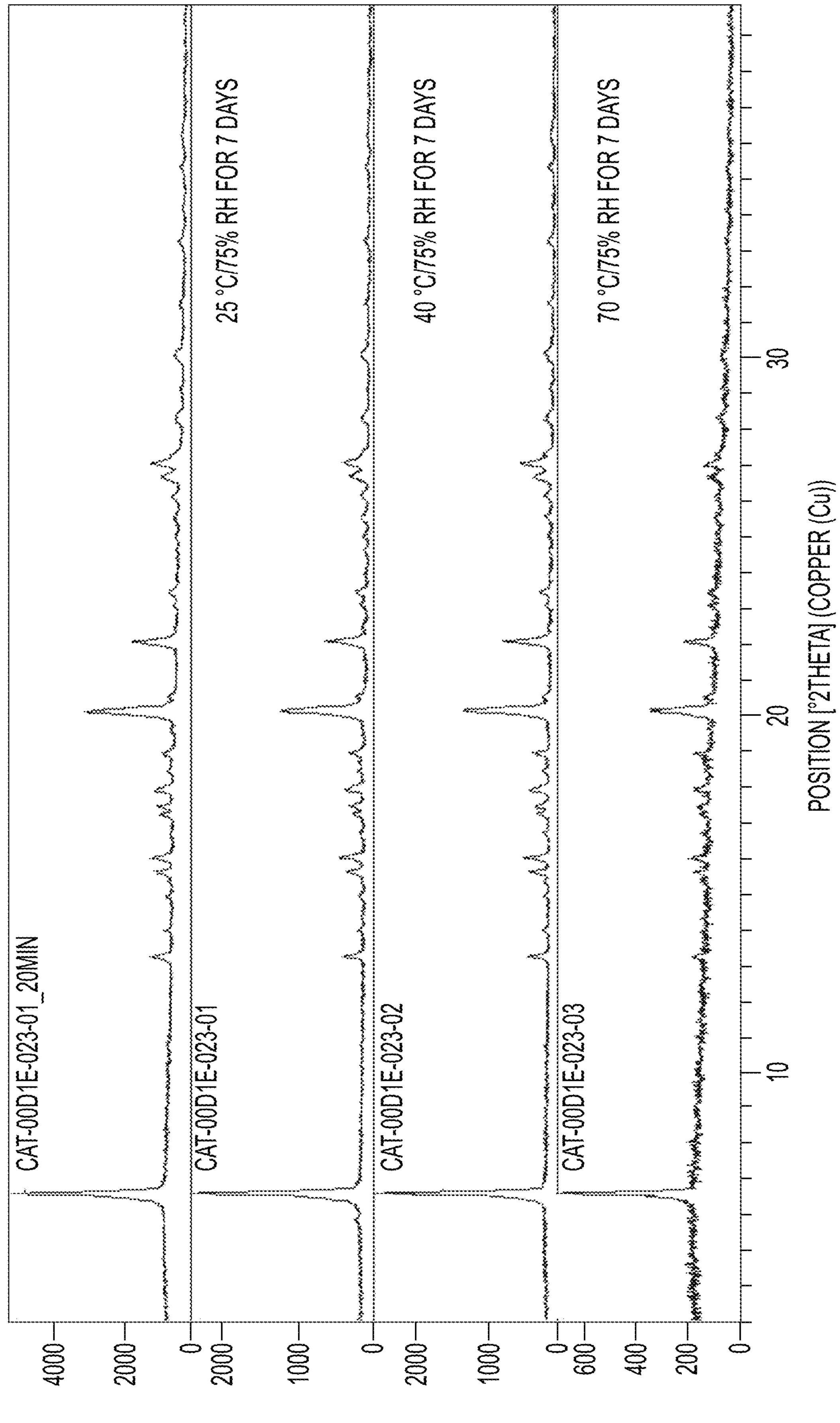
FIG. 70 provides an XRPD patterns of AAT-730 HCl salts post stressing.
Figure 71:
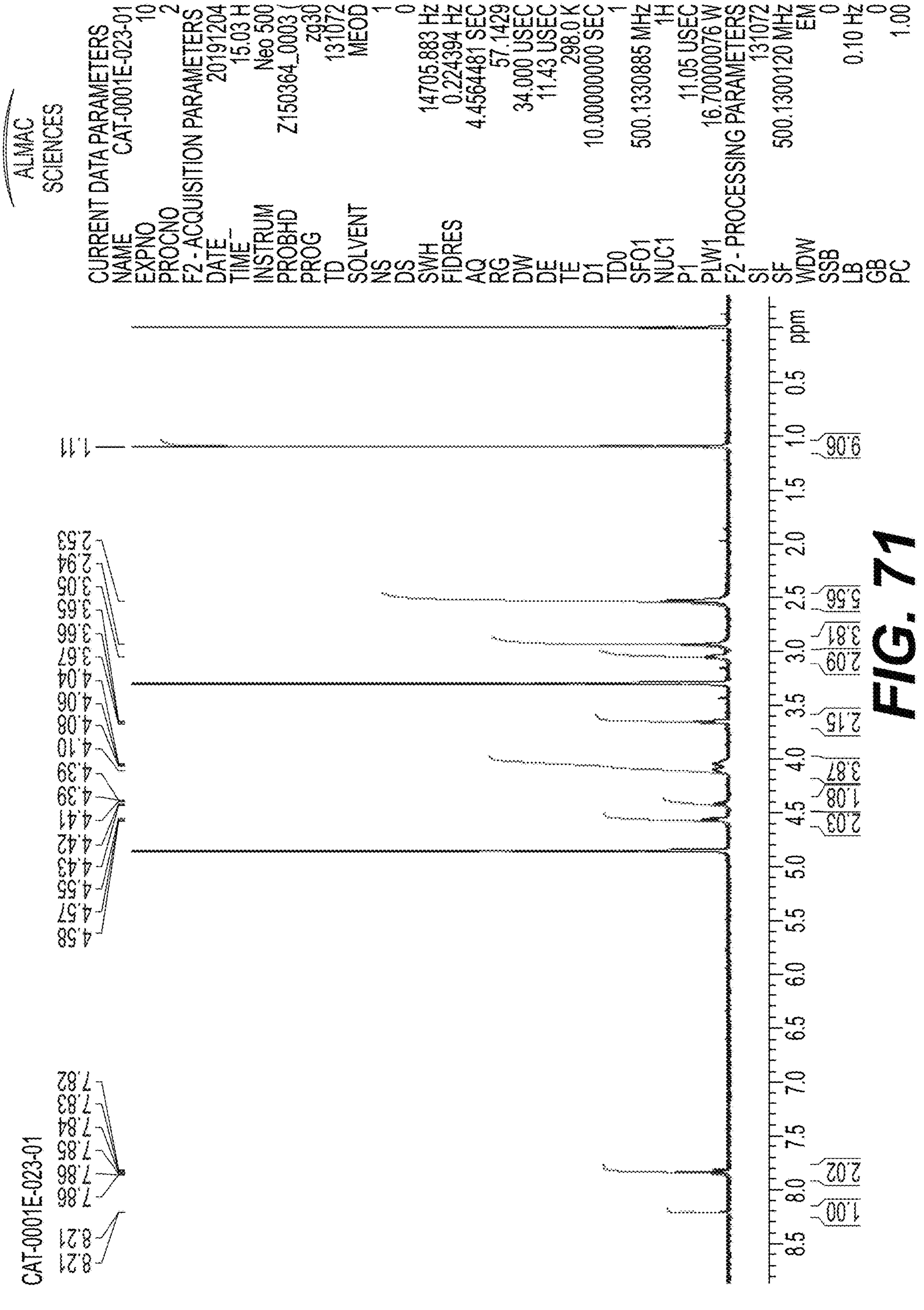
FIG. 71 provides a $^{1}H$ NMR analysis of AAT-730 HCl salt after stressing at 25° C./60% RH.
Figure 72:
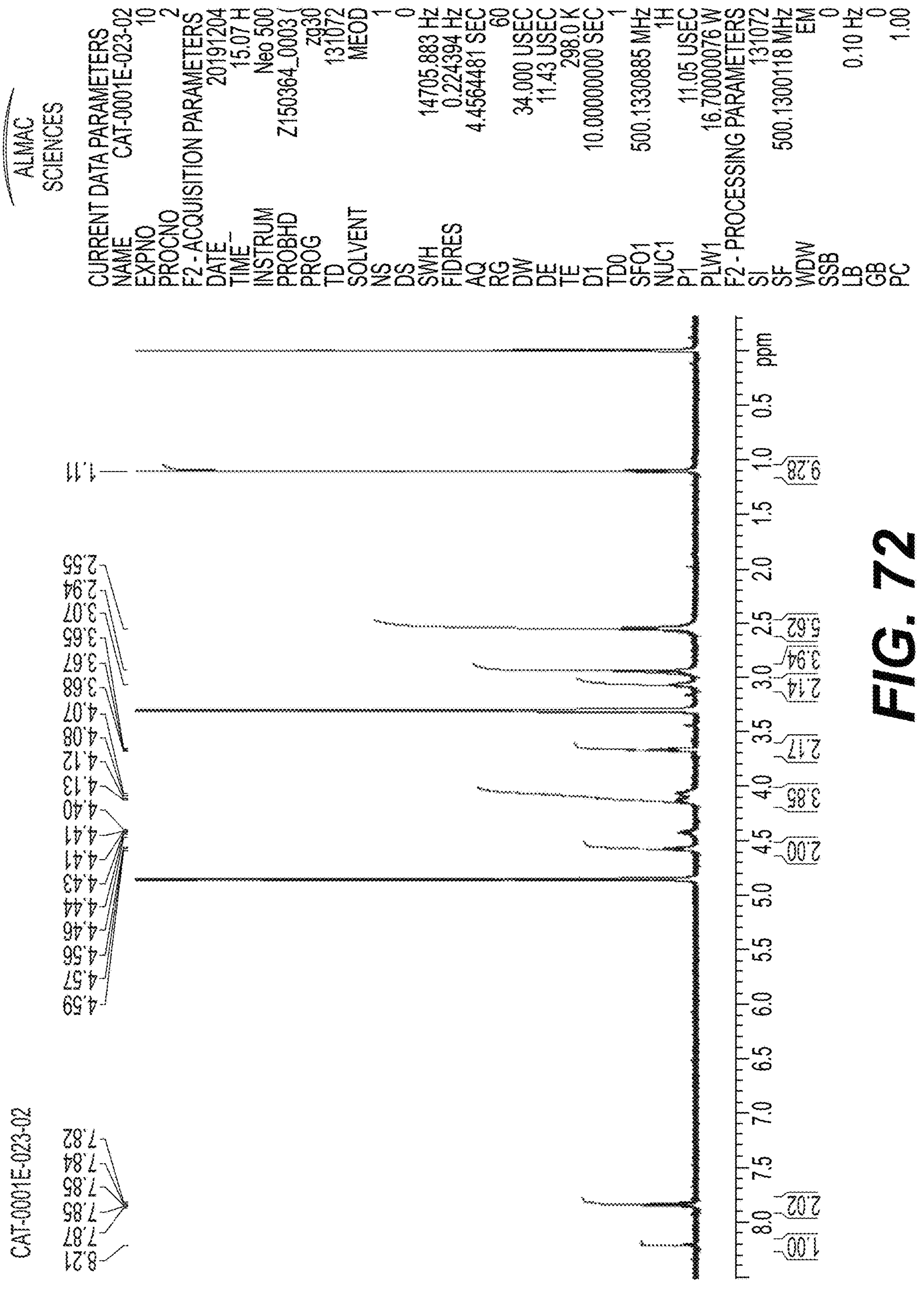
FIG. 72 provides a $^{1}H$ NMR analysis of AAT-730 HCl salt after stressing at 40° C./75% RH.
Figure 73:
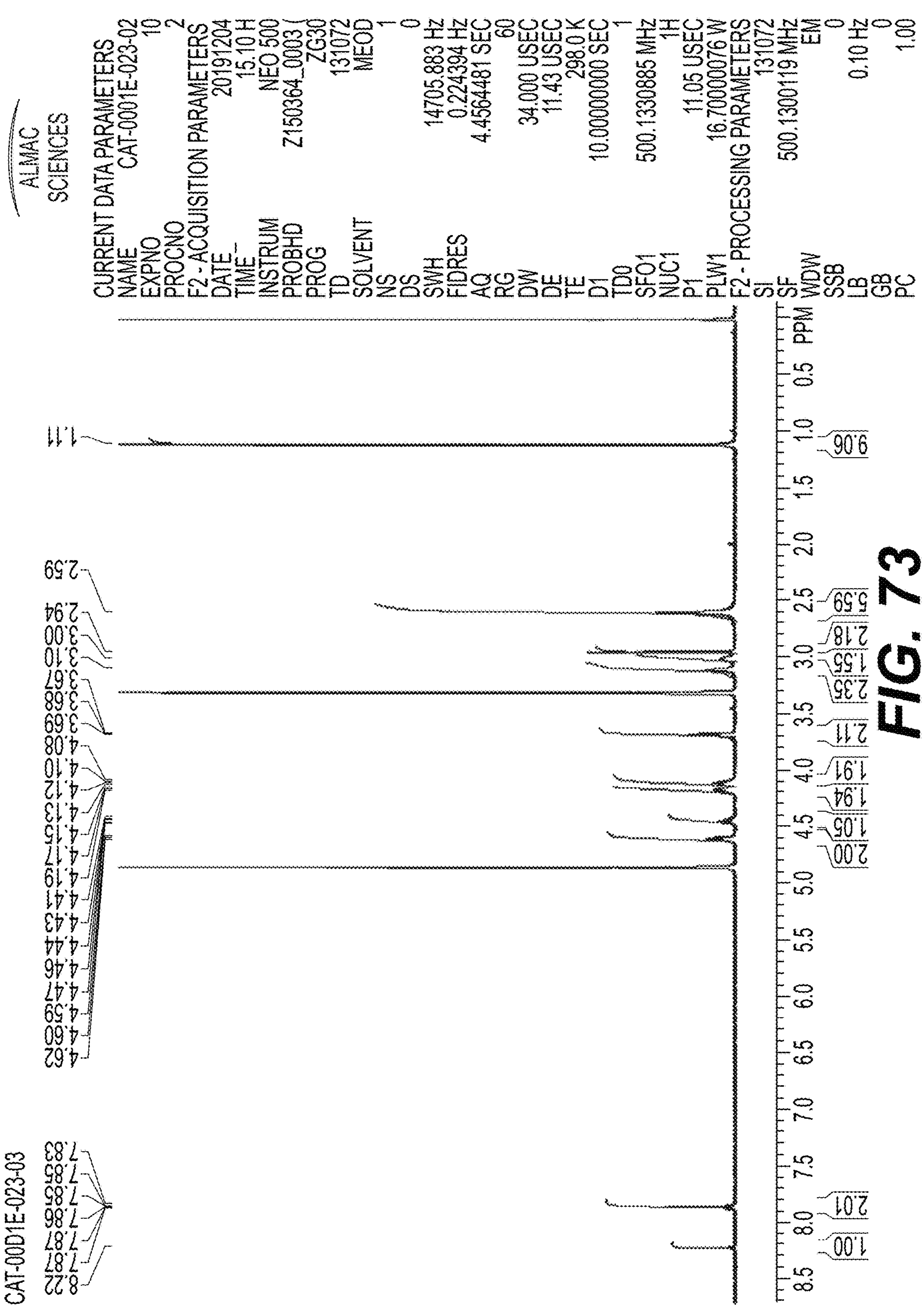
FIG. 73 provides a $^{1}H$ NMR analysis of AAT-730 HCl salt after stressing at 70° C./75% RH.

AAT-730 HCl salt (at most 20 mg) was added to each of the humidity chambers as described above. The XRPD patterns of the post stress samples are shown in FIG. 70. $^1$H NMR analysis (FIG. 71, FIG. 72, AND FIG. 73) of the post-stressed samples showed no change.

Table of Humidity Stressing Experiments

TABLE 4-2

| Sample No. (CAT-0001E-) | Conditions |
|---|---|
| 023-01 | 25° C./60% RH |
| 023-02 | 40° C./75% RH |
| 023-03 | 70° C./75% RH |

Example 4-4, Aqueous Equilibrium Solubility of AAT-730 (Compound A) HCl Salt

AAT-730 HCl salt (50 mg) was added to a vial and water (100 µL) was added. The mixture was stirred and after 30 minutes a thick suspension was formed. Further aliquots (20 µL) of water were added until a fine suspension was formed. This was stirred at 25° C. overnight and filtered to yield a clear solution. The solution was weighed and evaporated to constant weight to determine the solubility.

According to the above method, solubility of AAT-730 HCl salt was determined and was approximately 220 mg/mL in water at pH 6.6 to 7.0.

Example 4-5, Estimated Solubility of AAT-730 (Compound A) HCl Salt

The solubility of AAT-730 HCl salt was estimated in 10 solvent systems using the aliquot addition method. These included 4 aqueous/organic mixtures. The compound had a solubility of >20 mg/mL in 2 of the aqueous mixtures at ambient temperature. The solubility data obtained is shown in Table 4-3. Those experiments which did not show dissolution in at most 50 volumes were temperature cycled as described in Method 4-1. From this data and the solubility screen, the solvents were sorted into three groups outlined in Table 4-4 to define the scope of the screening experiments.

The solubility of AAT-730 HCl salt was assessed by aliquot addition and was found to have solubility greater than or equal to 20 mg/mL in DMSO/water and EtOH/water.

Solubility Estimates of AAT-730 HCl Salt at 20° C.

TABLE 4-3

| Solvent | Acronym | Solubility at 20° C. (mg/mL) | T dissolution (° C.) |
|---|---|---|---|
| acetone | — | <20 | — |
| acetonitrile | ACN | <21 | — |
| dichloromethane | DCM | <20 | — |
| ethanol | EtOH | <21 | — |
| methanol | MeOH | <20 | 40 |
| tetrahydrofuran | THF | <20 | — |
| DMSO/water (80/20, $A_w$ at most 0.27) | — | 22-25 | — |
| acetone/water (20/1, $A_w$ at most 0.6) | — | <20 | — |
| THF/water (13/1, $A_w$ at most 0.9) | — | <20 | 38 |
| EtOH/water (50/50) | — | 205-273 | — |

Solvent Systems Grouped into Categories

TABLE 4-4

| (A) - Solvents | (B) - Soluble with heating | (C) - Anti-solvents |
|---|---|---|
| DMSO/water (80/20, $A_w$ at most 0.27) | MeOH | acetone |
| EtOH/water (50:50) | THF/water (13/1, $A_w$ at most 0.9) | acetone/water (20/1, $A_w$ at most 0.6) |
| — | — | ACN |
| — | — | DCM |
| — | — | EtOH |
| — | — | THF |

Example 4-6, Determination of Chloride Content

AAT-730 HCl salt (6 mg) was added to a vial and water (1 mL) was added. A chloride test strip was added, and the solution allowed to travel up the strip. The level was recorded, and the chloride content calculated.

According to the above method, the strip read 2.8 which corresponded to a chloride content of 393 ppm. The theoretical concentration for a mono-HCl salt was 428 ppm. These results suggest that AAT-730 Pattern A is a mono-HCl salt (mono-hydrochloride).

Conclusions from Characterization of AAT-730 HCl Salt

1) XRPD analysis indicated that AAT-730 HCl was a crystalline material and polarized light microscopy concurred with this.
2) TG/DTA data showed 0.25% weight loss from 30-190° C., suggesting minimal moisture or residual solvent content, and shows that AAT-730 HCl salt remains thermally stable up to 220° C.
3) Heat rate studies by DSC indicated a melting onset of 192.46° C.
4) $^1$H NMR spectroscopy conformed to molecular structure and a small amount of residual THF was detected.
5) AAT-730 HCl salt was stressed for 7 days at 25° C./60% RH, 40° C./75% RH and 70° C./75% RH.
6) The post-stressed samples were analyzed by XRPD and $^1$H NMR analyses. No change in physical form was observed in all samples and $^1$H NMR suggested that it was chemically stable.
7) The solubility of AAT-730 HCl salt Pattern 1 was assessed by aliquot addition and was found to have solubility greater than or equal to 20 mg/mL in DMSO/water and EtOH/water. AAT-730 HCl salt had a solubility or up to approximately 220 mg/mL in water at pH 6.6 to 7.0.
8) Chloride analysis suggests that AAT-730 HCl Pattern A is a mono-HCl salt.

Example 4-7, Preparation of AAT-730 (Compound A) Maleate

AAT-730 (250 mg) and THF (1.25 mL) were stirred in a vial and a solution of maleic acid (69 mg) in THF (500 µL) was added dropwise. This was stirred at 400 rpm for up to 16 hours. A thick white precipitate formed immediately and a further portion (1 mL) of THF was added to assist stirring. The mixture was centrifuged, and the supernatant was removed. THF (at most 1 mL) was added and the mixture was agitated, centrifuged and solvent decanted. This was repeated and the solids were dried under $N_2$ overnight to yield the product as a white solid (198.7 mg, 62% yield).

Example 4-8, Characterization of AAT-730 (Compound A) Maleate

Figure 74:
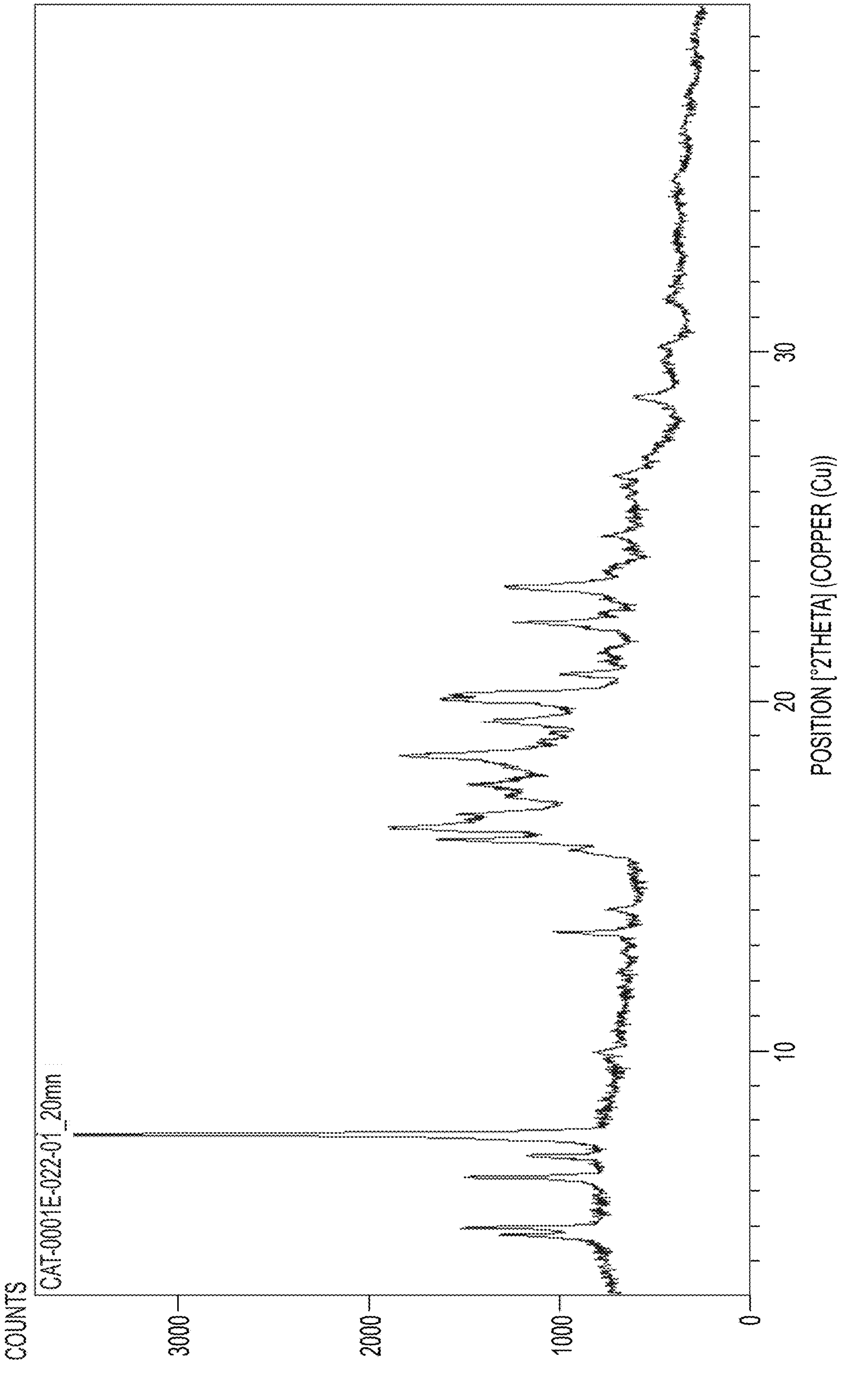
FIG. 74 provides an XRPD pattern of AAT-730 maleate.

AAT-730 maleate was isolated from a precipitation experiment in THE as described in Example 4-7. The solids were characterized as detailed below. The solids were crystalline by XRPD analysis (FIG. 74) and it was composed of the desired form which was previously isolated from the screening experiments.

KF analysis was carried out as described and the maleate had a water content of 0.77% w/w. The maleate is not a hydrate.

Figure 75:
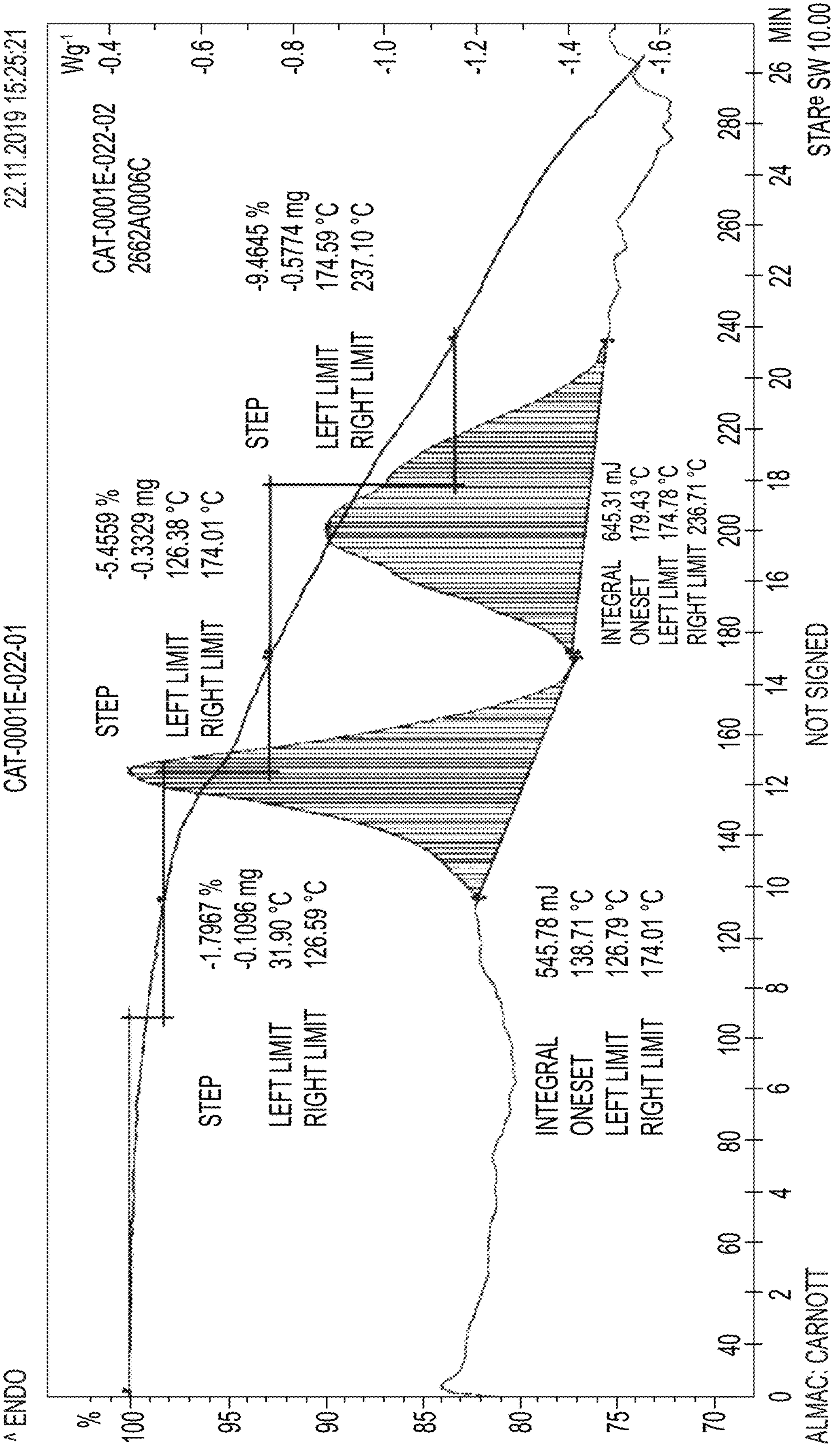
FIG. 75 provides a TG/DTA thermogram of AAT-730 maleate analyzed from 30 to 300° C. at 10° C. per minute.

Thermogravimetric/Differential Thermal Analysis (TG/DTA) was performed to determine the thermal profile and associated % weight changes of AAT-730 maleate (FIG. 75). The TG/DTA data showed a melting endotherm at onset up to 138° C. Weight loss of at most 1.8% w/w was observed between approximately 30 and 130° C. which is probably due to residual solvent or moisture. A second endotherm at onset up to 179° C. may be due to melting of another form. Weight loss of at most 5.45% w/w between approximately 130 and 175° C. may be due to loss of maleic acid which thermally decomposes at 135° C.

Figure 76:
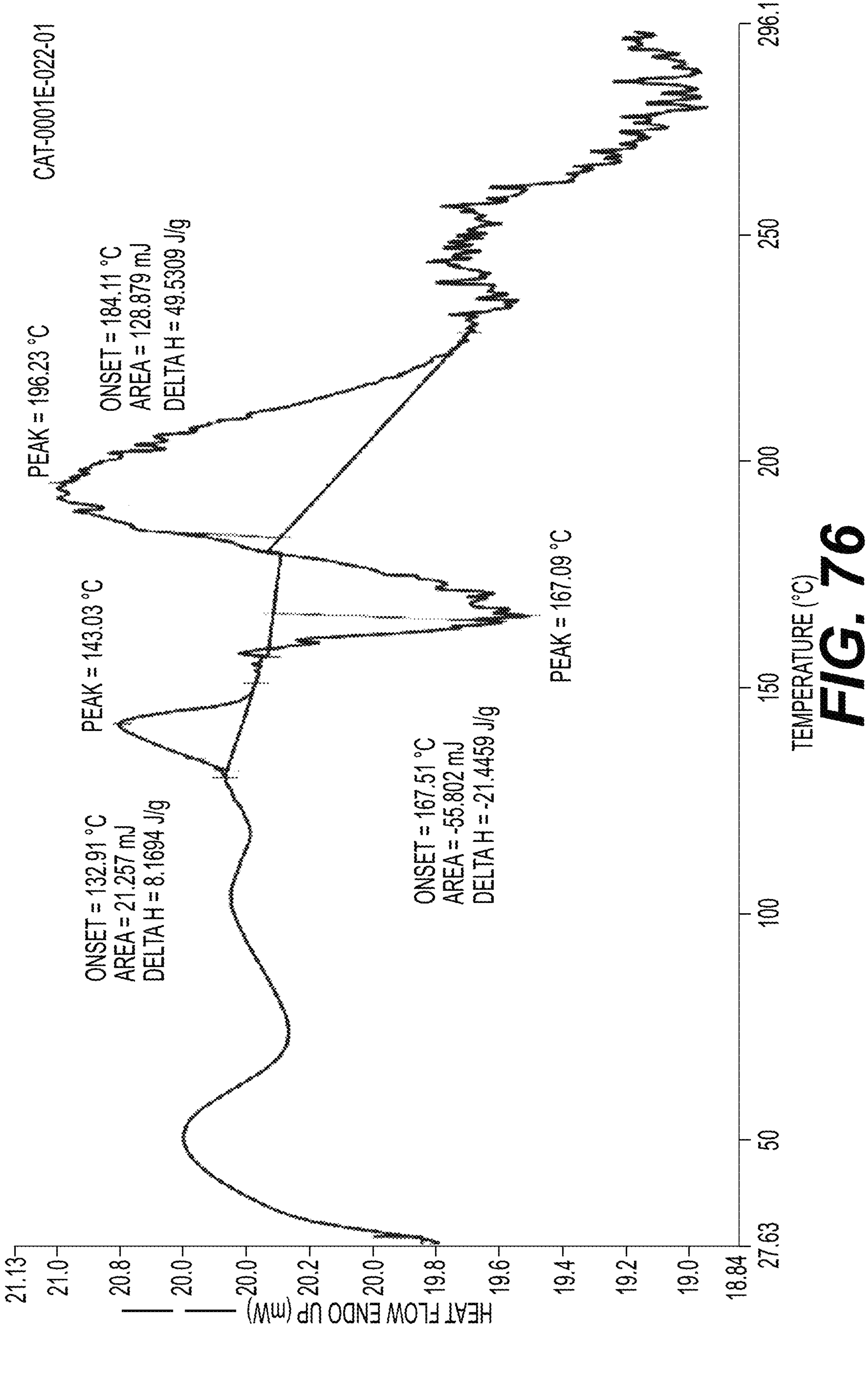
FIG. 76 provides a DSC thermogram for AAT-730 maleate analyzed from 30 to 300° C. at 10° C. per minute.

The DSC thermogram obtained for AAT-730 maleate at 10° C./min is shown in FIG. 76 and the melting onset is 132.91° C. Further thermal events are observed, an exotherm at onset up to 167° C. and another endotherm at onset up to 184° C. The exotherm may be due to recrystallisation of another form and then subsequent melting. This concurs with the hot-stage microscopy images (Table 4-4).

Figure 77:
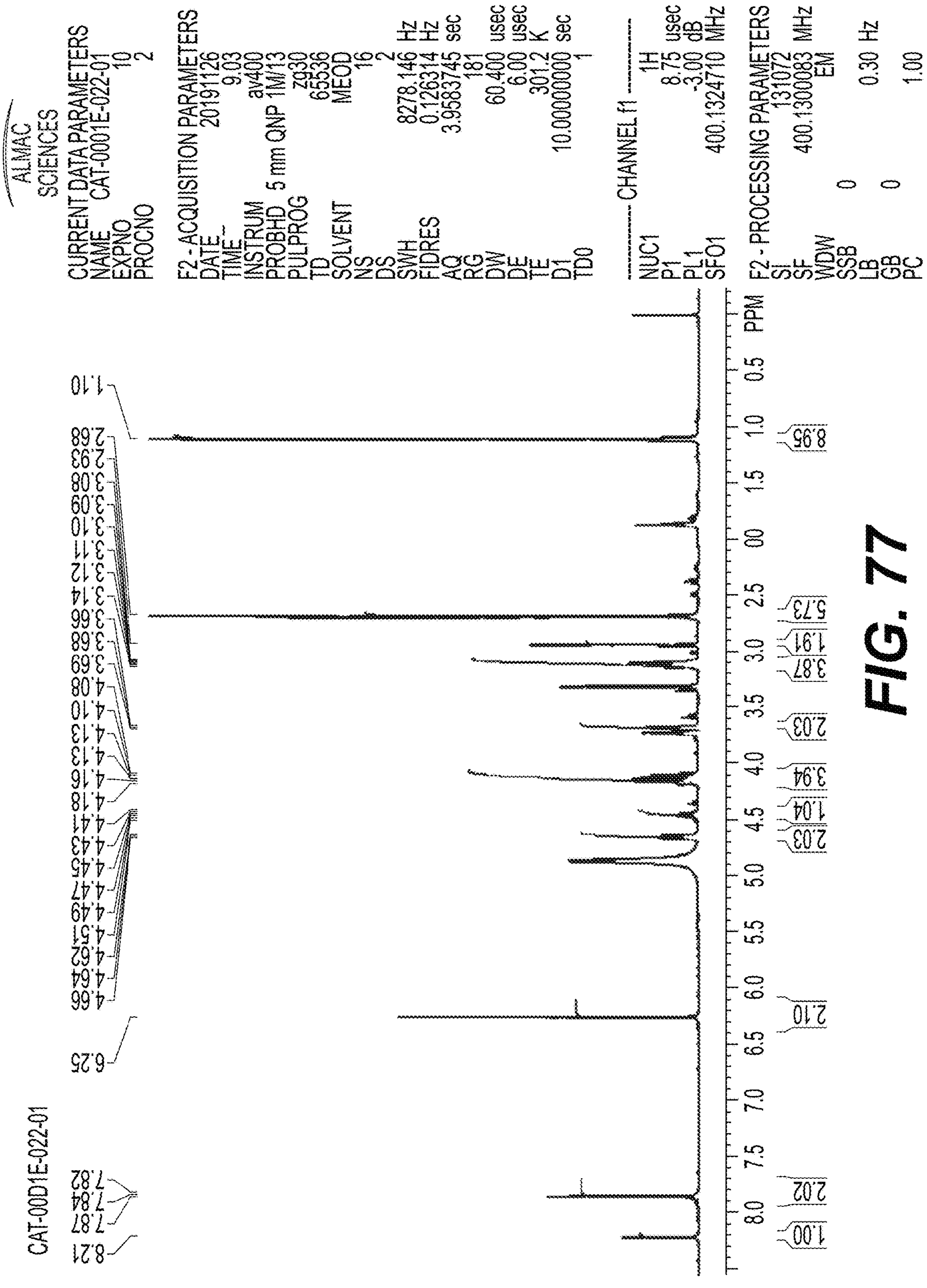
FIG. 77 provides a $^1$H NMR spectrum of suspected AAT-730 maleate.

$^1$H NMR analysis was carried out in $CD_3OD$ and the spectrum is shown in FIG. 77. It suggests formation of a mono-maleate. Residual solvent is detected in the spectrum.

Figure 78:
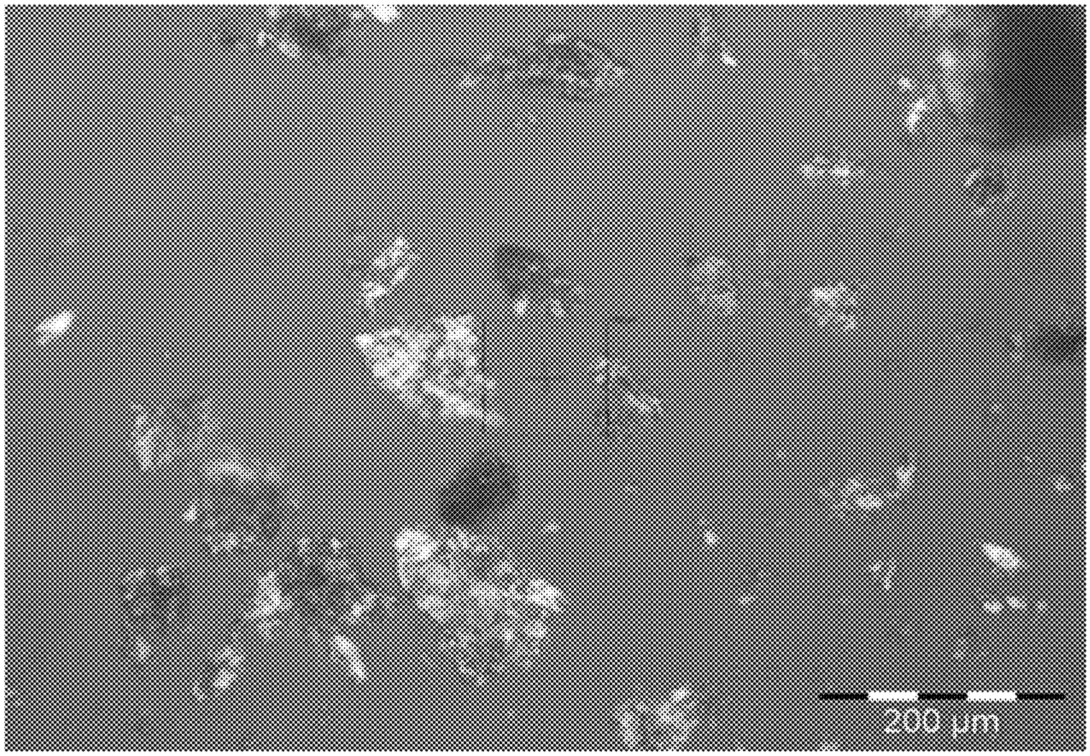
FIG. 78 provides a Photomicrograph of AAT-730 maleate.

A photomicrograph of AAT-730 maleate is shown in FIG. 78 and the material is composed of small irregular particles. Aggregation and/or agglomeration is also observed.

Figure 104:
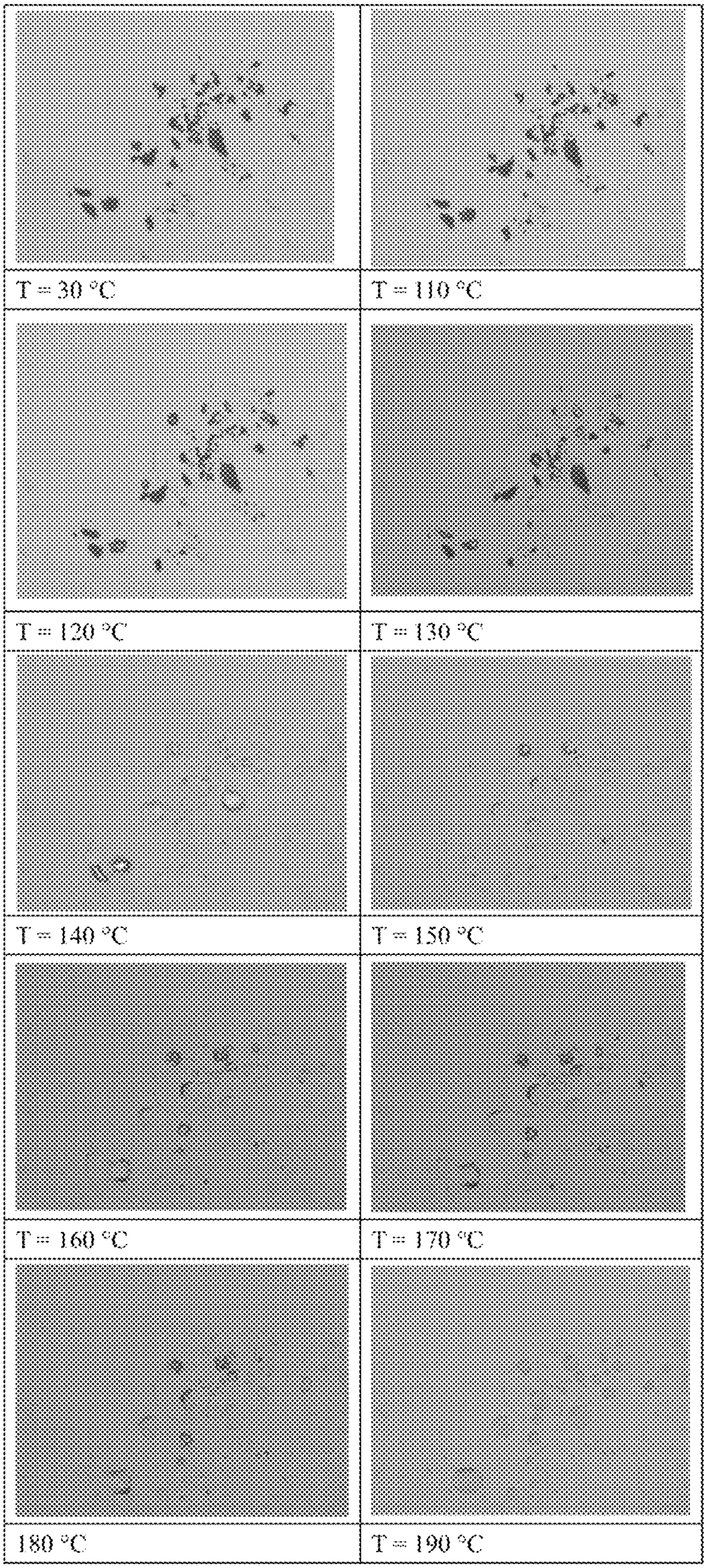
FIG. 104 provides hot-stage microscopy carried out using a Linkam hot-stage accessory and the photomicrographs of AAT-730 maleate.

Hot-stage microscopy was carried out using a Linkam hot-stage accessory and the photomicrographs are shown in FIG. 104. The material remains mostly unchanged on heating up to 110° C. Between 110° C. and 130° C. some changes in the bulk density can be observed as the solids begin to melt. At 140° C. the material has liquefied and some recrystallisation is observed. Between 150° C. and 180° C. further recrystallisation is observed and the material has liquified by 190° C.

Hot stage photomicrographs of AAT-730 maleate are shown in FIG. 104.

Example 4-9, Humidity Stress of AAT-730 (Compound A) Maleate (Maleic Acid Salt)

Sample of AAT-730 HCl salt was added to HPLC vials. The vials were placed, uncapped, into RH chambers as shown in Table 4-6.

The relative humidity of the chambers was controlled by supersaturated salt solutions. The samples were removed after 1 week and the XRPD patterns were acquired.

Figure 79:
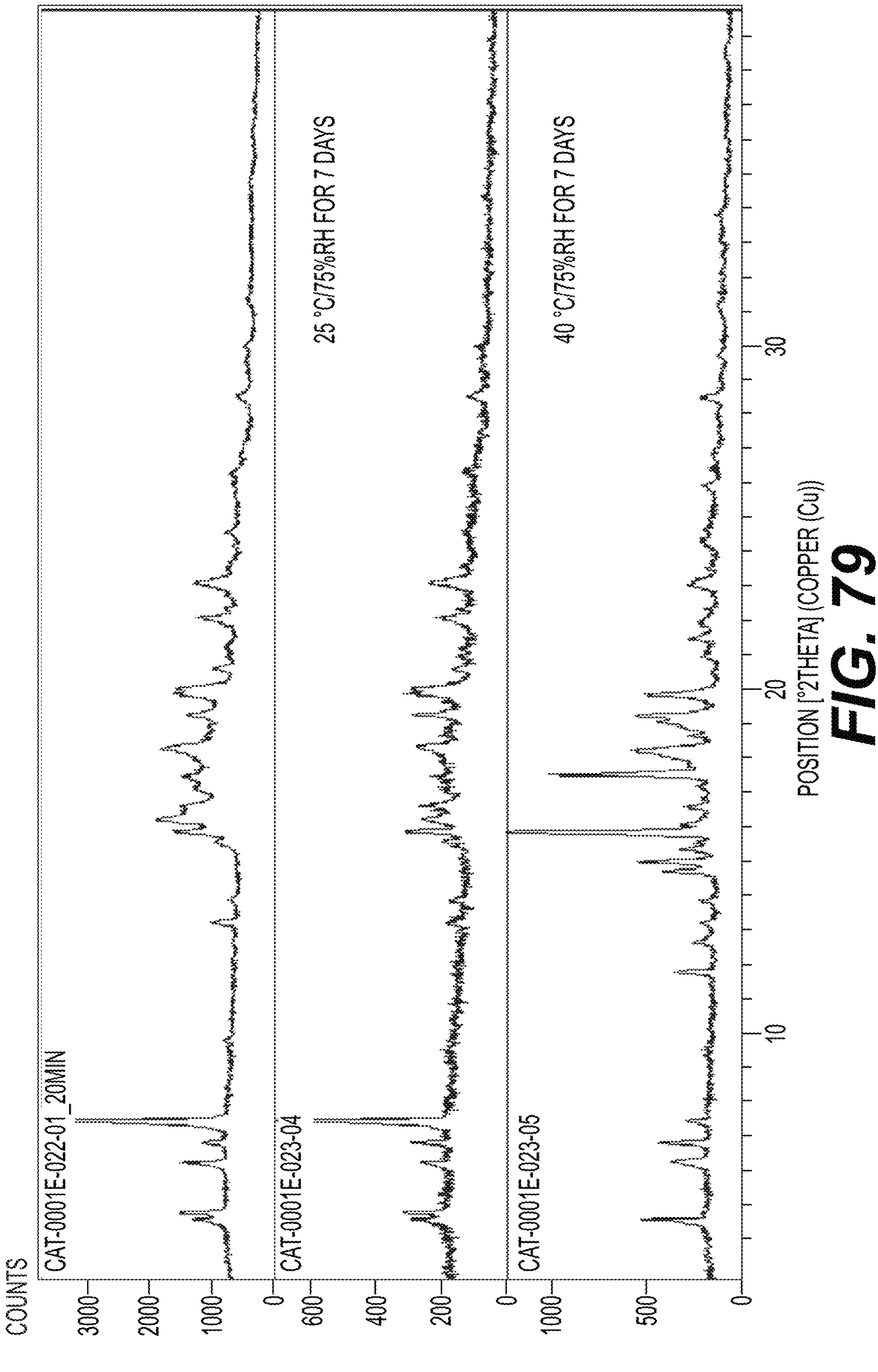
FIG. 79 provides an XRPD patterns for AAT-730 maleate post-stressing.
Figure 80:
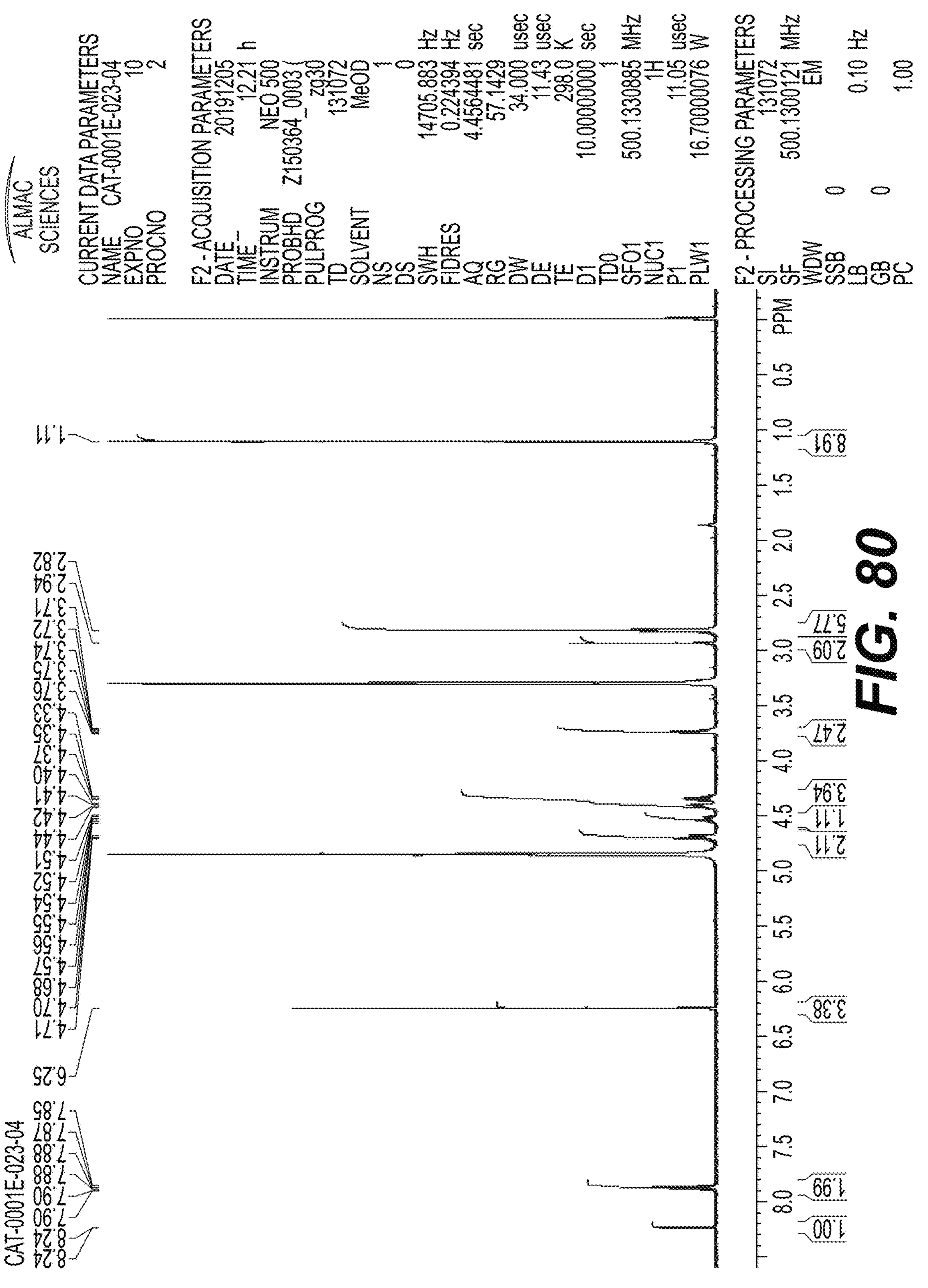
FIG. 80 provides a $^1$H NMR spectrum of AAT-730 maleate after stressing for 7 days at 25° C./60% RH.
Figure 81:
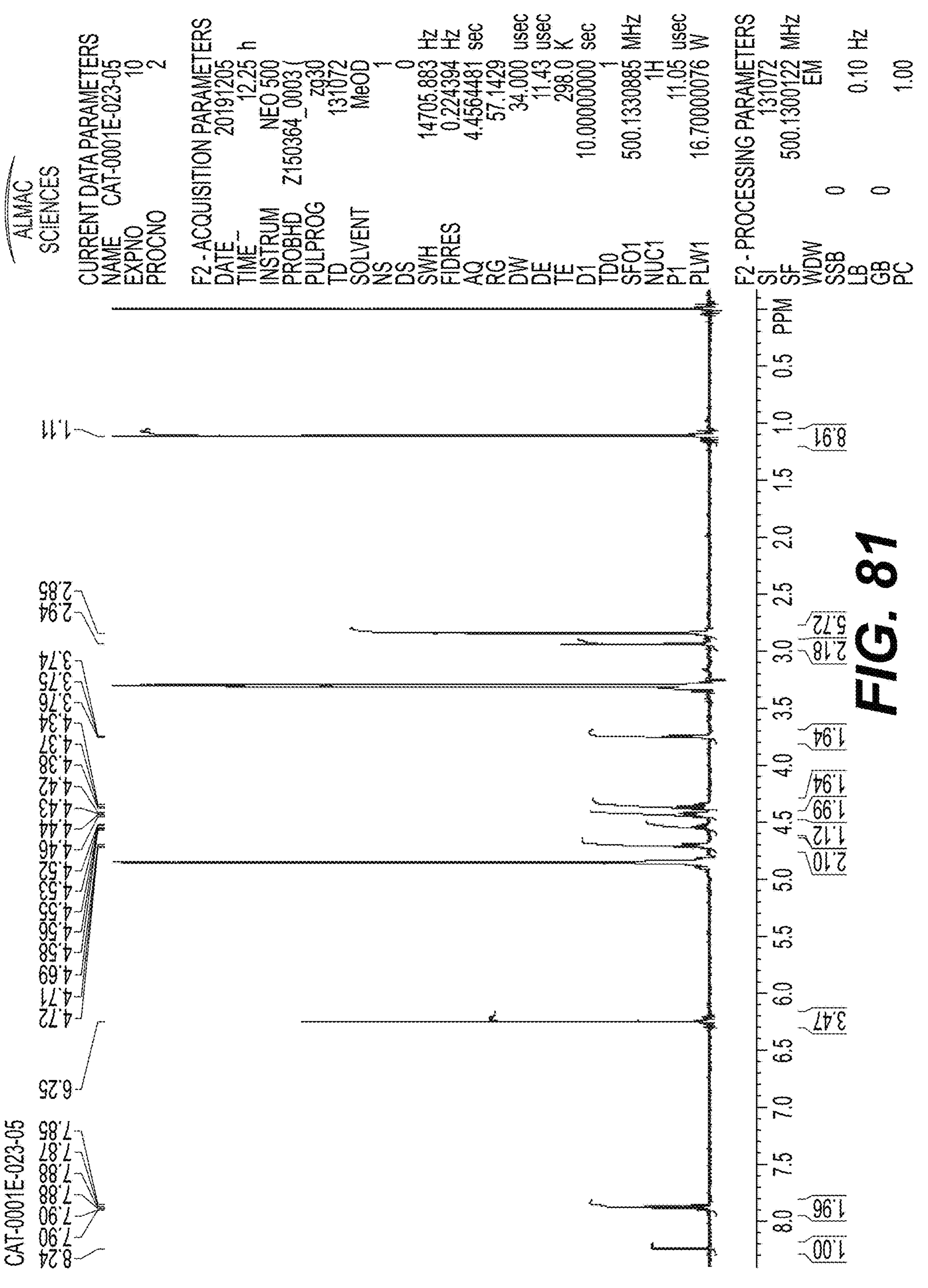
FIG. 81 provides a $^1$H NMR spectrum of AAT-730 maleate after stressing for 7 days at 40° C./75% RH.

AAT-730 maleate (at most 20 mg) was added to each of the humidity chambers as described above. The XRPD patterns of the post stress samples are shown in FIG. 79. At 70° C./75% RH, the material deliquesced. The XRPD diffractograms of the samples suggest changes in the physical form and $^1$H NMR analyses of the post-stressed samples shows that the ratio of maleic acid to API has changed (FIG. 80 and FIG. 81). These results would suggest that AAT-730 maleate is unstable to stressing at elevated relative humidity and would not be suitable for further development.

Table of Humidity Stressing Experiments

TABLE 4-6

| Sample No. (CAT-0001E-) | Conditions |
|---|---|
| 023-01 | 25° C./60% RH |
| 023-02 | 40° C./75% RH |
| 023-03 | 70° C./75% RH |

Example 4-10, Attempted Aqueous Equilibrium Solubility of AAT-730 (Compound A) Maleate AAT-730 maleate (50 mg) was added to a vial and water (100 μL) was added. A clear solution resulted and a further portion of AAT-730 maleate (20 mg) was added. This dissolved immediately. AAT-730 maleate had a solubility or >700 mg/mL in water at pH 6 to 7.

Conclusions from Characterization of AAT-730 (Compound A) Maleate

1) XRPD analysis indicated that AAT-730 maleate was a crystalline material and polarized light microscopy concurred with this.
2) TG/DTA data showed 1.8% weight loss from 30-130° C., suggesting some residual solvent content. Further weight loss is observed from up to 130° C. and shows that AAT-730 maleate may be thermally unstable.
3) Heat rate studies by DSC indicated a melting onset of 132.91° C.
4) $^1$H NMR spectroscopy conformed to molecular structure and suggested formation of a mono-maleate. Residual THF was detected.
5) AAT-730 maleate salt was stressed for 7 days at 25° C./60% RH, 40° C./75% RH and 70° C./75% RH. The post-stressed samples were analyzed by XRPD and $^1$H NMR analyses. Change in physical form was observed in all samples by XRPD analysis and $^1$H NMR analysis also suggested that AAT-730 maleate was unstable to stressing.
6) AAT-730 maleate salt had a solubility or >700 mg/mL in water at pH 6 to 7.

Example 5, Polymorph Screening of AAT-730 (Compound A) HCl Salt

A focused polymorph screen has been performed on AAT-730 HCl salt, the objective of which was to investigate the polymorphic landscape of AAT-730 HCl salt. The approach was to generate solids under a wide and diverse range of nucleation conditions, designed to mimic the process conditions and solvents used during development and formulation.

The XRPD pattern of AAT-730 HCl salt Pattern A is hereafter referred as to Pattern 1.

All solids from the crystallization experiments were analyzed by XRPD and the resulting patterns compared to that exhibited by the starting material. Novel XRPD patterns were assigned a descriptor in order of discovery (Pattern 2, Pattern 3, etc.). Where sufficient material was available, further analysis (e.g. $^1$H NMR or TGA) was conducted on solids with novel XRPD patterns to allow tentative assignment of the novel pattern as a polymorph, solvate, hydrate, degradant or mixture thereof. The starting material used in this study was AAT-730 HCl salt as prepared in Example 5-1.

Polymorph Screening Methods of Example 5

Method 5-1, Temperature Cycling

The Test Solvent (1 mL) was Added to a Sample of AAT-730 HCl Salt (at Most 20 mg) at Ambient Temperature and 15 Cycles of the Following Temperature Program was Performed Using the Clarity Crystallization Station:

Heating from 5° C. to 60° C. at 0.5° C./min (depending on boiling point of solvent)

Cooling to 5° C. at 0.5° C./min

Stirring speed-300 rpm

Method 5-2, Slow Evaporation

A solution of AAT-730 HCl salt was prepared in each solvent and evaporated in a fume hood at ambient temperature in a vial covered with perforated aluminum foil. After 2 weeks any samples which were still solutions were evaporated under a flow of nitrogen. The resulting solids were analyzed by XRPD.

Method 5-3, Crash Precipitation

AAT-730 HCl (at most 20 mg) salt was dissolved in water (100 µL) and filtered into anti-solvent (1 mL) with stirring. Experiments which did not result in precipitation were placed in the refrigerator for up to 7 days, then uncapped and left to evaporate in a fume hood at ambient temperature until solids were observed. The resulting solids were analyzed by XRPD.

Method 5-4, Slow Cooling

Sufficient solvent was added to AAT-730 HCl salt (20 mg) until dissolution at 60° C. The solutions were cooled with agitation at 0.2° C./min to a final temperature of 5° C. and any solids recovered by centrifugation and air dried prior to analysis by XRPD.

Method 5-5, Slurry Experiments

Sufficient AAT-730 HCl salt was added to a given solvent until undissolved solids remained at the desired temperature (5, 20, 40, and 50° C.). The vial was sealed and the slurry was maintained at the selected temperature and agitated by magnetic stirring for 5 to 7 days. Solids were isolated by centrifugation and air dried prior to analysis by XRPD.

Method 5-6, Sonication of Pastes

AAT-730 HCl salt (at most 20 mg) was added to a vial with 80 µL of the selected solvent to form a paste. The mixture was sonicated at 70% intensity using a Cole-Parmer 130 Watt ultrasonic processor using a pulsed program. In cases where the solids dissolved at ambient temperature, the sample was left uncapped to evaporate. The wet pastes recovered from these experiments were analyzed using XRPD.

Method 5-7, Crystalline Vapor Stress

Approximately 20 mg of crystalline AAT-730 HCl salt was added to a vial and placed unsealed inside a larger sealed vessel containing 1 mL of the selected solvent. After 7 days, the samples were removed and analyzed by XRPD.

Method 5-8, Amorphous Vapor Stress

Amorphous AAT-730 HCl salt was generated from evaporation of AAT-730 HCl salt from aqueous solution under a steady stream of $N_2$. The resulting solids were placed unsealed inside a larger sealed vessel containing 1 mL of the selected solvent. After 7 days, the samples were removed and analyzed by XRPD.

Method 5-9, Humidity Stress

Approximately 20 mg of Pattern 1 AAT-730 HCl salt was added to three individual vials and placed unsealed into the following relative humidity chambers (sealed cabinets with relative humidity conditions controlled by super-saturated salt solutions) for 7 days prior to analysis by XRPD:

Chamber 1-23% RH

Chamber 2-76% RH

Chamber 3-98% RH

Method 5-10, Planetary Milling

Approximately 20 mg of AAT-730 HCl salt was added to vials with steel milling balls. Vials were sealed and contents milled using a Fritsch Pulverisette 5 planetary mill and the following cycle:

Mill for 60 minutes at a rotation speed of 400 rpm.

Rest for 15 minutes.

Total time 18 hours

Solvent (30 µL) was added and the contents were milled again using the following cycle:

Mill for 60 minutes at a rotation speed of 400 rpm.

Rest for 15 minutes.

Total time 18 hours

Example 5-1, Preparation of AAT-730 (Compound A) HCl Salt Pattern 1

AAT-730 (2 g) and THF (10 mL) were added to a round bottom flask and stirred. Dissolution was incomplete after up to 10 minutes and a further portion (1 mL) of THF was added. The mixture was stirred to dissolution and HCl in dioxane (4 M, 1.5 mL) was added dropwise. A crust formed on the top and this was broken up with a pipette. Gumball formation was noted and a further portion (3 mL) of THE was added and the mixture was stirred to break up the solids. The solids were isolated by filtration, washed with THF (3 mL) and air dried in the Buchner funnel. The solids were transferred to a vial and dried to constant weight, under a flow of $N_2$, to yield the salt as a white solid (2.128 g, up to 98% yield).

Example 5-2, Generation of Amorphous AAT-730 (Compound A) HCl Salt

Freeze Drying

AAT-730 HCl salt (25 mg) was dissolved in water (1 mL), filtered through a 0.45 µm filter into a HPLC vial. This was frozen in liquid nitrogen and lyophilized under vacuum (0.08 millibar) for 18 hours. The amorphous material was not obtained.

Melt Quench

AAT-730 HCl salt (at most 20 mg) was added to a HPLC vial and flushed with $N_2$. This was heated to 200° C. and was quickly immersed in an ice/water bath. A dark brown solid was formed which had degraded. AAT-730 HCl salt (at most 20 mg) was added to a HPLC vial and flushed with $N_2$. This was heated up to 180° C. and was quickly immersed in an ice/water bath. A brown solid was formed which had degraded.

Evaporation

AAT-730 HCl salt (at most 20 mg) was added to a HPLC vial and water (1 mL) was added to form a solution. This was evaporated under a flow of nitrogen to yield amorphous material.

Example 5-3, Temperature Cycling

Samples were subjected to the temperature cycling program outlined in Method 5-1 and the results are shown in Table 5-1. Pattern 1 or Pattern 2 materials were isolated from the screening experiments and are discussed further in Example 5-12 and Example 5-13.

Screening Results from Temperature Cycling Experiments

TABLE 5-1

| Sample No. (TW-0012E-) | Solvent | Result | XRPD |
|---|---|---|---|
| 003-01 | acetone | solid | Pattern 1 |
| 003-02 | ACN | solid | Pattern 1 |
| 003-04 | EtOH | solid | Pattern 1 |
| 003-05 | THF | solid | Pattern 1 |
| 003-06 | acetone/water (20/1, $A_w$ at most 0.6) | solid | Pattern 1 |
| 003-07 | THF/water (13/1, $A_w$ at most 0.9) | solid | Pattern 1 |
| 003-08 | EtOH/water (50/50) | solid | Pattern 1 |
| 015-01 | 1-Butanol | solid | Pattern 2 |
| 015-02 | cyclohexane | solid | Pattern 2 |
| 015-03 | DIPE | solid | Pattern 2 |
| 015-04 | DMAc | solid | Pattern 2 |
| 015-05 | MEK | solid | Pattern 2 |
| 015-06 | MIBK | solid | Pattern 2 |
| 015-07 | MeOH | solution | N/A |
| 015-08 | IPA | solid | Pattern 2 |
| 015-09 | Dioxane | solid | Pattern 2 |
| 015-10 | i-PrOAc | solid | Pattern 2 |
| 015-11 | toluene | solid | Pattern 2 |
| 015-12 | heptane | solid | Pattern 2 |

Example 5-4, Slow Evaporation

Slow evaporation of AAT-730 HCl salt solutions were conducted as described in Method 5-2 and the results are shown in Table 5-2. Pattern 4 was isolated from the EtOH/water evaporation and this material was not further characterized but it was included in the interconversion and water activity experiments as detailed in Example 5-16. Amorphous material was isolated from the evaporation in water and this method was then used to prepare amorphous material for vapor stressing.

Screening Results from Evaporations in Vials

TABLE 5-2

| Sample No. (TW-0012E-) | Solvent | Result | XRPD |
|---|---|---|---|
| 008-01 | water | solid | amorphous |
| 008-02 | DMSO/water (80/20, $A_w$ at most 0.27) | solid | Pattern 3 + 2 |
| 008-03 | EtOH/water (50/50) | solid | Pattern 4 |

Example 5-5, Crash Precipitation

Crash precipitation experiments were carried out as detailed in Method 5-3 and the results are shown in Table 5-3. Most of the solids isolated contained amorphous material. Patterns 3 and 4 were isolated and these are discussed in Example 5-14 and Example 5-15.

Screening Results from Crash Precipitation Experiments

TABLE 5-3

| Sample No. (TW-0012E-) | Solvent | Anti-solvent | Result | XRPD |
|---|---|---|---|---|
| 009-01 | water | acetone | solid (after evap) | Amorphous + Pattern 4 |
| 009-02 | water | ACN | solid (after evap) | Amorphous |
| 009-03 | water | ethanol | gel (after evap) | N/A |
| 009-04 | water | MeOH | solid (after evap) | Pattern 4 |
| 009-05 | water | IPA | solid (after evap) | Pattern 3 |

TABLE 5-3-continued

| Sample No. (TW-0012E-) | Solvent | Anti-solvent | Result | XRPD |
|---|---|---|---|---|
| 009-06 | water | THF | solid (after evap) | Amorphous |
| 009-07 | water | dioxane | solid (after evap) | Amorphous + Pattern 1 |

Example 5-6, Slow Cooling

The slow increase in supersaturation allows more stable forms to nucleate. A sub-ambient final temperature also probes for stable solvates at temperatures typically accessed during cooling crystallization at plant scale. Table 5-4 shows the screening results from slow cooling experiments and Pattern 1 material was isolated from all experiments.

Screening Results from Slow Cooling Experiments

TABLE 5-4

| Sample No. (TW-0012E-) | Solvent | Result | XRPD |
|---|---|---|---|
| 016-01 | MeOH | solid | Pattern 1 |
| 016-02 | DMSO/water (80/20, $A_w$ at most 0.27) | solid | Pattern 1 + amorphous |
| 016-03 | THF/water (13/1, $A_w$ at most 0.9) | solid | Pattern 1 |

Example 5-7, Slurry Experiments

Suspensions of AAT-730 HCl salt Pattern 1 in various solvents were held at 5, 20° C. and 50° C. for 5-7 days prior to isolation and analysis by XRPD (Table 5-5). Pattern 1 or 2 materials were isolated from each experiment. Pattern 1 was isolated from most of the experiments at 5° C. Pattern 2 solids were isolated from the slurry experiments at 20 and 50° C. except for in aqueous solvents where either Pattern 1 or 2 was isolated.

Screening Results from Slurry Experiments

TABLE 5-5

| Sample No. (TW-0012E-) | Solvent | Temp. (° C.) | Days | Result | XRPD |
|---|---|---|---|---|---|
| 003-03 | DCM | 40 | 5 | solid | Pattern 1 |
| 004-01 | acetone | 5 | 5 | solid | Pattern 1 |
| 004-02 | ACN | 5 | 5 | solid | Pattern 1 |
| 004-03 | DCM | 5 | 5 | solid | Pattern 1 |
| 004-04 | EtOH | 5 | 5 | solid | Pattern 1 |
| 004-05 | THF | 5 | 5 | solid | Pattern 2 |
| 004-06 | DMSO/water (80/20, $A_w$ at most 0.27) | 5 | 5 | solid | Pattern 1 |
| 004-07 | acetone/water (20/1, $A_w$ at most 0.6) | 5 | 5 | solid | Pattern 2 |
| 004-08 | THF/water (13/1, $A_w$ at most 0.9) | 5 | 5 | solid | Pattern 1 |
| 005-01 | acetone | 20 | 5 | solid | Pattern 2 |
| 005-02 | ACN | 20 | 5 | solid | Pattern 2 |
| 005-03 | DCM | 20 | 5 | solid | Pattern 2 |
| 005-04 | EtOH | 20 | 5 | solid | Pattern 2 |
| 005-05 | THF | 20 | 5 | solid | Pattern 2 |
| 005-06 | DMSO/water (80/20, $A_w$ at most 0.27) | 20 | 5 | solid | Pattern 1 |
| 005-07 | acetone/water (20/1, $A_w$ at most 0.6) | 20 | 5 | solid | Pattern 2 |
| 005-08 | THF/water (13/1, $A_w$ at most 0.9) | 20 | 5 | solid | Pattern 1 |
| 006-01 | acetone | 50 | 7 | solid | Pattern 2 |
| 006-02 | ACN | 50 | 7 | solid | Pattern 2 |

TABLE 5-5-continued

| Sample No. (TW-0012E-) | Solvent | Temp. (° C.) | Days | Result | XRPD |
|---|---|---|---|---|---|
| 006-04 | EtOH | 50 | 7 | solid | Pattern 2 |
| 006-05 | THF | 50 | 7 | solid | Pattern 2 |

Example 5-8, Sonication of Pastes

Sonication experiments were carried out as detailed in Method 5-6 and the results are displayed in Table 5-6. Pattern 2 solids were isolated from the majority of the screening experiments and these are discussed in Example 5-13. Pattern 1 material was isolated from the sonication experiments in aqueous solvents and in MeOH.

Screening Results from Sonication Experiments

TABLE 5-6

| Sample No. (TW-0012E-) | Solvent | Result | XRPD |
|---|---|---|---|
| 010-01 | acetone | solid | Pattern 2 |
| 010-02 | ACN | solid | Pattern 2 |
| 010-03 | DCM | solid | Pattern 2 |
| 010-04 | EtOH | solid | Pattern 2 |
| 010-05 | THF | solid | Pattern 2 |

TABLE 5-6-continued

| Sample No. (TW-0012E-) | Solvent | Result | XRPD |
|---|---|---|---|
| 010-06 | DMSO/water (80/20, $A_w$ at most 0.27) | solid | Pattern 1 + amorphous |
| 010-07 | acetone/water (20/1, $A_w$ at most 0.6) | solid | Pattern 1 |
| 010-08 | MeOH | solid | Pattern 1 |

Example 5-9, Vapor and Humidity Stress

X-ray amorphous material generated from evaporation in water was exposed to air saturated in solvent vapor before analysis by XRPD. As amorphous material has lost long range order, it is in a high energy state. Exposure to vapor plasticizes the solid, allowing limited molecular mobility and is therefore an excellent method of generating meta-stable solvates and hydrates. Amorphous material crystallized to Pattern 1 material in all experiments. This may be aided by the residual water present in the amorphous material. Additional vapor and humidity stress experiments were setup using Pattern 1 material and the results are all shown in Table 5-7. In almost all cases Pattern 1 material converted to Pattern 2 on vapor stressing. Pattern 1 solids converted to Pattern 2 on stressing at less than or equal to 75% RH but remained as Pattern 1 at 98% RH.

Results from Vapor Stressing and Humidity Experiments

TABLE 5-7

| Input | Sample No. (TW-0012E-) | Solvent | Screen method | Result | XRPD |
|---|---|---|---|---|---|
| Pattern 1 | 012-01 | acetone | vapor stress | solid | Pattern 2 |
| Pattern 1 | 012-02 | ACN | vapor stress | solid | Pattern 2 |
| Pattern 1 | 012-03 | cyclohexane | vapor stress | solid | Pattern 2 |
| Pattern 1 | 012-04 | DIPE | vapor stress | solid | Pattern 2 |
| Pattern 1 | 012-05 | EtOH | vapor stress | solid | Pattern 2 |
| Pattern 1 | 012-06 | EtOAc | vapor stress | solid | Pattern 2 |
| Pattern 1 | 012-07 | MeOH | vapor stress | solid | Pattern 2 |
| Pattern 1 | 012-08 | MTBE | vapor stress | solid | Pattern 2 |
| Pattern 1 | 012-09 | MIBK | vapor stress | solid | Pattern 2 |
| Pattern 1 | 012-10 | IPA | vapor stress | solid | Pattern 2 |
| Pattern 1 | 012-11 | i-PrOAc | vapor stress | solid | Pattern 2 |
| Pattern 1 | 012-12 | Heptane | vapor stress | solid | Pattern 2 |
| Pattern 1 | 013-01 | none | 23% RH stress | solid | Pattern 2 |
| Pattern 1 | 013-02 | none | 75% RH stress | solid | Pattern 2 |
| Pattern 1 | 013-03 | none | 98% RH stress | solid | Pattern 1 |
| amorphous | 018-01 | acetone | vapor stress | solid | Pattern 1 |
| amorphous | 018-02 | ACN | vapor stress | solid | Pattern 1 |
| amorphous | 018-03 | DCM | vapor stress | solid | Pattern 1 |
| amorphous | 018-04 | EtOH | vapor stress | solid | Pattern 1 |
| amorphous | 018-05 | THF | vapor stress | solid | Pattern 1 |

Example 5-10, Planetary Milling

Planetary milling experiments were carried out as detailed in Method 5-10 and the results are shown in Table 5-8. Pattern 1 was isolated from most of these experiments.

Screening Results from Planetary Milling Experiments

TABLE 5-8

| Input | Sample No. (TW0012E-) | Solvent | Result | XRPD |
|---|---|---|---|---|
| Pattern 1 | 017-01 | acetone | solid | Disordered Pattern 1 |
| Pattern 1 | 017-02 | ACN | solid | Pattern 1 + very minor pattern 2 |
| Pattern 1 | 017-04 | Cyclohexane | solid | Disordered Pattern 1 |
| Pattern 1 | 017-05 | DCM | solid | Pattern 1 |
| Pattern 1 | 017-06 | dioxane | solid | Pattern 1 |
| Pattern 1 | 017-07 | DIPE | solid | Disordered Pattern 1 |
| Pattern 1 | 017-08 | EtOH | solid | Pattern 1 |
| Pattern 1 | 017-09 | EtOAc | solid | Pattern 1 |
| Pattern 1 | 017-10 | heptane | solid | Pattern 1 |
| Pattern 1 | 017-12 | MIBK | solid | Pattern 1 |
| Pattern 1 | 017-13 | IPA | solid | Pattern 1 |
| Pattern 1 | 017-14 | i-PrOAc | solid | Pattern 1 |
| Pattern 1 | 017-15 | toluene | solid | Pattern 1 |
| Pattern 1 | 017-16 | none | solid | Disordered Pattern 1 |

Conclusions from Polymorph Screening

1) Approximately 100 experiments were carried out using solvent and non-solvent based techniques.
2) Four crystalline XRPD patterns (Table 5-9) were observed during this study. Amorphous material was also generated from evaporation of a solution of AAT-730 HCl salt in water.

Summary of the Physical Forms Observed During this Study

TABLE 5-9

| Pattern | Comment |
|---|---|
| 1 | Isolated from preparation of AAT-730 HCl salt in THF |
| 2 | Novel polymorph, XRPD is similar to Pattern 1 |
| 3 | Novel polymorph, possible solvate or hydrate |
| 4 | Novel polymorph, isolated from water or water mixtures, possible hydrate |
| amorphous | Isolated from evaporation of AAT-730 HCl salt in water |

Figure 82:
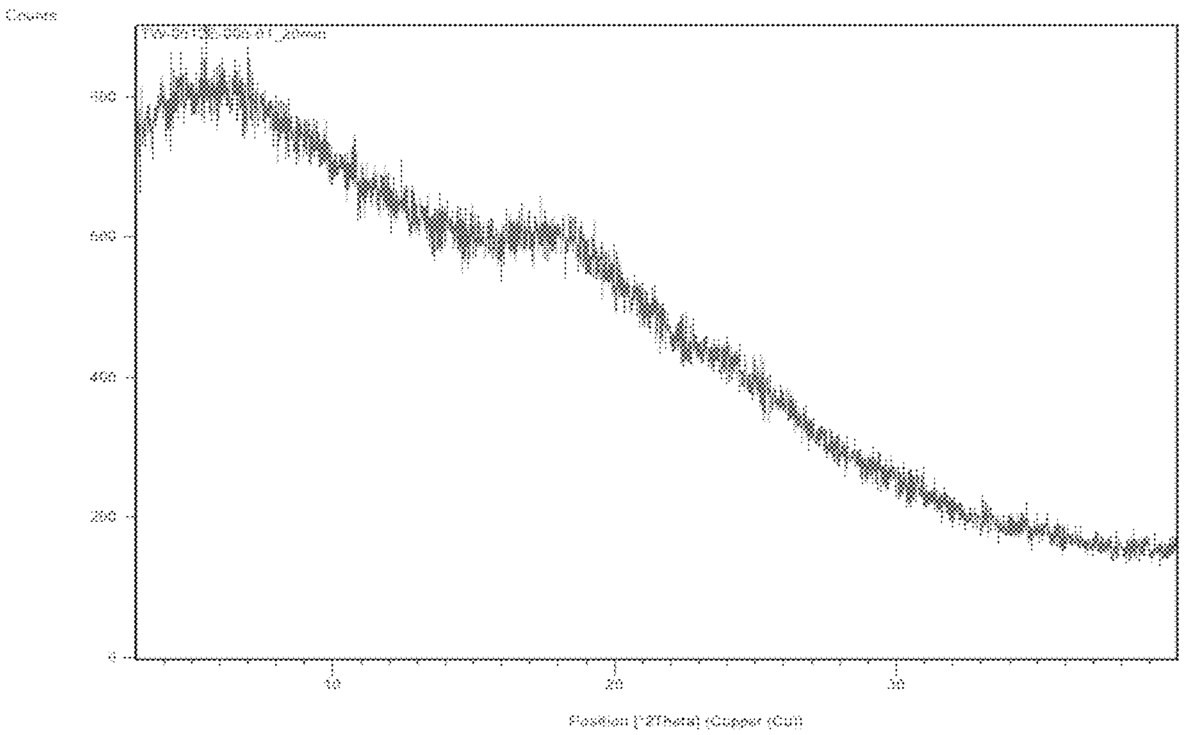
FIG. 82 provides an XRPD of amorphous material prepared by evaporation.

Example 5-11, Preparation and characterization of AAT-730 (Compound A) HCl salt amorphous form X-ray amorphous AAT-730 HCl salt was generated from evaporation of an aqueous solution of AAT-730 HCl salt under a steady stream of $N_2$. XRPD analysis displayed a halo pattern indicative of X-ray amorphous material (FIG. 82).

Physical stability of amorphous material was assessed by exposure to selected organic vapors and the material crystallized under organic vapor stress to Pattern 1 material.

Figure 83:
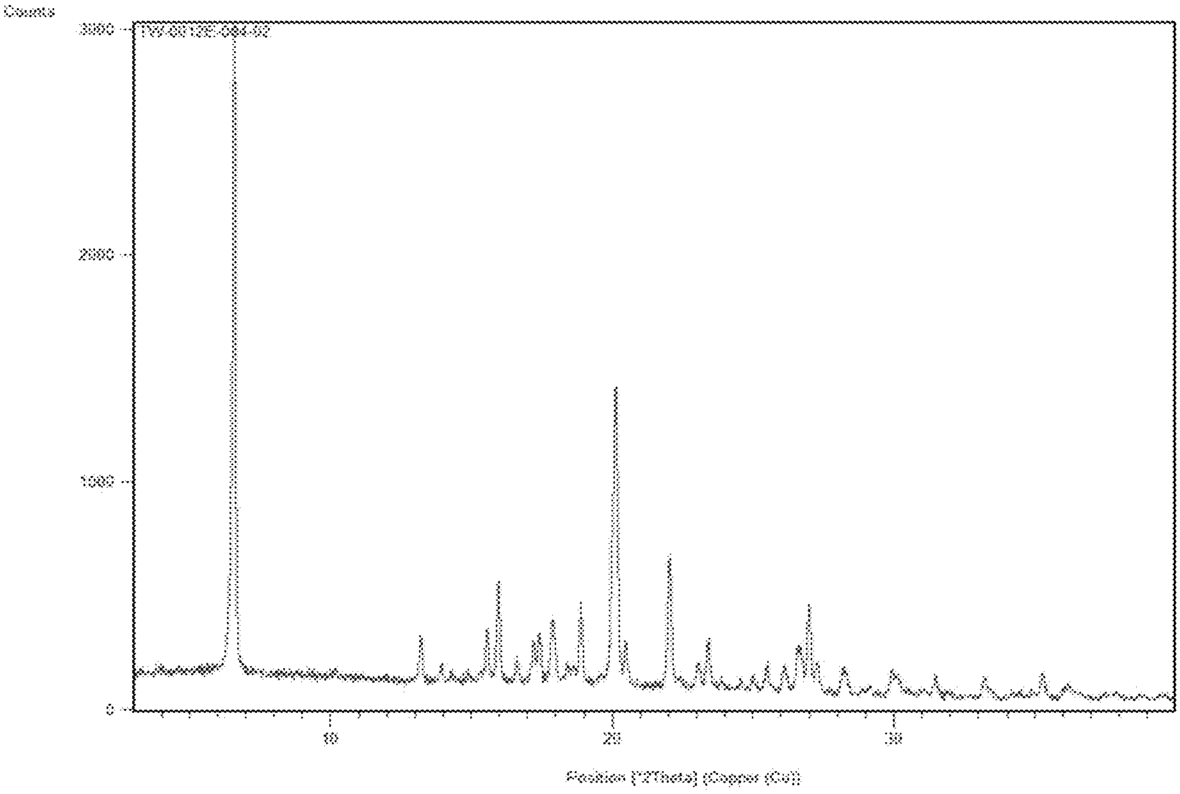
FIG. 83 provides an XRPD trace of AAT-730 HCl salt Pattern 1.
Figure 84:
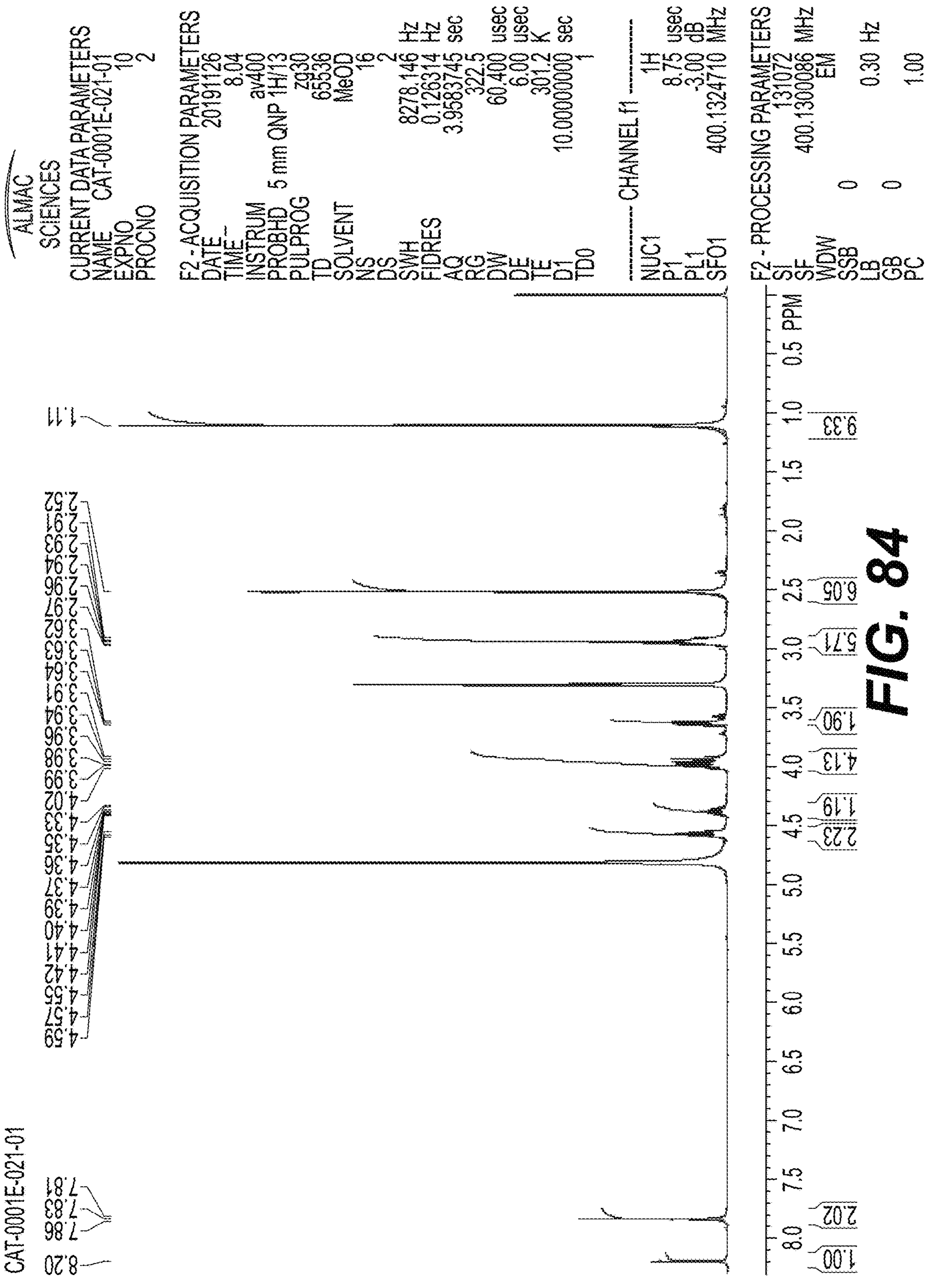
FIG. 84 provides a $^1$H NMR spectrum of AAT-730 HCl salt Pattern 1 analyzed in $CD_3OD$.
Figure 85:
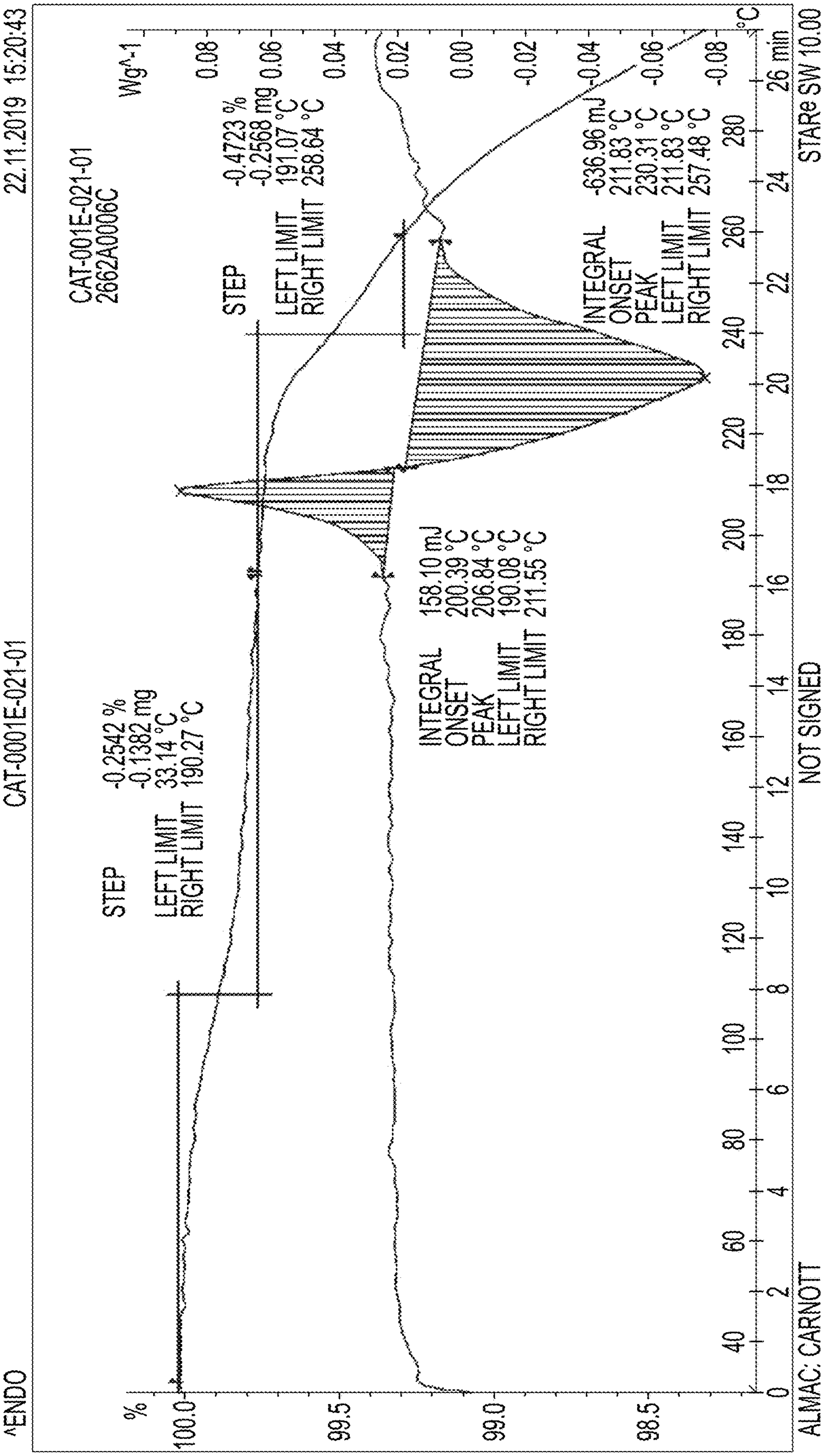
FIG. 85 provides a TG/DTA thermogram for AAT-730 HCl salt Pattern 1 between 3° and 300° C. at 10° C./min.

Example 5-12, Preparation and characterization of AAT-730 (Compound A) HCl salt Pattern 1 AAT-730 HCl salt Pattern 1 was isolated from the salt formation reaction and was frequently isolated throughout the polymorph screen (Table 5-10). XRPD analysis showed the material to be crystalline (FIG. 83). Proton NMR analysis performed on a sample isolated from the salt screen conformed to the molecular structure of the compound and no residual solvent was detected (FIG. 84). The TG/DTA data showed a melting endotherm at onset up to 200° C. (FIG. 85). Weight loss of at most 0.25% w/w was observed between approximately 30 and 190° C. which suggests an anhydrous material with a small amount of residual solvent/water, interconversion and water activity experiments disagree with this and suggest that Pattern 1 is a hydrate (Example 5-16). An exotherm at onset up to 212° C. may be due to crystallization to another form or decomposition.

Screening experiments which yielded Pattern 1 material

TABLE 5-10

| Input | Sample No (TW0012E-) | Solvent | Screen method | Result | XRPD |
|---|---|---|---|---|---|
| amorphous | 001-01 | THF | salt formation | solid | Pattern 1 |
| Lot No. 33-13 | 002-01 | THF | salt formation | solid | Pattern 1 |
| Pattern 1 | 003-01 | acetone | temp cycle | solid | Pattern 1 |
| Pattern 1 | 003-02 | ACN | temp cycle | solid | Pattern 1 |
| Pattern 1 | 003-03 | DCM | slurry (40° C.) | solid | Pattern 1 |
| Pattern 1 | 003-04 | EtOH | temp cycle | solid | Pattern 1 |
| Pattern 1 | 003-05 | THF | temp cycle | solid | Pattern 1 |
| Pattern 1 | 003-06 | acetone/water (20/1, $A_w$ at most 0.6) | temp cycle | solid | Pattern 1 |
| Pattern 1 | 003-07 | THF/water (13/1, $A_w$ at most 0.9) | temp cycle | solid (after evap) | Pattern 1 |
| Pattern 1 | 003-08 | EtOH/water (50/50) | temp cycle | solid (after evap) | Pattern 1 |
| Pattern 1 | 004-01 | acetone | slurry (5° C.) | solid | Pattern 1 |
| Pattern 1 | 004-02 | ACN | slurry (5° C.) | solid | Pattern 1 |
| Pattern 1 | 004-03 | DCM | slurry (5° C.) | solid | Pattern 1 |
| Pattern 1 | 004-04 | EtOH | slurry (5° C.) | solid | Pattern 1 |
| Pattern 1 | 004-06 | DMSO/water (80/20, $A_w$ at most 0.27) | slurry (5° C.) | solid | Pattern 1 |
| Pattern 1 | 004-08 | THF/water (13/1, $A_w$ at most 0.9) | slurry (5° C.) | solid | Pattern 1 |
| Pattern 1 | 005-06 | DMSO/water (80/20, $A_w$ at most 0.27) | slurry (20° C.) | solid | Pattern 1 |
| Pattern 1 | 005-08 | THF/water (13/1, $A_w$ at most 0.9) | slurry (20° C.) | solid | Pattern 1 |
| Pattern 1 | 010-07 | acetone/water (20/1, $A_w$ at most 0.6) | sonication | solid | Pattern 1 |
| Pattern 1 | 010-08 | MeOH | sonication | solid | Pattern 1 |
| Pattern 1 | 013-03 | none | 98% RH stress | solid | Pattern 1 |
| Pattern 1 | 016-01 | MeOH | slow cool | solid | Pattern 1 |
| Pattern 1 | 016-03 | THF/water (13/1, Aw at most 0.9) | slow cool | solid | Pattern 1 |

TABLE 5-10-continued

| Input | Sample No (TW0012E-) | Solvent | Screen method | Result | XRPD |
|---|---|---|---|---|---|
| Pattern 1 | 017-05 | DCM | Planetary milling | solid | Pattern 1 |
| Pattern 1 | 017-06 | dioxane | Planetary milling | solid | Pattern 1 |
| Pattern 1 | 017-08 | EtOH | Planetary milling | solid | Pattern 1 |
| Pattern 1 | 017-09 | EtOAc | Planetary milling | solid | Pattern 1 |
| Pattern 1 | 017-10 | heptane | Planetary milling | solid | Pattern 1 |
| Pattern 1 | 017-12 | MIBK | Planetary milling | solid | Pattern 1 |
| Pattern 1 | 017-13 | IPA | Planetary milling | solid | Pattern 1 |
| Pattern 1 | 017-14 | i-PrOAc | Planetary milling | solid | Pattern 1 |
| Pattern 1 | 017-15 | toluene | Planetary milling | solid | Pattern 1 |
| amorphous | 018-01 | acetone | Vapor stress | solid | Pattern 1 |
| amorphous | 018-02 | ACN | Vapor stress | solid | Pattern 1 |
| amorphous | 018-03 | DCM | Vapor stress | solid | Pattern 1 |
| amorphous | 018-04 | EtOH | Vapor stress | solid | Pattern 1 |
| amorphous | 018-05 | THF | Vapor stress | solid | Pattern 1 |
| Pattern 2 | 020-03 | EtOH/water (86/14, $A_w$ at most 0.6) | Water Activity experiments | solid | Pattern 1 |
| Pattern 2 | 020-04 | EtOH/water (68/32, $A_w$ at most 0.8) | Water Activity experiments | solid | Pattern 1 |

Figure 86:
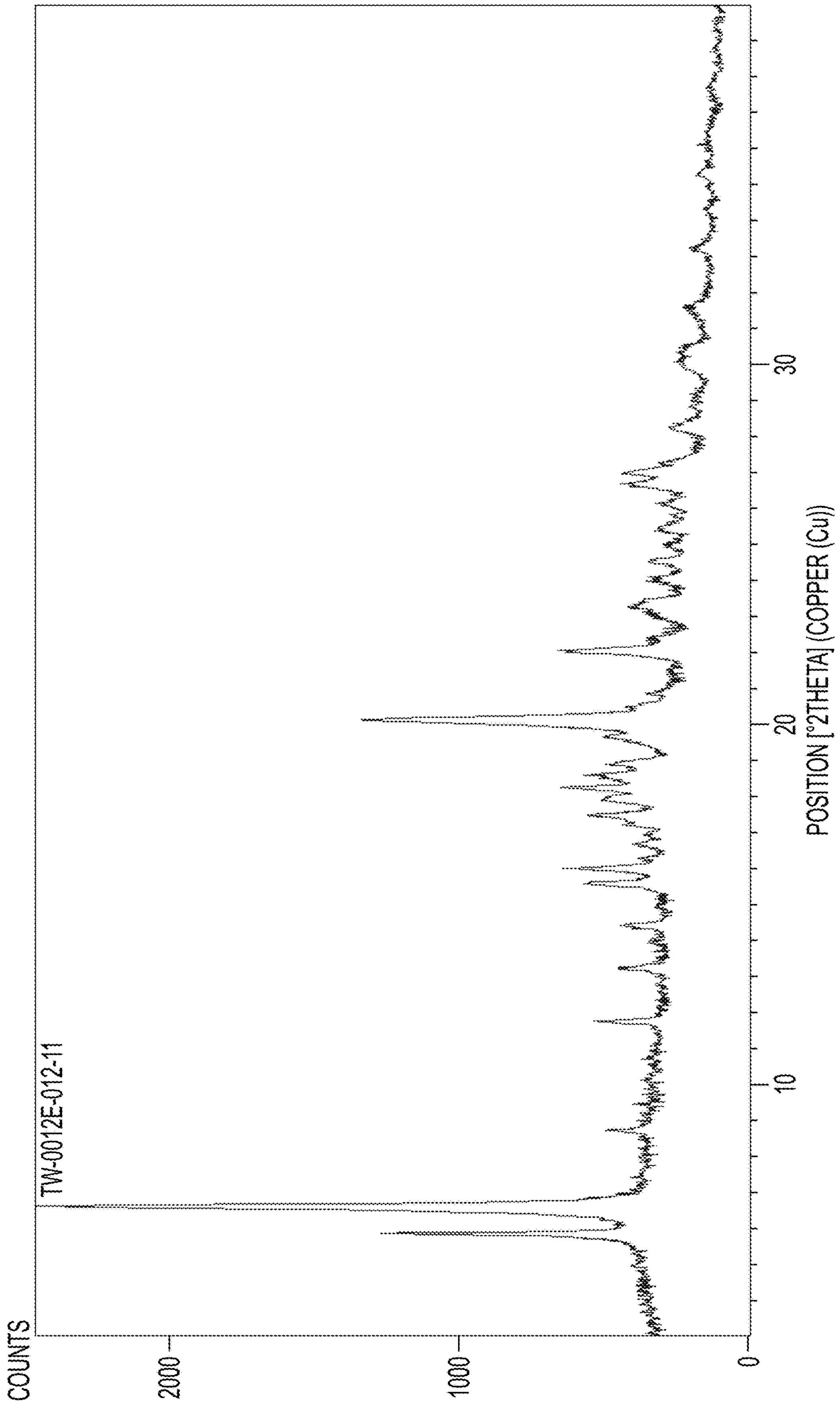
FIG. 86 provides an XRPD trace of AAT-730 HCl salt Pattern 2.
Figure 87:
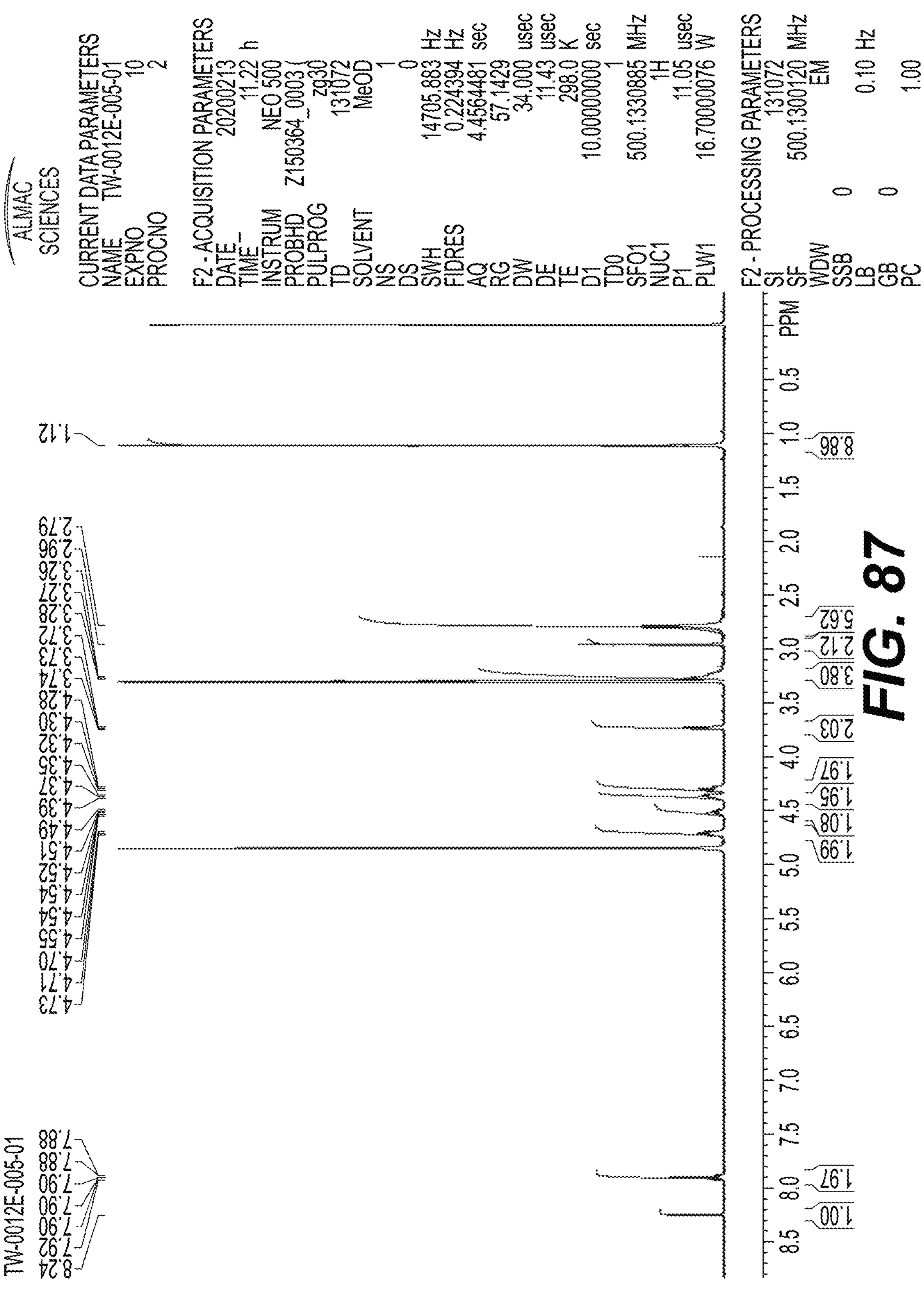
FIG. 87 provides a $^1$H NMR spectrum of AAT-730 HCl salt Pattern 2 analyzed in $CD_3OD$.
Figure 88:
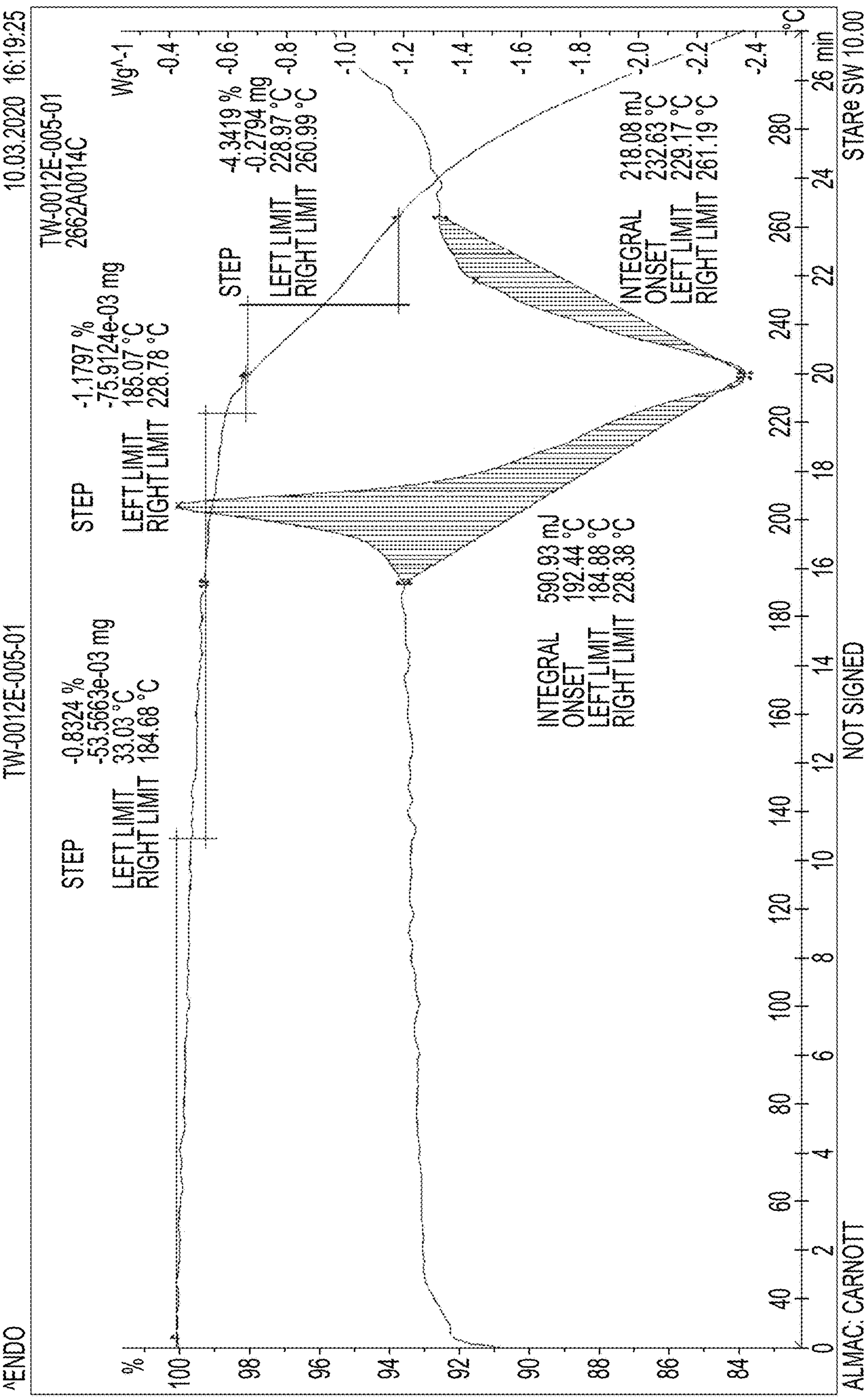
FIG. 88 provides a TG/DTA thermogram of AAT-730 HCl salt Pattern 2 analyzed between 30 and 300° C. at 10° C./min.
Figure 89:
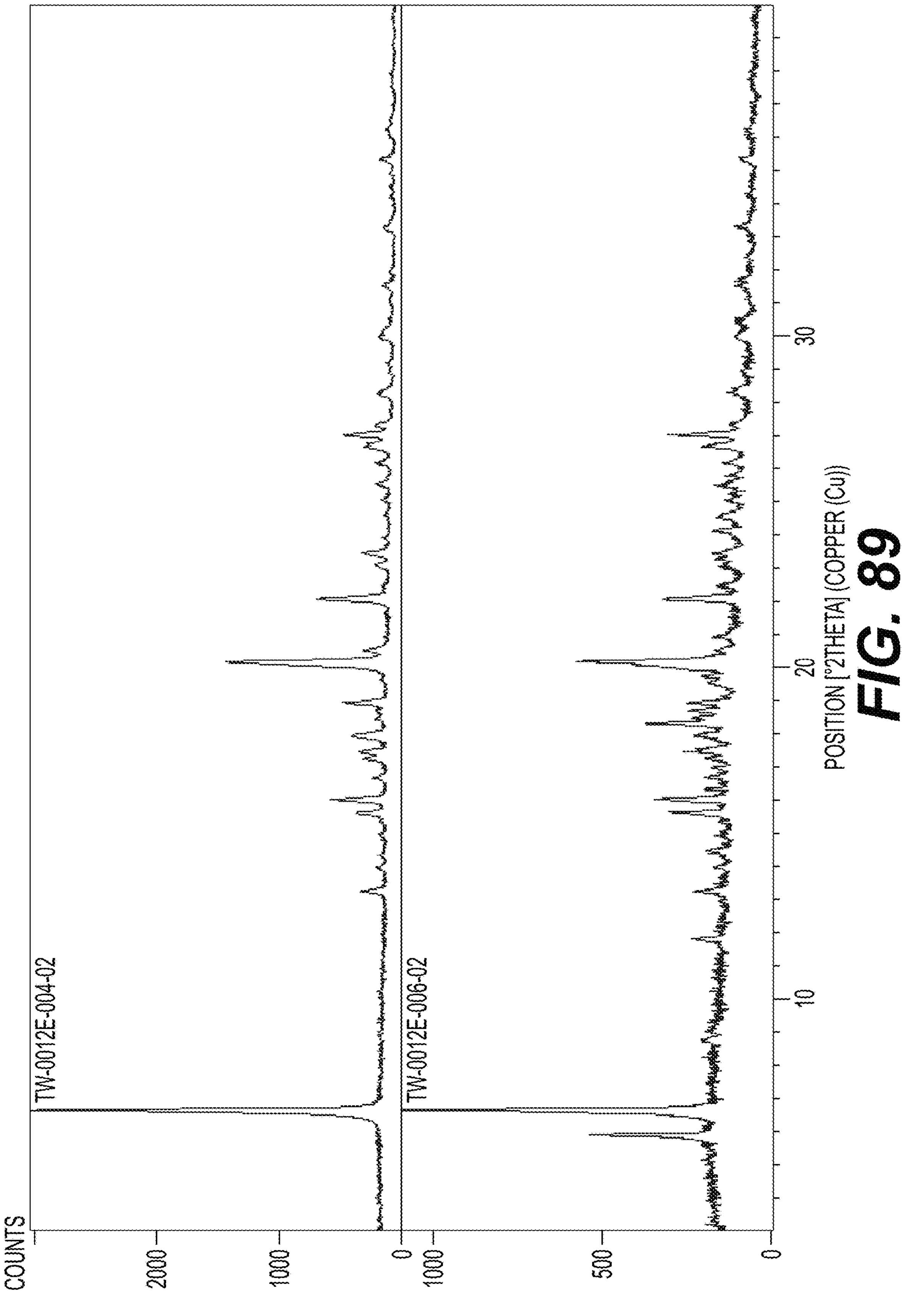
FIG. 89 provides an XRPD comparison of AAT-730 HCl salt Pattern 1 (top) with Pattern 2 (bottom).

Example 5-13, Preparation and characterization of AAT-730 (Compound A) HCl salt Pattern 2 AAT-730 HCl salt Pattern 2 was isolated from a large number of screening experiments (Table 5-11). XRPD analysis showed the material to be crystalline (FIG. 86). Proton NMR analysis (FIG. 87) conformed to the molecular structure of the compound and no residual solvent was detected. TG/DTA analysis (FIG. 88) performed on AAT-730 HCl salt Pattern 2 showed a melting endotherm at onset up to 192° C. Weight loss of at most 0.85% w/w was observed between approximately 30 and 180° C. which suggests an anhydrous material with a small amount of residual solvent/water. XRPD comparison of AAT-730 HCl salt Pattern 1 with Pattern 2 is shown in FIG. 89.

Screening Experiments which Yielded Pattern 2 Material

TABLE 5-11

| Input | Sample No. (TW-0012E-) | Solvent | Screen method | Result | XRPD |
|---|---|---|---|---|---|
| Pattern 1 | 004-05 | THF | slurry (5° C.) | solid | Pattern 2 |
| Pattern 1 | 004-07 | acetone/water (20/1, $A_w$ at most 0.6) | slurry (5° C.) | solid | Pattern 2 |
| Pattern 1 | 005-01 | acetone | slurry (20° C.) | solid | Pattern 2 |
| Pattern 1 | 005-02 | ACN | sluny (20° C.) | solid | Pattern 2 |
| Pattern 1 | 005-03 | DCM | slurry (20° C.) | solid | Pattern 2 |
| Pattern 1 | 005-04 | EtOH | slurry (20° C.) | solid | Pattern 2 |
| Pattern 1 | 005-05 | THF | slurry (20 ° C.) | solid | Pattern 2 |
| Pattern 1 | 005-07 | acetone/water (20/1, $A_w$ at most 0.6) | slurry (20° C.) | solid | Pattern 2 |
| Pattern 1 | 006-01 | acetone | slurry (50° C.) | solid | Pattern 2 |
| Pattern 1 | 006-02 | ACN | slurry (50° C.) | solid | Pattern 2 |
| Pattern 1 | 006-04 | EtOH | slurry (50° C.) | solid | Pattern 2 |
| Pattern 1 | 006-05 | THF | slurry (50° C.) | solid | Pattern 2 |
| Pattern 1 | 010-01 | acetone | sonication | solid | Pattern 2 |
| Pattern 1 | 010-02 | ACN | sonication | solid | Pattern 2 |
| Pattern 1 | 010-03 | DCM | sonication | solid | Pattern 2 |
| Pattern 1 | 010-04 | EtOH | sonication | solid | Pattern 2 |
| Pattern 1 | 010-05 | THF | sonication | solid | Pattern 2 |
| Pattern 1 | 012-01 | acetone | vapor stress | solid | Pattern 2 |
| Pattern 1 | 012-02 | ACN | vapor stress | solid | Pattern 2 |
| Pattern 1 | 012-03 | cyclohexane | vapor stress | solid | Pattern 2 |
| Pattern 1 | 012-04 | DIPE | vapor stress | solid | Pattern 2 |
| Pattern 1 | 012-05 | EtOH | vapor stress | solid | Pattern 2 |
| Pattern 1 | 012-06 | EtOAc | vapor stress | solid | Pattern 2 |
| Pattern 1 | 012-07 | MeOH | vapor stress | solid | Pattern 2 |
| Pattern 1 | 012-08 | MTBE | vapor stress | solid | Pattern 2 |
| Pattern 1 | 012-09 | MIBK | vapor stress | solid | Pattern 2 |
| Pattern 1 | 012-10 | IPA | vapor stress | solid | Pattern 2 |
| Pattern 1 | 012-11 | i-PrOAc | vapor stress | solid | Pattern 2 |
| Pattern 1 | 012-12 | heptane | vapor stress | solid | Pattern 2 |
| Pattern 1 | 013-01 | none | 23% RH stress | solid | Pattern 2 |
| Pattern 1 | 013-02 | none | 75% RH stress | solid | Pattern 2 |
| Pattern 1 | 015-01 | t-Butanol | temp cycle | solid | Pattern 2 |
| Pattern 1 | 015-02 | cyclohexane | temp cycle | solid | Pattern 2 |
| Pattern 1 | 015-03 | DIPE | temp cycle | solid | Pattern 2 |
| Pattern 1 | 015-05 | MEK | temp cycle | solid | Pattern 2 |
| Pattern 1 | 015-06 | MIBK | temp cycle | solid | Pattern 2 |
| Pattern 1 | 015-08 | IPA | temp cycle | solid | Pattern 2 |
| Pattern 1 | 015-09 | dioxane | temp cycle | solid | Pattern 2 |

TABLE 5-11-continued

| Input | Sample No. (TW-0012E-) | Solvent | Screen method | Result | XRPD |
|---|---|---|---|---|---|
| Pattern 1 | 015-10 | i-PrOAc | temp cycle | solid | Pattern 2 |
| Pattern 1 | 015-11 | toluene | temp cycle | solid | Pattern 2 |
| Pattern 1 | 015-12 | heptane | temp cycle | solid | Pattern 2 |
| Pattern 2 | 019-01 | THF | competitive slurry | solid | Pattern 2 |
| Pattern 2 | 019-02 | THF | competitive slurry | solid | Pattern 2 |
| Pattern 2 | 019-03 | THF | competitive slurry | solid | Pattern 2 |
| Pattern 2 | 020-01 | EtOH/water (97/3, $A_w$ at most 0.2) | water activity experiments | solid | Pattern 2 |

Figure 90:
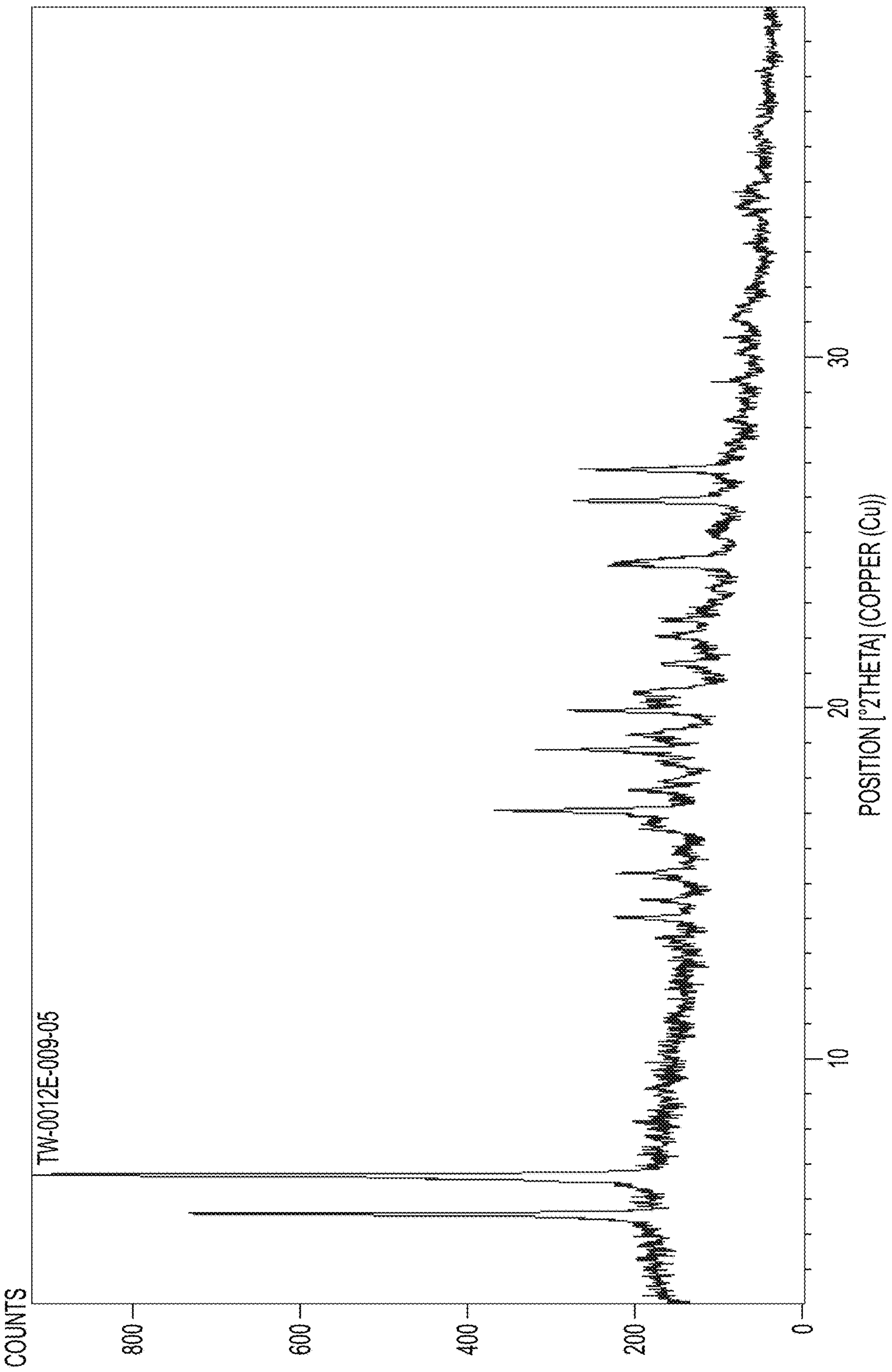
FIG. 90 provides an XRPD trace of AAT-730 HCl salt Pattern 3.
Figure 91:
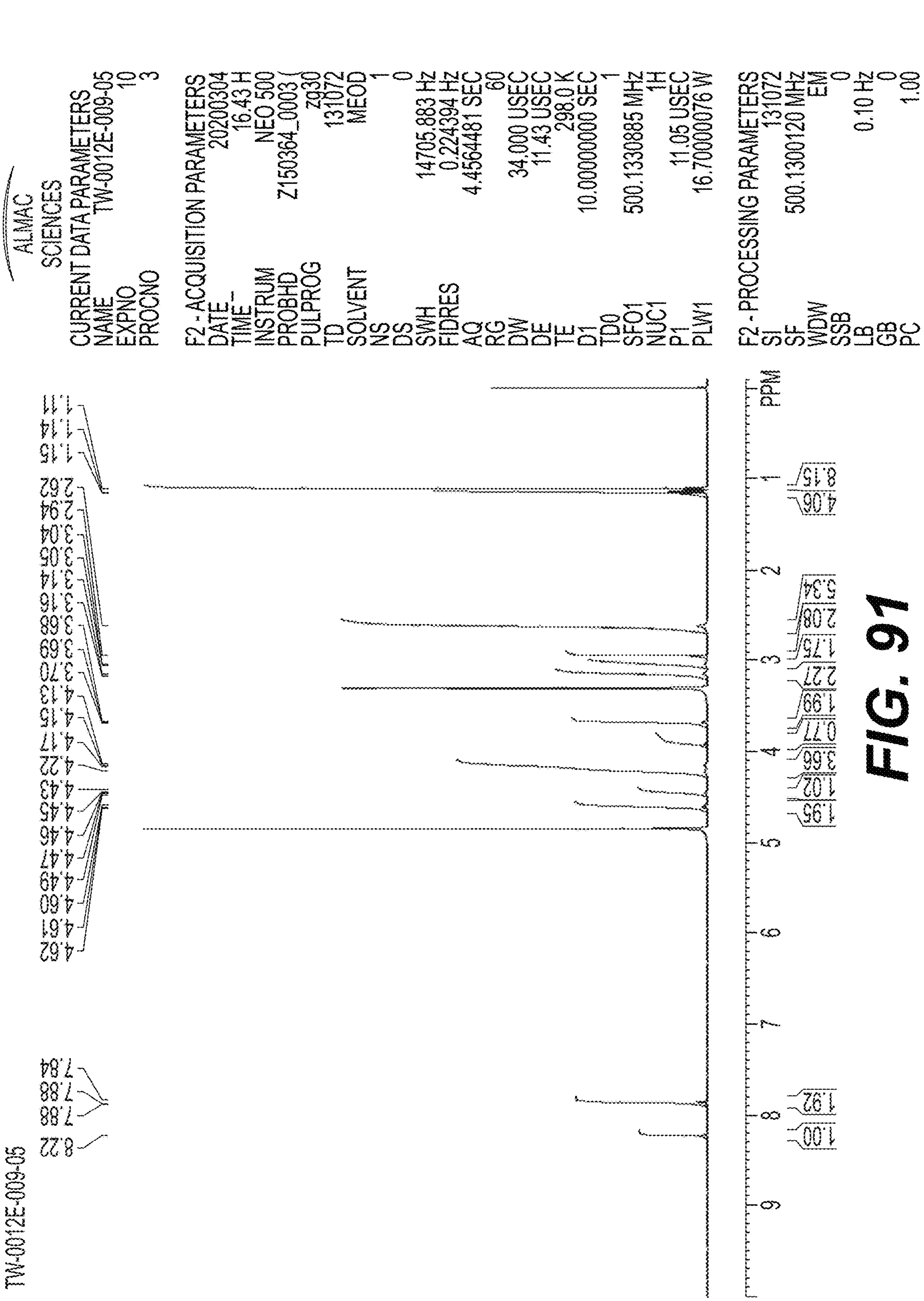
FIG. 91 provides a $^1$H NMR spectrum of AAT-730 HCl salt Pattern 3 analyzed in $CD_3OD$.
Figure 92:
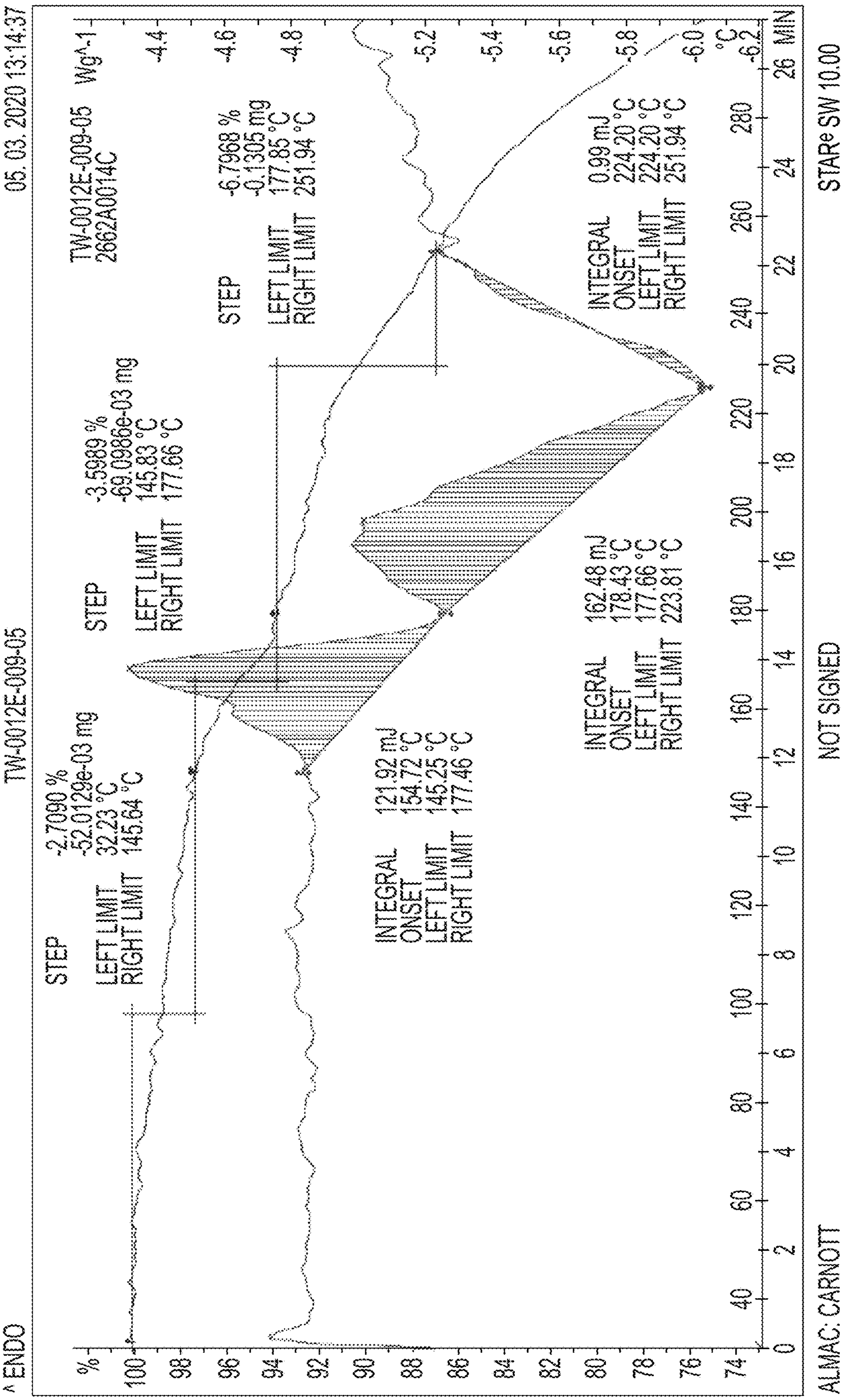
FIG. 92 provides a TG/DTA thermogram of AAT-730 HCl salt Pattern 3 analyzed between 30 and 300° C. at 10° C./min.

Example 5-14, Preparation and characterization of AAT-730 (Compound A) HCl salt Pattern 3 AAT-730 HCl salt Pattern 3 material was isolated from the experiments shown in Table 5-12. XRPD analysis (FIG. 90) showed the material to be crystalline. Proton NMR analysis of the sample isolated from the water/IPA crash precipitation experiment (FIG. 91) conformed to the molecular structure of the compound and IPA (at most 7.6% w/w) was detected. TG/DTA performed on the same sample of AAT-730 HCl salt Pattern 3 showed a weight loss of at most 2.7% w/w between approximately 30 and 145° C. and a further weight loss of 3.6% between approximately 145 and 180° C. (FIG. 92). The weight loss may be due to loss of IPA and/or water and suggests the compound may be a solvate/hydrate. The other Pattern 3 solids may be either hydrates or isostructural solvates.

Experiments which Yielded Pattern 3 Solids

TABLE 5-12

| Input | Sample No. (TW-0012E-) | Solvent | Antisolvent | Screen method | Result | XRPD |
|---|---|---|---|---|---|---|
| Pattern 1 | 008-02 | DMSO/water (80/20, $A_w$ at most 0.27) | none | slow evap | solid | Pattern 3 (PS) + 2 |
| Pattern 1 | 009-05 | water | IPA | crash pptn | solid (after evap) | Pattern 3 |
| Pattern 1 | 015-04 | DMAc | none | temp cycle | solid | Pattern 3 + peak |

Figure 93:
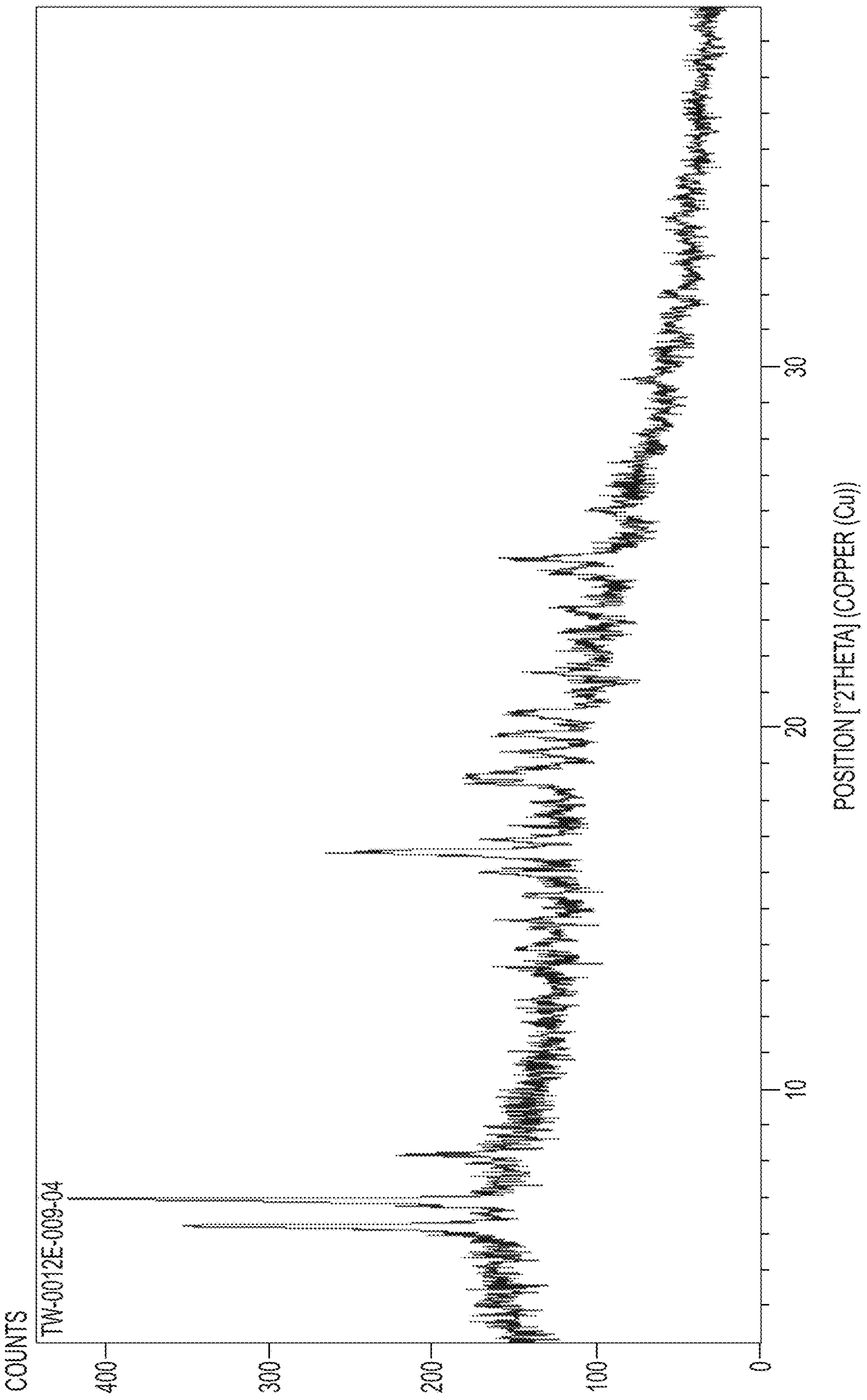
FIG. 93 provides an XRPD trace of AAT-730 HCl salt Pattern 4.

Example 5-15, Preparation and characterization of AAT-730 (Compound A) HCl salt Pattern 4 AAT-730 HCl salt Pattern 4 was isolated from the screening experiments shown in Table 5-13. The XRPD diffractogram is shown in FIG. 93 and is concordant with a crystalline material. Pattern 4 solids were not further analyzed as there was a very small amount of material, but it may be a hydrate. However, it was included in interconversion experiments (Example 5-16).

Screening Experiments which Yielded Pattern 4 Material

TABLE 5-13

| Input | Sample No. (TW-0012E-) | Solvent | Screen method | Result | XRPD |
|---|---|---|---|---|---|
| Pattern 1 | 008-03 | EtOH/water (50/50) | slow evap | solid-after evap | Pattern 4 |
| Pattern 1 | 009-04 | water | crash pptn | solid-after evap | Pattern 4 |
| Pattern 1 | 011-01 | water | freeze drying | solid | Pattern 4 |

Example 5-16, Determination of Most Stable Form

The most robust method for determining the thermodynamically most stable Form at a given temperature involves suspension of all observed forms in a saturated solution, as the system will naturally gravitate to the lowest free energy form. In solvent mediated conversions, seeds of all forms are present and there is no activation energy barrier to interconversion. This technique is used to identify the 'true' transition temperature and the thermodynamic relationship between the forms.

Interconversion Slurries of AAT-730 (Compound A) HCl Salt

Figure 94:
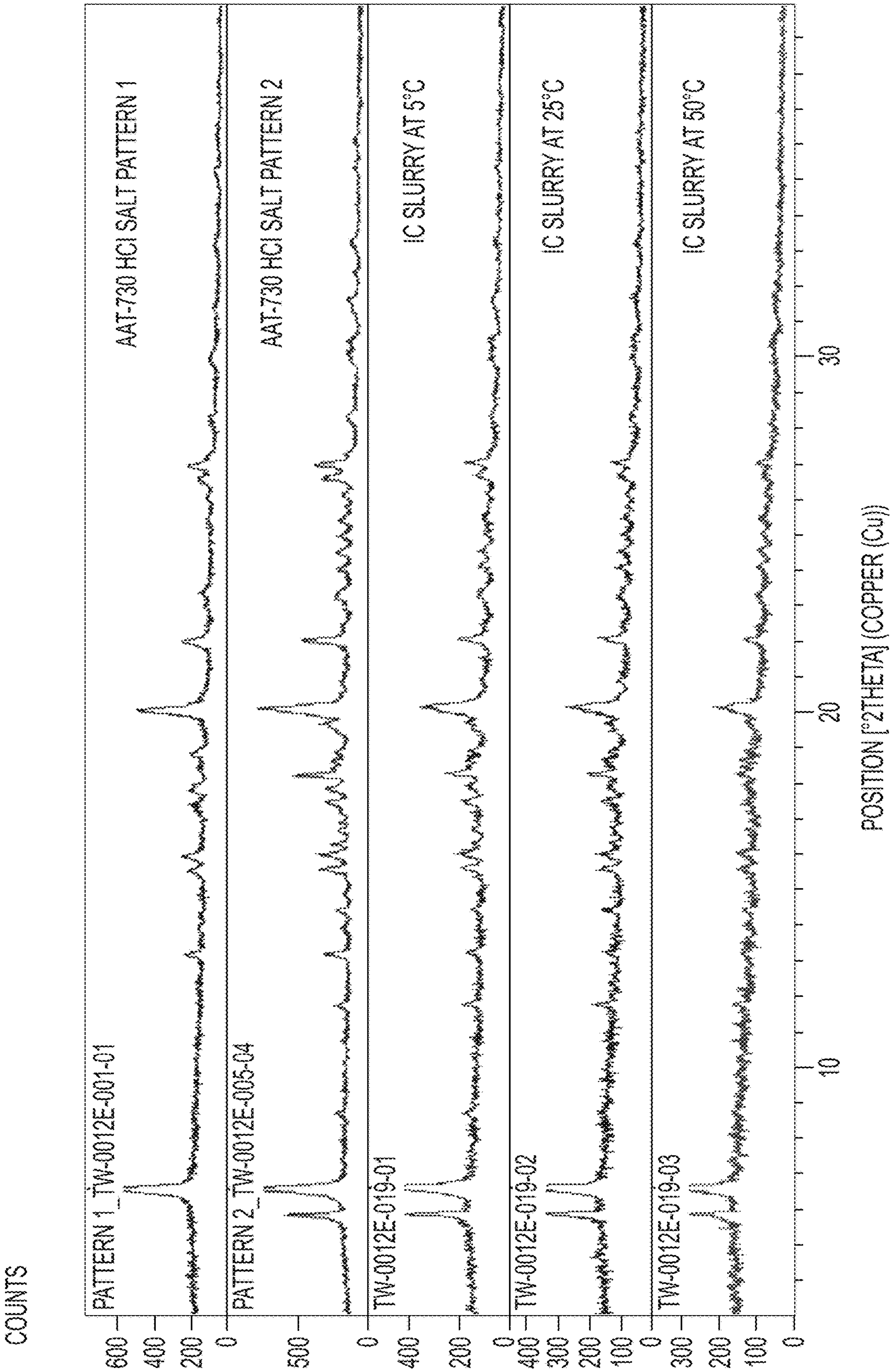
FIG. 94 provides an XRPD trace of interconversion slurry experiments.

Saturated slurries of Pattern 2 AAT-730 HCl salt were prepared in THF and stirred overnight. The slurry was seeded with Patterns 1, 2, 3, and 4 AAT-730 HCl salt and stirred for up to 10 days prior to isolation and analysis by XRPD (FIG. 94). The results are shown in Table 5-14 and suggest that Pattern 2 material is the most stable form in anhydrous solvent in the temperature range 5 to 50° C.

Results from Interconversion Slurry Experiments

TABLE 5-14

| Sample No. (TW-0012E-) | Solvent | Temp (° C.) | Seeds added | Result | XRPD |
|---|---|---|---|---|---|
| 019-01 | THF | 5 | Patterns 1, 2, 3 and 4 | solid | Pattern 2 |
| 019-02 | THF | 25 | Patterns 1, 2, 3 and 4 | solid | Pattern 2 |
| 019-03 | THF | 50 | Patterns 1, 2, 3 and 4 | solid | Pattern 2 |

Water Activity Experiments of AAT-730 (Compound A) HCl Salt

Figure 95:
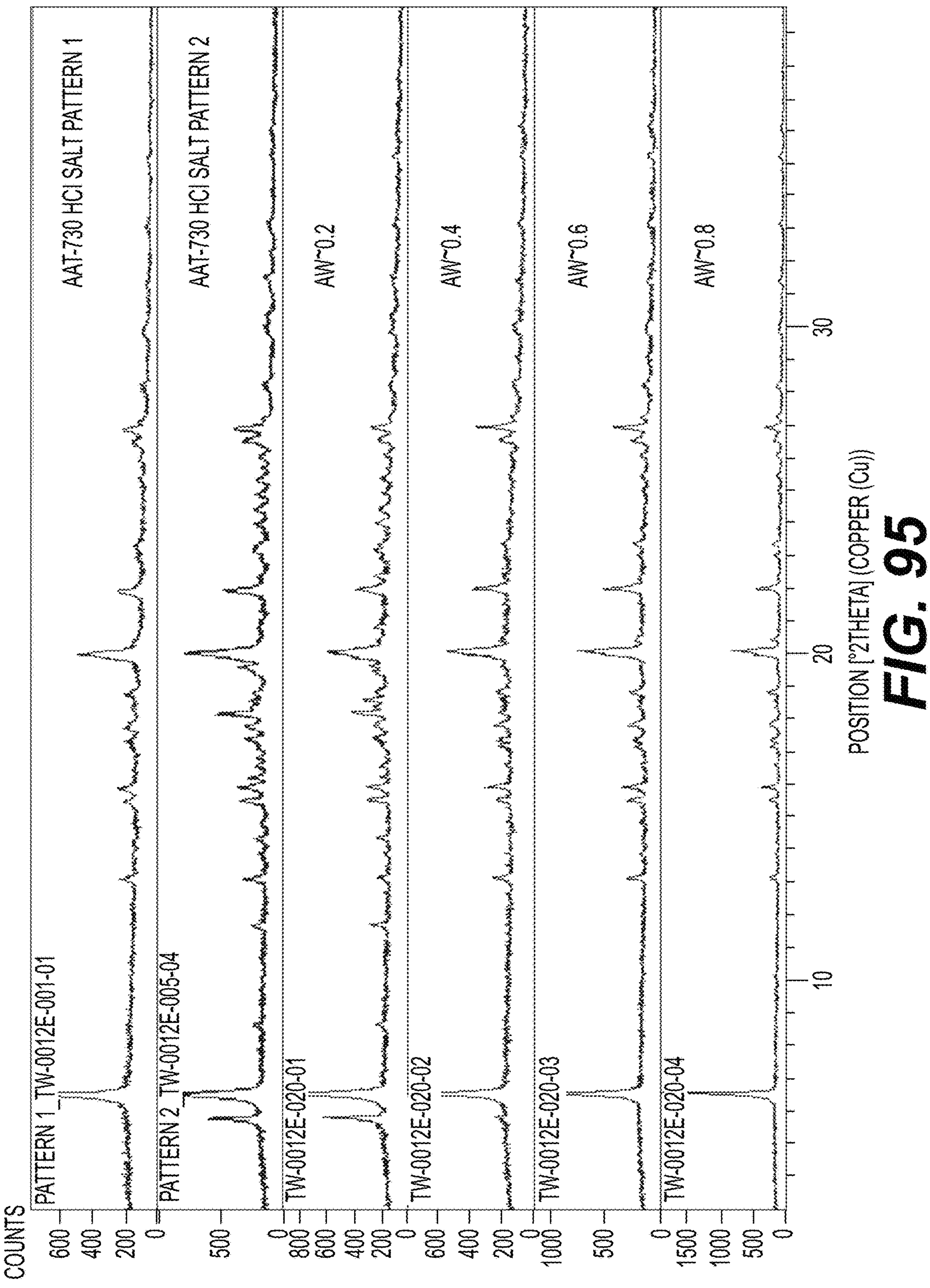
FIG. 95 provides an XRPD trace of water activity experiments.
Figure 96:
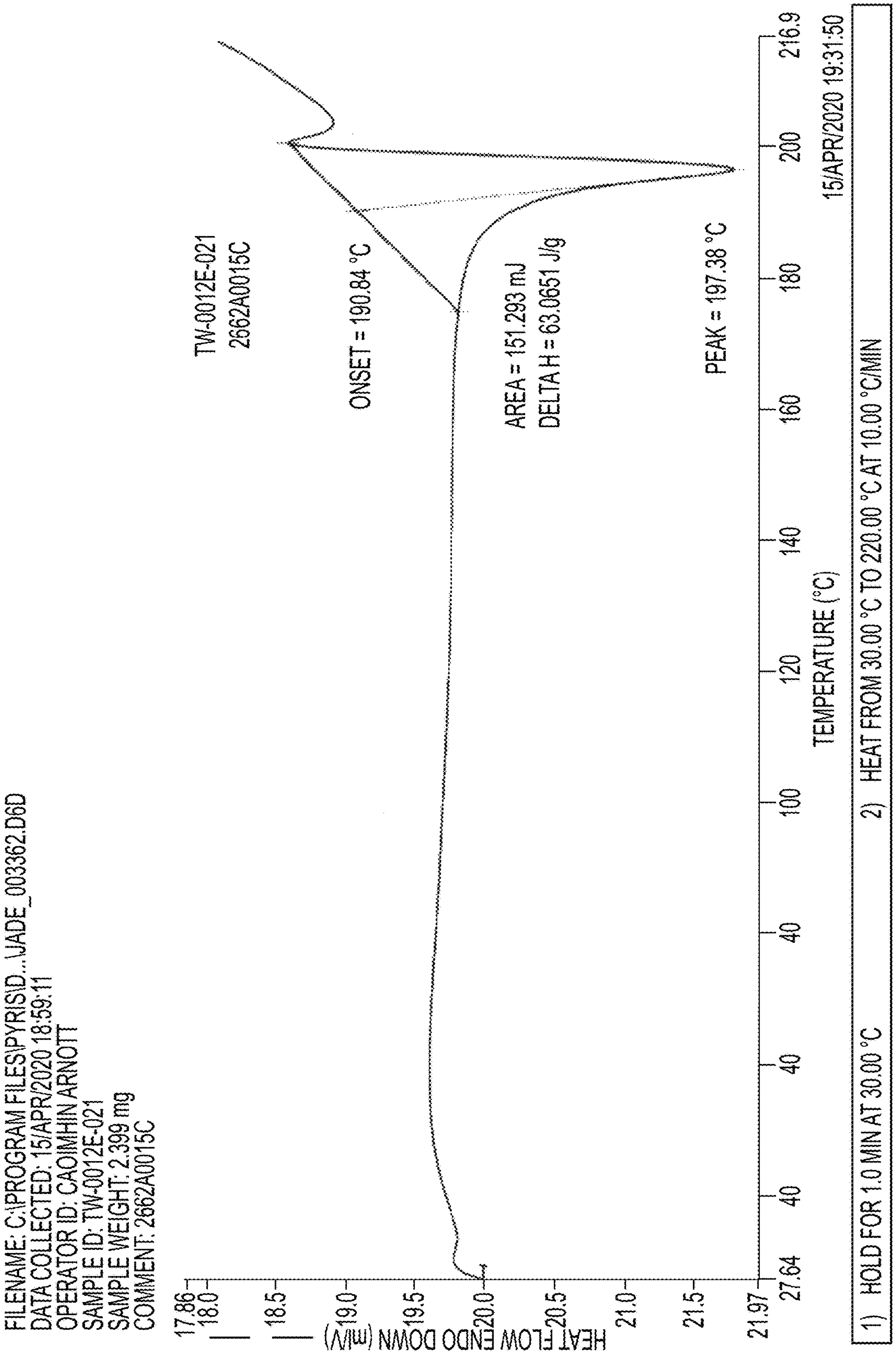
FIG. 96 provides a DSC thermogram of AAT-730 HCl salt Pattern 2 (sample used was a combined sample from the polymorph screen).

Water activity experiments were carried out to determine if the water activity of the solvent influenced which form was isolated. The results are shown in Table 5-15 and FIG. 95. At Aw at most 0.2, Pattern 2 was the most stable form. A mixture was isolated at Aw at most 0.4 and this may be close to the critical water activity. At Aw greater than or equal to 0.6, Pattern 1 was the more stable form. These results suggest that Pattern 1 may be a hydrate as its formation is influenced by water activity.

Results from Water Activity Experiments

TABLE 5-15

| Sample No. (TW-0012E-) | Solvent | Aw | Seeds added | Result | XRPD |
|---|---|---|---|---|---|
| 020-01 | EtOH/water (97/3) | 0.2 | Patterns 1, 2, 3 and 4 | solid | Pattern 2 |
| 020-02 | EtOH/water (93/7) | 0.4 | Patterns 1, 2, 3 and 4 | solid | Pattern 1 + small amount of Pattern 2 |
| 020-03 | EtOH/water (86/14) | 0.6 | Patterns 1, 2, 3 and 4 | solid | Pattern 1 |
| 020-04 | EtOH/water (68/32) | 0.8 | Patterns 1, 2, 3 and 4 | solid | Pattern 1 |

Example 5-17, Further characterization of AAT-730 (Compound A) HCl salt Pattern 2 AAT-730 HCl salt Pattern 2 was further characterized by DSC and humidity stressing. The aqueous solubility was also determined by aliquot addition.

The DSC thermogram obtained for AAT-730 HCl salt Pattern 2 at 10° C./min is shown in FIGS. 6-15 and shows a melting endotherm at onset 190.84° C. which is concordant with TG/DTA data.

Figure 97:
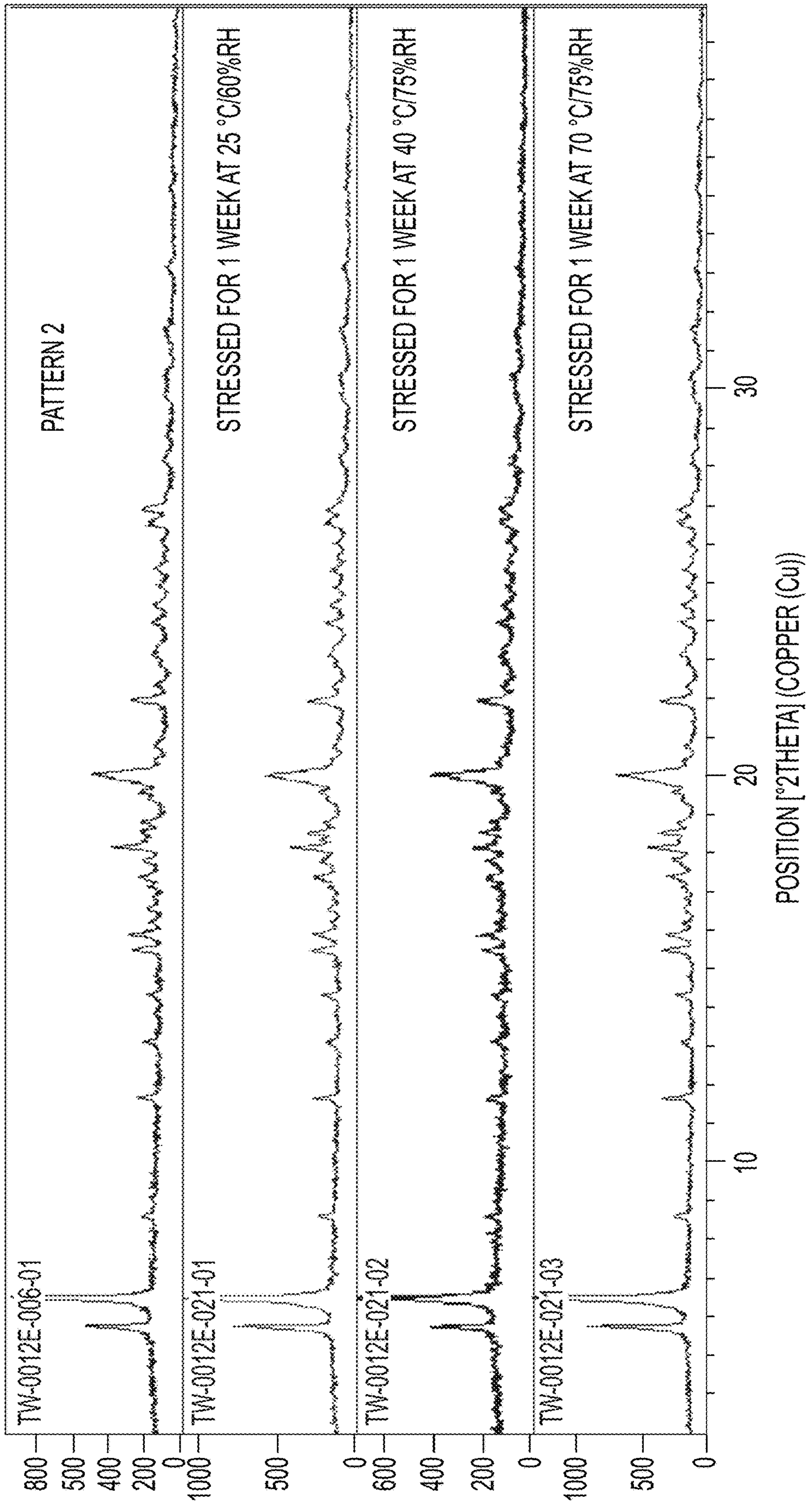
FIG. 97 provides an XRPD patterns of humidity stressed samples.
Figure 98:
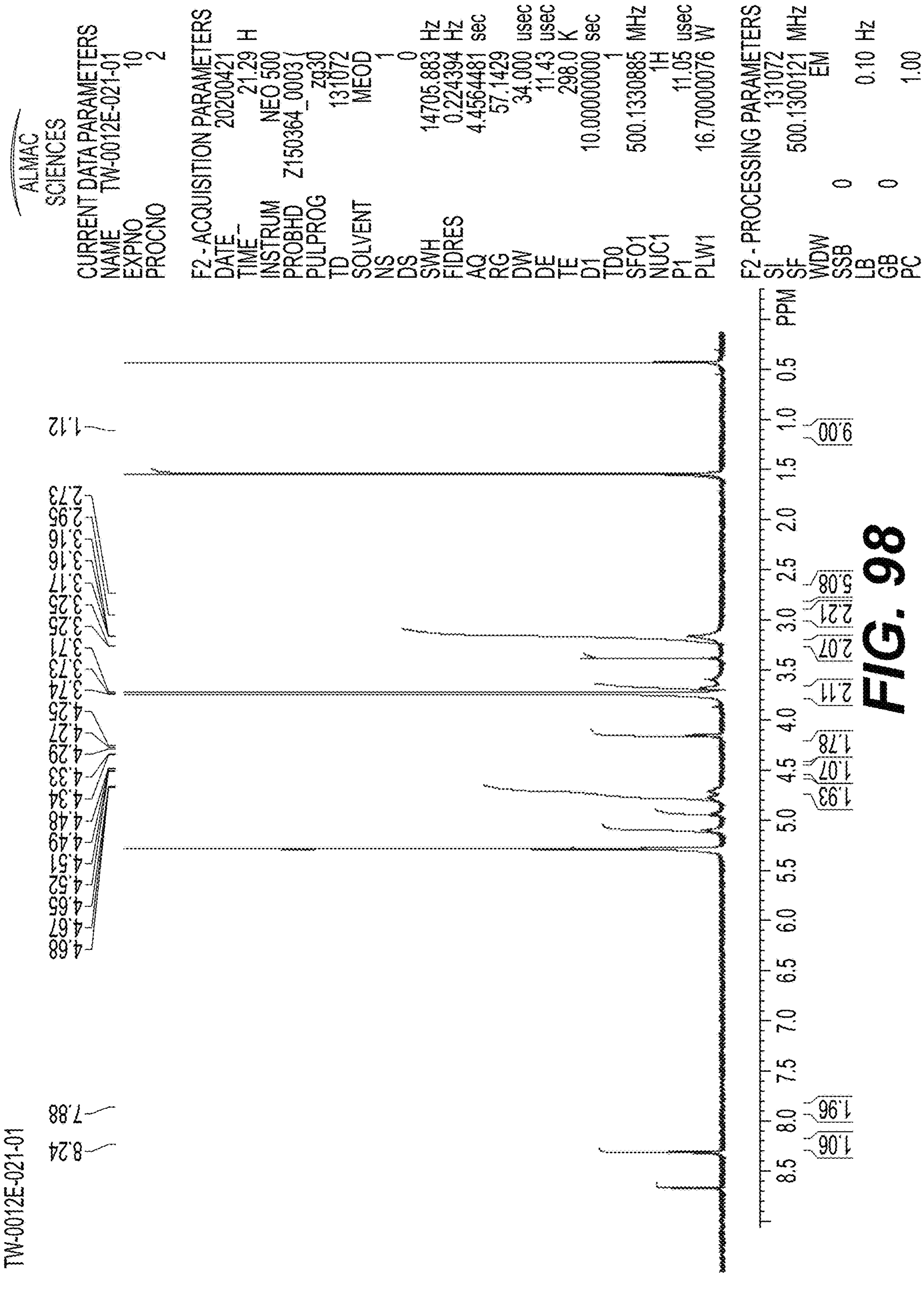
FIG. 98 provides a $^1$H NMR spectrum of AAT-730 HCl salt Pattern 2 (post 25° C./60% RH stressing) analyzed in $CD_3OD$.
Figure 99:
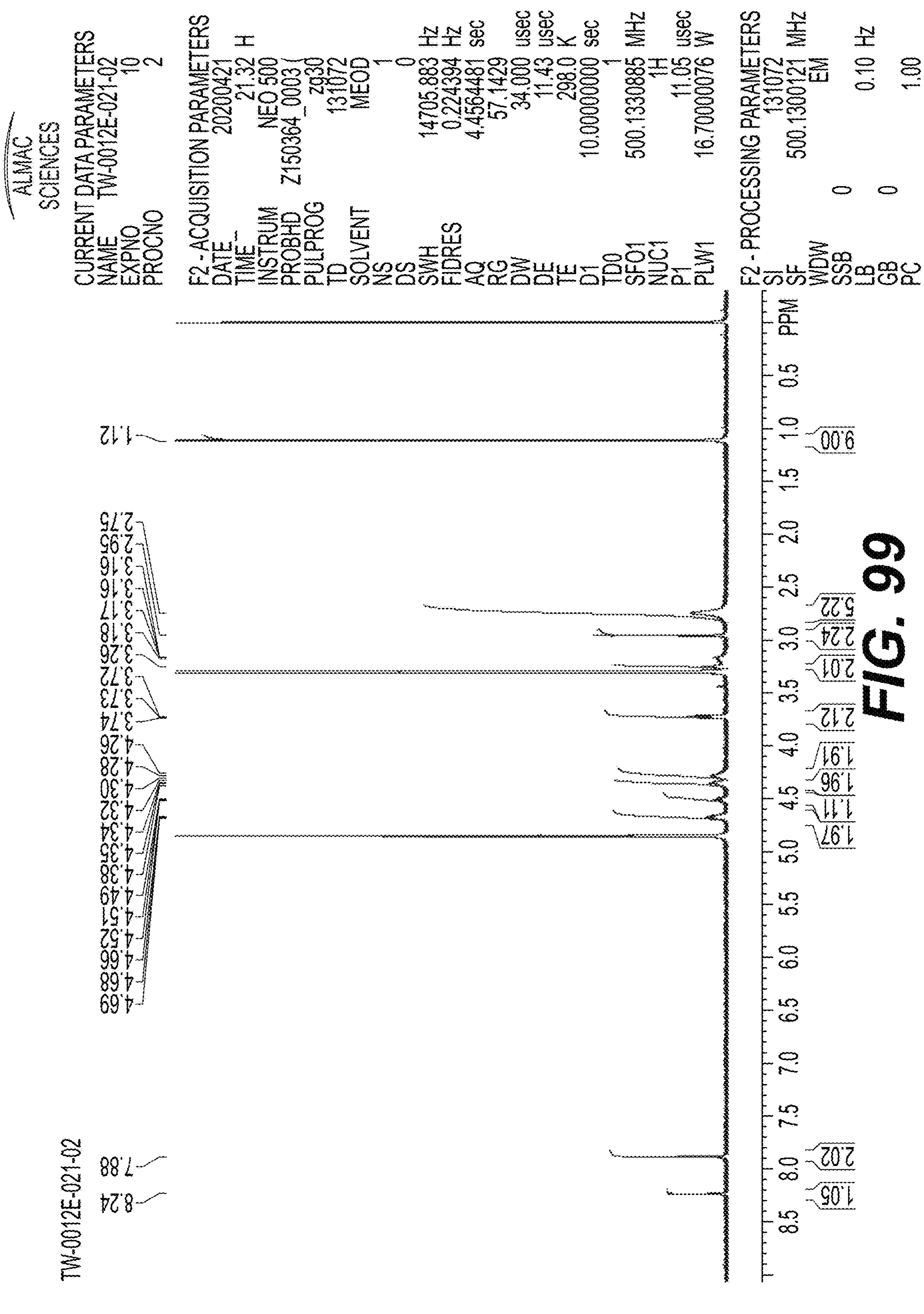
FIG. 99 provides a $^1$H NMR spectrum of AAT-730 HCl salt Pattern 2 (post 40° C./75% RH stressing) analyzed in $CD_3OD$.
Figure 100:
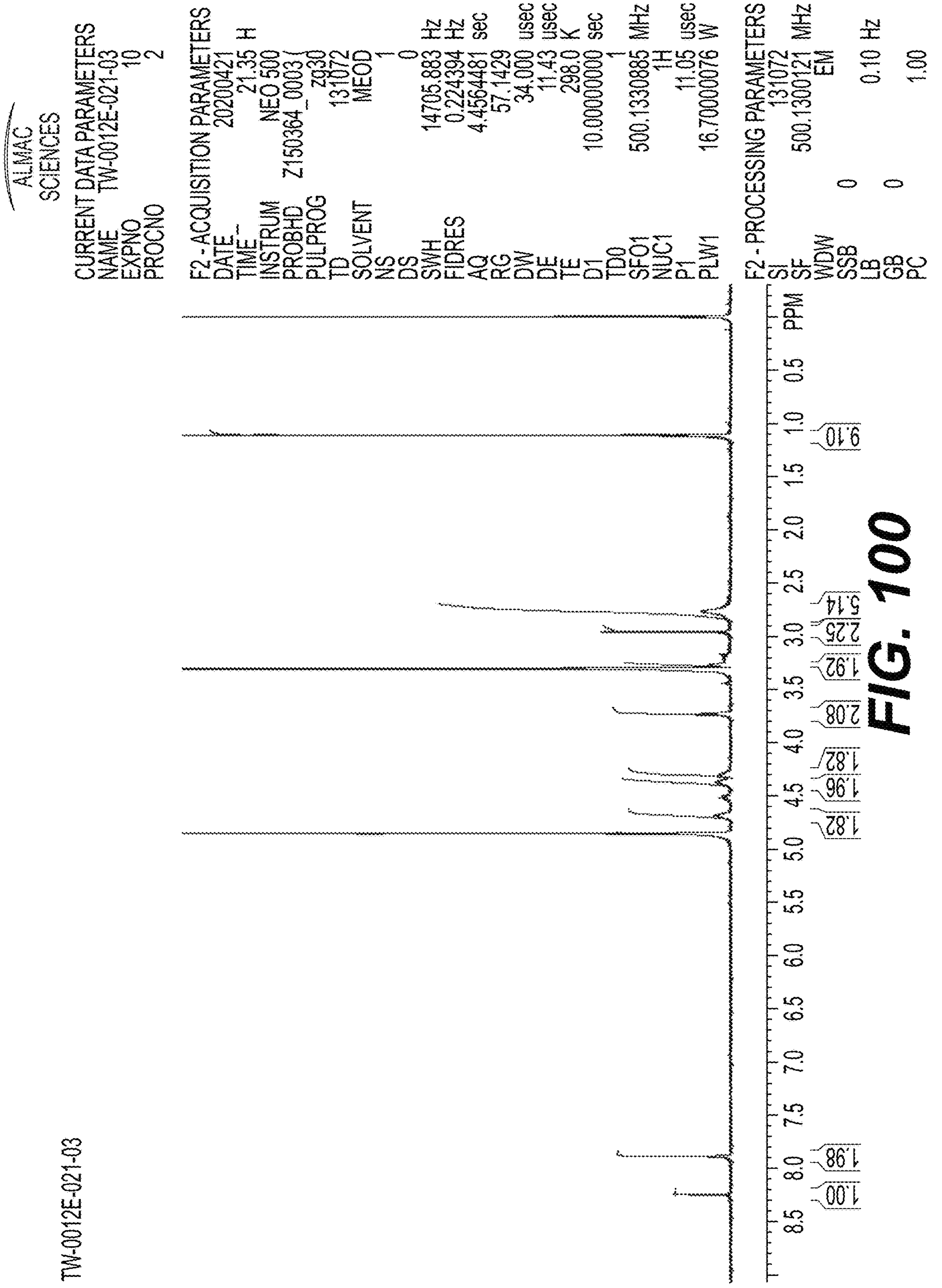
FIG. 100 provides a $^1$H NMR spectrum of AAT-730 HCl salt Pattern 2 (post 70° C./75% RH stressing) analyzed in $CD_3OD$.

AAT-730 HCl salt Pattern 2 was stressed at a range of relative humidity conditions for 7 days, as shown in Table 5-16. The salt was added to HPLC vials and placed, uncapped, into the relative humidity conditions shown in Table 5-16. The materials remained as Pattern 2 under the conditions tested (FIG. 97). $^1$H NMR analysis (FIG. 98, FIG. 99, and FIG. 100) of the post-stressed samples showed no change.

Results from RH Screening Experiments

TABLE 5-16

| Input | Sample No (TW0012E-) | Conditions | XRPD |
|---|---|---|---|
| Pattern 2 | 021-01 | 25° C./60% RH | Pattern 2 |
| Pattern 2 | 021-02 | 40° C./75% RH | Pattern 2 |
| Pattern 2 | 021-03 | 70° C./75% RH | Pattern 2 |

The aqueous solubility was determined as detailed in Method 4-1 by aliquot addition. The solubility of AAT-730 HCl salt Pattern 2 in water was 197-263 mg/mL at pH 6-7.

Conclusions

1) Four novel solids were isolated from the screening experiments. The XRPD diffractograms were all very similar suggesting that the solids all have a very similar crystal structure.
2) Interconversion slurries in dry solvent at 5, 25 and 50° C. yielded Pattern 2 material suggesting that this was the stable form in dry solvent between 5 and 50° C.
3) Water activity experiments yielded AAT-730 Pattern 1 at Aw greater than or equal to 0.6. Pattern 2 was stable at Aw at most 0.2 and at Aw at most 0.4, a mixture was isolated which suggests that the critical water activity is at most 0.4.
4) AAT-730 HCl salt Pattern 2 was a crystalline anhydrate with a melting onset of 190.84° C.
5) AAT-730 HCl salt Pattern 2 was stressed for 7 days at 25° C./60% RH, 40° C./75% RH and at 70° C./75% RH. The post-stressed samples were analyzed by XRPD and $^1$H NMR analyses. No change in physical form was observed in all samples and $^1$H NMR suggested that it was chemically stable.
6) The solubility of AAT-730 HCl salt Pattern 2 was 197-263 mg/mL (pH 6-7).

Example 6, Isolation of AAT-730 (Compound A) HCl Salt Pattern 2

AAT-730 (2 g) and THF (10 mL) were added to a round bottom flask and stirred. Dissolution was incomplete after up to 10 minutes and a further portion (1 mL) of THF was added. The mixture was stirred to dissolution and HCl in dioxane (4 M, 1.5 mL) was added dropwise. A crust formed on the top and this was broken up with a pipette. Gumball formation was noted and a further portion (3 mL) of THF was added and the mixture was stirred to break up the solids. The solids were isolated by filtration, washed with THF (3 mL) and air dried in the Buchner funnel. The solids were transferred to a vial and dried to constant weight, under a flow of $N_2$, to yield the salt as a white solid (2.128 g, up to 98% yield). XRPD analysis confirmed formation of AAT-730 HCl salt Pattern 1.

Figure 101:
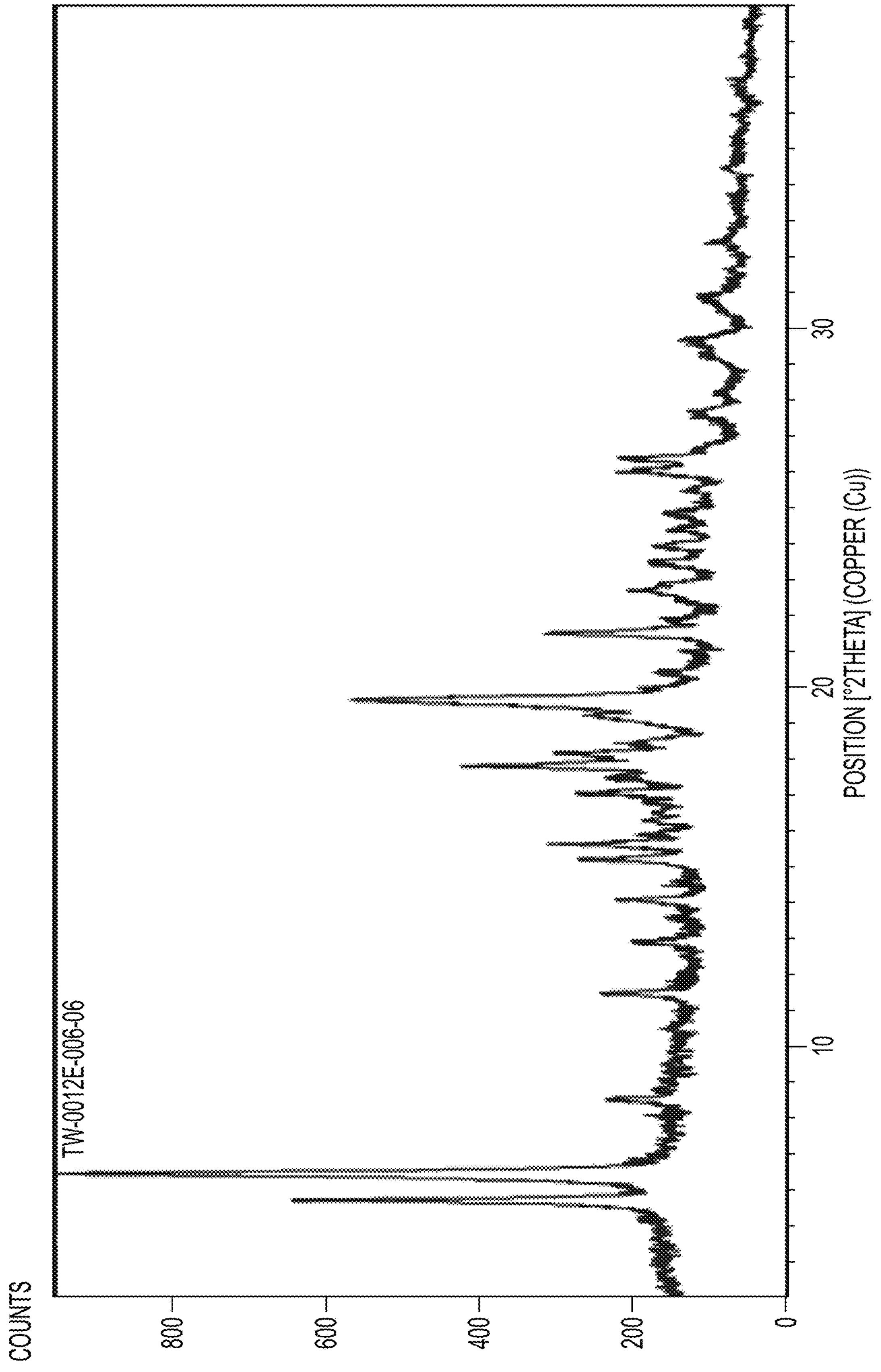
FIG. 101 provides an XRPD pattern of AAT-730 HCl salt Pattern 2.

AAT-730 HCl salt Pattern 1 was added to THF (10-20 volumes) and stirred for 5 days at 20° C. (temperatures between 5 and 50° C. were also suitable). The samples were isolated and air dried prior to analysis by XRPD (FIG. 101). AAT-730 HCl salt Pattern 2 was isolated. Pattern 2 material may be produced quicker by seeding the slurry.

The invention claimed is:

1. A crystalline form of a salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol with an acid, wherein the acid is selected from the group consisting of hydrochloric acid (HCl), maleic acid, and methanesulfonic acid.

2. The crystalline form of the salt according to claim 1, wherein the acid is HCl.

3. The crystalline form of the salt according to claim 1, wherein the salt is a maleic acid salt having a melting endotherm at onset 153° C. in thermogravimetry/differential thermal analysis (TG/DTA).

4. The crystalline form of the salt according to claim 1, wherein the salt is a methanesulfonic acid salt having a melting endotherm at onset 155° C. in thermogravimetry/differential thermal analysis (TG/DTA).

5. A crystalline form of an HCl salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol, wherein the crystalline form is characterized by a powder X-ray diffraction (XRPD) pattern comprising peaks in terms of 2-Theta, at 5.6, 6.7, 16.6, 17.1, 18.8, 19.9, 24.0, 25.9, and 26.8 degrees 2-Theta+/−0.2 degrees 2-Theta for each value.

6. The crystalline form of the HCl salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol according to claim 5, wherein the crystalline form is characterized by an XRPD pattern coinciding with the pattern shown by FIG. 7.

7. A crystalline form of an HCl salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol, wherein the crystalline form is characterized by a powder X-ray diffraction (XRPD) pattern comprising peaks in terms of 2-Theta, at 6.2, 7.0, 8.2, 16.6, 18.6, 19.3, 19.8, 20.4, 23.3, 24.4, and 24.7 degrees 2-Theta+/−0.2 degrees 2-Theta for each value.

8. The crystalline form of the HCl salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol according to claim 7, wherein the crystalline form is characterized by an XRPD pattern coinciding with the pattern shown by FIG. 8.

9. A crystalline form of a maleic acid salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol, wherein the crystalline form is characterized by an XRPD pattern coinciding with the pattern shown by FIG. 52.

10. A crystalline form of a methanesulfonic acid salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol, wherein the crystalline form is characterized by an XRPD pattern coinciding with the pattern shown by FIG. 55.

11. A pharmaceutical composition comprising the crystalline form of the salt according to claim 1.

12. A method for preventing or treating a disorder or condition selected from the group consisting of pain, inflammatory pain, nociceptive pain, neuropathic pain, fibromyalgia, chronic pain, visceral pain, migraine, cluster headache, cancer related pain, complex regional pain syndrome, neuralgias, multiple sclerosis, Alzheimer's disease, Parkinson's disease, amyotrophic lateral sclerosis, epilepsy, diabetes neuropathy, human immunodeficiency virus (HIV), polyneuropathy, a psychiatric disease, psychosis, autistic spectrum disorder, irritable bowel syndrome (IBS), inflammatory bowel disease (IBD), ulcerative colitis, Crohn's disease, gastroesophageal reflux disease (GERD), constipation, diarrhoea, functional gastrointestinal disorder, arthritis, rheumatoid arthritis, osteoarthritis, atherosclerosis, psoriatic arthritis disease, spondylitides, asthma, allergy, psoriasis, dermatitis, seasonal allergic rhinitis, systemic lupus erythematosus (SLE), acute allograft rejection, gingivitis, encephalitis, cutaneous T cell lymphoma, pancreatic cancer, systemic fibrosis, systemic sclerosis (SSc), vasculitis liver fibrosis, lung fibrosis, kidney fibrosis, keloids, hypertrophic scars, acute respiratory distress syndrome (ARDS), reversible airway obstruction, adult respiratory disease syndrome, chronic obstructive pulmonary disease (COPD), cryptogenic fibrosing alveolitis, bronchitis, glaucoma, age-related macular degeneration (AMD), geographic atrophy, diabetic retinopathy, uveitis, retinal vein occlusion, retinopathy of prematurity, ocular ischemic syndrome, glomerulonephritis, renal ischemia, nephritis, diabetic nephropathy, chronic allograft nephropathy, hepatitis, acute liver failure, liver cirrhosis, non-alcoholic steatohepatitis (NASH), myocardial infarction, cerebral ischemia, ischemia-reperfusion injury, heart failure, stroke, myocardial ischemia, cardiomyopathy, transient ischemic attack, diabetes, osteoporosis, regulation of bone mass, non-alcoholic fatty liver (NAFL), attention-deficit hyperactivity disorder (ADHD), anxiety, depression, insomnia/sleep disorder, obsessive compulsive disorder (OCD), post-traumatic stress disorder (PTSD), Tourette's syndrome, malaria, and pyrexia, the method comprising administering to a subject suffering from the disease or condition an affective amount of the crystalline form of the salt according to claim 1.

13. The method according to claim 12, wherein the disease or condition is selected from the group consisting of pain, inflammation, irritable bowel syndrome (IBS), inflammatory bowel disease (IBD) and colitis.

14. The method according to claim 12, wherein the neuralgia is trigeminal neuralgia.

15. A process for preparing a crystalline form of a pharmaceutically acceptable HCl, maleic acid or methanesulfonic acid salt of 2-[3-({1-[2-(dimethylamino)ethyl]-2-(2,2-dimethylpropyl)-1H-1,3-benzodiazol-5-yl}sulfonyl)azetidin-1-yl]ethan-1-ol, comprising dissolving 2-[3-({1-[2-(dimethylamino)ethyl]-2-(2,2-dimethylpropyl)-1H-1,3-benzodiazol-5-yl}sulfonyl)azetidin-1-yl]ethan-1-ol in a solvent.

16. The process according to claim 15, wherein the solvent is at least one selected from the group consisting of acetone, acetonitrile, 1-butanol, cyclohexane, dichloromethane, diisopropyl ether, dimethylacetamide, dimethyl sulfoxide, dioxane, ethanol, ethyl acetate, heptane, isopropyl acetate, methyl tert-butyl ether, methyl ethyl ketone, methyl isobutyl ketone, methanol, 2-propanol, toluene, tetrahydrofuran, water, and the mixture of the solvents thereof.

* * * * *